US012600985B2

(12) United States Patent
Deisseroth et al.

(10) Patent No.: US 12,600,985 B2
(45) Date of Patent: Apr. 14, 2026

(54) COMPOSITIONS AND METHODS FOR CONTROLLING PRODUCTION OF POLYPEPTIDES IN CELLS

(71) Applicant: The Board of Trustees of the Leland Stanford Junior University, Stanford, CA (US)

(72) Inventors: Karl A. Deisseroth, Stanford, CA (US); Charu Ramakrishnan, San Jose, CA (US); Yoon Seok Kim, Stanford, CA (US); Lief E. Fenno, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 923 days.

(21) Appl. No.: 17/796,839

(22) PCT Filed: Feb. 3, 2021

(86) PCT No.: PCT/US2021/016398
§ 371 (c)(1),
(2) Date: Aug. 1, 2022

(87) PCT Pub. No.: WO2021/158651
PCT Pub. Date: Aug. 12, 2021

(65) Prior Publication Data
US 2023/0064644 A1     Mar. 2, 2023

Related U.S. Application Data

(60) Provisional application No. 62/969,858, filed on Feb. 4, 2020.

(51) Int. Cl.
*C12N 15/85* (2006.01)
*C12N 15/66* (2006.01)

(52) U.S. Cl.
CPC ............. *C12N 15/85* (2013.01); *C12N 15/66* (2013.01); *C12N 2800/30* (2013.01)

(58) Field of Classification Search
CPC ...................................................... C12N 15/85
See application file for complete search history.

(56) References Cited

U.S. PATENT DOCUMENTS 6,774,279 B2     8/2004   Dymecki
6,852,530 B2     2/2005   Silver et al.
(Continued)

FOREIGN PATENT DOCUMENTS

CN          102373237          3/2012
CN          107699589          2/2018

OTHER PUBLICATIONS

Fenno et al., "INTRSECT: targeting specific cell types in the nervous System: A guide to creating and testing new INTRSECT constructs," Curr Protoc Neurosci, Author manuscript: available in PMC Dec. 4, 2019, entire document.*
(Continued)

*Primary Examiner* — Mark L Shibuya
(74) *Attorney, Agent, or Firm* — Rudy J. Ng; Darya Cheng; Bozicevic, Field & Francis LLP

(57) ABSTRACT

The present disclosure provides recombinant expression vectors for modulating production of polypeptides of interest in a target cell or target cell population. Aspects of the disclosure include recombinant expression vectors having coding sequences encoding portions of a polypeptide of interest, where the coding sequences are flanked by recombinase recognition sites. Also provided are methods for using the recombinant expression vectors as well as a device for monitoring expression of the polypeptide of interest.

25 Claims, 108 Drawing Sheets

Specification includes a Sequence Listing.

(56)                    References Cited

U.S. PATENT DOCUMENTS

| | | |
|---|---|---|
| 2003/0159160 A1 | 8/2003 | Chambon et al. |
| 2005/0003543 A1 | 1/2005 | Economides et al. |
| 2006/0253918 A1* | 11/2006 | Que .................. C12N 15/8213 |
| | | 800/278 |
| 2011/0223635 A1 | 9/2011 | Deisseroth |
| 2015/0275232 A1 | 10/2015 | Padidam |
| 2017/0183654 A1 | 6/2017 | Wong et al. |

OTHER PUBLICATIONS

Suzuki, VCre/VloxP and SCre/SloxP: new site-specific recombination systems for genome engineering, Nucleic Acids Research, Vo. 39, No. 8, pp. 1 to 11, Feb. 2011.*
Fenno et al., (2014) "INTRSECT: Single-Component Targeting of Cells using Multiple-Feature Boolean Logic," Nat Methods, 11(7):763-772.
Fenno et al., (2019) "INTRSECT: Targeting Specific Cell Types in the Nervous System", A Guide to Creating and Testing New INTRSECT Constructs, Curr Protoc Neurosci, 80: 38 pages.
Fenno et al., (2020). "Comprehensive Dual- and Triple-Feature Intersectiona | Single-Vector Delivery of Diverse Functional Payloads to Cells of Behaving Mammals," Neuron, 107(5):836-853.

* cited by examiner

FIG. 1A single intron INTRSECT constructs

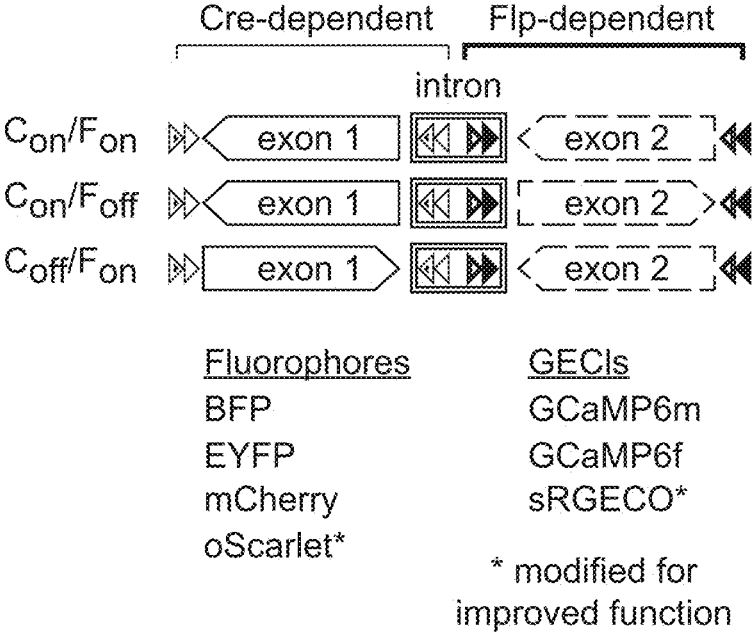

Cre-dependent    Flp-dependent intron $C_{on}/F_{on}$ $C_{on}/F_{off}$ $C_{off}/F_{on}$ exon 1    exon 2

<u>Fluorophores</u>
BFP
EYFP
mCherry
oScarlet*

<u>GECIs</u>
GCaMP6m
GCaMP6f
sRGECO*

* modified for
improved function

FIG. 1B

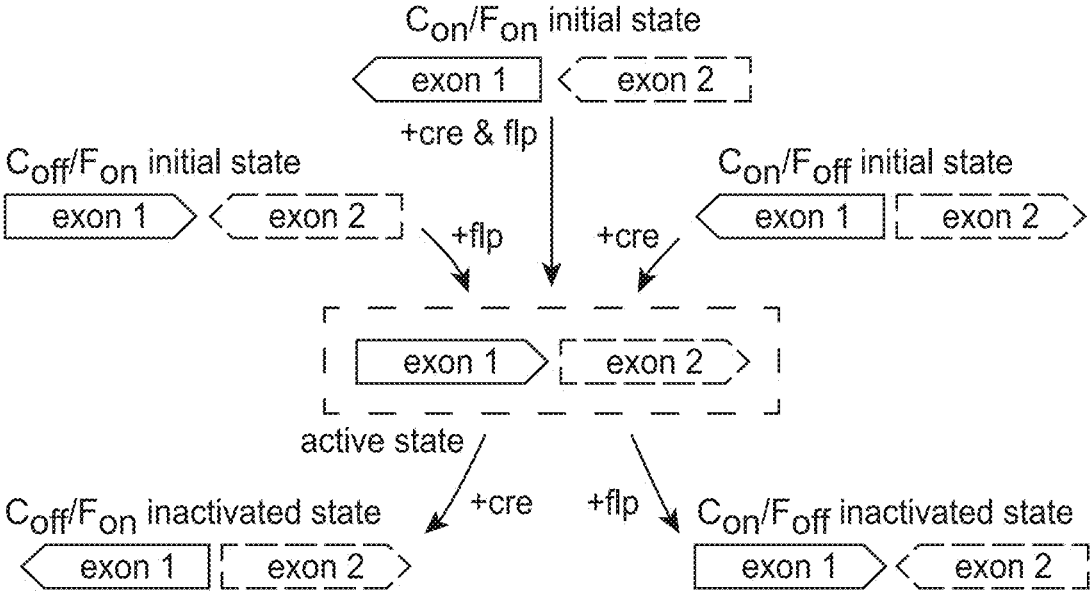

$C_{on}/F_{on}$ initial state
exon 1    exon 2
+cre & flp $C_{off}/F_{on}$ initial state
exon 1    exon 2

$C_{on}/F_{off}$ initial state
exon 1    exon 2

+flp    +cre exon 1    exon 2 active state $C_{off}/F_{on}$ inactivated state
exon 1    exon 2

+cre    +flp $C_{on}/F_{off}$ inactivated state
exon 1    exon 2 double intron INTRSECT constructs

Excitatory Opsins

ChR2 (H134R)-EYFP

ChR2 (ET/TC)-EYFP

ChR2 (H134R)-mCherry bReaChES-EYFP

ChRmine 3.3-p2a-oScarlet

Inhibitory Opsins

Arch 3.3-p2a-EYFP

NpHR 3.3-p2a-EYFP* iC++-EYFP

* modified for
improved function bReaChES-EYFP intron site replacement optimized bReaChES-EYFP

NpHR-EYFP rational protein engineering

NpHR(W179F)-EYFP

Hippocampus mPFC

FIG. 4C
$C_{on}/F_{on}$-EYEP + Flp-p2a-Cre day 5
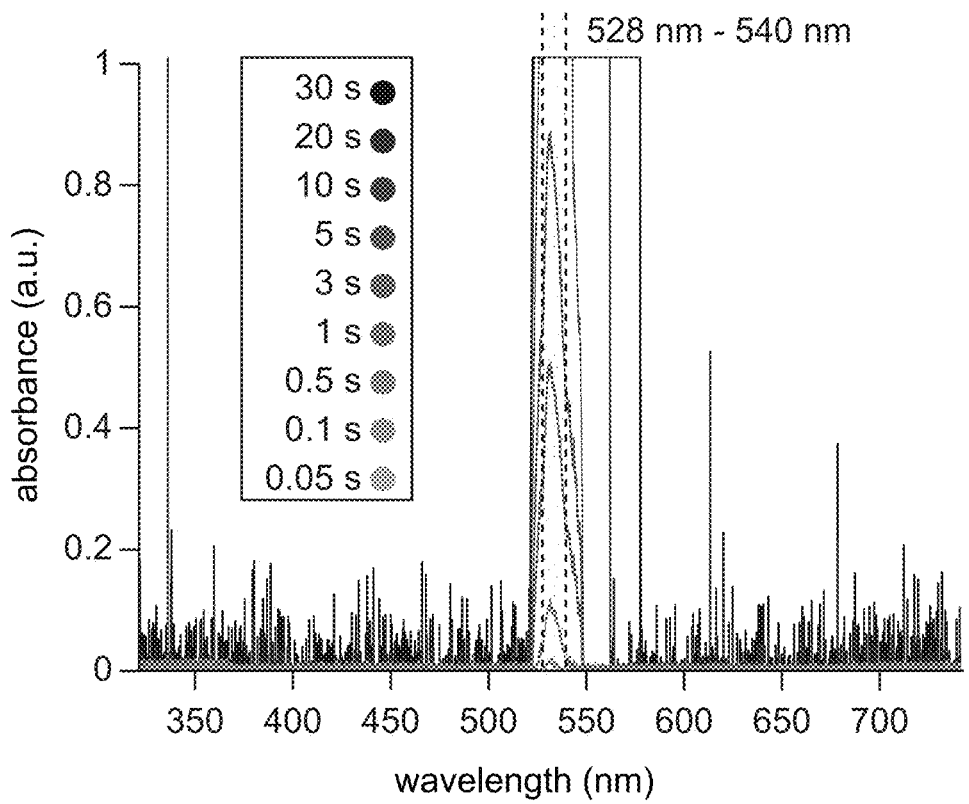
FIG. 4D
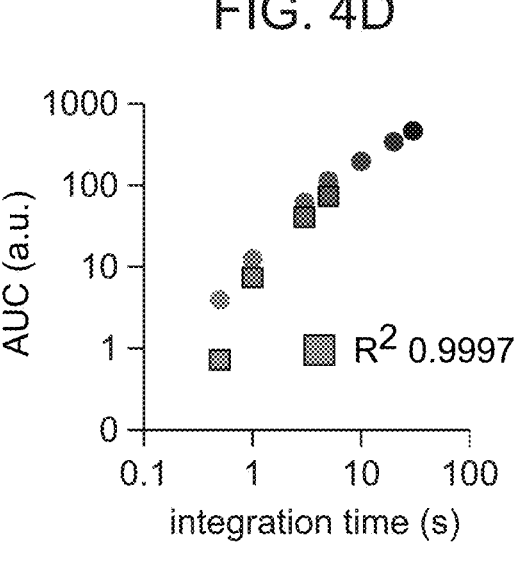
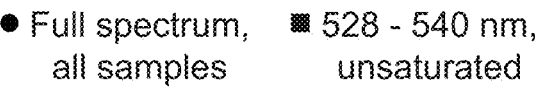
● Full spectrum,    ■ 528 - 540 nm,
   all samples         unsaturated
FIG. 4E
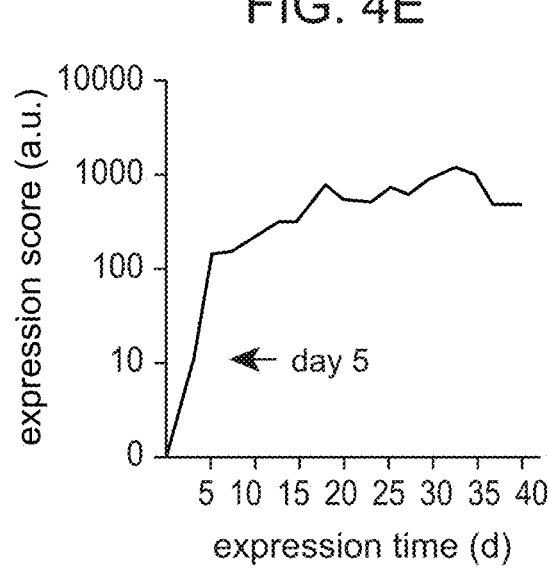

FIG. 4I
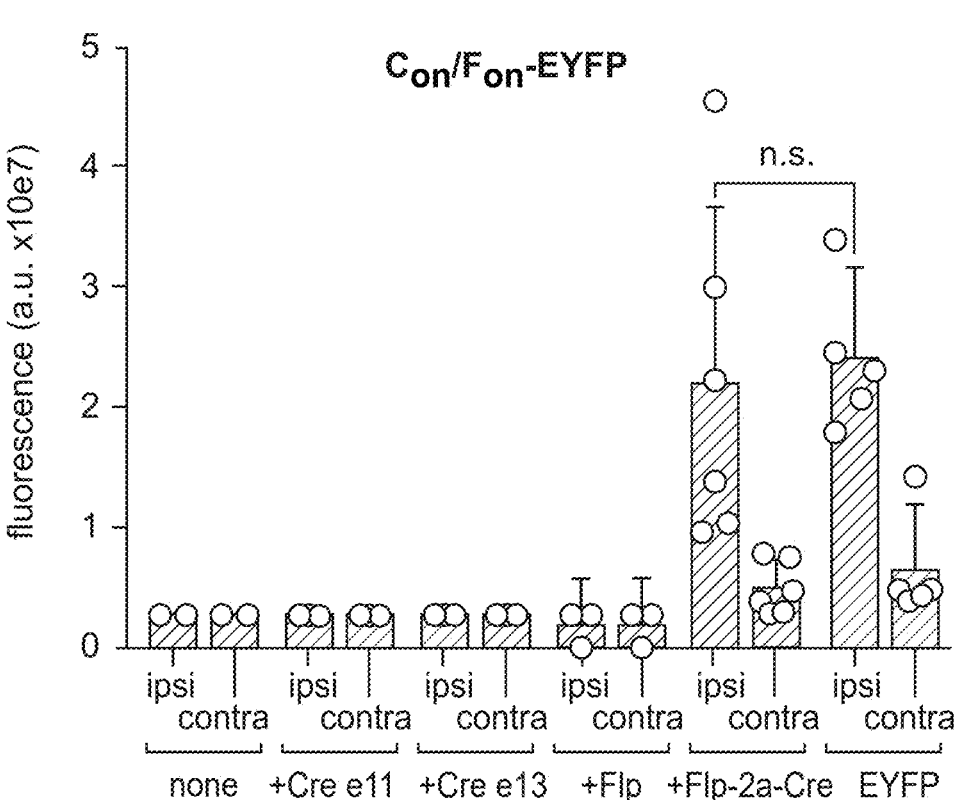
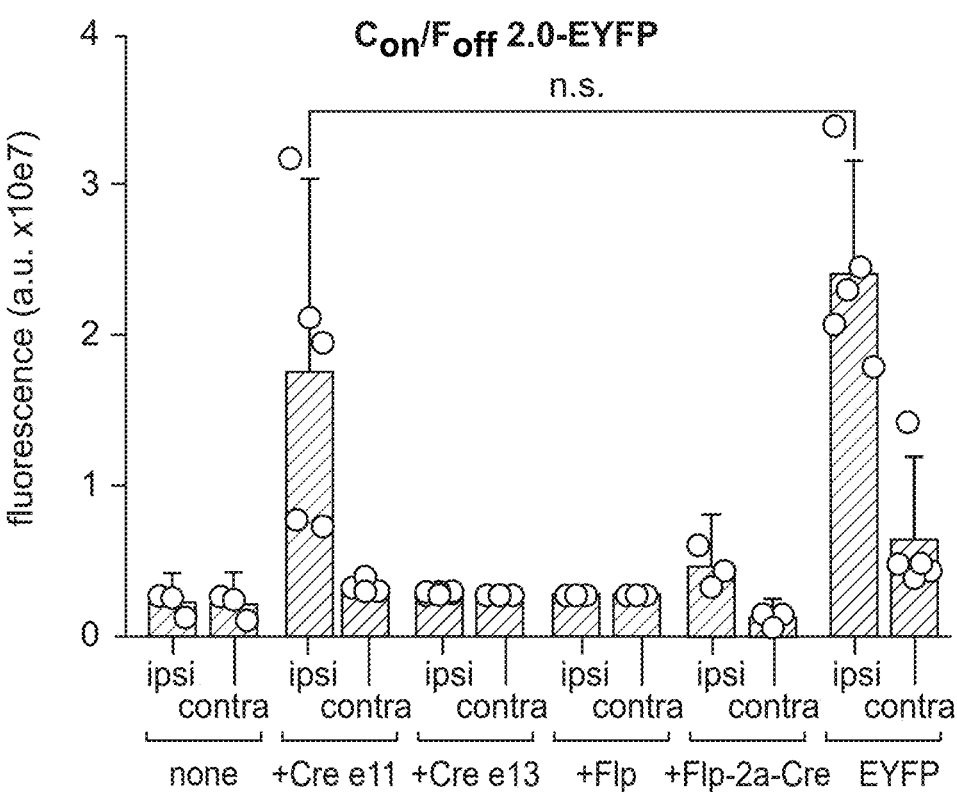

FIG. 5

| | Driver | Flp Gene | Construction | species | author | journal |
|---|---|---|---|---|---|---|
| 1 | Dlx5/6 | Myc-FlpE | Random integration | m | Miyoshi | Journal of Neuroscience |
| 2 | Actb | FlpE | Random integration | m | Rodriguez | Nature Genetics |
| 3 | Nkx2.1 | FlpO | IRES knock-in | m | He | Neuron |
| 4 | VIP | FlpO | IRES knock-in | m | He | Neuron |
| 5 | SST | FlpO | IRES knock-in | m | He | Neuron |
| 6 | Cag | FlpE | Random integration | m | Kanki | Experimental Animals |
| 7 | Phox2b | FlpO | BAC transgenic | m | Hirsch | Genesis |
| 8 | DbH | FlpO | START knock-in | m | Robertson | Nature Neuroscience |
| 9 | DbH | FlpO | START knock-in | m | Sun | PLOS One |
| 10 | DbH | FlpO | 2a knock-in | m | Sun | PLOS One |
| 11 | Pdx1 | FlpO | Random integration | m | Schönhuber | Nature Medicine |
| 12 | Pdx1 | FlpO | START knock-in | m | Wu | PLOS One |
| 13 | Pvalb | FlpE | 2a knock-in | m | Madisen | Neuron |
| 14 | Pvalb | FlpO | 2a knock-in | m | Madisen | Neuron |
| 15 | Wnt1 | Flp(F70L) | Random integration | m | Dymecki | Developmental Biology |
| 16 | Npy | FlpO | IRES knock-in | m | Daigle | Cell |
| 17 | Plxnd1 | dgFlpO | IRES knock-in | m | Daigle | Cell |
| 18 | Rasgrf2 | dgFlpO | 2a knock-in | m | Daigle | Cell |
| 19 | Rorb | FlpO | IRES knock-in | m | Daigle | Cell |
| 20 | Rorb | FlpO | 2a knock-in | m | Daigle | Cell |
| 21 | Slc17a6 | FlpO | IRES knock-in | m | Daigle | Cell |
| 22 | Slc32a1 | FlpO | IRES knock-in | m | Daigle | Cell |
| 23 | Slc32a1 | FlpO | 2a knock-in | m | Daigle | Cell |
| 24 | Crh | FlpO | IRES knock-in | m | Sabatini | Unpublished |
| 25 | Cdx2 | FlpO | Random integration | m | Abraira | Cell |
| 26 | Cdx2 | FlpO | Random integration | m | Britz | eLife |
| 27 | Advillin | FlpO | | | | Unpublished |
| 28 | TH | FlpO | 2a knock-in | m | Poulin | Nature Neuroscience |
| 29 | TH | FlpO | Random integration | m | Imayoshi | Neuroscience Research |
| 30 | Mrgprb4 | EGFP-2a-FlpO | 2a knock-in; driver knock-out | m | Vrontou | Nature |

FIG. 5 (Cont.)

| | Driver | Flp Gene | Construction | species | author | journal |
|---|---|---|---|---|---|---|
| (31) | Pet1 | FlpE | | m | Jensen | Nature Neuroscience |
| (32) | Pgk1 | Flpo | Random integration | m | Wu Y | Plos One |
| (33) | MMTV | FlpO | Random integration | m | Lüönd | Journal of Mammary Gland B |
| (34) | Cag | FlpE-ER | Random integration | m | Hunter | Genesis |
| (35) | Wnt1 | FlpE-ER | Random integration | m | Hunter | Genesis |
| (36) | Wnt1 | FlpE | Random integration | m | Awatramani | Nature Genetics |
| (37) | Gsh2 | FlpE | | m | | |
| (38) | Atoh1 | FlpO-ER | Random integration | m | Wojcinski | Neural Development |
| (39) | Bhlhe22 | FlpO | START knock-in | m | Cai | Developmental Biology |
| (40) | CamK2a | FlpE | | m | | |
| (41) | EF1A | Flp | Random integration | m | Takeuchi | Biochemical and Biophysica |
| (42) | Gad2 | FlpO | IRES knock-in | m | Alhadeff | Cell |
| (43) | VGlut2 | FlpO | IRES knock-in | m | Alhadeff | Cell |
| (44) | GFAP | FlpO | Random integration | m | Hara | Cancer Research |
| (45) | Hcrt | FlpO | 2a knock-in | m | Chowdhury | eLife |
| (46) | Hoxb8 | FlpO | Random integration | m | Zhang | The Journal of Clinical Invest |
| (47) | Htr3a | FlpO | IRES knock-in | m | Schuman | Journal of Neuroscience |
| (48) | Lbx1 | FlpO | START knock-in | m | Bourane | Science |
| (49) | Nestin | FlpO-ER | Random integration | m | Lao | Cell |
| (50) | Nphs1 | FlpO | Random integration | m | Goldberg | Journal of the American Soc |
| (51) | Pomc | FlpE | Random integration | m | Vooijs | Oncogene |
| (52) | Slc6a3 | FlpO | IRES knock-in | m | Fu | Unpublished |
| (53) | Slc6a4 | FlpO | IRES knock-in | m | Fu | Unpublished |
| (54) | Tbx21 | FlpE-ER | IRES knock-in | m | Gokmen | The Journal of Immunology |
| (55) | Trf | FlpE | | m | | |
| (56) | mGluR5 | FlpO | Random integration | m | Furukawa | Unpublished |
| (57) | Pvalb | FlpO | 2a knock-in | r | | Unpublished |
| (58) | Fezf2 | FlpO | 2a knock-in | m | Huang | Unpublished |
| (59) | PlexinD1 | FlpO | 2a knock-in | m | Huang | Unpublished |
| (60) | Tbr2 | FlpO-ER | 2a knock-in | m | Huang | Unpublished |

FIG. 5 (Cont.)

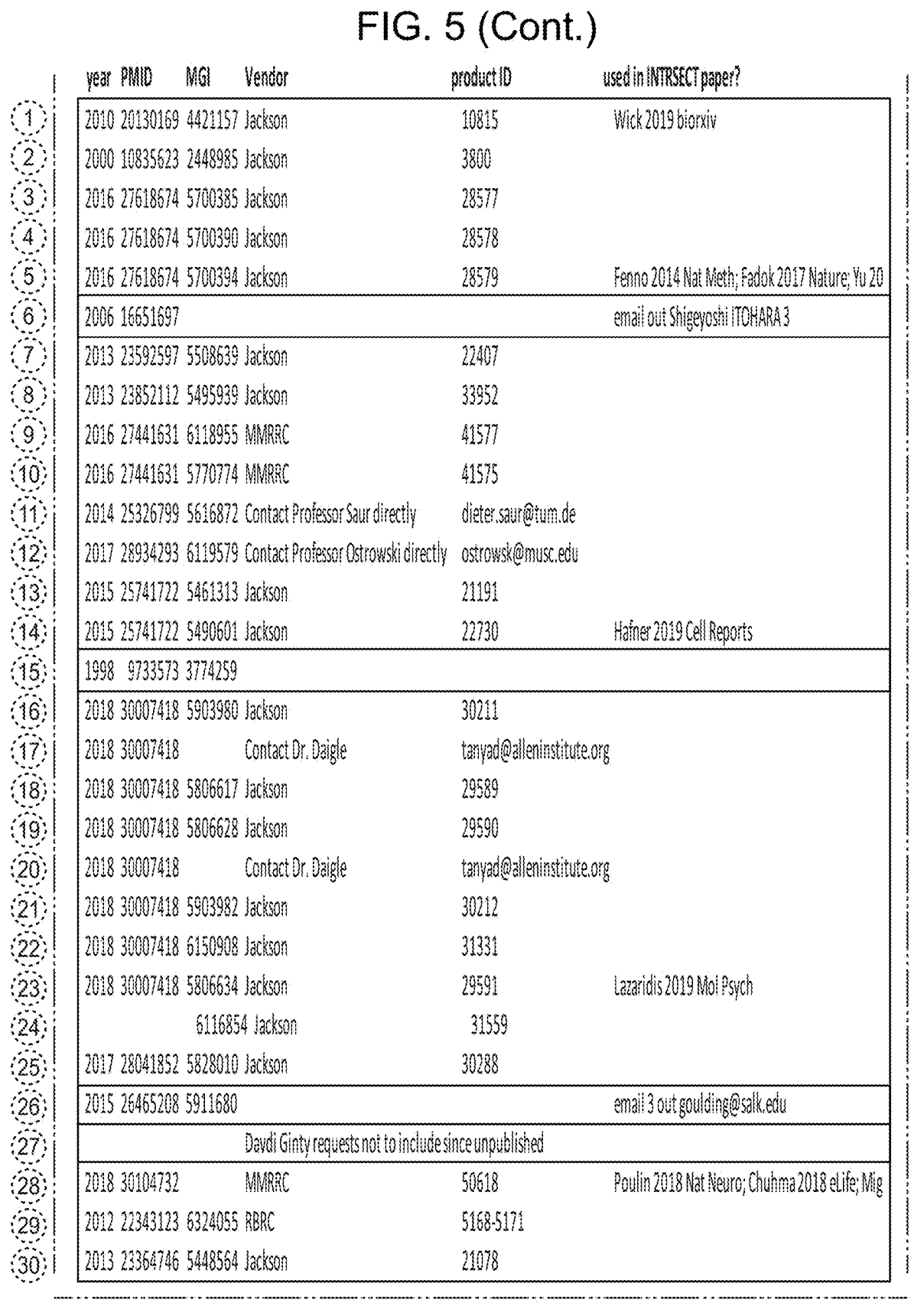

| | year | PMID | MGI | Vendor | product ID | used in INTRSECT paper? |
|---|---|---|---|---|---|---|
| 1 | 2010 | 20130169 | 4421157 | Jackson | 10815 | Wick 2019 biorxiv |
| 2 | 2000 | 10835623 | 2448985 | Jackson | 3800 | |
| 3 | 2016 | 27618674 | 5700385 | Jackson | 28577 | |
| 4 | 2016 | 27618674 | 5700390 | Jackson | 28578 | |
| 5 | 2016 | 27618674 | 5700394 | Jackson | 28579 | Fenno 2014 Nat Meth; Fadok 2017 Nature; Yu 20 |
| 6 | 2006 | 16651697 | | | | email out Shigeyoshi iTOHARA 3 |
| 7 | 2013 | 23592597 | 5508639 | Jackson | 22407 | |
| 8 | 2013 | 23852112 | 5495939 | Jackson | 33952 | |
| 9 | 2016 | 27441631 | 6118955 | MMRRC | 41577 | |
| 10 | 2016 | 27441631 | 5770774 | MMRRC | 41575 | |
| 11 | 2014 | 25326799 | 5616872 | Contact Professor Saur directly | dieter.saur@tum.de | |
| 12 | 2017 | 28934293 | 6119579 | Contact Professor Ostrowski directly | ostrowsk@musc.edu | |
| 13 | 2015 | 25741722 | 5461313 | Jackson | 21191 | |
| 14 | 2015 | 25741722 | 5490601 | Jackson | 22730 | Hafner 2019 Cell Reports |
| 15 | 1998 | 9733573 | 3774259 | | | |
| 16 | 2018 | 30007418 | 5903980 | Jackson | 30211 | |
| 17 | 2018 | 30007418 | | Contact Dr. Daigle | tanyad@alleninstitute.org | |
| 18 | 2018 | 30007418 | 5806617 | Jackson | 29589 | |
| 19 | 2018 | 30007418 | 5806628 | Jackson | 29590 | |
| 20 | 2018 | 30007418 | | Contact Dr. Daigle | tanyad@alleninstitute.org | |
| 21 | 2018 | 30007418 | 5903982 | Jackson | 30212 | |
| 22 | 2018 | 30007418 | 6150908 | Jackson | 31331 | |
| 23 | 2018 | 30007418 | 5806634 | Jackson | 29591 | Lazaridis 2019 Mol Psych |
| 24 | | | 6116854 | Jackson | 31559 | |
| 25 | 2017 | 28041852 | 5828010 | Jackson | 30288 | |
| 26 | 2015 | 26465208 | 5911680 | | | email 3 out goulding@salk.edu |
| 27 | | | | Davdi Ginty requests not to include since unpublished | | |
| 28 | 2018 | 30104732 | | MMRRC | 50618 | Poulin 2018 Nat Neuro; Chuhma 2018 eLife; Mig |
| 29 | 2012 | 22343123 | 6324055 | RBRC | 5168-5171 | |
| 30 | 2013 | 23364746 | 5448564 | Jackson | 21078 | |

FIG. 5 (Cont.)

| | year | PMID | MGI | Vendor | product ID | used in INTRSECT paper? |
|---|---|---|---|---|---|---|
| (31) | 2008 | | | | | |
| (32) | 2009 | 19956655 | 4415609 | Jackson | 11065 | |
| (33) | 2019 | 30209717 | | Contact Professor Christofori directly | gerhard.christofori@unibas.ch | |
| (34) | 2005 | 15729687 | 5432116 | | | email 3 out dymecki |
| (35) | 2005 | 15729687 | 5432117 | | | email 3 out dymecki |
| (36) | 2003 | 12923530 | 3774259 | | | email 3 out dymecki |
| (37) | | | | CARD | 2114 | email 3 out tamamaki@kumamoto-u.ac.jp |
| (38) | 2019 | 30764875 | 6331265 | Contact Professor Joyner directly | joynera@mskcc.org | |
| (39) | 2016 | 27151208 | 6369826 | Contact Professor Ross directly | saross@pitt.edu | |
| (40) | 2012 | | 5440165 | Taconic - Not available | | |
| (41) | 2002 | 12051751 | | RBRC | 1251,1252 | |
| (42) | 2018 | 29570993 | 6156370 | Contact Professor Hantman directly | hantmana@janelia.hhmi.org | |
| (43) | 2018 | 29570993 | 6156365 | Contact Professor Hantman directly | hantmana@janelia.hhmi.org | |
| (44) | 2019 | 31315836 | 6294098 | Jackson | 33116 | |
| (45) | 2019 | 31159922 | 6357834 | Contact Professor Yamanaka directly | yamank@riem.nagoya-u.ac.jp | |
| (46) | 2018 | 29893745 | 6147797 | EMMA | 11094 | |
| (47) | 2019 | 30413647 | | Jackson | 30755 | |
| (48) | 2015 | 26516282 | 5770780 | | | email 3 out goulding@salk.edu |
| (49) | 2012 | 22884371 | 5532191 | Contact Professor Joyner directly | joynera@mskcc.org | |
| (50) | 2010 | 20150535 | 5431870 | Contact Professor Miner directly | minerj@wustl.edu | |
| (51) | 1998 | 9671308 | 4353097 | No longer maintained or available | | |
| (52) | | | 6316964 | Jackson | 33673 | |
| (53) | | | 6316965 | Jackson | 33674 | |
| (54) | 2013 | | 5575639 | Contact Professor Lord directly | Graham.lord@manchester.ac.uk | |
| (55) | 2012 | | 5440434 | Taconic - Not available | | |
| (56) | | | | RBRC | 9715 | |
| (57) | | | | Contact Professor Berke directly | joshua.berke@ucsf.edu | |
| (58) | | | | Contact Professor Huang directly | huangj@cshl.edu | |
| (59) | | | | Contact Professor Huang directly | huangj@cshl.edu | |
| (60) | | | | Contact Professor Huang directly | huangj@cshl.edu | |

FIG. 5 (Cont.)

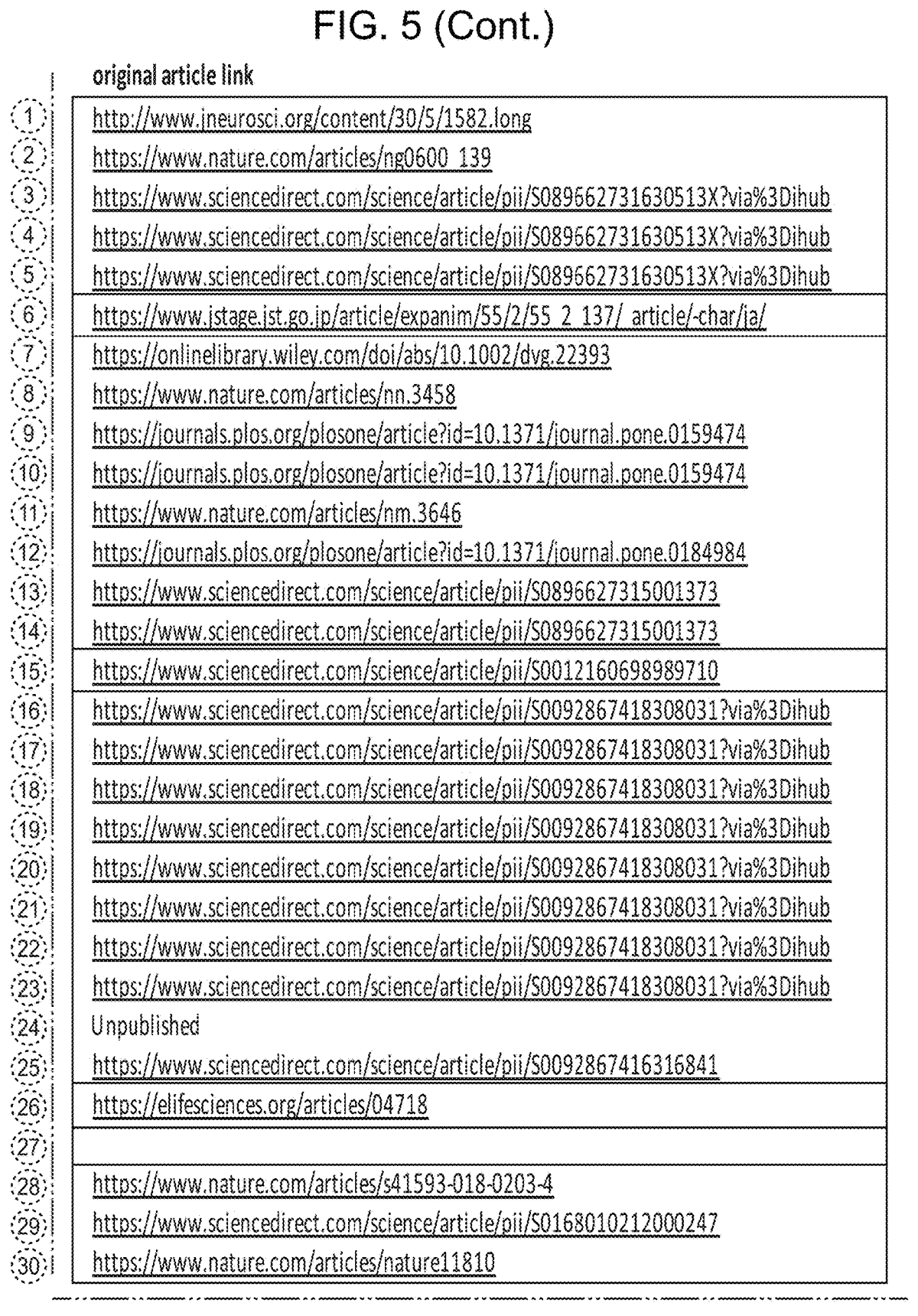

original article link

| # | |
|---|---|
| 1 | http://www.jneurosci.org/content/30/5/1582.long |
| 2 | https://www.nature.com/articles/ng0600_139 |
| 3 | https://www.sciencedirect.com/science/article/pii/S089662731630513X?via%3Dihub |
| 4 | https://www.sciencedirect.com/science/article/pii/S089662731630513X?via%3Dihub |
| 5 | https://www.sciencedirect.com/science/article/pii/S089662731630513X?via%3Dihub |
| 6 | https://www.jstage.jst.go.jp/article/expanim/55/2/55_2_137/_article/-char/ja/ |
| 7 | https://onlinelibrary.wiley.com/doi/abs/10.1002/dvg.22393 |
| 8 | https://www.nature.com/articles/nn.3458 |
| 9 | https://journals.plos.org/plosone/article?id=10.1371/journal.pone.0159474 |
| 10 | https://journals.plos.org/plosone/article?id=10.1371/journal.pone.0159474 |
| 11 | https://www.nature.com/articles/nm.3646 |
| 12 | https://journals.plos.org/plosone/article?id=10.1371/journal.pone.0184984 |
| 13 | https://www.sciencedirect.com/science/article/pii/S0896627315001373 |
| 14 | https://www.sciencedirect.com/science/article/pii/S0896627315001373 |
| 15 | https://www.sciencedirect.com/science/article/pii/S0012160698989710 |
| 16 | https://www.sciencedirect.com/science/article/pii/S0092867418308031?via%3Dihub |
| 17 | https://www.sciencedirect.com/science/article/pii/S0092867418308031?via%3Dihub |
| 18 | https://www.sciencedirect.com/science/article/pii/S0092867418308031?via%3Dihub |
| 19 | https://www.sciencedirect.com/science/article/pii/S0092867418308031?via%3Dihub |
| 20 | https://www.sciencedirect.com/science/article/pii/S0092867418308031?via%3Dihub |
| 21 | https://www.sciencedirect.com/science/article/pii/S0092867418308031?via%3Dihub |
| 22 | https://www.sciencedirect.com/science/article/pii/S0092867418308031?via%3Dihub |
| 23 | https://www.sciencedirect.com/science/article/pii/S0092867418308031?via%3Dihub |
| 24 | Unpublished |
| 25 | https://www.sciencedirect.com/science/article/pii/S0092867416316841 |
| 26 | https://elifesciences.org/articles/04718 |
| 27 | |
| 28 | https://www.nature.com/articles/s41593-018-0203-4 |
| 29 | https://www.sciencedirect.com/science/article/pii/S0168010212000247 |
| 30 | https://www.nature.com/articles/nature11810 |

FIG. 5 (Cont.)

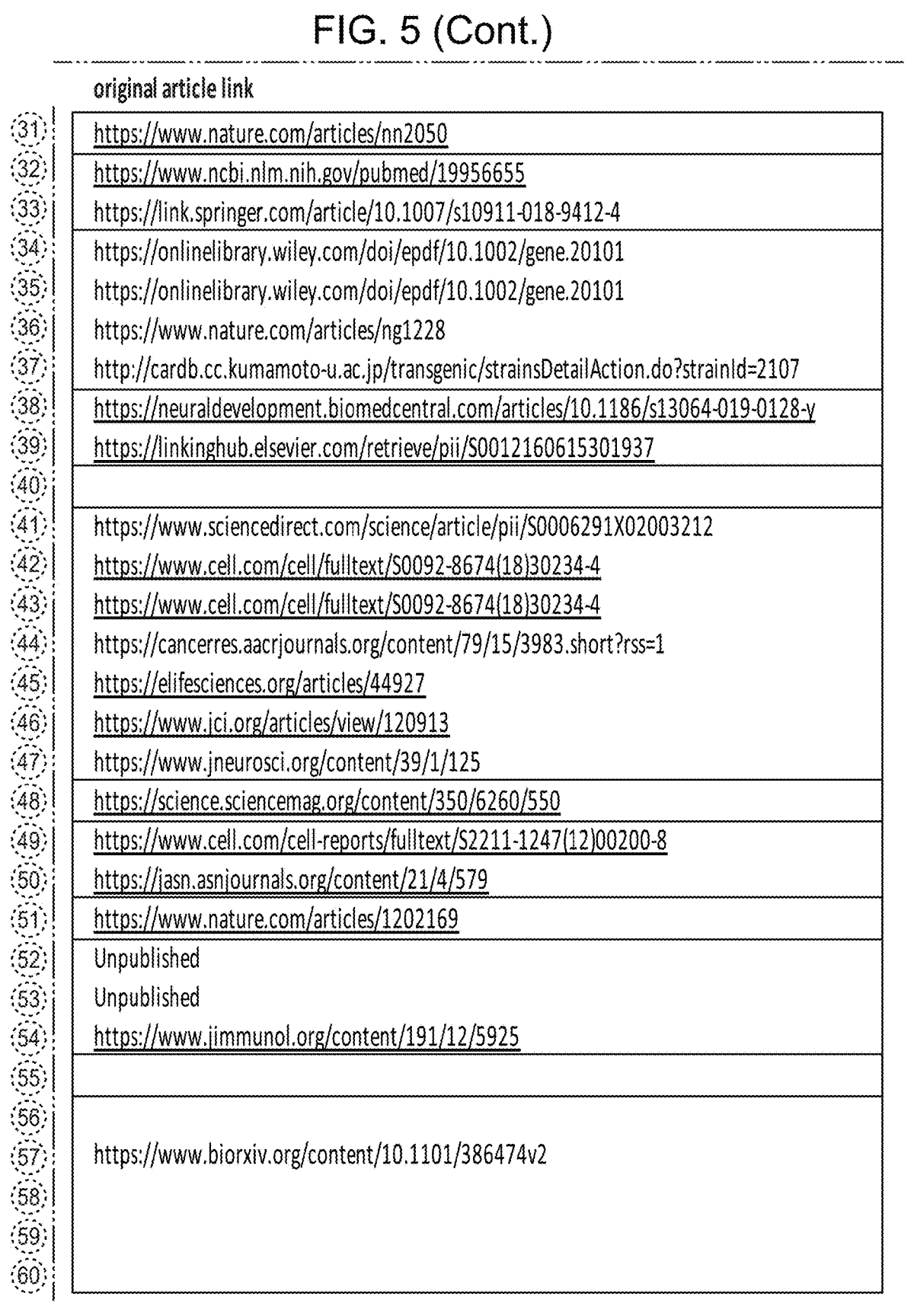

original article link

| # | link |
|---|------|
| 31 | https://www.nature.com/articles/nn2050 |
| 32 | https://www.ncbi.nlm.nih.gov/pubmed/19956655 |
| 33 | https://link.springer.com/article/10.1007/s10911-018-9412-4 |
| 34 | https://onlinelibrary.wiley.com/doi/epdf/10.1002/gene.20101 |
| 35 | https://onlinelibrary.wiley.com/doi/epdf/10.1002/gene.20101 |
| 36 | https://www.nature.com/articles/ng1228 |
| 37 | http://cardb.cc.kumamoto-u.ac.jp/transgenic/strainsDetailAction.do?strainId=2107 |
| 38 | https://neuraldevelopment.biomedcentral.com/articles/10.1186/s13064-019-0128-y |
| 39 | https://linkinghub.elsevier.com/retrieve/pii/S0012160615301937 |
| 40 | |
| 41 | https://www.sciencedirect.com/science/article/pii/S0006291X02003212 |
| 42 | https://www.cell.com/cell/fulltext/S0092-8674(18)30234-4 |
| 43 | https://www.cell.com/cell/fulltext/S0092-8674(18)30234-4 |
| 44 | https://cancerres.aacrjournals.org/content/79/15/3983.short?rss=1 |
| 45 | https://elifesciences.org/articles/44927 |
| 46 | https://www.jci.org/articles/view/120913 |
| 47 | https://www.jneurosci.org/content/39/1/125 |
| 48 | https://science.sciencemag.org/content/350/6260/550 |
| 49 | https://www.cell.com/cell-reports/fulltext/S2211-1247(12)00200-8 |
| 50 | https://jasn.asnjournals.org/content/21/4/579 |
| 51 | https://www.nature.com/articles/1202169 |
| 52 | Unpublished |
| 53 | Unpublished |
| 54 | https://www.jimmunol.org/content/191/12/5925 |
| 55 | |
| 56 | |
| 57 | https://www.biorxiv.org/content/10.1101/386474v2 |
| 58 | |
| 59 | |
| 60 | |

Cre

AND

Flp

AND

VCre

FIG. 6C

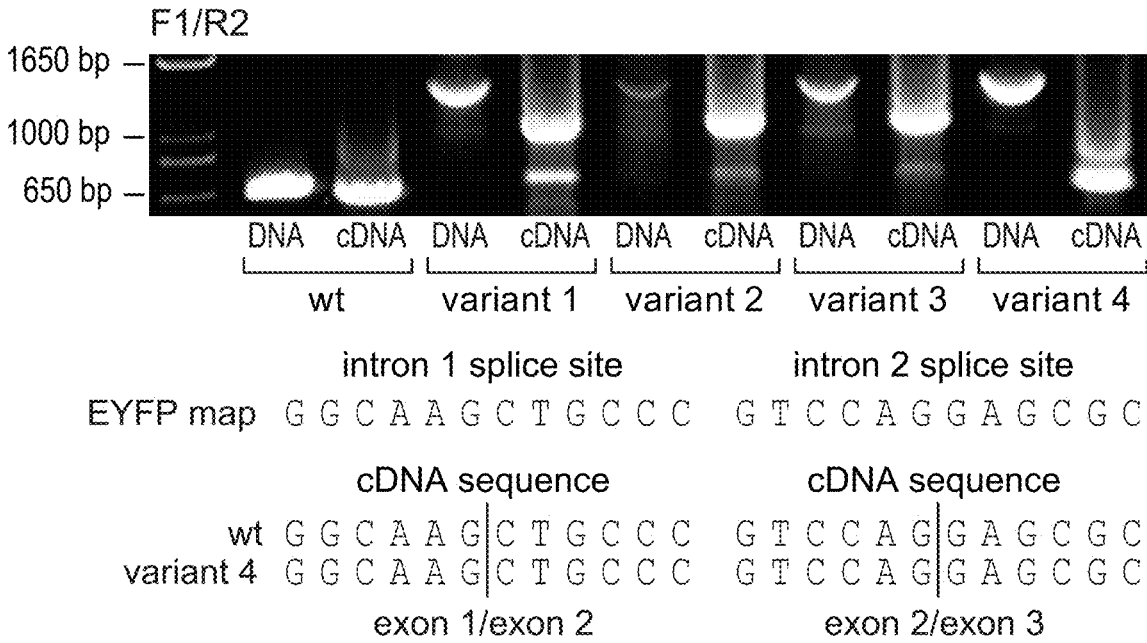

F1/R2

1650 bp —
1000 bp —
650 bp —

DNA  cDNA  DNA  cDNA  DNA  cDNA  DNA  cDNA  DNA  cDNA wt        variant 1    variant 2    variant 3    variant 4 intron 1 splice site              intron 2 splice site

EYFP map  G G C A A G C T G C C C    G T C C A G G A G C G C cDNA sequence                        cDNA sequence wt  G G C A A G|C T G C C C    G T C C A G|G A G C G C
variant 4  G G C A A G|C T G C C C    G T C C A G|G A G C G C exon 1/exon 2                        exon 2/exon 3

FIG. 6D

HEK293 culture transfection (variant +Cre +Flp +VCre)

wt            variant 1        variant 2

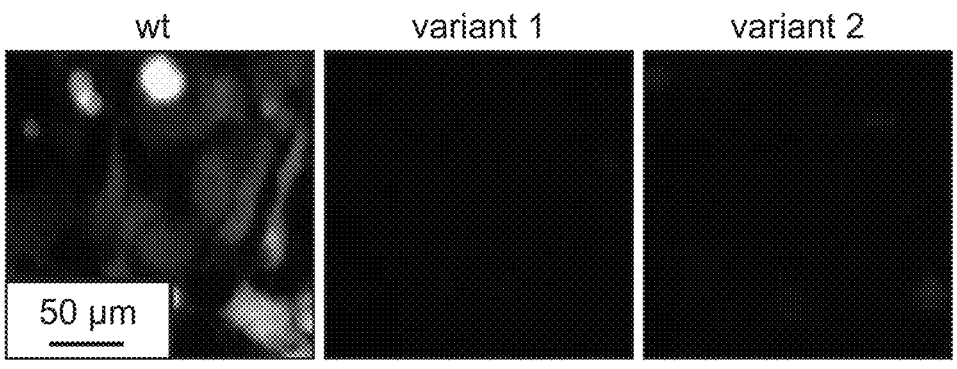

50 µm variant 3        variant 4

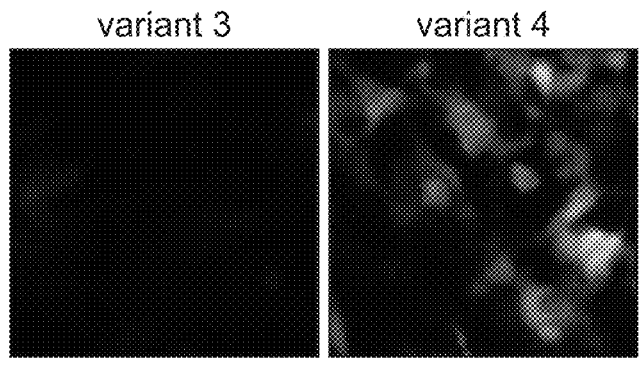

FIG. 6I
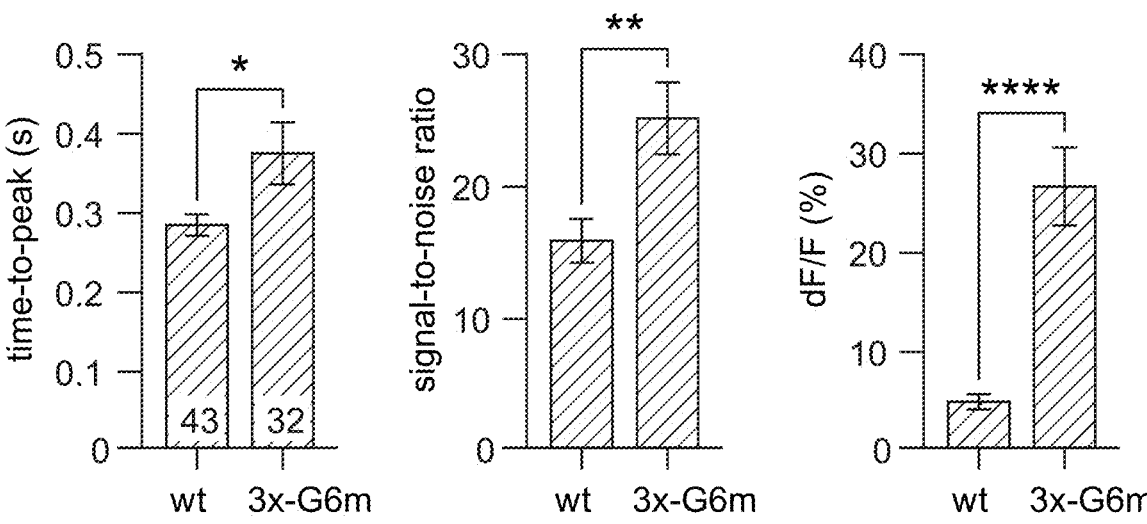
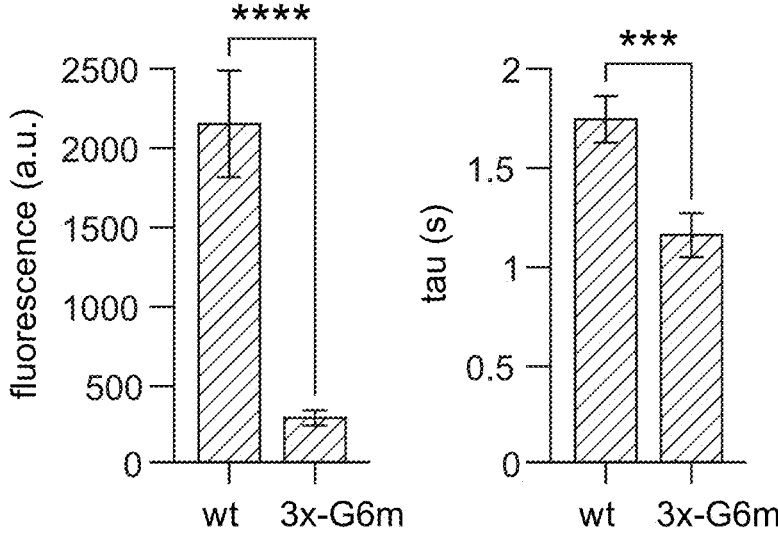

novel object exploration

| | |
|---|---|
| ■ TH-Cre +3x-G6m +Flp +VCre | ■ TH-Cre +3x-G6m +VCre |
| ■ TH-Cre +3x-G6m +Flp | ■ WT +3x-G6m +Flp +VCre | novel object exploration onset 500 ms

FIG. 7E
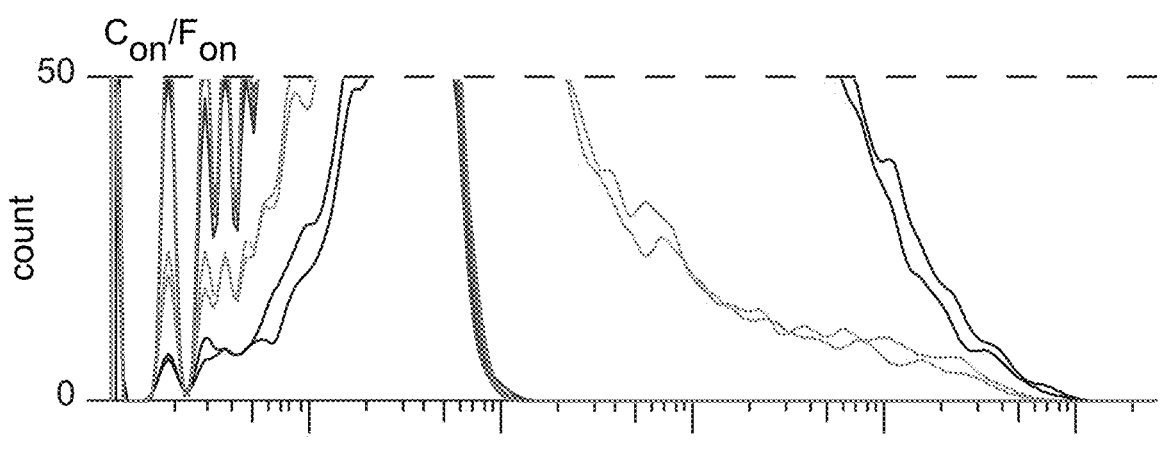
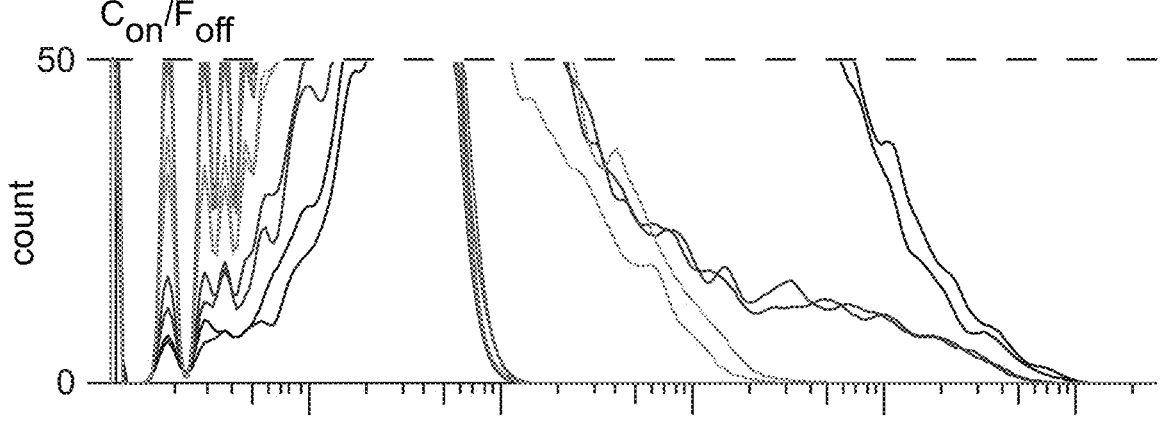
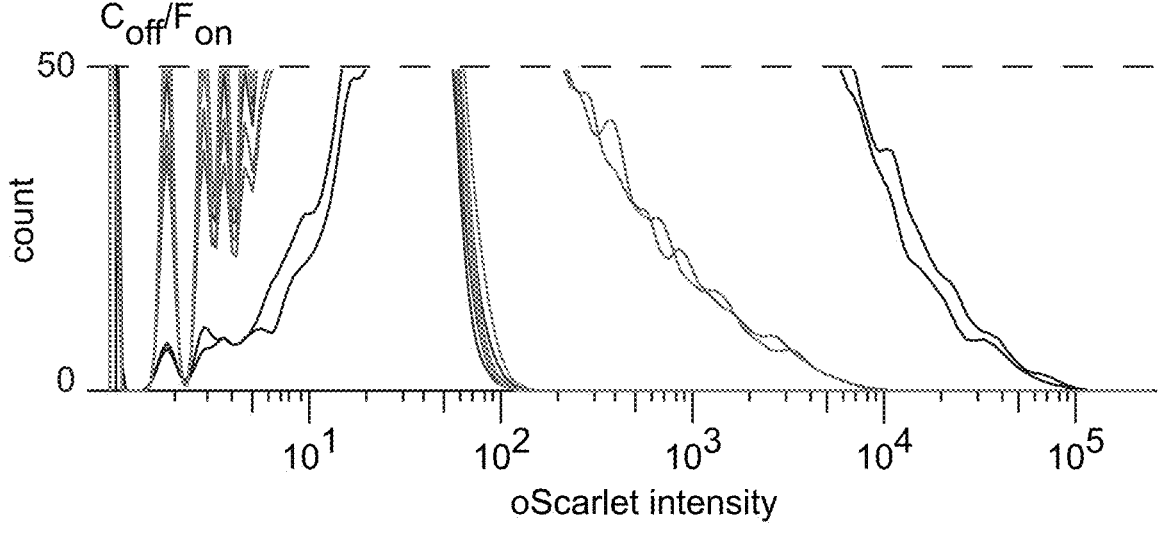
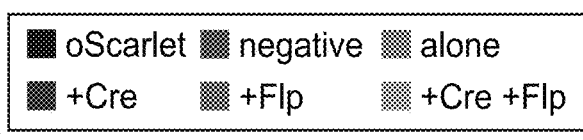

oScarlet    $C_{on}/F_{on}$    $C_{on}/F_{off}$    $C_{off}/F_{on}$

50 μm

FIG. 7H
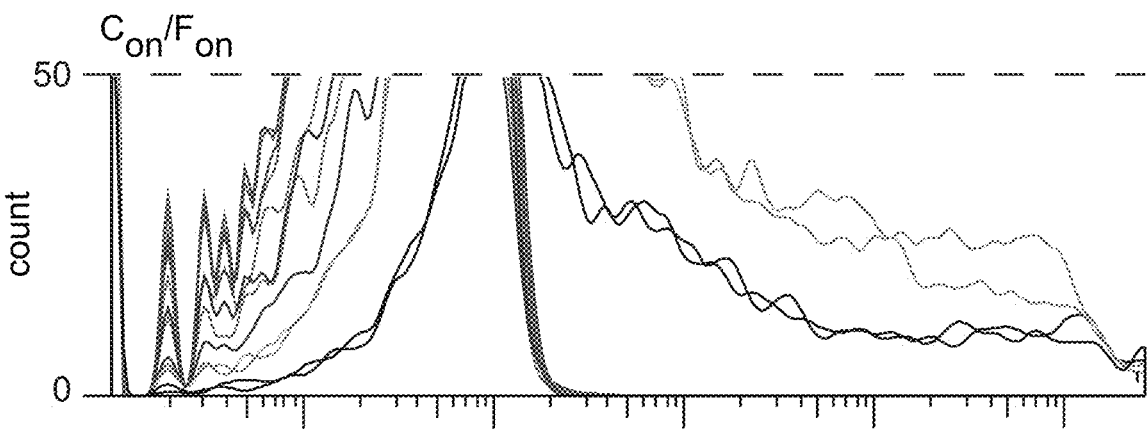
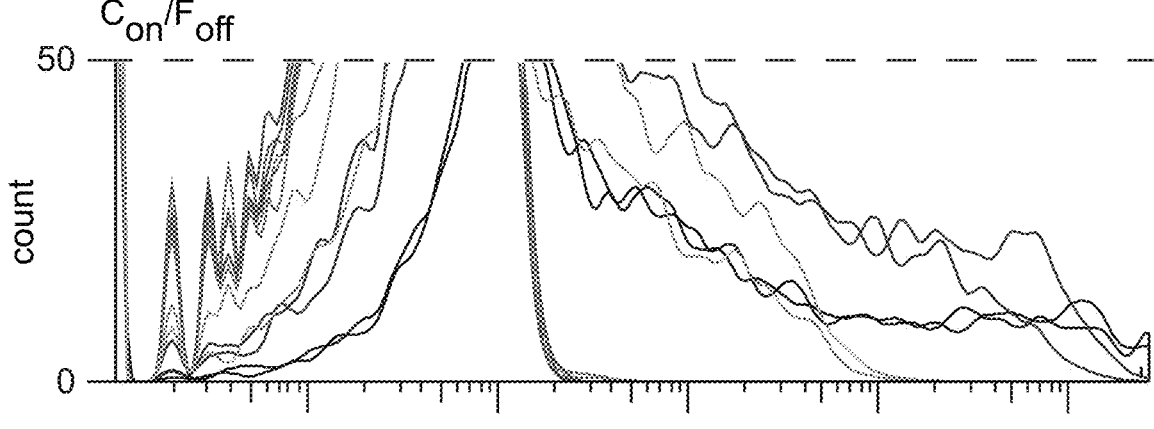
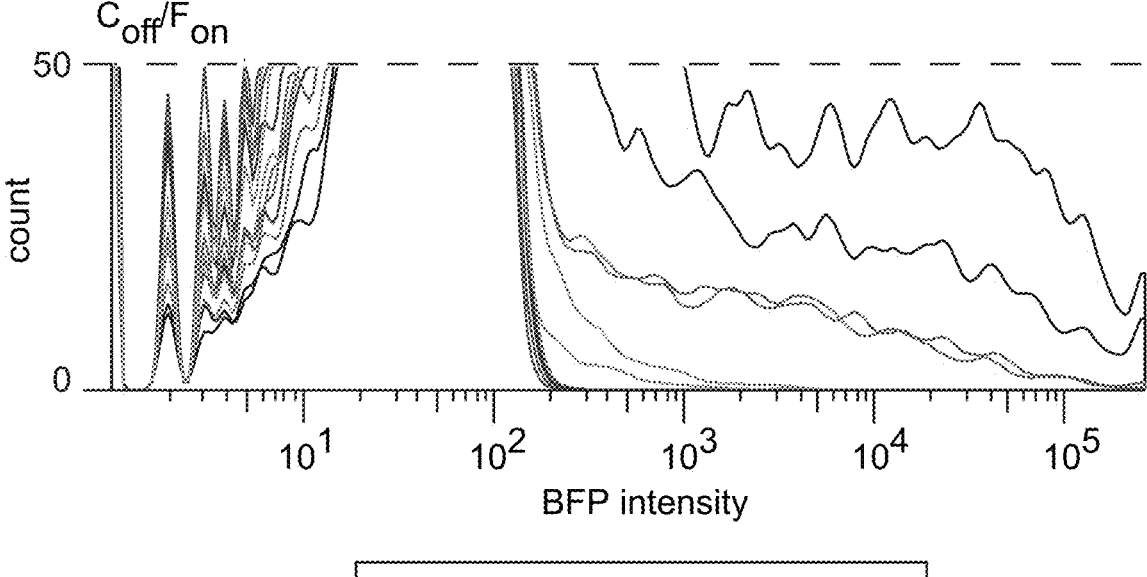
BFP intensity oScarlet          $C_{on}/F_{on}$          $C_{on}/F_{off}$          $C_{off}/F_{on}$ 50 μm primers F1          intron          F2

MCherry$_N$                    MCherry$_C$ 342 bp    R2          369 bp    R1

F1/R2

300 bp —

DNA    cDNA    DNA    cDNA    DNA    cDNA    DNA    cDNA
wt          $C_{on}/F_{on}$       $C_{on}/F_{off}$       $C_{off}/F_{on}$ mCherry map    C C C A G G A C T C cDNA sequence $C_{on}/F_{on}$    C C C A G | G A C T C $C_{on}/F_{off}$    C C C A G | G A C T C $C_{off}/F_{on}$    C C C A G | G A C T C exon 1/exon 2

DNA

R2/F2    R2/R1    F1/F2

500 bp —

$C_{on}/F_{on}$              $C_{off}/F_{on}$ $C_{on}/F_{off}$

FIG. 7K
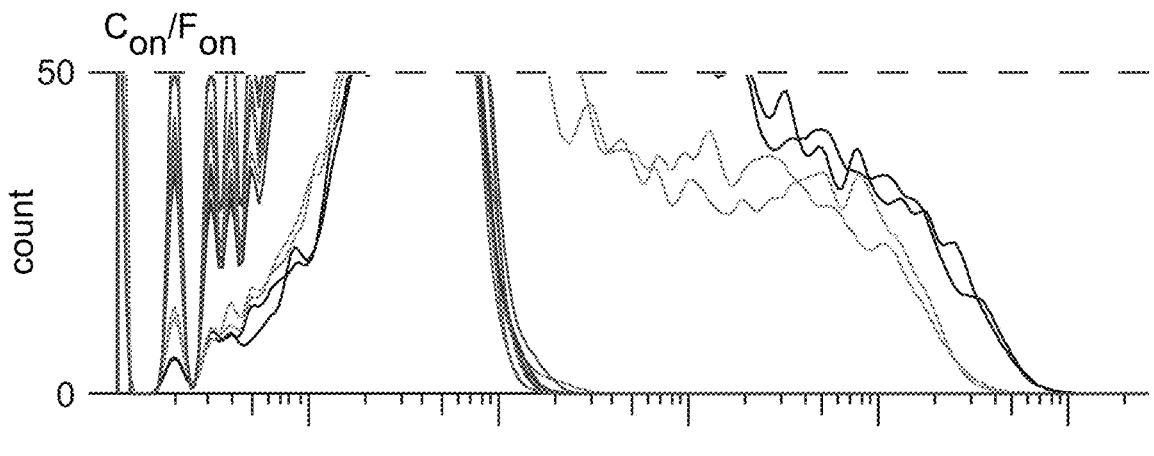
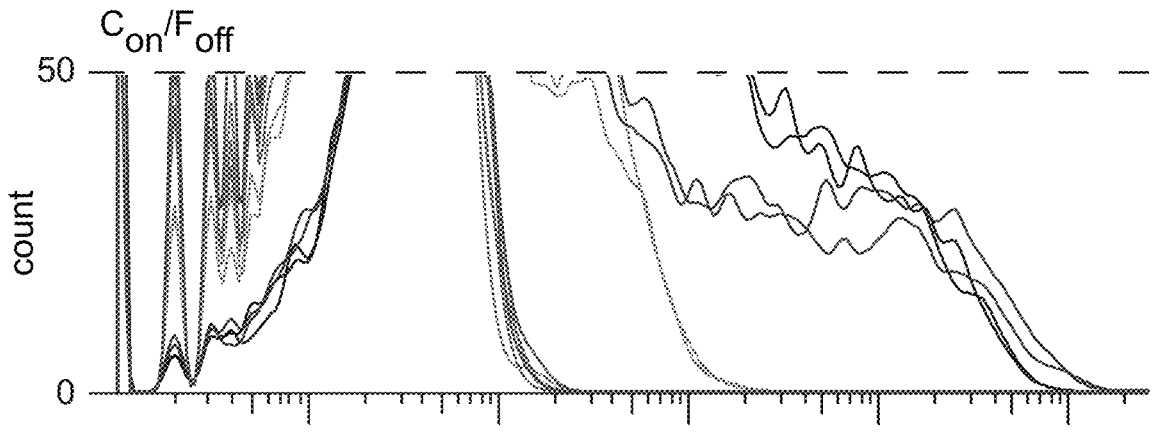
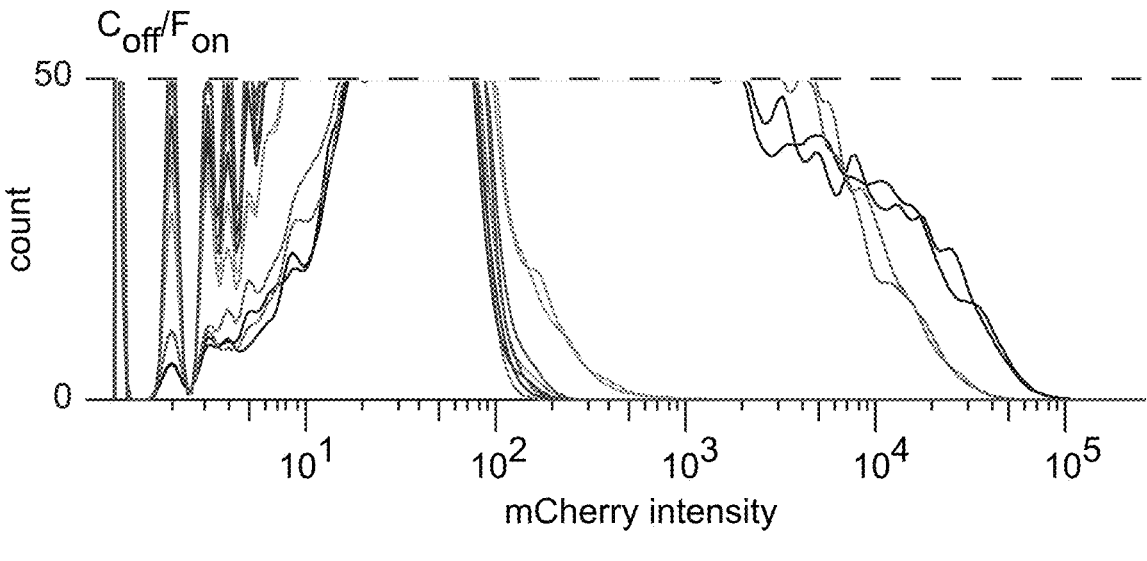
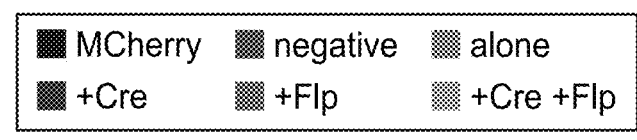

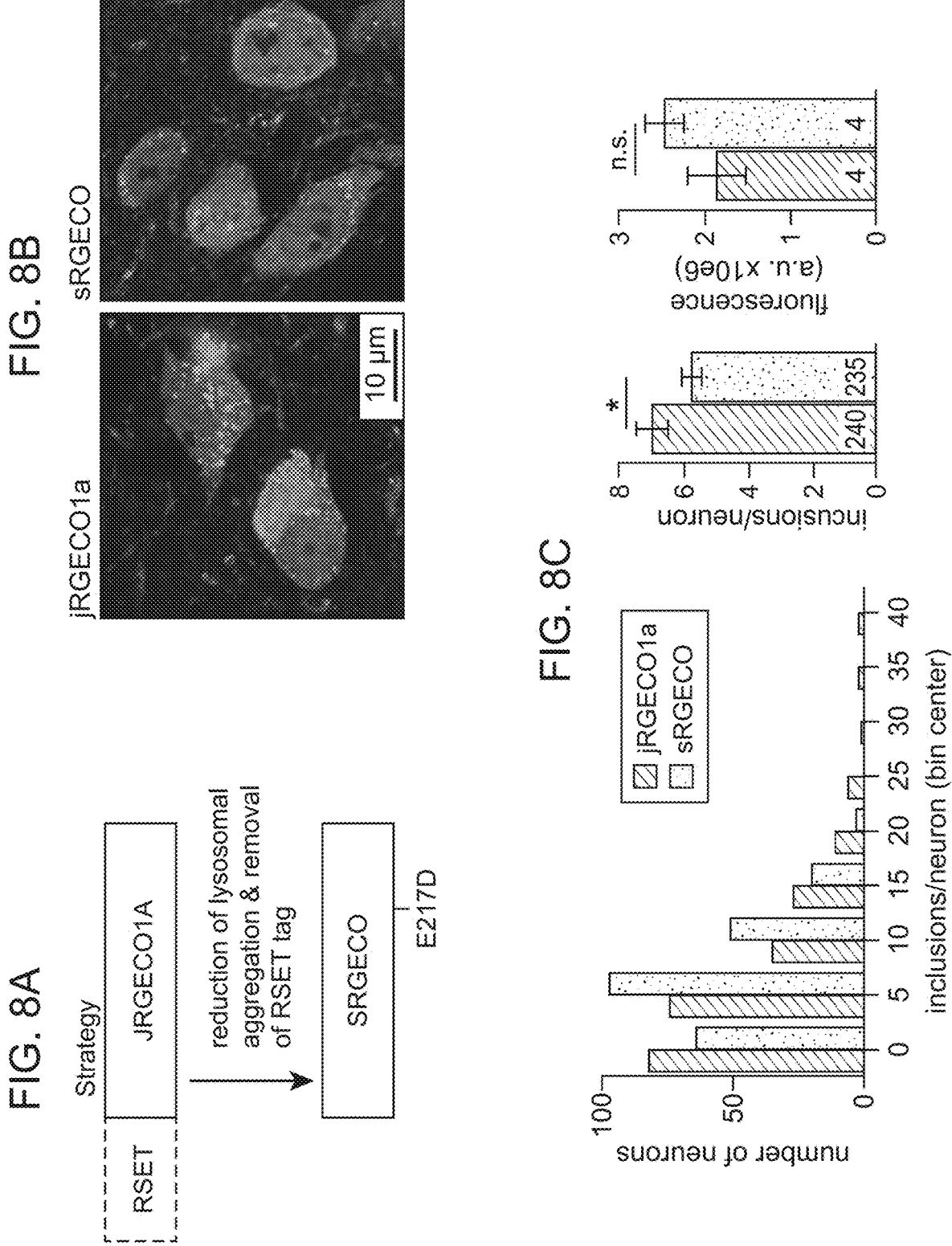

FIG. 8F

FIG. 8G
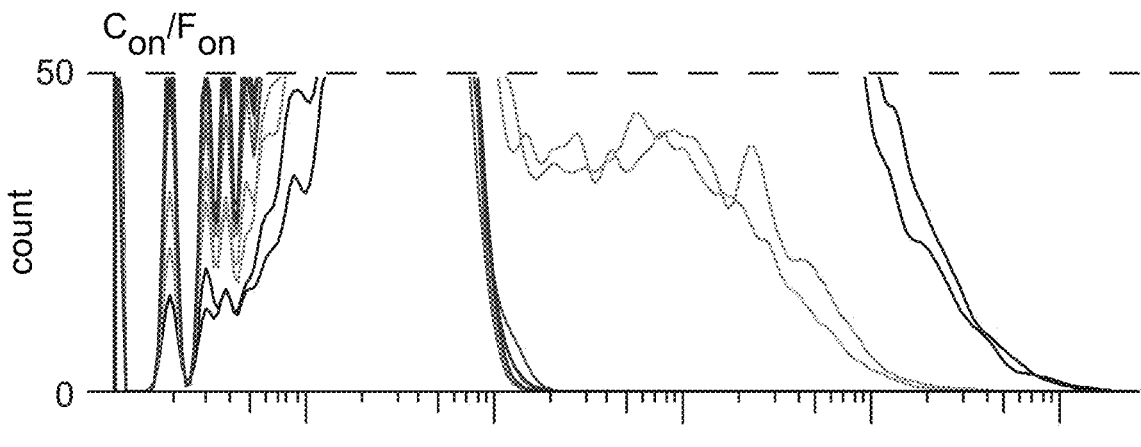
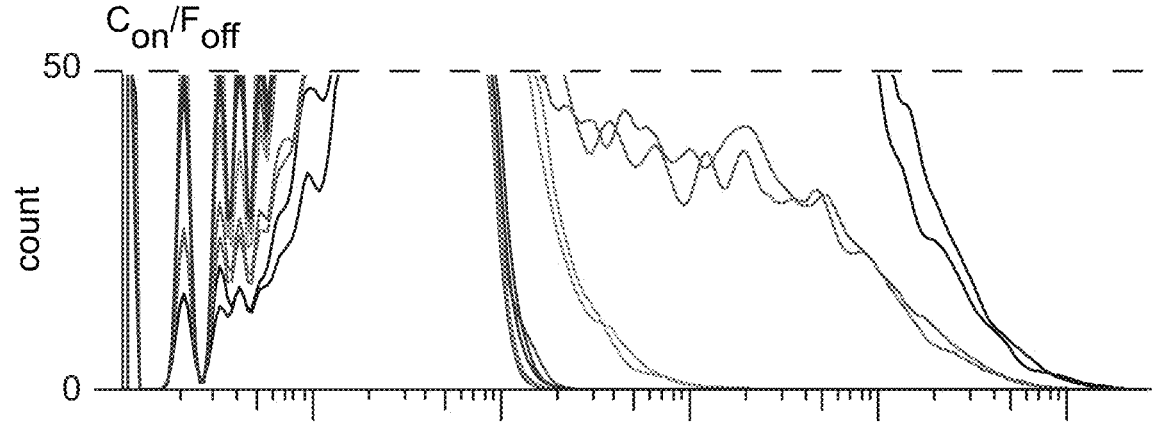
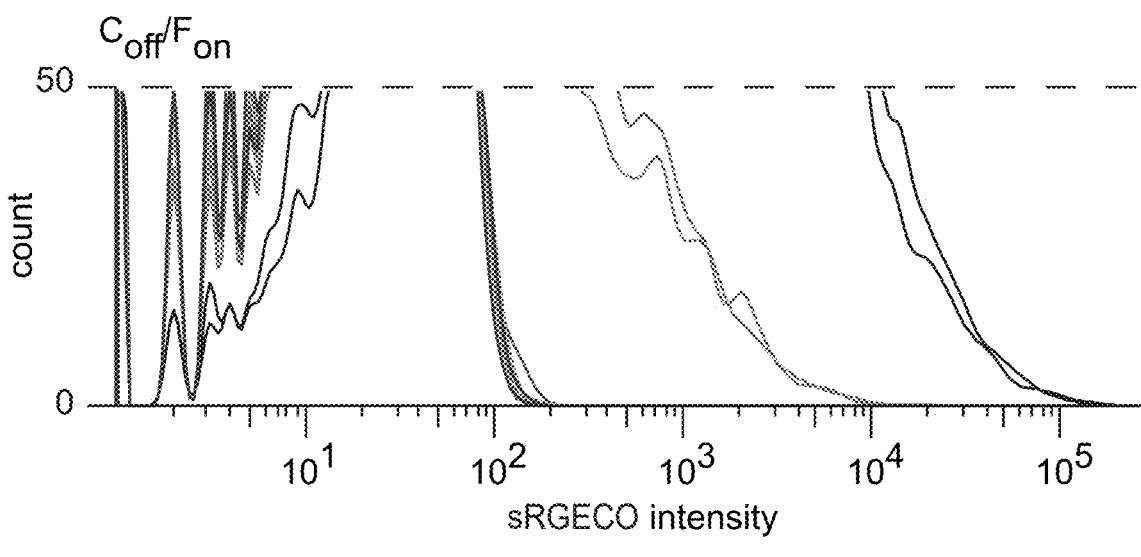
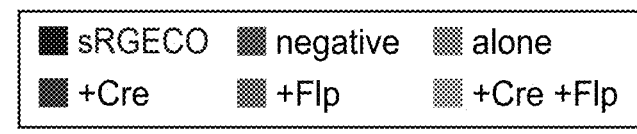

FIG. 8I

FIG. 8J
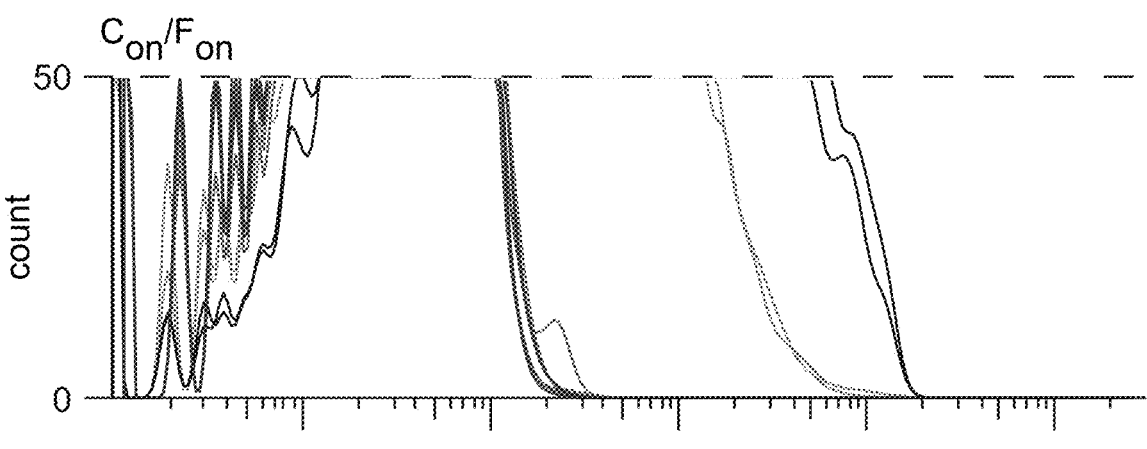
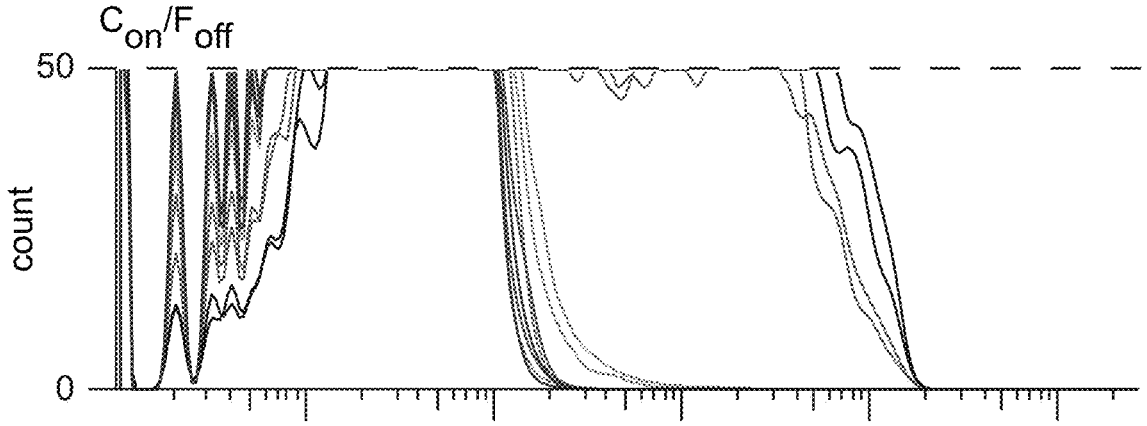
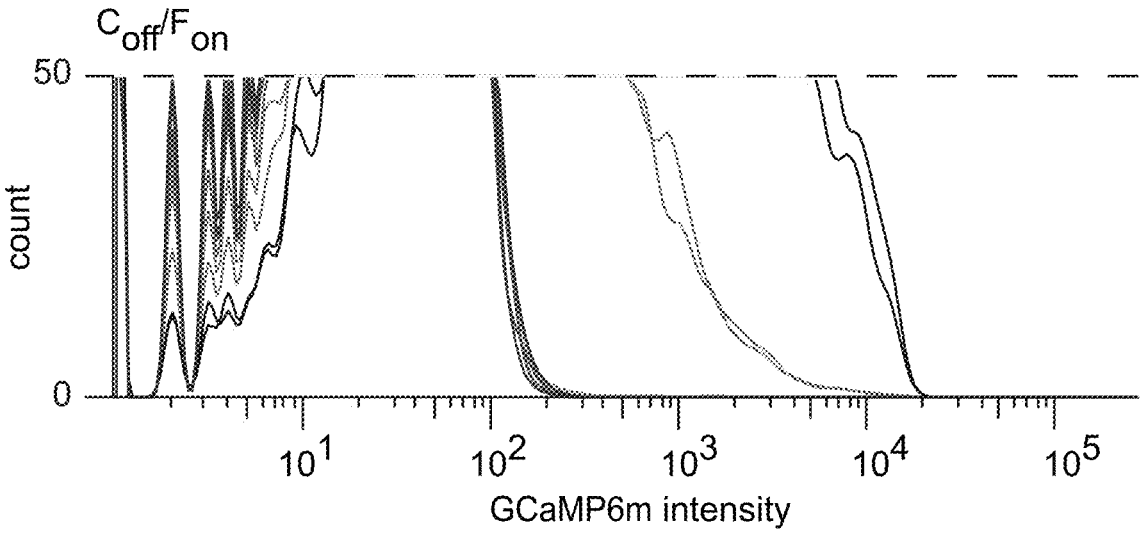
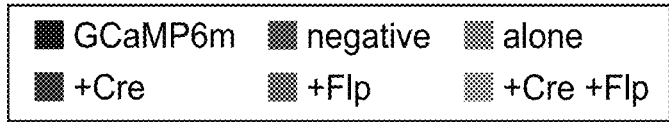

FIG. 8K
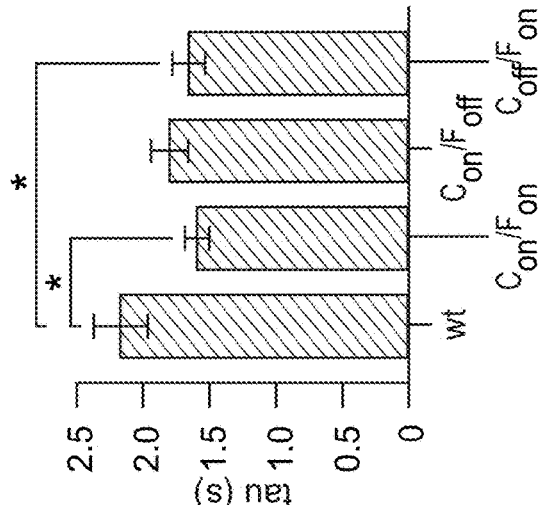
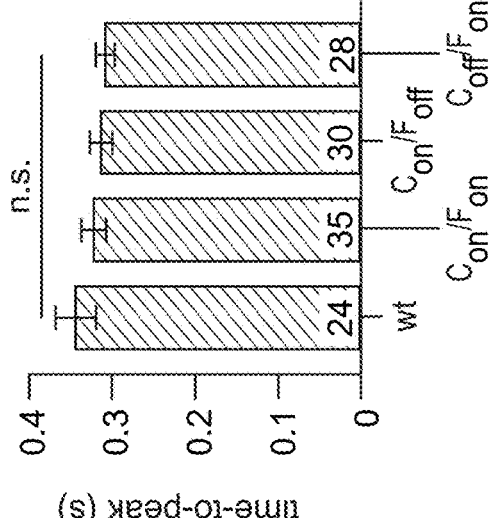
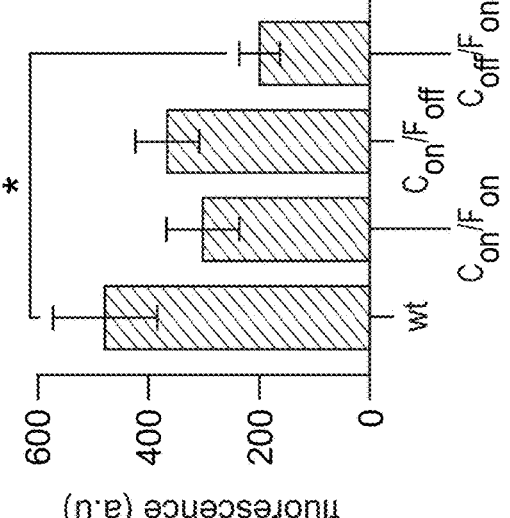

FIG. 8L

FIG. 8M
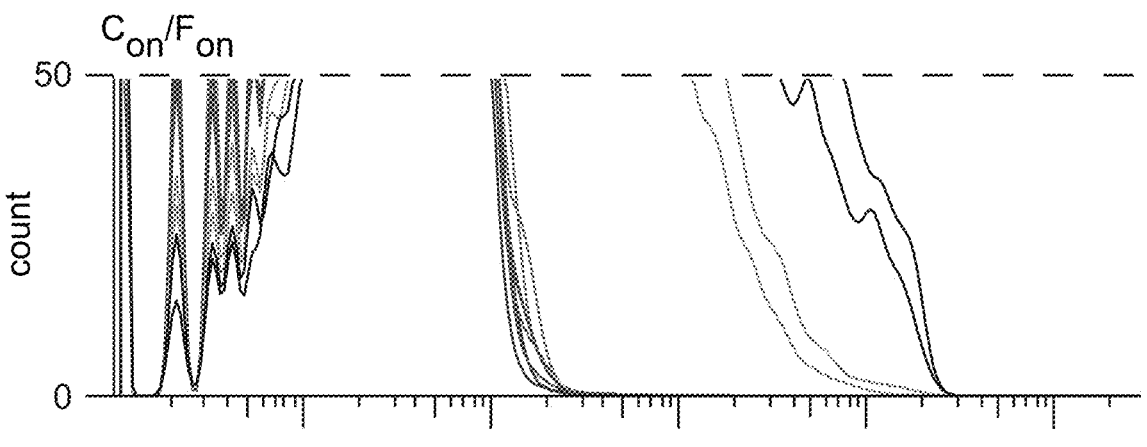
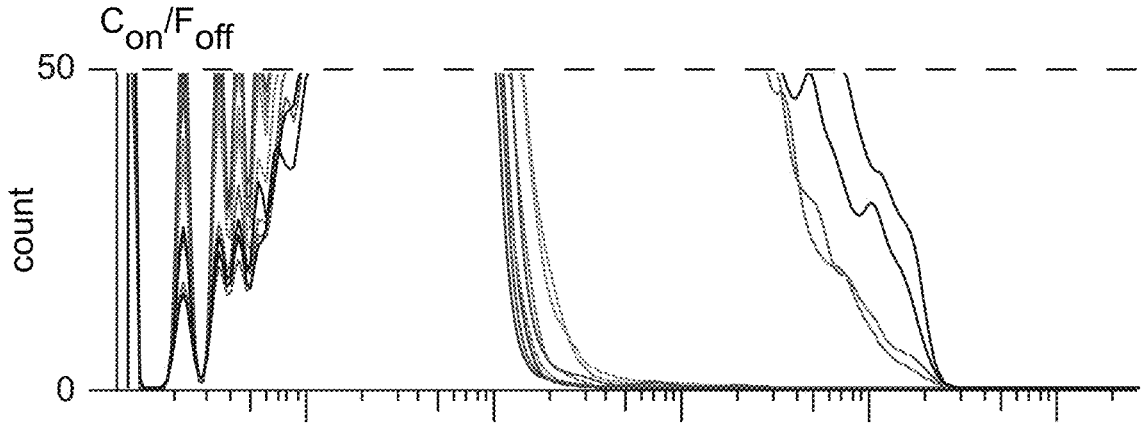
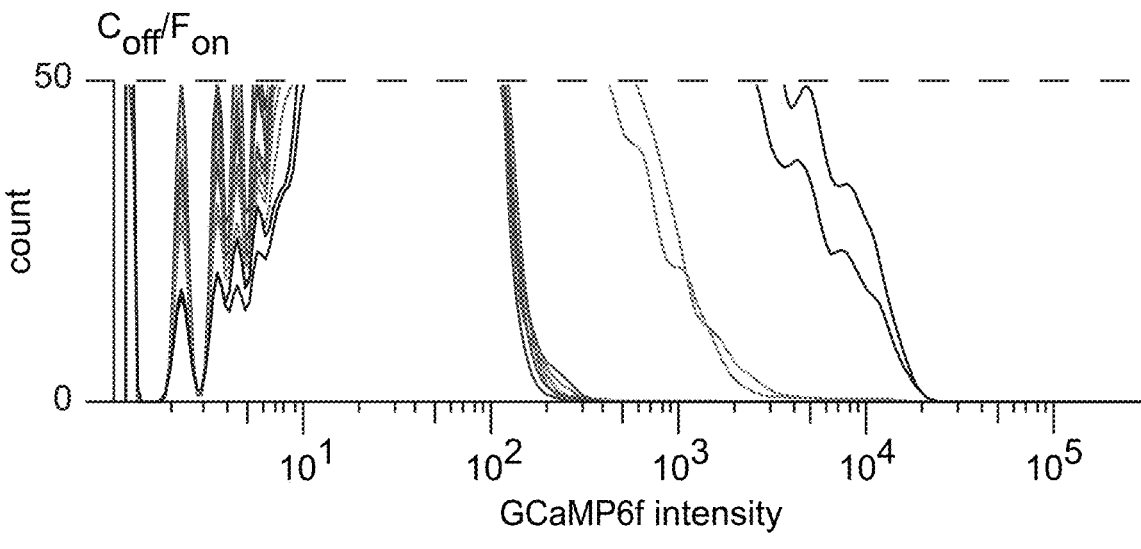
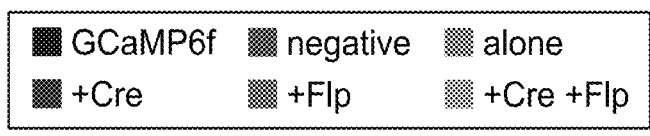

FIG. 8N
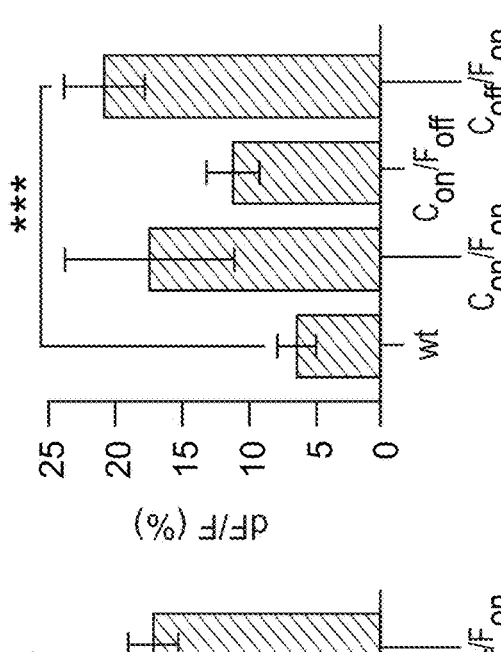
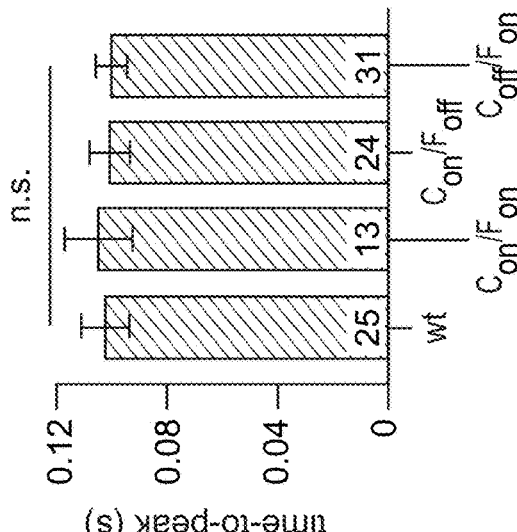
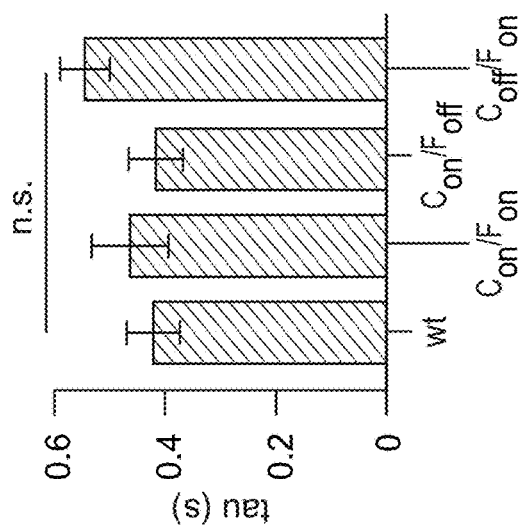
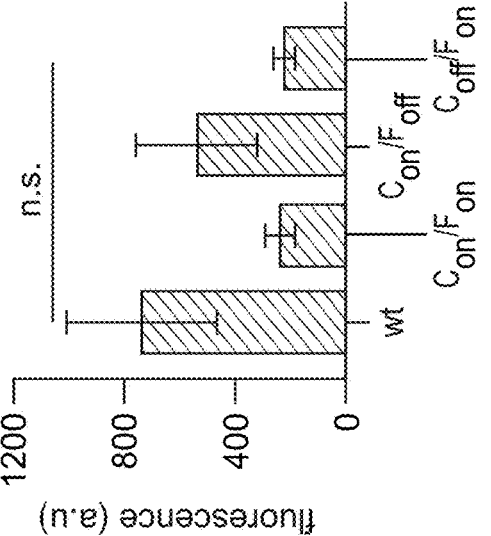

FIG. 9B
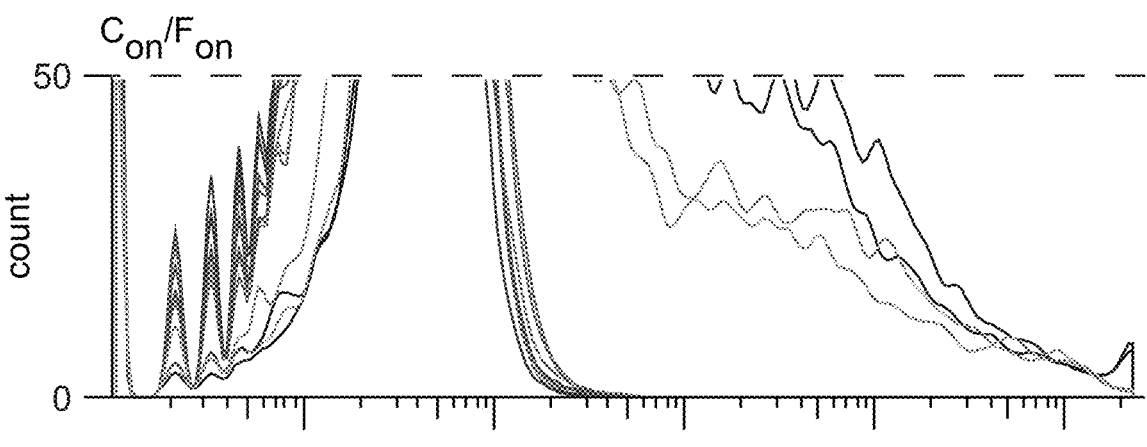
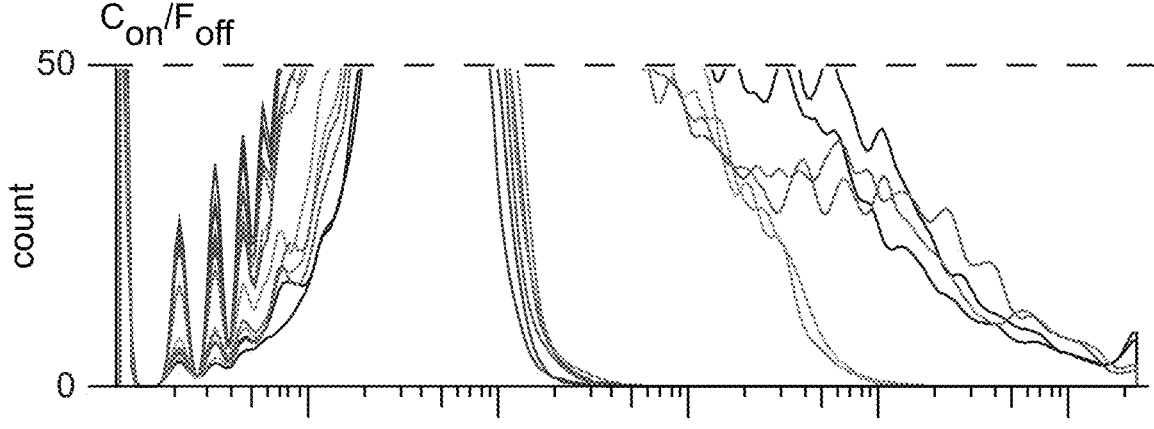
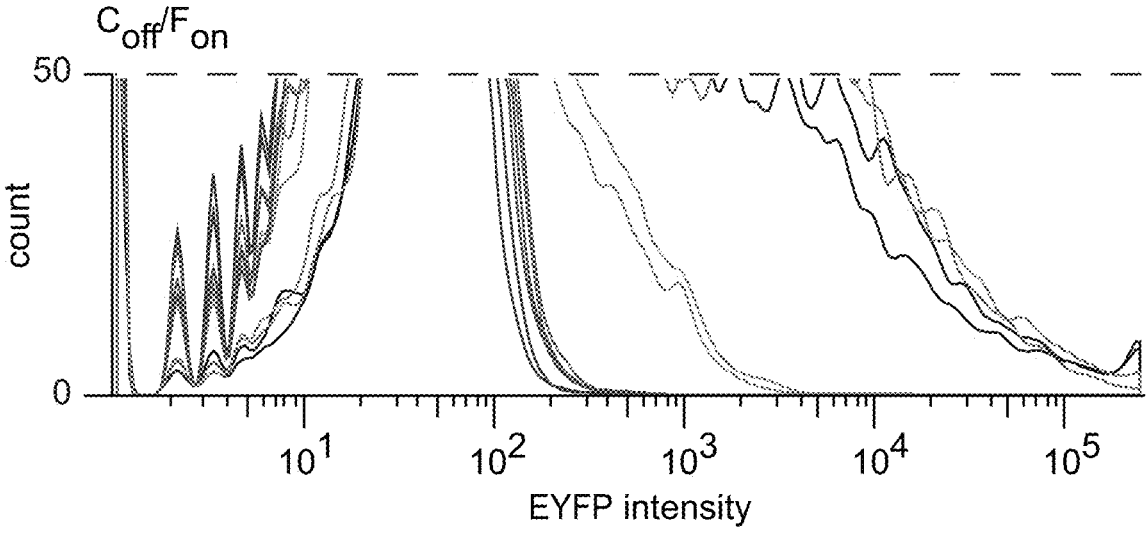
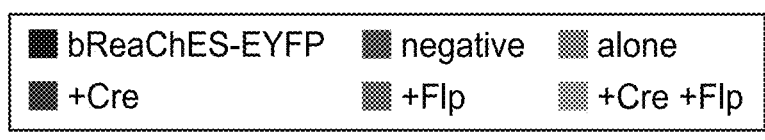

FIG. 9H
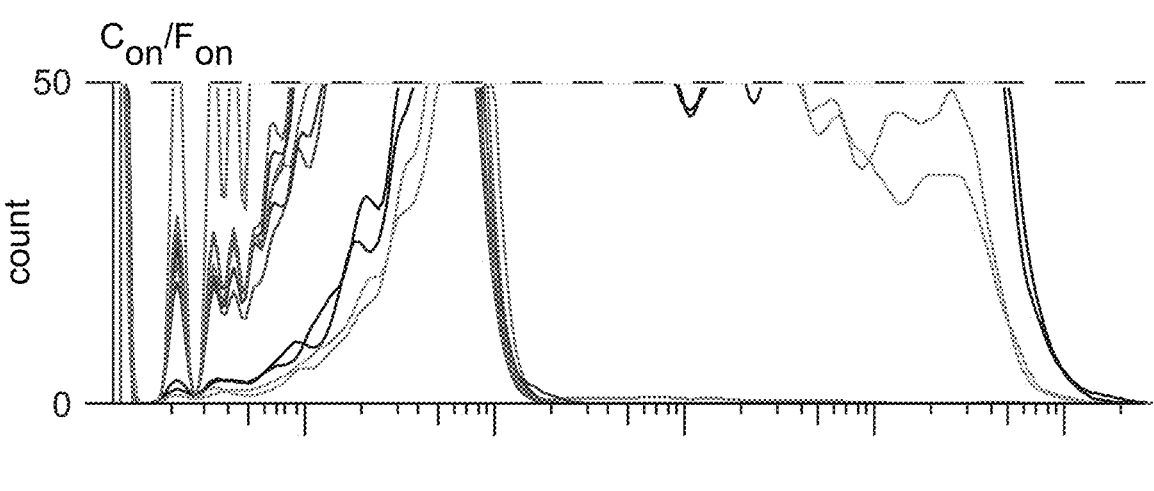
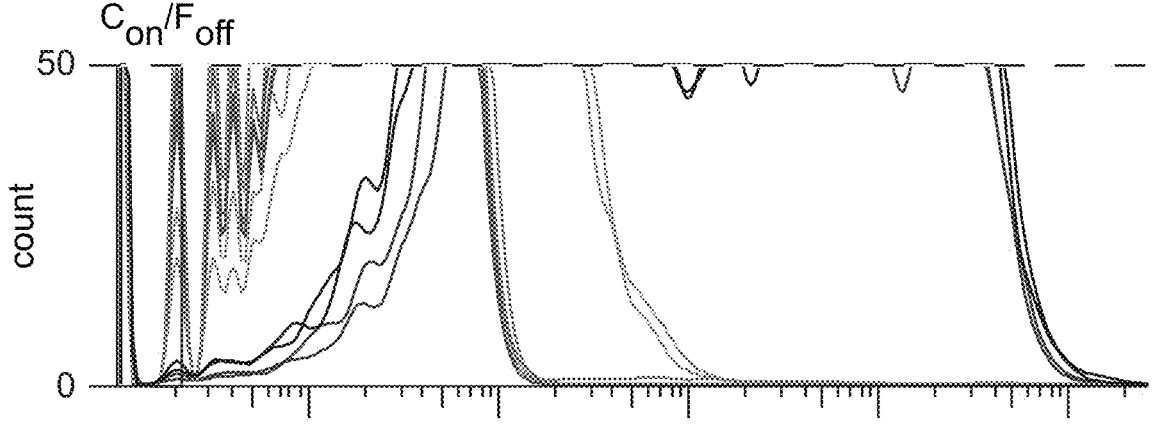
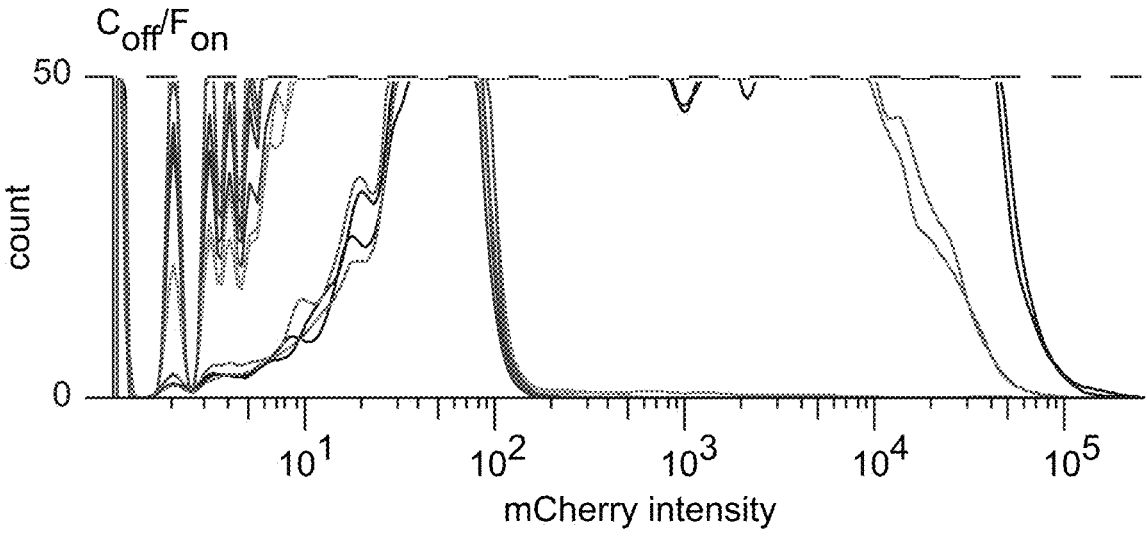
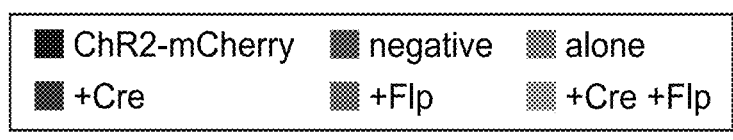

FIG. 9K
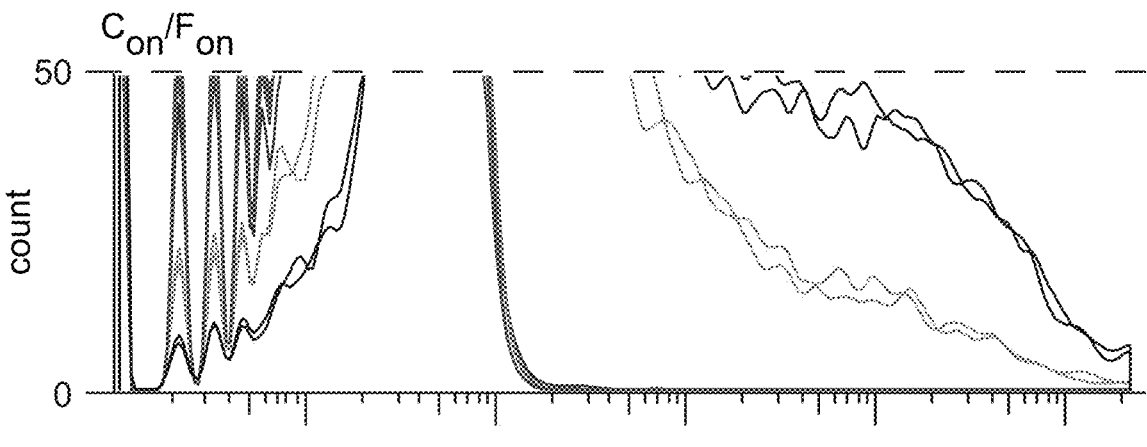
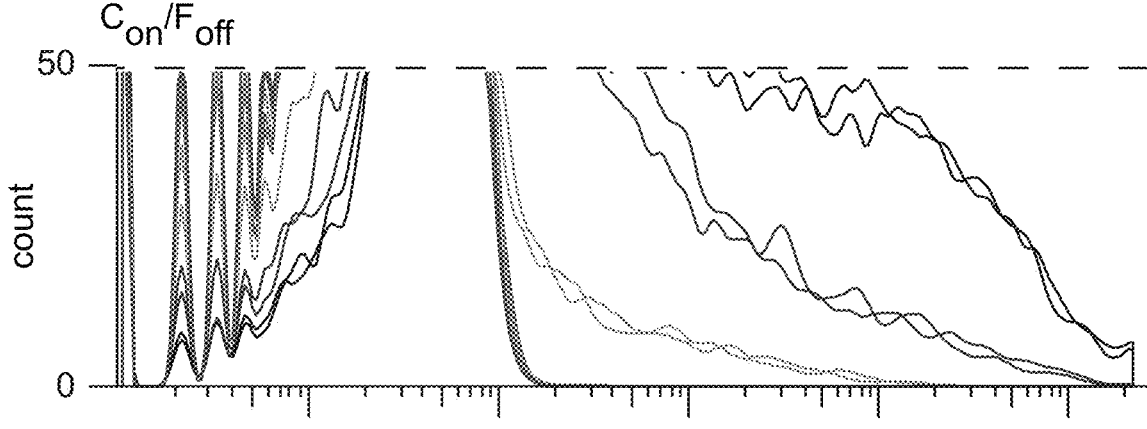
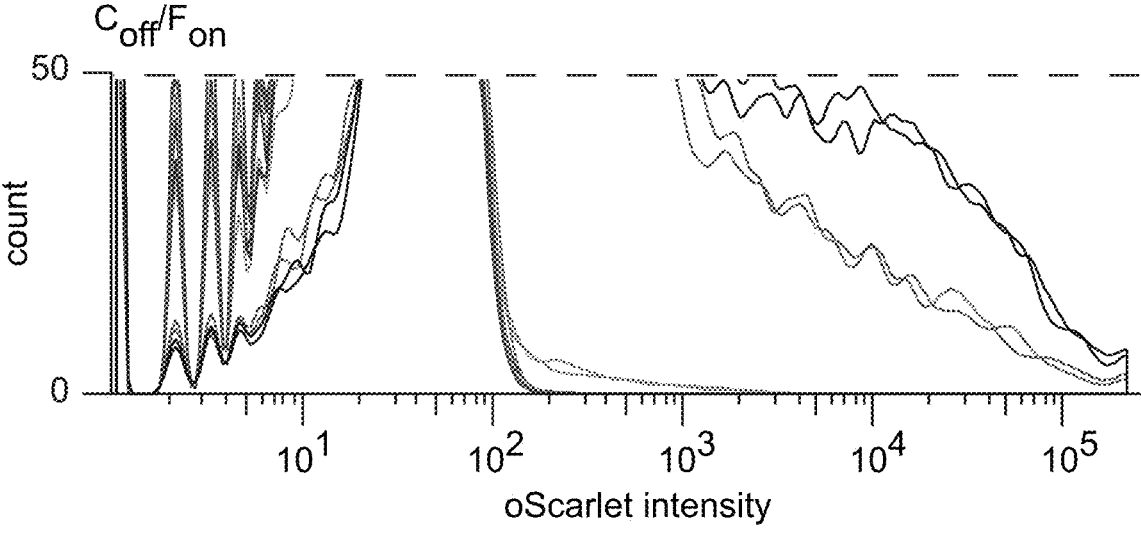
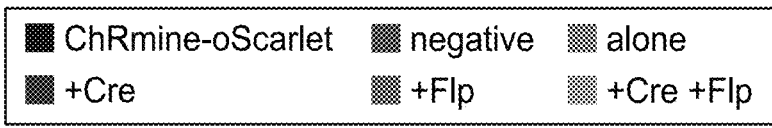

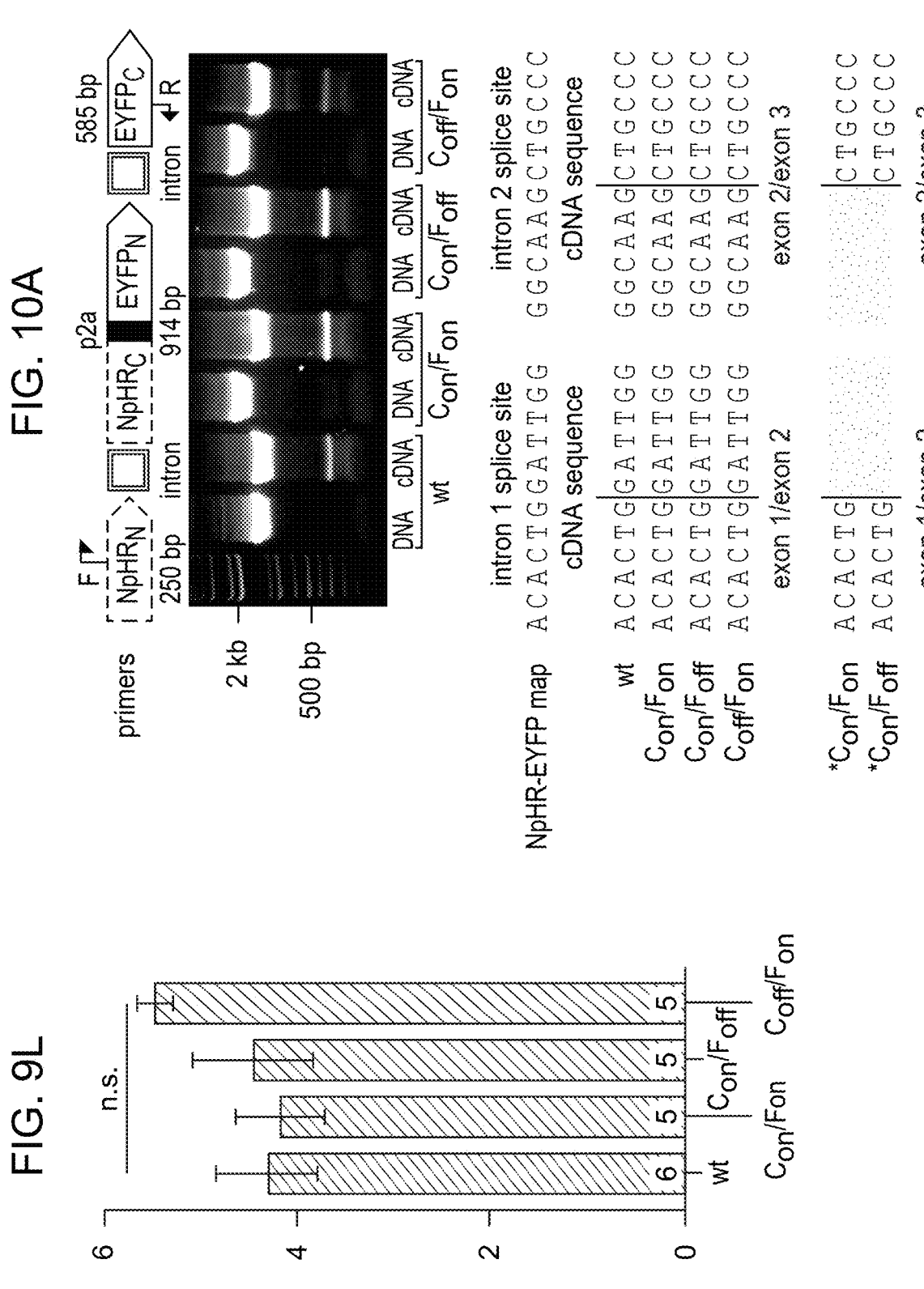

FIG. 10B
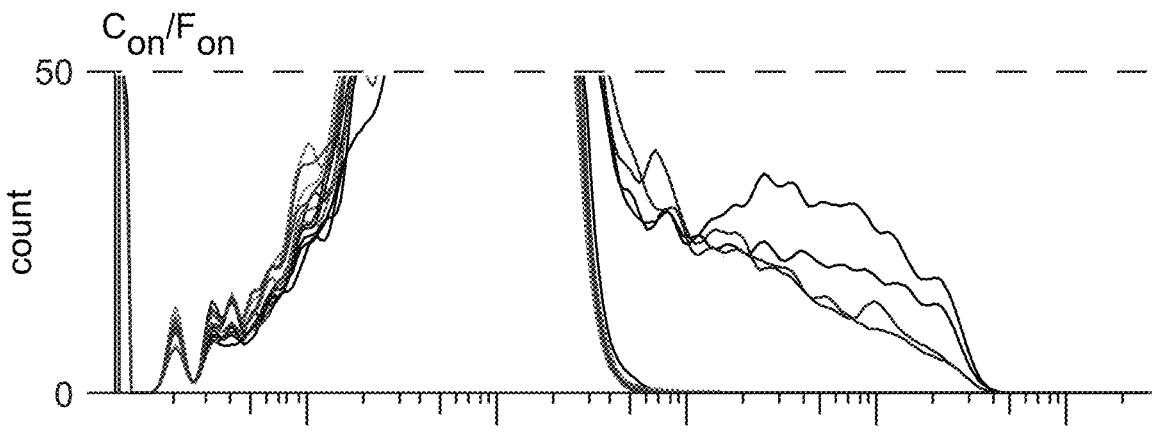
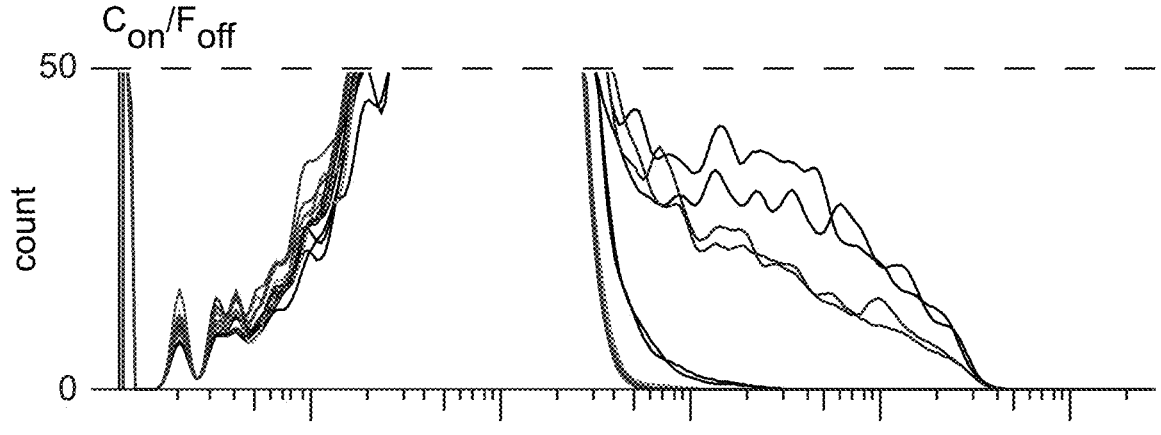
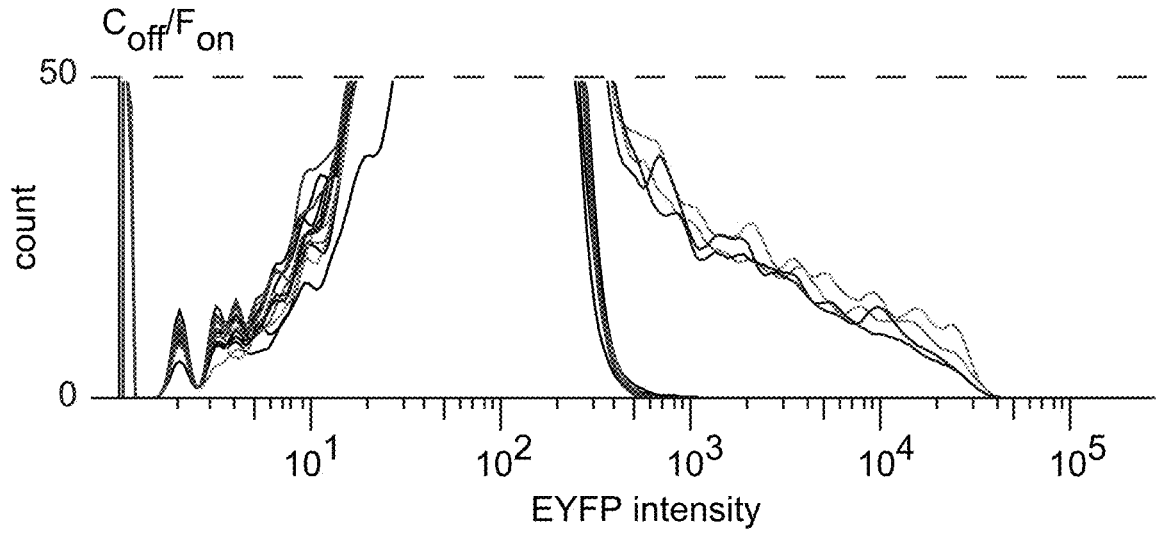
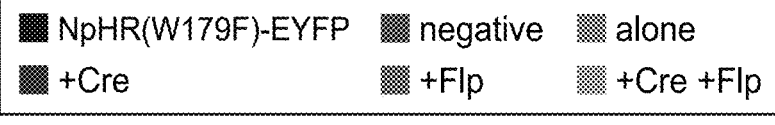

FIG. 10E
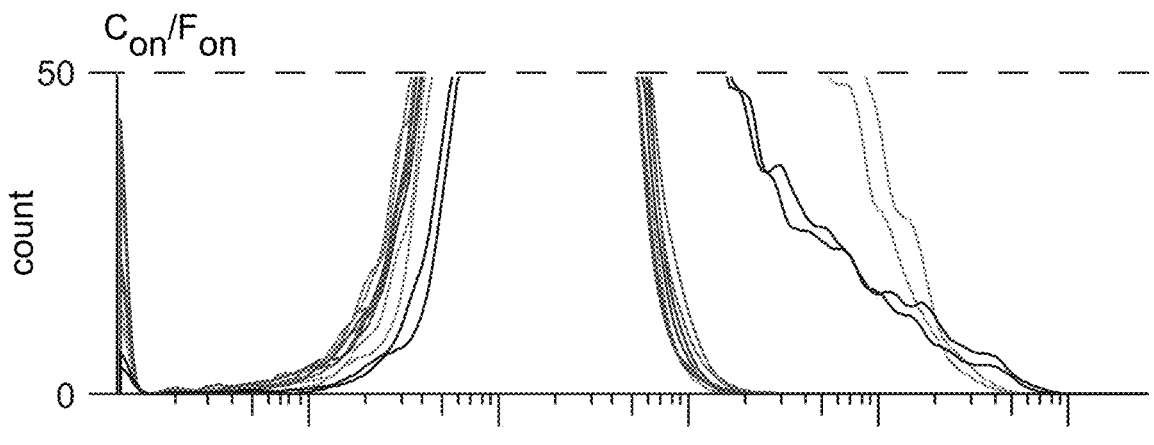
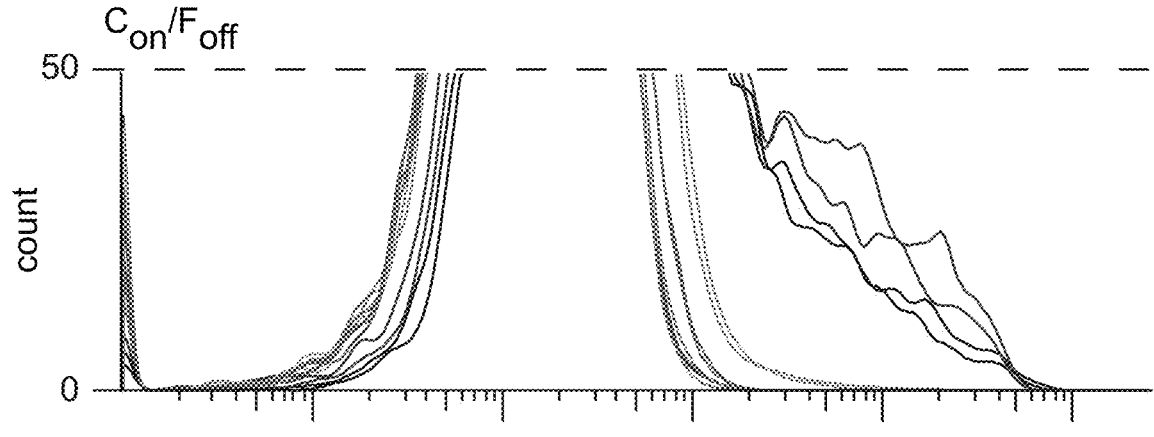
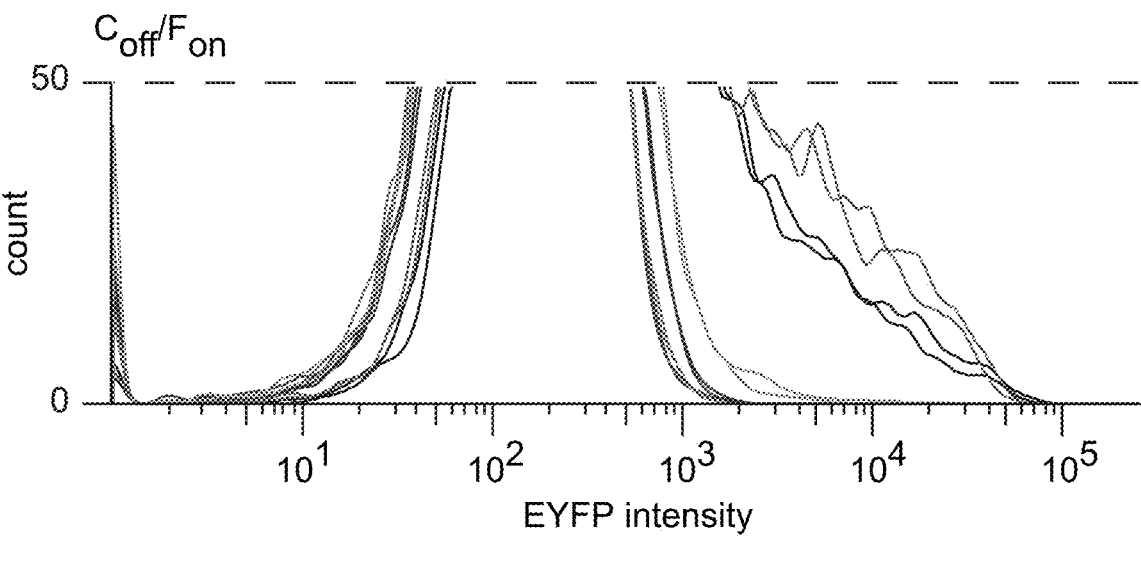
EYFP intensity
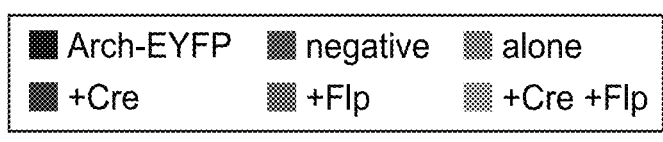

FIG. 10H
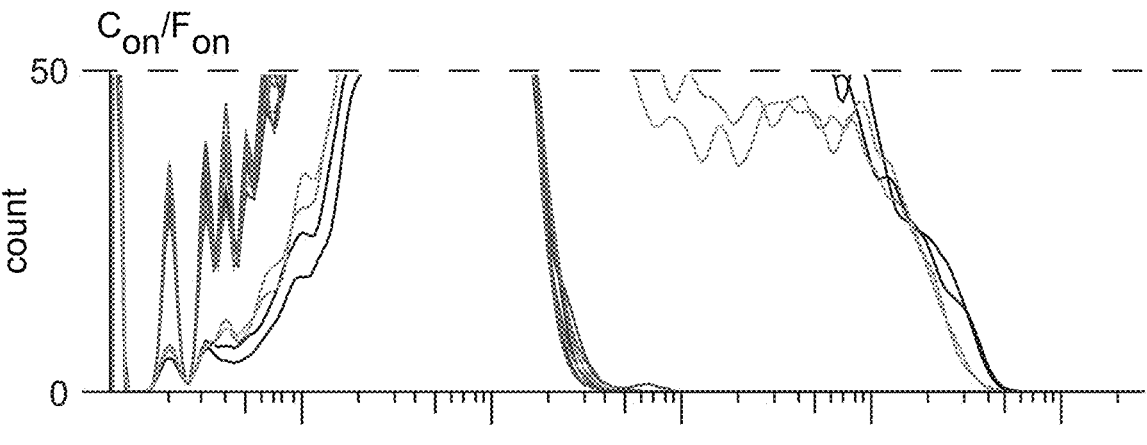
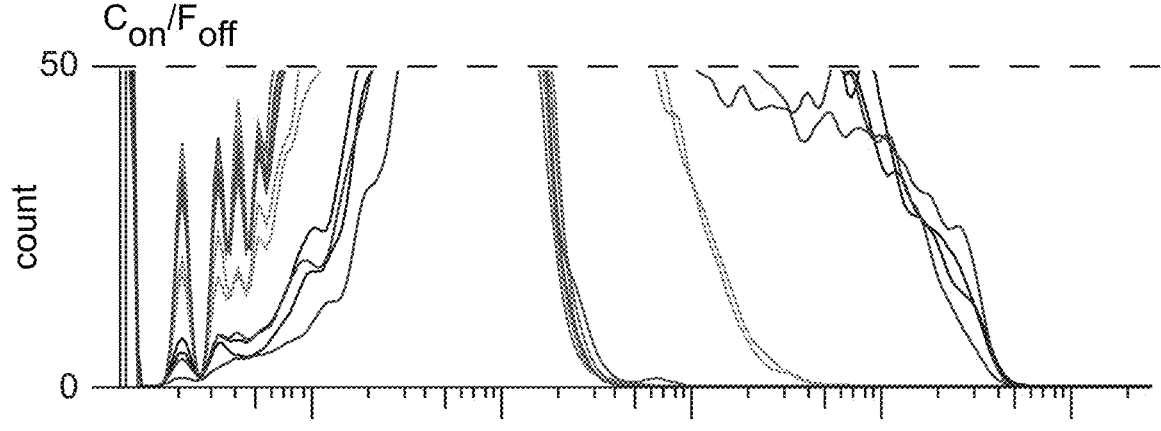
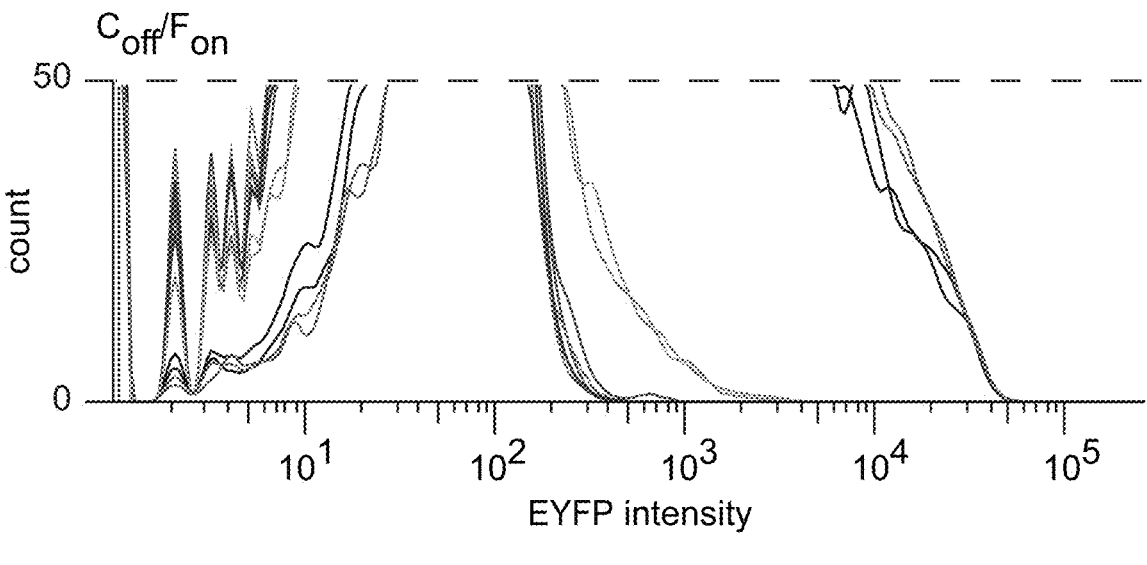
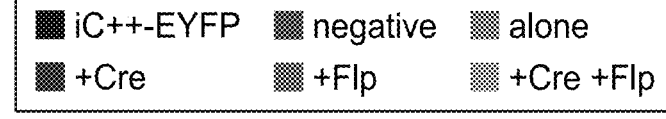

FIG. 11B
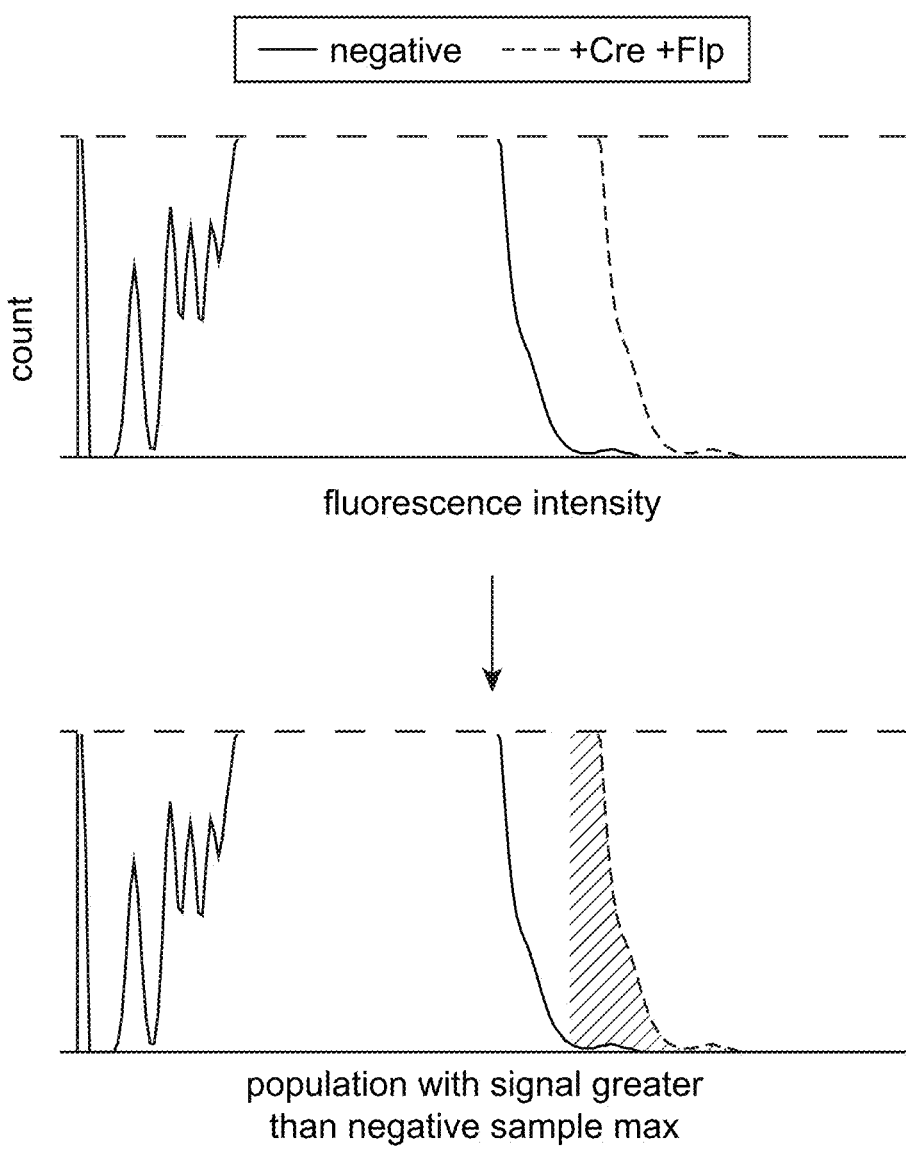

FIG. 11C
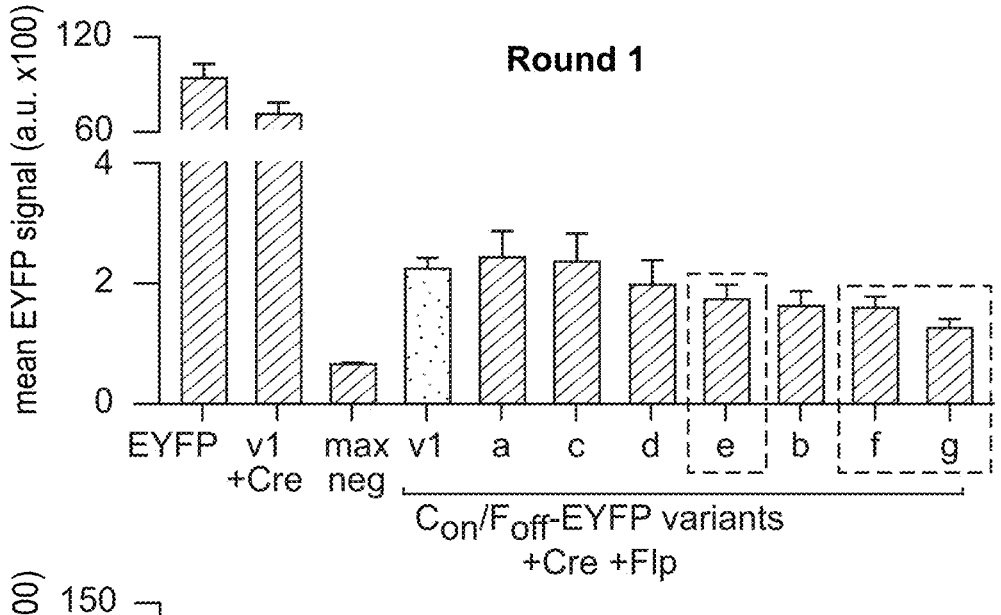
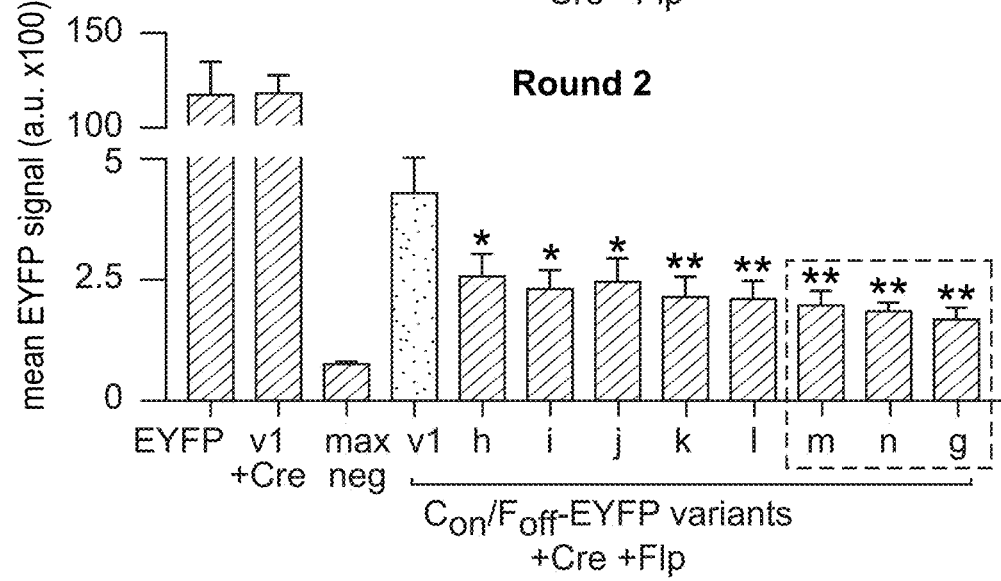
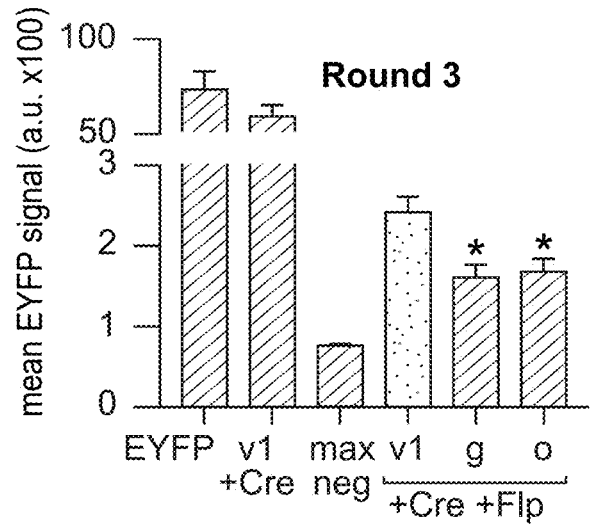

$C_{on}/F_{off}$ all tools +Cre $C_{on}/F_{off}$ all tools +Cre +Flp $C_{on}/F_{off}$ 2.0-EYFP +Cre (1.35e13)

| | |
|---|---|
| ● | $C_{on}/F_{off}$-EYFP 2.8e13 |
| ○ | $C_{on}/F_{off}$-EYFP 2.8e12 |
| ◔ | $C_{on}/F_{off}$-EYFP 2.8e11 |

EYFP $C_{on}/F_{on}$ + Flp-2a-Cre $F_{on}/C_{off}$ +Flp $C_{on}/F_{off}$-2.0 + Cre e13

$C_{on}/F_{off}$-2.0 + Cre e12

$C_{on}/F_{off}$-2.0 + Cre e11

FIG. 12B
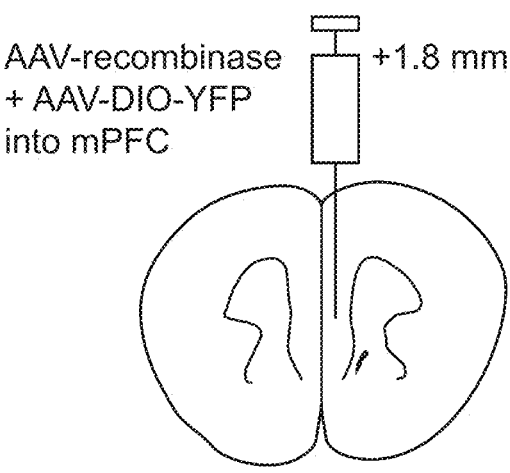
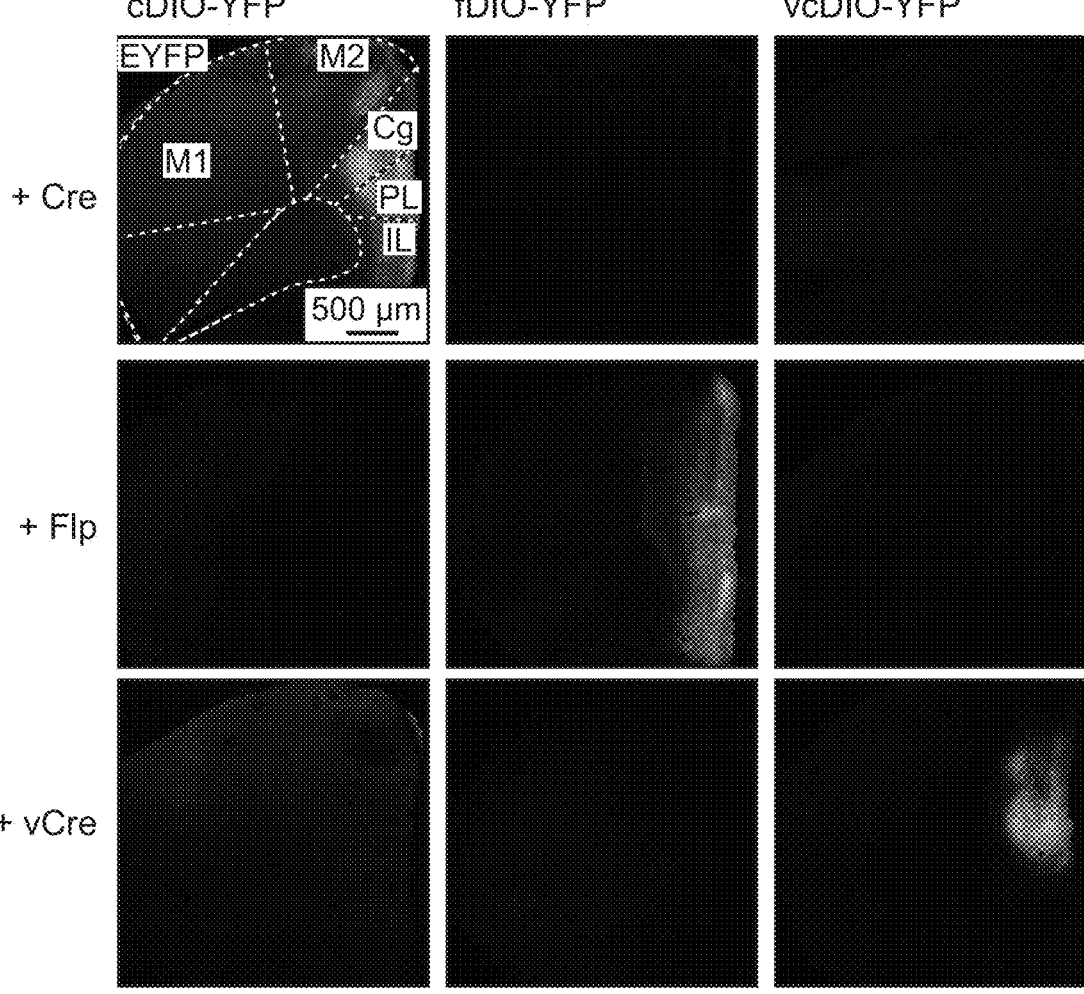

GCaMPK (SEQ ID NO:28)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGYVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLYNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKYTDSEEEIGEAFRYFDKDGNGYISAAELR
HVMTNLGEKLTDEEVDEMIREADIDGDGQVNYEEFVQMMTAK

FIG. 13B

GCaMP2 (SEQ ID NO:29)

MRGSHHHHHHGMASMTGGQQMGRDLYDDDDKDLATMVDSSRRKWNKTG
HAVRAIGRLSSLENYYIMADKQKNGIKANFKIRHNIEDGGYQLAYHYQQNTP
IGDGPYLLPDNHYLSTQSKLSKDPNEKRDHMVLLEFVTAAGITLGMDELYK
GGTGGSMYSKGEELFTGYVPILVELDGDVNGHKFSYSGEGEGDATYGKLTL
KFICTTGKLPVPWPTLVTTLTYGYQCFSRYPDHMKQHDFFKSAMPEGYIQER
TIFFKDDGNYKTRAEVKFEGDTLYNRIELKGIDFKEDGNILGHKLEYNTRDQ
LTEEQIAEFKEAFSLFDKDGDGTITTKELGTYMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13C

GCaMP2.1 (SEQ ID N0:30)

MGSHHHHHHGMASMTGGQQMGRDLYDDDDKDLATMVDSSRRKWNKTG
HAYRAIGRLSSLENYYIMADKQKNGIKANFKIRHNIEDGGVQLAYHYQQNTP
IGDGPYLLPDNHYLSTQSKLSKDPNEKRDHMVLLEFYTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 13D

GCaMP2.2a (SEQ ID N0:31)

MGSHHHHHHGMASMTGGQQMGRDLYDDDDKDLATMVDSSRRKWNKTG
HAYRAIGRLSSLENYYIMADKQKNGIKANFKIRHNIEDGGVQLAYHYQQNTP
IGDGPVLLPDNHYLSVQSKLSKDPNEKRDHMVLLEFYTAAGITLGMDELYK
GGTGGSMYSKGEELFTGVVPILVELDGDVNGHKFSVSGEGEGDATYGKLTL
KFICTTGKLPYPWPTLVTTLTYGYQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTYMRSLGQNPTEAELQDMINEV
DADGNGTIDFPEFLTMMARKMKDTDSEEEIREAFRVFDKDGNGYISAAELRH
VMTNLGEKLTDEEYDEMIREADIDGDGQVNYEEFVQMMTAK

FIG. 13E

GCaMP2.2b (SEQ ID NO:32)

MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQCKLSKDPNEKRDHMVLLEFVTAAGITLGMDELYK
GGTGGSMVSKGEELFTGYVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLYNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRYFDKDGNGYISAAELRH
YMTNLGEKLTDEEVDEMIREADIDGDGQVNYEEFVQMMTAK

FIG. 13F

GCaMP2.3 (SEQ ID NO: 33)

MGSHHHHHHGMASMTGGQQMGRDLYDDDDKDLATMVDSSRRKWNKTG
HAVRAIGRLSSLENYYIKADKQKNGIKANFKIRHNIEDGGVQLAYHYQQNTP
IGDGPYLLPDNHYLSVQSKLSKDPNEKRDHMVLLEFYTAAGITLGMDELYK
GGTGGSMYSKGEELFTGVVPILVELDGDVNGHKFSYSGEGEGDATYGKLTL
KFICTTGKLPYPWPTLVTTLTYGYQCFSRYPDHMKQHDFFKSAMPEGYIQER
TIFFKDDGNYKTRAEVKFEGDTLYNRIELKGIDFKEDGNILGHKLEYNTRDQ
LTEEQIAEFKEAFSLFDKDGDGTITTKELGTYMRSLGQNPTEAELQDMINEV
DADGNGTIDFPEFLTMMARKMKDTDSEEEIREAFRVFDKDGNGYISAAELRH
VMTNLGEKLTDEEYDEMIREADIDGDGQVNYEEFVQMMTAK

FIG. 13G

GCaMP2.4 (SEQ ID N0:34)

MGSHHHHHHGMASMTGGQQMGRDLYDDDDKDLATMVDSSRRKWNKTG
HAYRAIGRLSSLENYYIMADKQKNGIKANFKIRHNIEDGGVQLAYHYQQNTP
IGDGPYLLPDNHYLSYQSKLSKDPNEKRDHMVLLEFVTAAGITLGMDELYK
GGTGGSMVSKGEELFTGYVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLYNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRYFDKDGNGYISAAELRH
YMTNLGEKLTDEEVDEMIREADIDGDGQVNYEEFVQMMTAK

FIG. 13H

GCaMP3 (SEQ ID NO:35)

MGSHHHHHHGMASMTGGQQMGRDLYDDDDKDLATMVDSSRRKWNKTG
HAVRAIGRLSSLENYYIKADKQKNGIKANFKIRHNIEDGGVQLAYHYQQNTP
IGDGPYLLPDNHYLSVQSKLSKDPNEKRDHMVLLEFYTAAGITLGMDELYK
GGTGGSMYSKGEELFTGYVPILVELDGDVNGHKFSYSGEGEGDATYGKLTL
KFICTTGKLPYPWPTLVTTLTYGYQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTYMRSLGQNPTEAELQDMINEV
DADGDGTIDFPEFLTMMARKMKDTDSEEEIREAFRVFDKDGNGYISAAELRH
VMTNLGEKLTDEEYDEMIREADIDGDGQVNYEEFVQMMTAK

FIG. 13I

GCaMP5g (SEQ ID NO:36)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGYVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLYNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYTDSEEEIREAFRVFDKDGNGYISAAELRHY
MTNLGEKLTDEEVDEMIREADIDGDGQYNYEEFVQMMTAK

FIG. 13J

GCaMP6m (SEQ ID NO:37)

MGSHHHHHHGMASMTGGQQMGRDLYDDDDKDLATMVDSSRRKWNKTG
HAVRAIGRLSSLENYYIKADKQKNGIKANFKIRHNIEDGGVQLAYHYQQNTP
IGDGPYLLPDNHYLSVQSKLSKDPNEKRDHMVLLEFYTAAGITLGMDELYK
GGTGGSMYSKGEELFTGYVPILVELDGDVNGHKFSYSGEGEGDATYGKLTL
KFICTTGKLPYPWPTLVTTLTYGYQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTYMRSLGQNPTEAELQDMINEVD
ADGDGTIDFPEFLTMMARKGSYRDTEEEIREAFGVFDKDGNGYISAAELRHV
MTNLGEKLTDEEVDEMIREADIDGDGQVNYEEFVQMMTAK

FIG. 13K

GCaMP6s (SEQ ID NO:38)

MGSHHHHHHGMASMTGGQQMGRDLYDDDDKDLATMVDSSRRKWNKTG
HAVRAIGRLSSLENVYIKADKQKNGIKANFHIRHNIEDGGVQLAYHYQQNTP
IGDGPYLLPDNHYLSYQSKLSKDPNEKRDHMYLLEFYTAAGITLGMDELYK
GGTGGSMVSKGEELFTGYYPILYELDGDVNGHKFSVSGEGEGDATYGKLTL
KFICTTGKLPYPWPTLYTTLTYGVQCFSRYPDHMKQHDFFKSAMPEGYIQER
TIFFKDDGNYKTRAEYKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYRDTEEEIREAFGVFDKDGNGYISAAELRH
YMTNLGEKLTDEEVDEMIREADIDGDGQVNYEEFVQMMTAK

FIG. 13L

GCaMP6f (SEQ ID NO:39)

MGSHHHHHHGMASMTGGQQMGRDLYDDDDKDLATMYDSSRRKWNKTG
HAYRAIGRLSSLENYYIKADKQKNGIKANFKIRHNIEDGGVQLAYHYQQNTP
IGDGPYLLPDNHYLSVQSKLSKDPNEKRDHMVLLEFYTAAGITLGMDELYK
GGTGGSMYSKGEELFTGYVPILVELDGDVNGHKFSYSGEGEGDATYGKLTL
KFICTTGKLPYPWPTLYTTLTYGYQCFSRYPDHMKQHDFFKSAMPEGYIQER
TIFFKDDGNYKTRAEVKFEGDTLYNRIELKGIDFKEDGNILGHKLEYNLPDQL
TEEQIAEFKEEFSLFDKDGDGTITTKELGTVMRSLGQNPTEAELQDMINEYD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 13M

GEM-GECO1 (GenBank ID: JN258409) (SEQ ID NO:40)

MVDSSRRKWNKTGHAVRAIGRLSSPENVYIKADEQKNGIKAYFKIRHNIEGG
GVQLAYHYQQITPIGDGPVLLPDNHYLSVQSILSKDPNEKRDHMVLLEFVTA
AGITLGMDELYKGGSGGMVSKGEELFfGVYPIQVELDGDVNGHKFSYSGEG
EGDATYGKLTLKFICTTGKLPYPWPTLVTTLSYGVQCFSRYPDHMKQHDFFK
SAMPEGYIQERTIFFKDDGNYKTRAEVKFEGDTLVNRIELKGIDFKEDGNILG
HKLEYSTRDQLTEEQIAEFKEAFSLFDKDGDGTITTKELGTVMRSLGQNPTE
AELQDMINEVDADGDGTIDFPEFLTMMAPKMQDTDSEEEIREAFRYFDKDG
NGYIGAAELRHVMTNLGEKLTDEEVDEMIRVADIDGDGQVNYEEFYQMMT
AK

FIG. 13N

GEX-GECO1 (GenBank ID: JN258410) (SEQ ID NO:41)

MVDSSRRKWNKTGHAVRAIGRLSSLENVYIKADEQKNGIKANFKIRHNIEDG
GVQLAYHYQQNTPIGDGPVLLPDNHYLSYQSILSKDPNEKRDHMVLLEFVT
AAGITLGMDELYKGGTGGSMVSKGEELFfGVVPIQVELDGDVNGHKFSVSG
EGEGDATYGKLTLKFICTTGKLPVPWPTLVTTLSYGYQCFSRYPDHMKQHDF
FKSAMPEGYIQERTIFFKDDGNYKTRAEYKFEGDTLVNRIELKGIDFKEDGNI
LGHKLEYNTRDQLTEEQIAELKEAFSLFDKDGDGTITTKELGTYMRSLGQNP
TEAELQDMINEVDADGDGTIDLPEFQTMMARKMNDTDSEEEIREAFRVFDK
DGNGYIGAAELRHVMTNLGEKLTDEEVDEMIRVADIDGDGQVNYEEFVQM
MTAK

FIG. 13O

R-GECOl (GenBank ID: JN258411) (SEQ ID NO:42)

MVDSSRRKWNKAGHAVRAIGRLSSPVVSERMYPEDGALKSEIKKGLRLKDG
GHYAAEVKTTYKAKKPVQLPGAYIVDIKLDIVSHNEDYTIVEQCERAEGRHS
TGGMDELYKGGTGGSLVSKGEEDNMAIIKEFMRFKVHMEGSVNGHEFEIEG
EGEGRPYEAFQTAKLKVTKGGPLPFAWDILSPQFMYGSKAYIKHPADIPDYF
KLSFPEGFRWERYMNFEDGGIIHYNQDSSLQDGVFIYKVKLRGTNFPPDGPV
MQKKTMGWEATRDQLTEEQIAEFKEAFSLFDKDGDGTITTKELGTYMRSLG
QNPTEAELQDMINEVDADGDGTFDFPEFLTMMARKMNDTDSEEEIREAFRV
FDKDGNGYIGAAELRHYMTDLGEKLTDEEVDEMIRVADIDGDGQVNYEEFY
QMMTAK

FIG. 13P

B-GECOl (GenBank ID: JN258412) (SEQ ID NO:43)

MYDSPRRKWNKTGHAYRAIGRLSSPENVYIKADKQKNGIKANFKJRHNIEG
GGYQLAYHYQQNTPIGDGPYLLPDNHYLSVQSILSKDPNEKRDHMVLLEFV
TAAGITLGMDELYKGGTGGSESMVSKGEELFTGVVPIQVELDGDVNGHKFS
VSGEGEGDATYGKLTLKFICTTGKLPVPWPTLVTTLSHGVQCFSRYPDHMKQ
HDFFKSAMPGGYIQERTIFFKDDGNYKTRAEVKFEGDTLYNRIELKGIDFKED
GNILGHKLEYNTRGQLTEEQIAEFKEAFSLFDKDGDGTITTKELGTYMRSLG
QNPTEAELQDMINEVDADGDGTIDFPEFLTMMAPKMQDTDSEEEIREAFRYF
DKDGNGYIGAAELRHVMTNLGEKLTDEEVDEMIREADIDGDGQYNYEEFV
QMMTAK

FIG. 13Q

G-GECO1 (GenBank ID: JN258413) (SEQ ID N0:44)

MVDSSRRKWNKTGHAVRAIGRLSSLENVYIKADKQKNGIKANFKIRHNIED
GGVQLAYHYQQNTPIGDGPVLLPDNHYLSVQSILSKDPNEKRDHMVLLEFV
TAAGITLGMDELYKGGTGGSMVSKGEELFTGVVPIQVELDGDVNGHKFSVS
GEGEGDATYGKLTLKFICTTGKLPVPWPTLVTTLTYGVQCFSRYPDHMKQHD
FFKSAMPEGYIQERTIFFKDDGNYKTRAEVKFEGDTLVNRIELKGIDFKEDGN
ILGHKLEYNTRDQLTEEQIAEFKEAFSLFDKDGDGTITTKELGTVMRSLGQNP
TEAELQDMINEVDADGDGTIDFPEFLTMMARKMKDTDSEEEIREAFRVFDK
DGNGYIGAAELRHVMTNLGEKLTDEEVDEMIRVADIDGDGQVNYEEFVQM
MTAK

FIG. 13R

G-GECO1.1 (GenBank ID: JN258414) (SEQ ID N0:45)

MVDSSRRKWNKTGHAVRAIGRLSSLENVYIKADEQKNGIKAYFKIRHNIEGG
GYQLAYHYQQNTPIGDGPVLLPDNHYLSYQSILSKDPNEKRDHMVLLEFVT
AAGITLGMDELYKGGTGGSMYSKGEELFTGVYPIQVELDGDVNGHKFSVSG
EGEGDATYGKLTLKFICTTGKLPYPWPTLVTTLTYGVQCFSRYPDHMKQHDF
FKSAMPEGYIQERTIFFKDDGNYKTRAEYKFEGDTLVNRIELKGIDFKEDGNI
LGHKLEYNTRDQLTEEQIAEFKEAFSLFDKDGDGTITTKELGTYMRSLGQNP
TEAELQDMINEVDADGDGTIDFPEFLTMMARKMNDTDSEEEIREAFRVFDK
DGNGYIGAAELRHVMTNLGEKLTDEEVDEMIRVADIDGDGQVNYEEFVQM
MTAK

FIG. 13S

G-GECO1.2 (GenBank ID: JN258415) (SEQ ID NO: 46)

MVDSSRRKWNKTGHAYRAIGRLSSLENVYIKADEQKNGIKAYFKIRHNIEGG
GVQLAYHYQQNTPIGDGPVLLPDNHYLSYQSMLSKDPNEKRDHMYLLEFVT
AAGITLGMDELYKGGTGGSESMVSKGEELFTGVVPIQVELDGDVNGHKFSV
SGEGEGDATYGKLTLKFICTTGKLPVPWPTLVTTLTYGYQCFSRYPDHMKQH
DFFKSAMPEGYIQERTIFFKGDGNYKTRAEVKFEGDTLVNRIELKGIDFKEDG
NILGHKLEYNTRDQLTEEQIAEFKEAFSLFDKDGDGTITIKELGTVMRSLGQ
NPTEAELQDMINEYDADGDGTIDFPEFLTMMARKMKDTDSEEEIREAFRVFD
KDGNGYIGAAELRHVMTNLGEKLTDEEVDEMIRVADIDGDGQYNYEEFVQ
MMTAK

FIG. 14A

TN-XXL (SEQ ID NO:47)

MVSKGEELFTGYVPILVELDGDYNGHKFSVRGEGEGDATNGKLTLKFICTTG
KLPVPWPTLVTTLTWGVQCFSRYPDHMKQHDFFKSAMPEGYVQERTIFFKD
DGNYKTRAEVKFEGDTLV NRIELKGIDFKEDGNILGHKLEYNYISHNVYITA
DKQKNGIKAHFKIRHNIEDGSVQLADHYQQNTPIGDGPVLLPDNHYLSTQSK
LSKDPNEKRDHMYLLEFYTAARMLSEEELANCFRIFDKDANGFIDIEELGEIL
RATGEHVTEEDIEDLMKDSDKNNDGRIDFDEFLKMMEGYQGTSEEELANCF
RIFDKDANGFIDIEELGEILRATGEHVTEEDIEDLMKDSDKNNDGRIDFDEFL
KMMEGYQELMGGYQLADHYQQNTPIGDGPYLLPDNHYLSYQSKLSKDPNE
KRDHMVLLEFVTAAGITLGMDELYKGGTGGSMVSKGEELFTGVYPILVELD
GDYNGHKFSYRGEGEGDATNGKLTLKFICTTGKLPYPWPTLVTTLGYGLMC
FARYPDHMKQHDFFKSAMPEGYVQERTIFFKDDGNYKTRAEVKFEGDTLVN
RIELKGIDFKEDGNILGHKLEYNYNSHNVYIMADKQKNGIKANFKIRHNIED

FIG. 14B

YC3.6 (SEQ ID NO:48)

MVSKGEELFTGVYPILVELDGDYNGHRFSYSGEGEGDATYGKLTLKFICTTG
KLPVPWPTLVTTLTWGYQCFSRYPDHMKQHDFFKSAMPEGYYQERTIFFKD
DGNYKTRAEVKFEGDTLV NRIELKGIDFKEDGNILGHKLEYNYISHNVYITA
DKQKNGIKAHFKIRHNIEDGSVQLADHYQQNTPIGDGPYLLPDNHYLSTQSA
LSKDPNEKRDHMVLLEFYTAARMHDQLTEEQIAEFKEAFSLFDKDGDGTITT
KELGTVMRSLGQNPTEAELQDMINEVDADGNGTIYFPEFLTMMARKMKDT
DSEEEIREAFRVFDKDGNGYISAAQLRHYMTNLGEKLTDEEVDEMIREADID
GDGQVNYEEFVQMMTAKGGKRRWKKNFIAVSAANRFKKISSSGALELMDG
GVQLADHYQQNTPIGDGPYLLPDNHYLSYQSALSKDPNEKRDHMVLLEFVT
AAGITLGMDELYKGGSGGMVSKGEELFTGVVPILYELDGDY NGHKFSVSGE
GEGDATYGKLTLKLICTTGKLPVPWPTLVTTLGYGLQCFARYPDHMKQHDFF
KSAMPEGYYQERTIFFKDDGNYKTRAEVKFEGDTLVNRIELKGIDFKEDGNI
LGHKLEYNYNSHNVYITADKQKNGIKANFKIRHNIELSRGPGTSAEIYACRLE
ISN

FIG. 14C

D3CPVenus polypeptide (SEQ ID NO:49)

MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSYQLADHYQQNTPIGDGPYLLPDNHYLSTQSA
LSKDPNEKRDHMVLLEFVTAARMHDQLTEEQIAEFKEAFSLLDKDGDGTITT
KELGTALRSLGQNPTEAELQDMINEVDADGNGTIYFPEFLTMMARKMKDTD
SEEEIREAFRVFDKDGNGYISAAELRHVMTNLGEKLTDEEVDEMIREADIDG
DGQVNYEEFYQMMTAKGGKRRWQKTGHAVRAFGRLKKISSSGALELMDG
GVQLADHYQQNTPIGDGPYLLPDNHYLSYQSALSKDPNEKRDHMVLLEFVT
AAGITLGMDELYKGGSGGMVSKGEELFTGVYPILVELDGDVNGHKFSVSGE
GEGDATYGKLTLKLICTTGKLPVPWPTLVTTLGYGLQCFARYPDHMKQHDFF
KSAMPEGYYQERTIFFKDDGNYKTRAEVKFEGDTLYNRIELKGIDFKEDGNI
LGHKLEYNYNSHNVYITADKQKNGIKANFKIRHNIE

FIG. 15A

Amino acid sequence of ChR1  (SEQ ID NO: 50)

MSRRPWLLALALAVALAAGSAGASTGSDATVPVATQDGPDYVFHRAHERML
FQTSYTLENNGSYICIPNNGQCFCLAWLKSNGTNAEKLAANILQWITFALSAL
CLMFYGYQTWKSTCGWEEIYYATIEMIKFIIEYFHEFDEPAYIYSSNGNKTVW
LRYAEWLLTCPYILIHLSNLTGLANDYNKRTMGLLVSDIGTIVWGTTAALSKG
YVRVIFFLMGLCYGIYTFFNAAKVYIEAYHTVPKGICRDLVRYLAWLYFCSW
AMFPVLFLLGPEGFGHINQFNSAIAHAILDLASKNAWSMMGHFLRVKIHEHI
LLYGDIRKKQKVNVAGQEMEVETMYHEEDD

FIG. 15B

Amino acid sequence of ChR2 (SEQ ID NO: 51)

MDYGGALSAVGRELLFYTNPVVVNGSYLVPEDQCYCAGWIESRGTNGAQT
ASNYLQWLAAGFSILLLMFYAYQTWKSTCG WEEIYVCAIEMVKYILEFFFEF
KNPSMLYLATGHRYQWLRYAEWLLTCPVILIHLSNLTGLSNDYSRRTMGLLY
SDIGTIVWGATSAMATGYVKYIFFCLGLCYGANTFFHAAKAYIEGYHTVPKG
RCRQYVTGMAWLFFYSWGMFPILFILGPEGFGVLSYYGSTYGHTIIDLMSKN
CWGLLGHYLRYLIHEHILIHGDIRKTTKLNIGGTEIEYETLVEDEAEAGAYP

FIG. 15C

Amino acid sequence of ChR2 SFO  (SEQ ID NO: 52)

MDYGGALSAVGRELLFYTNPYYVNGSYLVPEDQCYCAGWIESRGTNGAQT
ASNVLQWLAAGFSILLLMFYAYQTWKSTCGWEEIY VCAIEMY KVILEFFFEF
KNPSMLYLATGHRVQWLRYAEWLLTSPVILIHLSNLTGLSNDYSRRTMGLLV
SDIGTIYWGATSAMATGYVKVIFFCLGLCYGANTFFHAAKAYIEGYHTVPKG
RCRQVYTGMAWLFFYSWGMFPILFILGPEGFGVLSYYGSTVGHTIIDLMSKN
CWGLLGHYLRVLIHEHILIHGDIRKTTKLNIGGTEIEVETLVEDEAEAGAVP

FIG. 15D

Amino acid sequence of ChR2_SSFO (SEQ ID NO:53)

MDYGGALSAVGRELLFVTNPVVVNGSVLVPEDQCYCAGWIESRGTNGAQT
ASNVLQWLAAGFSILLLMFYAYQTWKSTCGWEEIY VCAIEMV KVILEFFFEF
KNPSMLYLATGHRVQWLRYAEWLLTSPVILIHLSNLTGLSNDYSRRTMGLLV
SAIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 15E

Amino acid sequence of VChR1 (SEQ ID NO:54)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 15F

Amino acid sequence of VChR1 SFO (SEQ ID NO: 55)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTSPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 15G

Amino acid sequence of VChR1 SSFO (SEQ ID NO:56)

MDYPVARSLIVRYPTDLGNGTVCMPRGQCYCEGWLRSRGTSIEKTIAITLQW
VVFALSVACLGWYAYQAWRATCGWEEVYVALIEMMKSIiEAFHEFDSPATLW
LSSGNGVVWMRYGEWLLTCPVLLIHLSNLTGLKDDYSKRTMGLLVSAYGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGYLG
NYLRVKIHEHILLYGDIRKKQKITIAGQEMEVETLVAEEED

FIG. 15H

Amino acid sequence of CIVl (SEQ ID NO: 57)

MSRRPWLLALALAYALAAGSAGASTGSDATYPVATQDGPDYVFHRAHERML
FQTSYTLENNGSYICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPYLLIHLSNLTGLKDDYSKRTMGLLVSDVGCIVWGATSAMCT
GWTKILFFLISLSYGMYTYFHAAKVYIEAFHTVPKGICRELVRVMAWTFFVA
WGMFPVLFLLGTEGFGHISPYGSAIGHSILDLIAKNMWGYLGNYLRVKIHEH
ILLYGDIRKKQKITIAGQEMEVETLYAEEED

FIG. 15I

Amino acid sequence of CIC2 (SEQ ID NO: 58)

MSRRPWLLALALAYALAAGSAGASTGSDATYPVATQDGPDYVFHRAHERML
FQTSYTLENNGSYICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPYILIHLSNLTGLANDYNKRTMGLLYSDIGTIYWGTTAALSKG
YVRVIFFLMGLCYGIYTFFNAAKYYIEAYHTVPKGRCRQVVTGMAWLFFYS
WGMFPILFILGPEGFGVLSVYGSTYGHTIIDLMSKNCWGLLGHYLRVLIHEHI
LIHGDIRKTTKLNIGGTEIEVETLVEDEAEAGAV

FIG. 15J

Amino acid sequence of SdChR (SEQ ID NO:59)

MGGAPAPDAHSAPPGNDSAGGSEYHAPAGYQVNPPYHPVHGYEEQCSSIYI
YYGALWEQETARGFQWFAVFLSALFLAFYGWHAYKASVGWEEVYVCSVEL
IKVILEIYFEFTSPAMLFLYGGNITPWLRYAEWLLTCPVILIHLSNITGLSEEYN
KRTMALLVSDLGTICMGVTAALATGWVKWLFYCIGLVYGTQTFYNAGIIYV
ESYYIMPAGGCKKLVLAMTAVYYSSWLMFPGLFIFGPEGMHTLSYAGSTIGH
TIADLLSKNIWGLLGHFLRIKIHEHIIMYGDIRRPVSSQFLGRKVDVLAFVTEE
DKV

FIG. 15K

Amino acid sequence of CnChR2 (SEQ ID NO:60)

MEPVLGLASTAVRELTAGGSGNPYESYKPPEDPCALTPFGCLTNFWCDPQFG
LADAKYDYCYVKAAYGELAIVETSRLPWLYSHGSDAEHQGALAMQWMAF
ALCIICLVFYAYHSWKATTGWEEVYVCVVELVKVLLEIYKEFESPASIYLPTA
NAALWLRYGEWLLTCPVILIHLSNITGLKDDYNKRTMQLLVSDIGCVVWGIT
AAFSVGWLKWVFFVLGLLYGSNTYFHAAKVYIESYHTVPKGHCRLIVRLMA
YCFYVAWTMYPILFILGPEGLGHMSAYMSTALHGVADMLSKQIWGLLGHHL
RVKIFEHILIHGDIRKTTTMQVGGQMVQVEEMVDEEDEDTI

FIG. 15L

Amino acid sequence of CsChrimson (SEQ ID NO:61)

MSRLVAASWLLALLLCGITSTTTASSAPAASSTDGTAAAAVSHYAMNGFDEL
AKGAVVPEDHFVCGPADKCYCSAWLHSRGTPGEKIGAQVCQWIAFSIAIALL
TFYGFSAWKATCGWEEVYVCCVEVLFVTLEIFKEFSSPATVYLSTGNHAYCL
RYFEWLLSCPVILIKLSNLSGLKNDYSKRTMGLIVSCVGMIVFGMAAGLATD
WLKWLLYIVSCIYGGYMYFQAAKCYVEANHSVPKGHCRMVVKLMAYAYF
ASWGSYPILWAVGPEGLLKLSPYANSIGHSICDIIAKEFWTFLAHHLRIKIHEHI
LIHGDIRKTTKMEIGGEEV EVEEFVEEEDEDTV

FIG. 15M

Amino acid sequence of ShChR1 (SEQ ID NO:62)

METAATMTHAFISAVPSAEATIRGLLSAAAVVTPAADAHGETSNATTAGADH
GCFPHINHGTELQHKIAVGLQWFTVIVAIVQLIFYGWHSFKATTGWEEYYVC
VIELVKCFIELFHEYDSPATVYQTNGGAYIWLRYSMWLLTCPYILIHLSNLTGL
HEEYSKRTMTILVTDIGNIYWGITAAFTKGPLKILFFMIGLFYGVTCFFQIAKV
YIESYHTLPKGVCRKICKIMAYVFFCSWLMFPVMFIAGHEGLGLITPYTSGIG
HLILDLISKNTWGFLGHHLRVKIHEHILIHGDIRKTTTINVAGENMEIETFVDE
EEEGGV

FIG. 15N

Amino acid sequence of Arch (SEQ ID NO:63)

MDPIALQAGYDLLGDGRPETLWLGIGTLLMLIGTFYFLYRGWGVTDKDARE
YYAVTILVPGIASAAYLSMFFGIGLTEYTYGGEMLDIYYARYADWLFITPLLL
LDLALLAKVDRVTIGTLVGVDALMIVTGLIGALSHTAIARYSWWLFSTICMIY
VLYFLATSLRSAAKERGPEYASTFNTLTALVLVLWTAYPILWIIGTEGAGYVGL
GIETLLFMVLDVTAKVGFGFILLRSRAILGDTEAPEPSAGADYSAAD

FIG. 15O

Amino acid sequence of ArchT (SEQ ID NO:64)

MDPIALQAGYDLLGDGRPETLWLGIGTLLMLIGTFYFIVKGWGVTDKEARE
YYSITILVPGIASAAYLSMFFGIGLTEVTVAGEYLDIYYARYADWLFITPLLLL
DLALLAKYDRVSIGTLYGYDALMIYTGLIGALSHTPLARYSWWLFSTICMIV
VLYFLATSLRAAAKERGPEYASTFNTLTALVLYLWTAYPILWIIGTEGAGVYGL
GIETLLFMVLDVTAKVGFGFILLRSRAILGDTEAPEP

FIG. 15P

Amino acid sequence of GtR3 (SEQ ID N0: 65)

ASSFGKALLEFVFIVFACITLLLGINAAKSKAASRVLFPATFVTGIASIAYFSMA
SGGGWVIAPDCRQLFVARYLDWLITTPLLLIDLGLVAGVSRWDIMALCLSDV
LMIATGAFGSLTVGNVKWVWWFFGMCWFLHIIFALGKSWAEAAKAKGGDS
ASVYSKIAGITVITWFCYPVVWVFAEGFGNFSVTFEVLIYGVLDVISKAVFGLI
LMSGAATGYESI

FIG. 15Q

Amino acid sequence of Oxy (SEQ ID NO: 66)

MAPLAQDWTYAEWSAVYNALSFGIAGMGSATIFFWLQLPNVTKNYRTALTIT
GIVTLIATYHYFRIFNSWVAAFNVGLGVNGAYEVTVSGTPFNDAYRYVDWLL
TVPLLLVELILVMKLPAKETVCLAWTLGIASAVMVALGYPGEIQDDLSVRWF
WWACAMVPFVYVVGTLVVGLGAATAKQPEGVVDLVSAARYLTVVSWLTYP
FVYIVKNIGLAGSTATMYEQIGYSAADVTAKAVFGVLIWAIANAKSRLEEEG
KLRA

FIG. 15R

Amino acid sequence of Mac (SEQ ID NO: 67)

MIVDQFEEVLMKTSQLFPLPTATQSAQPTHVAPVPTVLPDTPIYETVGDSGSK
TLWVVFVLMLIASAAFTALSWKIPVNRRLYHVITTIITLTAALSYFAMATGHG
VALNKIVIRTQHDHVPDTYETVYRQVYYARYIDWAITTPLLLLDLGLLAGMS
GAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYA
VLDVLAKGVFGAWLLVTHANLRESDVELNGFWANGLNREGAIRIGEDDGA

FIG. 15S

Amino acid sequence of NpHR (SEQ ID NO:68)

VTQRELFEFVLNDPLLASSLYINIALAGLSILLFVFMTRGLDDPRAKLIAVSTIL
VPVVSIASYTGLASGLTISVLEMPAGHFAEGSSVMLGGEEVDGVVTMWGRY
LTWALSTPMILLALGLLAGSNATKLFTAITFDIAMCVTGLAAALTTSSHLMRW
FWYAISCACFLVVLYILLVEWAQDAKAAGTADMFNTLKLLTVVMWLGYPIV
WALGVEGIAVLPVGVTSWGYSFLDIVAKYIFAFLLLNYLTSNESVVSGSILDV
PSASGTPADD

FIG. 15T

Amino acid sequence of DsChR (SEQ ID NO: 69)

MRRRESQLAYLCLFVLIAGWAPRLTESAPDLAERRPPSERNTPYANIKKVPNI
TEPNANVQLDGWALYQDFYYLAGSDKEWVVGPSDQCYCRAWSKSHGTDR
EGEAAVYWAYIYFAICIYQLYYFMFAAWKATVGWEEVYYNIIELVHIALYIWV
EFDKPAMLYLNDGQMVPWLRYSAWLLSCPVILIHLSNLTGLKGDYSKRTMG
LLVSDIGTIYFGTSAALAPPNHVKVILFTIGLLYGLFTFFTAAKVYIEAYHTVP
KGQCRNLYRAMAWTYFYSWAMFPILFILGREGFGHITYFGSSIGHFILEIFSKN
LWSLLGHGLRYRIRQHiliHGNLTKKNKINIAGDNVEVEEYYDSNDKDSDV

FIG. 15U

Amino acid sequence of Champ (SEQ ID NO:70)

MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIYTGLIGALSHTAIARYSWWLFSTICMIV
VLYFLATSLRSAAKERGPEVASTFNTLTALVLVLWTAYPILWIIGTEGAGVVGL
GIETLLFMYLDVTAKYGFGFILLRSRAILGDTEAPEPSAGADVSAADKSRITSE
GEYIPLDQIDINVGAPGSGATNFSLLKQAGDVEENPGPMDLKESPSEGSLQPS
SIQIFANTSTLHGIRHIFVYGPLTIRRVLWAYAFYGSLGLLLYESSERYSYYFSY
QHVTKVDEVVAQSLVFPAVTLCNLNGFRFSRLTTNDLYHAGELLALLDVNLQ
IPDPHLADPTVLEALRQKANFKHYKPKQFSMLEFLHRVGHDLKDMMLYCKF
KGQECGHQDFTTYFTKYGKCYMFNSGEDGKPLLTTVKGGTGNGLEIMLDIQ
QDEYLPIWGETEETTFEAGVKVQIHSQSEPPFIQELGFGVAPGFQTFVATQEQR
LTYLPPPWGECRSSEMGLDFFPVYSITACRIDCETRYIVENCNCRMVHMPGD
APFCTPEQHKECAEPALGLLAEKDSNYCLCRTPCNLTRYNKELSMVKIPSKTS
AKYLEKKFNKSEKYISENILVLDIFFEALNYETIEQKKAYEVAALLGDIGGQM
GLFIGASLLTILELFDYIYELIKEKLLDLLGKEEEEGSHDENMSTCDTMPNHSE
TISHTVNYPLQTALGTLEEIACAAAKSRITSEGEYIPLDQIDINYVSKGEELFTG
VVPILVELDGDYNGHKFSVSGEGEGDATYGKLTLKFICTTGKLPVPWPTLVT
TFGYGLQCFARYPDHMKQHDFFKSAMPEGYVQERTIFFKDDGNYKTRAEVK
FEGDTLYNRIELKGIDFREDGNILGHKLEYNYNSHNVYIMADKQKNGIKVNF
KIRHNIEDGSVQLADHYQQNTPIGDGPVLLPDNHYLSYQSALSKDPNEKRDH
MYLLEFYTAAGITLGMDELYKFCYENEV

FIG. 16

KEY RESOURCES TABLE

| REAGENT or RESOURCE | SOURCE | IDENTIFIER |
|---|---|---|
| Antibodies | | |
| Chicken Anti-TH | Aves Labs | Cat# TH |
| Alexa Cy3 anti-chicken | Jackson ImmunoResearch | Cat# 703-165-155 |
| Bacterial and Virus Strains | | |
| One Shot Stbl3 *e-coli* | ThermoFisher | Cat# C737303 |
| Adeno-Associated Virus Coat Protein 2/8 | Stanford GVVC | AAV8 |
| Adeno-Associated Virus Coat Protein 2/retro | Stanford GVVC | AAV-retro |
| pAAV-EF1a-FlpO-p2a-Cre | This Paper | Stanford GVVC AAV8 |
| pAAV-EF1a-FlpO | | Stanford GVVC AAV8 |
| pAAV-EF1a-FlpO | | Stanford GVVC AAV-retro |
| pAAV-EF1a-Cre | | Stanford GVVC AAV8 |
| pAAV-EF1a-VCre | Fenno et al. 2014 | Stanford GVVC AAV8 |
| pAAV-EF1a-VCre | Fenno et al. 2014 | Stanford GVVC AAV-retro |
| pAAV-cDIO-EYFP | | Stanford GVVC AAV8 |
| pAAV-fDIO-EYFP | | Stanford GVVC AAV8 |
| pAAV-vcDIO-EYFP | Fenno et al. 2014 | Stanford GVVC AAV8 |
| pAAV-Ef1a-EYFP | | Stanford GVVC AAV8 |
| pAAV-Ef1a-Con/Fon-EYFP | Fenno et al. 2014 | Stanford GVVC AAV8 |
| pAAV-Ef1a-Con/Foff-EYFP | Fenno et al. 2014 | Stanford GVVC AAV8 |
| pAAV-Ef1a-Coff/Fon-EYFP | Fenno et al. 2014 | Stanford GVVC AAV8 |
| pAAV-Ef1a-Con/Foff 2.0-EYFP | | Stanford GVVC AAV8 |
| pAAV-nEF-3x-EYFP | | Addgene Cat# 137163 |
| pAAV-Ef1a-3x-GCaMP6M | | Addgene Cat# 137164 |
| Experimental Models: Organisms/Strains | | |
| WT C57/BL6 mice | Jackson Laboratories | Cat# 000664 |
| SST-Cre C57/BL6 transgenic mice | Jackson Laboratories | Cat# 013044 |
| Sprague-Dawley rat pups | Charles River | |
| Oligonucleotides | | |
| Sequencing nEF F GACCCTGCTTGCTCAACTCT | IDT DNA | N/A |
| Sequencing EF1a F TGGAATTTGCCCTTTTTTGAG | IDT DNA | N/A |
| Sequencing Intron 1 F GGGACGACATGACTTAACCAG | IDT DNA | N/A |

FIG. 16 (Cont.)

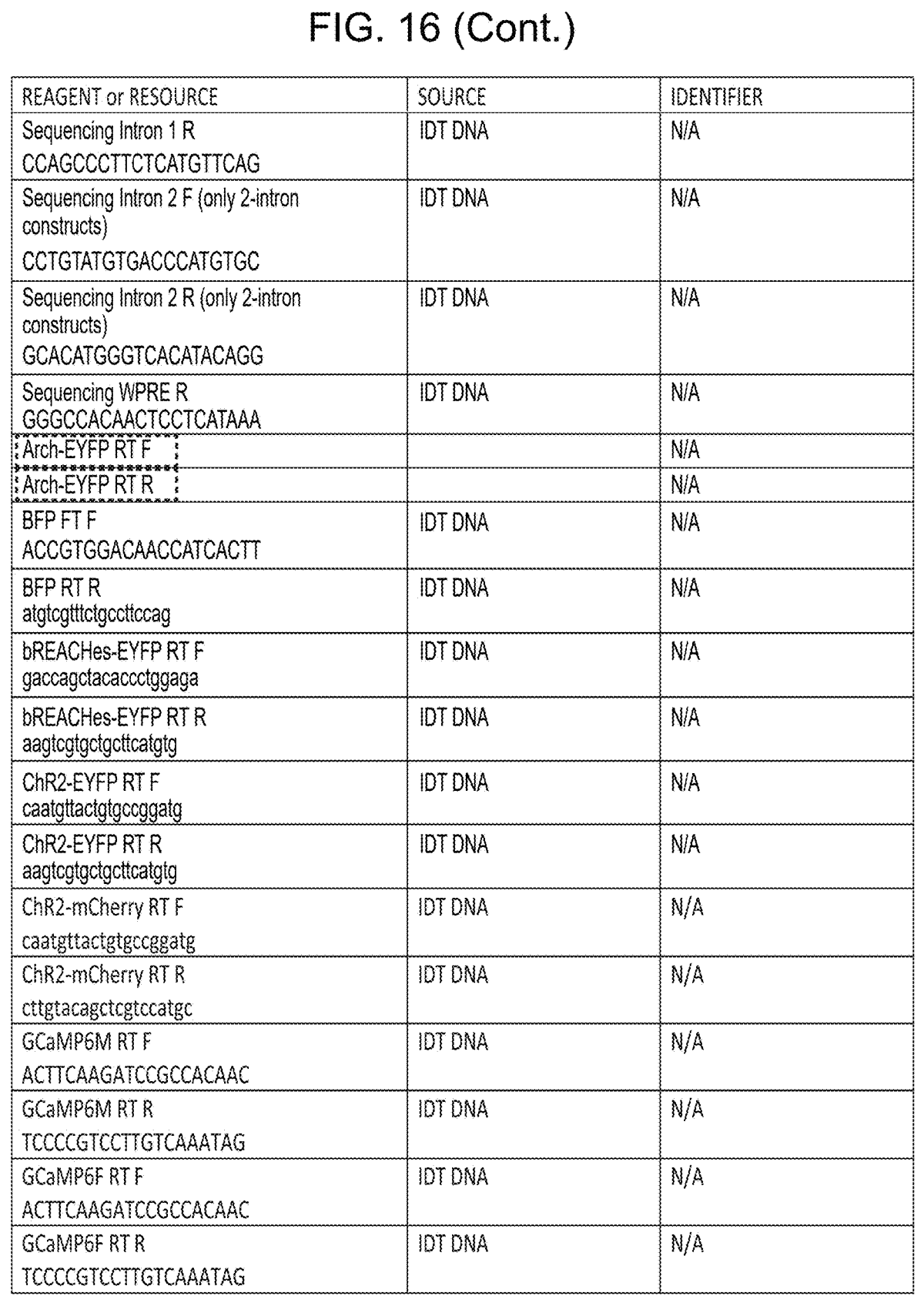

| REAGENT or RESOURCE | SOURCE | IDENTIFIER |
|---|---|---|
| Sequencing Intron 1 R<br>CCAGCCCTTCTCATGTTCAG | IDT DNA | N/A |
| Sequencing Intron 2 F (only 2-intron constructs)<br>CCTGTATGTGACCCATGTGC | IDT DNA | N/A |
| Sequencing Intron 2 R (only 2-intron constructs)<br>GCACATGGGTCACATACAGG | IDT DNA | N/A |
| Sequencing WPRE R<br>GGGCCACAACTCCTCATAAA | IDT DNA | N/A |
| Arch-EYFP RT F | | N/A |
| Arch-EYFP RT R | | N/A |
| BFP FT F<br>ACCGTGGACAACCATCACTT | IDT DNA | N/A |
| BFP RT R<br>atgtcgtttctgccttccag | IDT DNA | N/A |
| bREACHes-EYFP RT F<br>gaccagctacaccctggaga | IDT DNA | N/A |
| bREACHes-EYFP RT R<br>aagtcgtgctgcttcatgtg | IDT DNA | N/A |
| ChR2-EYFP RT F<br>caatgttactgtgccggatg | IDT DNA | N/A |
| ChR2-EYFP RT R<br>aagtcgtgctgcttcatgtg | IDT DNA | N/A |
| ChR2-mCherry RT F<br>caatgttactgtgccggatg | IDT DNA | N/A |
| ChR2-mCherry RT R<br>cttgtacagctcgtccatgc | IDT DNA | N/A |
| GCaMP6M RT F<br>ACTTCAAGATCCGCCACAAC | IDT DNA | N/A |
| GCaMP6M RT R<br>TCCCCGTCCTTGTCAAATAG | IDT DNA | N/A |
| GCaMP6F RT F<br>ACTTCAAGATCCGCCACAAC | IDT DNA | N/A |
| GCaMP6F RT R<br>TCCCCGTCCTTGTCAAATAG | IDT DNA | N/A |

FIG. 16 (Cont.)

| REAGENT or RESOURCE | SOURCE | IDENTIFIER |
|---|---|---|
| iC++-EYFP RT F<br>aacaagcgtaccatgggtct | IDT DNA | N/A |
| iC++-EYFP RT R<br>aagtcgtgctgcttcatgtg | IDT DNA | N/A |
| mCherry RT F<br>cctgtcccctcagttcatgt | IDT DNA | N/A |
| mCherry RT R<br>cttcagcttcagcctctgct | IDT DNA | N/A |
| NpHR-EYFP RT F<br>gttgttcgagttcgtgctga | IDT DNA | N/A |
| NpHR-EYFP RT R<br>aagtcgtgctgcttcatgtg | IDT DNA | N/A |
| oScarlet RT F<br>CCATGAACGGCCACGAGTTCG | IDT DNA | N/A |
| oScarlet RT R<br>GTCCAACTTGCGGTCCACGTTG | IDT DNA | N/A |
| srGECO RT F<br>CAACGAGGACTACACCATCG | IDT DNA | N/A |
| srGECO RT R<br>GTCCTCGAAGTTCATCACGC | IDT DNA | N/A |
| 3xEYFP RT F | IDT DNA | N/A |
| 3xEYFP RT R | IDT DNA | N/A |
| 3xGCaMP6M RT F | IDT DNA | N/A |
| 3xGCaMP6M RT R | IDT DNA | N/A |
| Recombinant DNA | | |
| pAAV-EF1a-Con/Fon-GCaMP6M | | Addgene Cat# 137119 |
| pAAV-Ef1a-Con/Foff-GCaMP6M | | N/A |
| pAAV-Ef1a-Con/Foff 2.0-GCaMP6M | | Addgene Cat# 137120 |
| pAAV-Ef1a-Coff/Fon-GCaMP6M | | Addgene Cat# 137121 |
| pAAV-Ef1a-Con/Fon-GCaMP6F | | Addgene Cat# 137122 |
| pAAV-Ef1a-Con/Foff-GCaMP6F | | N/A |
| pAAV-Ef1a-Con/Foff 2.0-GCaMP6F | | Addgene Cat# 137123 |
| pAAV-Ef1a-Coff/Fon-GCaMP6F | | Addgene Cat# 137124 |
| pAAV-Ef1a-sRGECO | | Addgene Cat# 137125 |
| pAAV-Ef1a-Con/Fon-sRGECO | | Addgene Cat# 137126 |

FIG. 16 (Cont.)

| REAGENT or RESOURCE | SOURCE | IDENTIFIER |
|---|---|---|
| pAAV-Ef1a-Con/Foff-sRGECO | | N/A |
| pAAV-Ef1a-Con/Foff 2.0-sRGECO | | Addgene Cat# 137127 |
| pAAV-Ef1a-Coff/Fon-sRGECO | | Addgene Cat# 137128 |
| pAAV-Ef1a-Con/Fon-BFP | | Addgene Cat# 137129 |
| pAAV-Ef1a-Con/Foff-BFP | | N/A |
| pAAV-Ef1a-Con/Foff 2.0-BFP | | Addgene Cat# 137130 |
| pAAV-Ef1a-Coff/Fon-BFP | | Addgene Cat# 137131 |
| pAAV-Ef1a-Con/Fon-mCherry | | Addgene Cat# 137132 |
| pAAV-Ef1a-Con/Foff-mCherry | | N/A |
| pAAV-Ef1a-Con/Foff 2.0-mCherry | | Addgene Cat# 137133 |
| pAAV-Ef1a-Coff/Fon-mCherry | | Addgene Cat# 137134 |
| pAAV-Ef1a-oScarlet | | Addgene Cat# 137135 |
| pAAV-Ef1a-Con/Fon-oScarlet | | Addgene Cat# 137136 |
| pAAV-Ef1a-Con/Foff-oScarlet | | N/A |
| pAAV-Ef1a-Con/Foff 2.0-oScarlet | | Addgene Cat# 137137 |
| pAAV-Ef1a-Coff/Fon-oScarlet | | Addgene Cat# 137138 |
| pAAV-nEF-Con/Fon-ChR2(ET/TC)-EYFP | | Addgene Cat# 137139 |
| pAAV-nEF-Con/Foff-ChR2(ET/TC)-EYFP | | N/A |
| pAAV-nEF-Con/Foff 2.0-ChR2(ET/TC)-EYFP | | Addgene Cat# 137140 |
| pAAV-nEF-Coff/Fon-ChR2(ET/TC)-EYFP | | Addgene Cat# 137141 |
| pAAV-nEF-Con/Fon-ChR2-mCherry | | Addgene Cat# 137142 |
| pAAV-nEF-Con/Foff-ChR2-mCherry | | N/A |
| pAAV-nEF-Con/Foff 2.0-ChR2-mCherry | | Addgene Cat# 137143 |
| pAAV-nEF-Coff/Fon-ChR2-mCherry | | Addgene Cat# 137144 |
| pAAV-nEF-Con/Fon-bREACHes-EYFP | | Addgene Cat# 137145 |
| pAAV-nEF-Con/Foff-bREACHes-EYFP | | N/A |
| pAAV-nEF-Con/Foff 2.0-bREACHes-EYFP | | Addgene Cat# 137146 |
| pAAV-nEF-Coff/Fon-bREACHes-EYFP | | Addgene Cat# 137147 |
| pAAV-nEF-Con/Fon-Arch3.3-p2a-EYFP | | Addgene Cat# 137148 |
| pAAV-nEF-Con/Foff-Arch3.3-EYFP | | N/A |
| pAAV-nEF-Con/Foff 2.0-Arch3.3-EYFP | | Addgene Cat# 137149 |
| pAAV-nEF-Coff/Fon-Arch3.3-p2a-EYFP | | Addgene Cat# 137150 |
| pAAV-nEF-NpHR3.3-EYFP | | Addgene Cat# 137151 |

FIG. 16 (Cont.)

| REAGENT or RESOURCE | SOURCE | IDENTIFIER |
|---|---|---|
| pAAV-nEF-Con/Fon-NpHR3.3-EYFP | | Addgene Cat# 137152 |
| pAAV-nEF-Con/Foff-NpHR3.3-EYFP | | N/A |
| pAAV-nEF-Con/Foff 2.0-NpHR3.3-EYFP | | Addgene Cat# 137153 |
| pAAV-nEF-Coff/Fon-NpHR3.3-EYFP | | Addgene Cat# 137154 |
| pAAV-nEF-Con/Fon-iC++-EYFP | | Addgene Cat# 137155 |
| pAAV-nEF-Con/Foff-iC++-EYFP | | N/A |
| pAAV-nEF-Con/Foff 2.0-iC++-EYFP | | Addgene Cat# 137156 |
| pAAV-nEF-Coff/Fon-iC++-EYFP | | Addgene Cat# 137157 |
| pAAV-nEF-ChRmine-mScarlet | | Addgene Cat# 137158 |
| pAAV-nEF-Con/Fon-ChRmine-oScarlet | | Addgene Cat# 137159 |
| pAAV-nEF-Coff/Fon-ChRmine-oScarlet | | Addgene Cat# 137160 |
| pAAV-nEF-Con/Foff-ChRmine-oScarlet | | N/A |
| pAAV-nEF-Con/Foff 2.0-ChRmine-oScarlet | | Addgene Cat# 137161 |
| pAAV-Ef1a-Con/Foff 2.0-EYFP | | Addgene Cat# 137162 |
| pAAV-nEF-Con/Foff 2.0-ChR2-EYFP | | Addgene Cat# 137163 |
| pAAV-nEF-3x-EYFP | | Addgene Cat# 137164 |
| pAAV-Ef1a-3x-GCaMP6M | | Addgene Cat# 137165 |

COMPOSITIONS AND METHODS FOR CONTROLLING PRODUCTION OF POLYPEPTIDES IN CELLS

CROSS REFERENCE TO RELATED APPLICATIONS

This application claims priority pursuant to 35 U.S.C. § 119(e) to the filing date of U.S. Provisional Application Ser. No. 62/969,858, filed Feb. 4, 2020, the disclosure of which is incorporated herein by reference.

INTRODUCTION

Neuroscience research has accelerated dramatically with the rapid and ongoing development of genetically-encoded, molecular tools that function based on visible light. These include optogenetic tools that control action potentials with millisecond resolution, calcium indicators that report neuron activity, and a palette of fluorescent proteins. As detailed neuronal transcriptomes and connectomes become more refined, the application of these molecular approaches is limited by researcher's ability to selectively express them in defined cellular sub-populations.

SUMMARY

The present disclosure provides recombinant expression vectors for modulating production of polypeptides of interest in a target cell or target cell population. Aspects of the disclosure include recombinant expression vectors having coding sequences encoding portions of a polypeptide of interest, where the coding sequences are flanked by recombinase recognition sites. Also provided are methods for using the recombinant expression vectors as well as a device for monitoring expression of the polypeptide of interest.

BRIEF DESCRIPTION OF THE DRAWINGS

FIGS. 1A-1G depicts the INTRSECT strategy, function, and engineering pipeline.

FIGS. 2A-2H depicts standardized approaches to the INTRSECT design and implementation. The sequences of FIG. 2F are set forth from top to bottom in SEQ ID NOs: 1 and 2.

FIGS. 4A-4I depicts chronic monitoring of viral expression.

FIG. 5 depicts published Flp-expressing transgenic mouse lines.

FIGS. 6A-6L depicts engineering, optimization, testing, and in vivo function of three-recombinase-dependent INTRSECT 3x constructs. The sequences of FIG. 6C are set forth in SEQ ID NOs: 3-4.

FIGS. 7A-7L depicts INTRSECT fluorophore development. The sequences of FIG. 7D are set forth in SEQ ID NO: 5. The sequences of FIG. 7G are set forth in SEQ ID NO: 6. The sequences of FIG. 7J are set forth in SEQ ID NO:7.

FIGS. 9A-9L depicts INTRSECT excitatory opsin development. The sequences of FIG. 9A are set forth from left to right in SEQ ID NOs: 8 and 3. The sequences of FIG. 9D are set forth from left to right in SEQ ID NOs: 9 and 3. The sequences of FIG. 9G are set forth from left to right in SEQ ID NOs: 9 and 10. The sequences of FIG. 9J are set forth from left to right in SEQ ID NOs: 11 and 12.

FIGS. 10A-10I depicts INTRSECT inhibitory opsin development. The sequences of FIG. 10A are set forth in SEQ ID NO: 13 (intron 1 splice site) and 3 (intron 2 splice site). The sequences of FIG. 10D are set forth in SEQ ID NO: 14 (intron 1 splice site) and 3 (intron 2 splice site). The sequences of FIG. 10G are set forth in SEQ ID NO: 15 (intron 1 splice site) and 3 (intron 2 splice site).

FIGS. 11A-11G depicts optimization of the Con/Foff INTRSECT backbone.

FIG. 13A-13S provide amino acid sequences of single-fluorescent protein genetically encoded calcium indicators.

FIG. 14A-14C provide amino acid sequences of multi-fluorescent protein genetically encoded calcium indicators.

FIG. 15A-15U provide amino acid sequences of various light-responsive polypeptides.

FIG. 16 provides a table of various exemplary reagents and constructs. The oligonucleotide sequences are set forth from top to bottom in SEQ ID NOs: 71 to 99.

DEFINITIONS

Figure 1C:
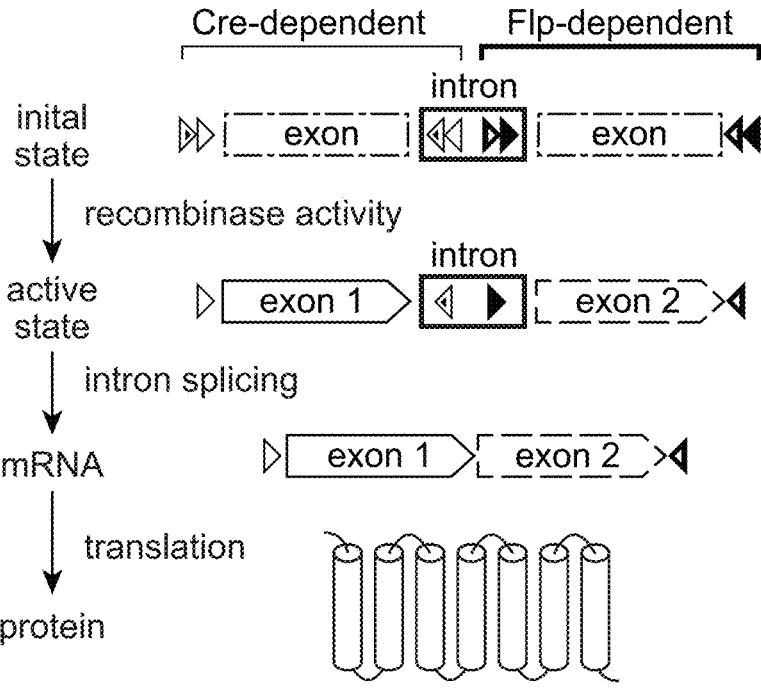

As used herein, the term "reverse complement" or a sequence in "reverse complement orientation" refers to a sequence that will anneal/base pair or substantially anneal/base pair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUUGC would be 5'-GCAAAUU. Alternative base pairing schemes, including but not limited to G-U pairing, can also be included in reverse complements.

An "exon" refers to a defined section of nucleic acid that encodes for a protein or portion thereof, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA.

An "intron" refers to a nucleic acid region, e.g., within a gene, that is not translated into a protein. An intron is a non-coding section that is transcribed into a precursor mRNA (pre-mRNA), and subsequently removed by splicing during formation of the mature RNA.

A "recombinase," as used herein in, is a site-specific enzyme that recognizes short DNA sequence(s), which sequence(s) are typically between about 30 base pairs (bp) and 40 bp, and that mediates the recombination between these recombinase recognition sequences (RRS), which results in the excision, integration, inversion, or exchange of DNA fragments between the recombinase recognition sequences. Exemplary recombinases include, but are not limited to, Cre, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, A118, spoIVCA, PhiMR11, SCCmec, TndX, XerC, XerD, XisA, Hin, Cin, mrpA, beta, PhiFC1, Fre, Clp, sTre, FimE, and HbiF. Exemplary RRS include, but are not limited to, loxP, loxN, lox511, lox5171, lox2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.

The outcome of recombination depends, in part, on the location and orientation of two short repeated DNA sequences (e.g., RRS) that are to be recombined, typically less than 30 bp long. The site-specific recombinases bind to these repeated sequences, which are specific to each recombinase, and are herein referred to as "recombinase recognition sequences" or "recombinase recognition sites." Thus, as used herein, a recombinase is "specific for" a recombinase recognition site when the recombinase can mediate inversion or excision between the repeat DNA sequences. As used herein, a recombinase may also be said to recognize its "cognate recombinase recognition sites," which flank an intervening genetic element (e.g., promoter, terminator, or target gene). A genetic element is said to be "flanked" by recombinase recognition sites when the element is located between and immediately adjacent to two repeated DNA sequences. In some embodiments, the recombinase recognition sites do not overlap each other. However, in other embodiments, recombinase recognition sites do overlap each other, such as described herein below, which permits greatly increased combinatorial complexity.

Inversion recombination happens between two short, inverted, repeated DNA sequences. Without wishing to be bound by theory, a DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA.

As used herein, the term "modulating" means increasing, reducing or inhibiting an attribute of a biological system such as, e.g., expression or production of a polypeptide. In some cases, "modulate" or "modulating" or "modulation" may be measured using an appropriate in vitro assay, cellular assay or in vivo assay. In some cases, the increase or decrease is 10% or more relative to a reference, e.g., 10% or more, 20% or more, 30% or more, 40% or more, 50% or more, 60% or more, 70% or more, 80% or more, 90% or more, 95% or more, 97% or more, 98% or more, up to 100% relative to a reference. For example, the increase or decrease may be 2 or more times, 3 times or more, 4 times or more, 5 times or more, 6 times or more, 7 times or more, 8 times or more, 9 times or more, 10 times or more, 50 times or more, or 100 times or more relative to a reference.

As used herein, "naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation. A wild-type organism or cell refers to an organism or cell that has not been intentionally modified by human manipulation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a recombinase" includes a plurality of such recombinases and reference to "the opsin" includes reference to one or more opsins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant expression vectors for modulating production of polypeptides of interest in a target cell or target cell population. Aspects of the disclosure include recombinant expression vectors having coding sequences encoding portions of a polypeptide of interest, where the coding sequences are flanked by recombinase recognition sites. Also provided are methods for using the recombinant expression vectors as well as a device for monitoring expression of the polypeptide of interest.

In further describing various aspects of the invention, the recombinant expression vectors are reviewed first in greater detail, followed by a review of methods. Devices for monitoring expression of polypeptides of interest is also provided in greater detail below.

Recombinant Expression Vectors

The present disclosure provides a recombinant expression vector that provides for controlling or modulating production of polypeptides in a target cell or target cell population. Aspects of the recombinant expression vector include one or more coding sequences, e.g., exons, that encode a portion of a polypeptide of interest. The orientation of a coding sequence (e.g., in a sense orientation or reverse complement orientation) in the recombinant expression vector may modulate expression or production of the polypeptide of interest. The orientation of the coding sequence(s) may be inverted during recombination by one or more recombinases such that the coding sequence(s) is subsequently oriented in a sense orientation or a reverse complement orientation. The recombinant expression vectors may further include one or more non-coding sequences, e.g., introns, that may be inserted between the one or more coding sequences. The recombinant expression vector may further include enzyme recognition sites, e.g., recombinase recognition sites, that are recognized by one or more enzymes, e.g., recombinases, to catalyze recombination of the sequences of the vector. The one or more coding sequences may encode a polypeptide of interest, where the polypeptide includes any one of, e.g., a fluorescent polypeptide, a calcium indicator, an excitatory opsin, and an inhibitory opsin, as described in further detail below.

As summarized above, coding sequences in a recombinant expression vector may be subjected to recombination by one or more recombinases. In some instances, the orientation of the coding sequence(s) is inverted during recombination by one or more recombinases. In some instances, the orientation of one or more coding sequences in reverse complement orientation is inverted during recombination by one or more recombinases such that the coding sequences are in a sense orientation or an orientation that allows expression of the polypeptide or portion thereof encoded by the coding sequences. In some instances, the orientation of one or more coding sequences in a sense orientation is inverted during recombination by one or more recombinases such that the coding sequences are in a reverse complement orientation or an orientation which inhibits expression of the polypeptide or portion thereof encoded by the coding sequences.

The recombinant expression vector may include any suitable number of coding sequences, e.g., exons, where any one of the coding sequences may be in a sense orientation or a reverse complement orientation. In some cases, the recombinant expression vector includes one, two, three, four, five, six, seven, eight, nine, or ten coding sequences. In some cases, the recombinant expression vector includes a first coding sequence and a second coding sequence. In some cases, the recombinant expression vector includes a first coding sequence, a second coding sequence, and a third coding sequence. In some cases, the first coding sequence is in reverse complement orientation. In some cases, the second coding sequence is in reverse complement orientation. In some cases, the third coding sequence is in reverse complement orientation. In some cases, the first coding sequence and the second coding sequence are in reverse complement orientation. In some cases, the second coding sequence and the third coding are in reverse complement orientation. In some cases, the first coding sequence and third coding sequence are in reverse complement orientation. In some cases, every coding sequence of the recombinant expression vector, e.g., the first coding sequence, the second coding sequence, and the third coding sequence, is in reverse complement orientation.

The recombinant expression vector may include any suitable arrangement of recombinase recognition sites. In some instances, the recombinant expression vector includes recombinase recognition sites configured for a double-floxed inverse orientation approach (e.g., DIO approach). In some instances, the recombinant expression vector includes recombinase recognition sites configured for a double-floxed orientation approach (e.g., DO approach). The recombinant expression vectors may include one or more recombinase recognition sites positioned 5' or 3' to a terminal coding sequence. In some instances, one or more recombinase recognition sites are positioned 5' to the first coding sequence. In some instances, one or more recombinase recognition sites are positioned 3' to the last coding sequence in a sequence of coding sequences. The number of recombinase recognition sites positioned 5' or 3' to a coding sequence may range from 1 to 10 including, e.g., from 1 to 9, from 1 to 8, from 1 to 7, from 1 to 6, from 1 to 5, from 1 to 4, from 1 to 3, or from 1 to 2. The recombinant expression vector may further include one or more recombinase recognition sites in a non-coding sequence, as described in detail below. The recombinase recognition sites may include a recombinase recognition site variant, as described in detail below.

In certain embodiments, a recombinant expression vector of the present disclosure comprises: a) a first coding sequence encoding a portion of a polypeptide of interest, wherein a first recombinase recognition site is positioned 5' to the first coding sequence; b) a second coding sequence positioned 3' to the first coding sequence, the second coding sequence encoding a portion of the polypeptide of interest, wherein a second recombinase recognition site is positioned 3' to the second coding sequence; and c) a non-coding sequence comprising a first recombinase recognition site and a second recombinase recognition site positioned between the first coding sequence and the second coding sequence. In some cases, the first recombinase recognition site is positioned 5' to the second recombinase recognition site in the non-coding sequence. In some cases, the first recombinase recognition site is positioned 3' to the second recombinase recognition site in the non-coding sequence.

In certain embodiments, a recombinant expression vector of the present disclosure comprises a) a first coding sequence encoding a portion of a polypeptide of interest, wherein a first recombinase recognition site is positioned 5' to the first coding sequence; b) a second coding sequence positioned 3' to the first coding sequence, the second coding sequence encoding a portion of the polypeptide of interest; c) a first non-coding sequence comprising a second recombinase recognition site positioned between the first coding sequence and the second coding sequence; d) a third coding sequence positioned 3' to the second coding sequence, the third coding sequence encoding a portion of the polypeptide of interest, wherein a first recombinase recognition site is positioned 3' to the third coding sequence; and e) a second non-coding sequence comprising a second recombinase recognition site positioned between the second coding sequence and the third coding sequence.

In certain embodiments, a recombinant expression vector of the present disclosure comprises: a) a first coding sequence encoding a portion of a polypeptide of interest, wherein a first recombinase recognition site is positioned 5' to the first coding sequence; b) a second coding sequence positioned 3' to the first coding sequence, the second coding sequence encoding a portion of the polypeptide of interest; c) a first non-coding sequence comprising a first recombinase recognition site and a second recombinase recognition site positioned between the first coding sequence and the second coding sequence; d) a third coding sequence positioned 3' to the second coding sequence, the third coding sequence encoding a portion of the polypeptide of interest, wherein a third recombinase recognition site is positioned 3' to the third coding sequence; and e) a second non-coding sequence comprising a second recombinase recognition site and third recombinase recognition site positioned between the second coding sequence and the third coding sequence. In some cases, the first recombinase recognition site is positioned 5' to the second recombinase recognition site in the first non-coding sequence. In some cases, the first recombinase recognition site is positioned 3' to the second recombinase recognition site in the first non-coding sequence. In some cases, the second recombinase recognition site is positioned 5' to the third recombinase recognition site in the second non-coding sequence. In some cases, the second recombinase recognition site is positioned 3' to the third recombinase recognition site in the second non-coding sequence.

As summarized above, aspects of the present disclosure include a recombinant expression vector comprising a nucleotide sequence encoding a polypeptide of interest, e.g., a light-activated polypeptide or any variant thereof as described herein. Suitable expression vectors include vectors comprising a nucleotide sequence that encodes an RNA (e.g., an mRNA). Vectors which may be used include, without limitation, lentiviral, herpes simplex virus, adenoviral, and adeno-associated virus (AAV) vectors. Lentiviral vectors include, but are not limited to human immunodeficiency virus (HIV)-based vectors. Lentiviral vectors may be pseudotyped with the envelope proteins of other viruses, including, but not limited to vesicular stomatitis virus (VSV), rabies, Mo-murine leukemia virus (MLV), baculovirus and Ebola. Such vectors may be prepared using standard methods in the art.

AAV Vector

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety.

Introns

As summarized above, one or more non-coding sequences, e.g. introns, may be inserted between the coding sequences of the recombinant expression vector. The non-coding sequences may include one or more recombinase recognition sites including, e.g., a first recombinase recognition site and a second recombinase recognition site. In some instances, the non-coding sequence(s) are removed from the recombinant expression vector, e.g., after recombination, by splicing. In some instances, the splicing produces a construct where all coding sequences are present in the sense orientation to allow for expression of a functional polypeptide. In some instances, the splicing produces a construct having one or more coding sequences in the reverse complement orientation which inhibits expression of a functional polypeptide.

The recombinant expression vector may include any suitable number of non-coding sequences inserted between the coding sequences. In some cases, the non-coding sequences are arranged such that one non-coding sequence is inserted between two coding sequences. The number of non-coding sequences may range from 1 to 10 including, e.g., from 1 to 9, from 1 to 8, from 1 to 7, from 1 to 6, from 1 to 5, from 1 to 4, from 1 to 3, or from 1 to 2. In some cases, the recombinant expression vector includes a first non-coding sequence and a second non-coding sequence. In some cases, the first non-coding sequence includes a first recombinase recognition site and a second recombinase recognition site. The first non-coding sequence may be positioned between a first coding sequence and a second coding sequence positioned 3', e.g., directly 3', to the first coding sequence. In some cases, the second non-coding sequence includes a second recombinase recognition site and third recombinase recognition site. The second non-coding sequence may be positioned between a second coding sequence and a third coding sequence positioned 3', e.g., directly 3', to the second coding sequence.

In some cases, the intron is derived from the CMV IE gene. For example, an intron can have the following nucleotide sequence:

```
                                        (SEQ ID NO: 100)
gtaAgtgtcggggtttgtgcccccccttttttttataaaattgtattaa
tgttatatacatatctcctgtatgtgacccatgtgcttatgactctatt
tctcatgtgtttag.
```

In some cases, the intron has the following nucleotide sequence

```
                                        (SEQ ID NO: 101)
gtgagtacaggaggtggagagtggccagcccttctcatgttcagagaac
atggttaactggttaagtcatgtcgtcccacag.
```

Other suitable introns include, e.g., a β-actin intron; mouse igE intron 3; CMV Towne Variant intron B; Intron 1: CMV Towne Variant intron B (GenBank M60321); Intron 2: Mouse IgE intron 3 (GenBank X01857.1).

Splice sequences are provided at the exon/intron borders, such that the intron can be excised during mRNA processing. For example, in some cases, the intron comprises consensus sequences for splicing. For example, in some cases, an exon-intron-exon includes: i) an exon comprising, at its 3' end, the sequence (A/C)AG; ii) an intron including, at its 5' end, the sequence GT(A/G)AGT; and, at its 3' end, the sequence (C/T)AG; and iii) an exon comprising, at its 5' end, a G.

An intron may include a recognition site(s) for a recombinase; e.g., a FRT site recognized by a Flp recombinase; a Lox site recognized by a Cre recombinase; etc. The first recombinase recognition site of a recombinant expression vector of the present disclosure may be any of a Cre recombinase recognition site, Flp recombinase recognition site, vCre recombinase recognition site, Dre recombinase recognition site, or sCre recombinase recognition site. In some cases, the first recombinase recognition site is a Cre recombinase recognition site. In some cases, the first recombinase recognition site is a Flp recombinase recognition site. In some cases, the first recombinase recognition site is a vCre recombinase recognition site. The second recombinase recognition site of a recombinant expression vector of the present disclosure may be any of a Cre recombinase recognition site, Flp recombinase recognition site, vCre recombinase recognition site, Dre recombinase recognition sites, or sCre recombinase recognition site. In some cases, the second recombinase recognition site is a Flp recombinase recognition site. In some cases, the second recombinase recognition site is a Cre recombinase recognition site. In some cases, the second recombinase recognition site is a vCre recombinase recognition site. The third recombinase recognition site of a recombinant expression vector of the present disclosure may be any of a Cre recombinase recognition site, Flp recombinase recognition sites, vCre recombinase recognition site, Dre recombinase recognition sites, or sCre recombinase recognition site. In some cases, the third recombinase recognition site is a vCre recombinase recognition site. In some cases, the third recombinase recognition site is a Cre recombinase recognition site. In some cases, the third recombinase recognition site is a Flp recombinase recognition site.

The non-coding sequences may include any suitable number of recombinase recognition sites. The number of recombinase recognition sites in a non-coding sequence may range from 1 to 10 including, e.g., from 1 to 9, from 1 to 8, from 1 to 7, from 1 to 6, from 1 to 5, from 1 to 4, from 1 to 3, or from 1 to 2.

The recombinase recognition sites may have any suitable orientation. The orientation of the recombinase recognition sites may determine whether a sequence is subjected to, e.g., inversion, excision, insertion or translocation by a recombinase. In some cases, two corresponding recombinase recognition sites, e.g., two loxP sites flanking a sequence, are oriented in the same direction. In some cases, two corresponding recombinase recognition sites are oriented in different directions.

The recombinase recognition sites may have any suitable sequence. A recombinase recognition site may include a sequence that is recognized by a particular recombinase. In some instances, the recombinase recognition site is a recombinase recognition site variant including one or more modifications. The modifications may include sequence variations including, e.g., a change in a nucleotide sequence (e.g., a mutation) and/or length of a nucleotide sequence. The modification may be present in a left recognition region, spacer region, and/or right recognition region of a recombinase recognition site. The modifications may modulate, e.g., increase or decrease, recognition of the site by a recombinase. In some instances, a non-coding sequence includes a first recombinase recognition site variant. In some instances, a non-coding sequence includes a second recombinase recognition site variant. In some instances, a non-coding sequence includes a third recombinase recognition site variant. In some instances, a non-coding sequence includes one or more first recombinase recognition site variants, one or more second recombinase recognition site variants, one or more third recombinase recognition site variants, or a combination thereof. In some instances, a non-coding sequence includes a combination of naturally-occurring recombinase recognition sites and recombination recognition site variants.

A 34-base pair minimal FRT site has the following sequence: 5'-GAAGTTCCTATTCtctagaaaGtATAG-GAACTTC-3' (SEQ ID NO:102). The Flp recombinase binds to both 13-bp 5'-GAAGTTCCTATTC-3' (SEQ ID NO:103) arms flanking the 8 bp spacer. In some cases, the Flp recombinase recognition site includes a F3 sequence, F5 sequence, FRT sequence, variant FRT sequence, or F72 sequence.

A Lox site can be a 34-bp sequence comprising 5'-

```
                                        (SEQ ID NO: 104)
ATAACTTCGTATANNNTANNNTATACGAAGTTAT-3'
``` this sequence includes: i) a 13-bp recognition region; ii) an 8 bp spacer (underlined); and iii) a 13-bp recognition region. The 8-bp recognition region can be ATGTATGC (SEQ ID NO:105); or any of a variety of well-known variations thereof. Variations of the 13-bp recognition region are known in the art and can be used in a subject recombinant expression vector; examples include: i) ATAACTTCGTATA (SEQ ID NO:106); ii) ATAACTTCGTATA (SEQ ID NO:10'7); iii) ATAACTTCGTATA (SEQ ID NO:108); and iv) ATAACTTCGTATA (SEQ ID NO:109), for the 5' 13-bp recognition region, and the complement thereof (e.g., i) TATACGAAGTTAT (SEQ ID NO:110); ii) TATACGAAGTTAT (SEQ ID NO:111); iii) TATACGAAGTTAT (SEQ ID NO:112); and iv) TATACGAAGTTAT (SEQ ID NO:113)) for the 3' 13-bp recognition region. In some cases, the Cre recombinase recognition site includes a variant loxP site. In some cases, the Cre recombinase recognition site includes a loxP sequence, lox2722 sequence, loxN sequence, vloxP sequence, or vlox2722 sequence.

Recombinases

Any suitable recombinase may be used to catalyze a site-specific recombination event. In some instances, the recombinase orients, e.g., inverts, the coding sequence(s) of the recombinant expression vector in a sense orientation or a direction such that a polypeptide of interest may be expressed from the recombinant expression vector. In some instances, the recombinase orients the coding sequence(s) of the recombinant expression vector in a reverse complement orientation or an orientation such that a polypeptide may not be expressed from the recombinant expression vector. Suitable recombinases include Cre recombinases, Flp recombinases, Dre recombinases, SCre recombinases, and VCre recombinases.

Any suitable double or triple combination of the recombinases disclosed herein may be used to catalyze the recombination of the sequences in the recombinant expression vector. In some cases, a combination of Cre and Flp is used. In some cases, a combination of Cre and vCre is used. In some cases, a combination of vCre and Flp is used. In some cases, a triple combination of Cre, Flp, and VCre is used. In some cases, the combination of recombinases is introduced to a target cell or population of target cells, e.g., by introducing a recombinant expression vector encoding one or more of a Cre recombinase, Flp recombinase, and vCre recombinase into the target cell or target cell population.

Suitable combinations include:

Cre AND Flp ($C_{on}/F_{on}$)

Cre NOT Flp ($C_{on}/F_{off}$)

Flp NOT Cre($C_{off}/F_{on}$)

Cre AND vCre ($C_{on}/VC_{on}$)

Cre NOT vCre ($C_{on}/VC_{off}$)

vCre NOT Cre($C_{off}/VC_{on}$)

vCre AND Flp ($VC_{on}/F_{on}$)

vCre NOT Flp ($VC_{on}/F_{off}$)

Flp NOT vCre ($VC_{off}/F_{on}$)

Cre AND Flp AND VCre ($C_{on}/F_{on}/VC_{on}$);

Cre NOT Flp NOT VCre ($C_{on}/F_{off}/VC_{off}$);

Flp NOT Cre NOT VCre ($C_{off}/F_{on}/VC_{off}$);

VCre NOT Flp NOT Cre ($C_{off}/F_{off}/VC_{on}$);

Cre AND Flp NOT VCre ($C_{on}/F_{off}/VC_{on}$);

VCe AND Cre NOT Flp ($VC_{on}/C_{on}/F_{off}$);

Flp AND VCe NOT Cre $F_{on}/VC_{on}/C_{off}$).

Polypeptides of Interest

As summarized above, the recombinant expression vectors may include one or more coding sequences that encode a polypeptide of interest or a portion thereof. Polypeptides of interest include, but are not limited to, fluorescent polypeptides, genetically encoded calcium indicators (GECI), opsins (e.g., hyperpolarizing opsins; depolarizing opsins), receptors, and polypeptides in biosynthetic pathways. In some cases, the one or more coding sequences encode a fusion polypeptide including, e.g., one or more fluorescent polypeptides, calcium indicators, excitatory opsins, and inhibitor opsins.

Fluorescent Proteins

Suitable fluorescent polypeptides include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dE-GFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

GECI

A GECI comprises a fluorescent protein, a calcium-binding domain (e.g., calmodulin, troponin C, and the like), and a domain that binds the calcium-binding domain (e.g., the M13 domain of the myosin light chain kinase, which binds calmodulin). Suitable GECI polypeptides include, e.g., GCaMP6f, GCaMP6m, sRGECO1a, Pericams, Cameleons, GCaMP, TN-XXL, and Twitch. GECIs comprise a calcium-binding domain such as calmodulin or troponin C, fused to one or more (e.g., one, two, three, four, or more) fluorescent proteins (FPs). In single-FP GECIs, upon calcium binding, the fluorescence intensity of a circularly permutated FP (cpFP) may be modulated by calcium binding-dependent changes in the chromophore environment. In multiple-FP GECIs (e.g., two-FP GECIs, three-FP GECIs, four-FP GECIs), calcium binding modulates Förster resonance energy transfer (FRET) between FPs.

For example, in some cases, single-FP GECIs may find use in combination with light-responsive polypeptides as tools for the effective mapping of functional connection between brain regions. Single-FP GECIs that find use in the present disclosure may be a fusion product of a fluorescent protein, calmodulin and an M13 peptide sequence (e.g., GFP calmodulin-M13 GECI (GCaMP)), including, but are not limited to, GCaMPK (SEQ ID NO:28), GCaMP2 (SEQ ID NO:29), GCaMP2.1 (SEQ ID NO:30), GCaMP2.2a (SEQ ID NO:31), GCaMP2.2b (SEQ ID NO:32), GCaMP2.3 (SEQ ID NO:33), GCaMP2.4 (SEQ ID NO:34), GCaMP3 (SEQ ID NO:35), GCaMP5g (SEQ ID NO:36), GCaMP6m (SEQ ID NO:37), GCaMP6s (SEQ ID NO:38), GCaMP6f (SEQ ID NO:39), and the like Amino acid sequences of such GECIs are provided in FIG. 13A-13L. Other single-FP GECIs that find use in the present disclosure include genetically encoded calcium indicators for optical imaging (GE-COs) such as, the green fluorescing indicators G-GECO1 (SEQ ID NO:44), G-GECO1.1 (SEQ ID NO:45) and G-GECO1.2 (SEQ ID NO:46), the red fluorescing indicator R-GECO1 (SEQ ID NO:42), the blue fluorescing indicator B-GECO1 (SEQ ID NO:43), the emission ratiometic indicator GEM-GECO1 (SEQ ID NO:40), and the excitation ratiometric GEX-GECO1 (SEQ ID NO:41), and the like Amino acid sequences of such GECIs are provided in FIG. 13M-13S.

Single-FP GECIs that are suitable for use include, but are not limited to those that comprise an amino acid sequence having at least 75%, at least 80%, at least 85%, at least 90%, at least 95%, at least 98%, or at least 99%, amino acid sequence identity to the amino acid sequences depicted in FIG. 13A-FIG. 13S.

For example, in some cases, multi-FP GECIs (e.g., two-FP GECIs, three-FP GECIs, four-FP GECIs) may find use in combination with a light-responsive polypeptide of the present disclosure as tools for the effective mapping of functional connection between brain regions. Multi-FP GECIs that find use in the present disclosure include, but are not limited to, TN-XXL (depicted in FIG. 14A), Yellow Cameleons (e.g., YC3.6 (depicted in FIG. 14B)), D3CPVenus (depicted in FIG. 14C), and the like.

Multi-FP GECIs that are suitable for use comprise an amino acid sequence having at least 75%, at least 80%, at least 85%, at least 90%, at least 95%, at least 98%, or at least 99%, amino acid sequence identity to the amino acid sequences depicted in FIG. 14A-14C.

Light-Responsive Polypeptides

Suitable light-responsive polypeptides include depolarizing opsins and hyperpolarizing opsins. In some cases, a light-responsive polypeptide is a depolarizing light-responsive polypeptide. In some cases, a light-responsive polypeptide is a depolarizing light-responsive polypeptide that is activated by blue light, by yellow light, by green light, or by orange light. In some cases, a light-responsive polypeptide is a hyperpolarizing light-responsive polypeptide. In some cases, a light-responsive polypeptide is a hyperpolarizing light-responsive polypeptide that is activated by blue light, by yellow light, by green light, or by orange light.

In some cases, a depolarizing light-responsive polypeptide is a channelrhodopsin (ChR1—NCBI Gene ID: 5724518, ChR2—NCBI Gene ID: 5727376) derived from *Chlamydomonas reinhardtii*, wherein the polypeptide is capable of transporting cations across a cell membrane when the cell is illuminated with light. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some cases, activation of the light-responsive cation channel derived from *Chlamydomonas reinhardtii* with light pulses having a temporal frequency of about 100 Hz can cause depolarization of the excitable cells, e.g., neurons, expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable channelrhodopsin is a ChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 15A (SEQ ID NO:50). In some cases, a suitable channelrhodopsin is a ChR2 polypeptide that comprises an amino acid sequence having at least 75%, at least 80%, at least 85%, at least 90%, or 100%, at least 95%, at least 98%, or at least 99%, amino acid sequence identity to the amino acid sequence depicted in FIG. 15B (SEQ ID NO:51).

In other cases, the light-responsive polypeptide is a step function opsin (SFO) protein or a stabilized step function opsin (SSFO) protein that can have specific amino acid substitutions at key positions in the retinal binding pocket of the amino acid sequence of ChR2. Further disclosure related to SFO or SSFO proteins can be found in International Patent Application Publication No. WO 2010/056970, the disclosure of which is hereby incorporated by reference in its entirety. In some cases, a suitable ChR2 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 15C (SEQ ID NO:52). In some cases, a suitable ChR2 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 15D (SEQ ID NO:53).

In some cases, a suitable light-responsive polypeptide is a cation channel derived from *Volvox carteri* (VChR1—NCBI Gene ID: 9619570) and is activated by illumination with light of a wavelength of from about 500 nm to about 600 nm, e.g., from about 525 nm to about 550 nm, e.g., 545 nm. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a excitable cell in response to light. In some cases, a suitable cation channel derived from *Volvox carteri* is a VChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 15E (SEQ ID NO:54).

In other instances, the light-responsive polypeptide is a SFO or an SSFO based on VChR1. In some cases, an SFO or SSFO protein is capable of mediating a depolarizing current in the cell when the cell is illuminated with blue light. In some cases, the light has a wavelength of about 560 nm. Additionally, in some cases the light is delivered as a single pulse of light or as spaced pulses of light due to the prolonged stability of SFO and SSFO photocurrents. In some cases, activation of the SFO or SSFO protein with single pulses or spaced pulses of light can cause depolarization of an excitable cell, e.g., neuron, expressing the SFO or SSFO protein. In some embodiments, each of the disclosed step function opsin and stabilized step function opsin proteins can have specific properties and characteristics for use in depolarizing the membrane of an excitable cell in response to light. In some cases, a suitable VChR1 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 15F (SEQ ID NO:55). In some cases, a suitable VChR1 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 15G (SEQ ID NO:56).

In other instances, the light-responsive cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some cases, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another instance, the portion of the intracellular loop domain of the C1V1 chimeric protein can be replaced with the corresponding portion from ChR1 extending to amino acid residue A145 of the ChR1. In other cases, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1.

In some cases, the C1V1 protein mediates a depolarizing current in the cell when the cell is illuminated with green light. In some cases, the light has a wavelength of between about 540 nm to about 560 nm. In some cases, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include C1V1 chimeric light-responsive proteins that can have specific amino acid substitutions at key positions throughout the retinal binding pocket of the VChR1 portion of the chimeric polypeptide. In some cases, a suitable C1V1 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15H (SEQ ID NO:57).

In other instances, the light-responsive cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable C1C2 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15I (SEQ ID NO:58).

In some aspects, a depolarizing light-responsive polypeptide is a SdChR polypeptide (GenBank Accession No.: AHH02138) derived from *Scherffelia dubia*, wherein the SdChR polypeptide is capable of transporting cations across a cell membrane when the cell is illuminated with light. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane. In some cases, a suitable SdChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15J (SEQ ID NO:59).

In some aspects, a depolarizing light-responsive polypeptide can be, e.g. CnChR2 (Genbank Accession No.: AHH02139), derived from *Chlamydomonas noctigama*, wherein the CnChR2 polypeptide is capable of transporting cations across a cell membrane when the cell is illuminated with light. The light used to activate the CnChR2 polypeptide can have a wavelength between about 560 and about 630 nm or can have a wavelength of about 600 nm. The CnChR2 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR2 protein to regulate the polarization state of the plasma membrane of the cell. In some cases, the CnChR2 protein comprises one or more conservative amino acid substitutions and/or one or more non-conservative amino acid substitutions. The CnChR2 protein containing substitutions, deletions, and/or insertions introduced into the native amino acid sequence suitably retains the ability to transport cations across a cell membrane. In some cases, a suitable CnChR2 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15K (SEQ ID NO:60).

In other instances, the light-responsive cation channel protein is a CsChrimson chimeric protein derived from a CsChR (Genbank Accession No.: AHH02144) protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane. In some cases, a suitable CsChrimson protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15L (SEQ ID NO:61).

In some aspects, a depolarizing light-responsive polypeptide can be, e.g. ShChR1 (Genbank Accession No.: AHH02106), derived from *Stigeoclonium helveticum*, wherein the ShChR1 polypeptide is capable of transporting cations across a cell membrane when the cell is illuminated with light. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane. In some cases, a suitable ShChR1 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15M (SEQ ID NO:62).

In some cases, a suitable hyperpolarizing light-responsive polypeptide is an Archaerhodopsin (Arch—Genbank Accession No.: ADB03111) proton pump (e.g., a proton pump derived from *Halorubrum sodomense*) that can transport one or more protons across the plasma membrane of a cell when the cell is illuminated with light. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light. In some cases, a suitable Arch protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15N (SEQ ID NO:63).

In some cases, a suitable light-activated protein is an Archaerhodopsin (ArchT—Genbank Accession No.: ABT17417) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light. In some cases, a suitable ArchT protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15O (SEQ ID NO:64).

In some cases, the light-responsive polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The GtR3 (NCBI Gene ID: 17301498) protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of an excitable cell, e.g., neuron, in response to light. In some cases, a suitable GtR3 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15P (SEQ ID NO:65).

In some cases, a light-activated protein is an *Oxyrrhis marina* (Oxy—Genbank Accession No.: ADY17806) proton pump that can transport one or more protons across the plasma membrane of a cell when the cell is illuminated with light. The light can have a wavelength between about 500 and about 560 nm or can have a wavelength of about 530 nm. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light. In some cases, a suitable Oxy protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15Q (SEQ ID NO:66).

In some cases, the light-responsive proton pump protein (referred to herein as "Mac protein"—NCBI Gene ID: 13287905) is responsive to light and is derived from *Leptosphaeria macularis*, wherein the Mac proton pump protein is capable of pumping protons across the membrane of a cell when the cell is illuminated with 520 nm to 560 nm light. The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of an excitable cell, e.g., neuron, in response to light. In some cases, a suitable Mac protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15R (SEQ ID NO:67).

In some cases, a suitable light-responsive chloride pump protein is derived from *Natronomonas pharaonic*; such a protein is referred to herein as an "NpHR protein" or an "NpHR polypeptide." In some embodiments, the NpHR (NCBI Gene ID: 3702828) protein can be responsive to amber light as well as red light and can mediate a hyperpolarizing current in the excitable cell, e.g., the neuron, when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. An NpHR protein containing substitutions, deletions, and/or insertions introduced into the native amino acid sequence suitably retains the ability to hyperpolarize the plasma membrane of an excitable cell in response to light. In some cases, a suitable NpHR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15S (SEQ ID NO:47).

Further disclosure related to light-responsive chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

In some cases, a suitable light-responsive ion channel protein is, e.g., a DsChR protein (Genbank Accession No.: AEY68833) derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of an excitable cell, e.g., a neuron, in response to light. In some cases, a suitable DsChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15T (SEQ ID NO:69).

In some cases, the light-responsive protein is a chimeric protein comprising Arch-TS-p2A-ASIC 2a-TS-EYFP-ER-2

(Champ). A Champ protein of the present disclosure comprises an Arch domain and an Acid-sensing ion channel (ASIC)-2a domain. Light activation of Champ activates a proton pump (Arch domain) that activates the ASIC-2a proton-activated cation channel (ASIC-2a domain) In some cases, a suitable Champ protein comprises an amino acid sequence having at least 75%, at least 80%, at least 85%, at least 90%, at least 95%, at least 98%, or at least 99%, or 100%, amino acid sequence identity to the amino acid sequence depicted in FIG. 15U (SEQ ID NO:70).

In some cases, a hyperpolarizing light-responsive ion channel is based on a depolarizing light-responsive ion channel, as described in, e.g., PCT App. No. PCT/US2015/23087, which is incorporated herein by reference. In some cases, a light-responsive anion channel polypeptide is based on a C1C2 protein (Genbank Accession No. AHA49646). In some cases, a suitable hyperpolarizing light-responsive polypeptide is based on the amino acid sequence of the protein ChR2 (Genbank Accession No. AER29835). In some cases, a suitable hyperpolarizing light-responsive polypeptide is based on the amino acid sequence of the protein C1V1 (Genbank Accession No. AEL28924).

Methods

As described above, aspects of the present disclosure provide methods for controlling or modulating production of polypeptides of interest, e.g., exogenous polypeptides, in a target cell or target cell population. The methods may include introducing a recombinant expression vector as described herein into the target cell or target cell population. The target cell or target cell population may express one or more recombinases that recognize recombinase recognition sites in the recombinant expression vector. A recombinase may catalyze a site-specific recombination event. In some instances, the method produces a construct having a polynucleotide sequence in the sense orientation such that a functional polypeptide may be expressed from the construct. In some instances, the method produces a construct having a polynucleotide sequence in the reverse complement orientation such that a functional polypeptide cannot be expressed from the construct. In some instances, the method further includes introducing an expression vector encoding one or more recombinases to the target cell or target cell population.

In practicing embodiments of the methods, a method for modulating production of a polypeptide of interest in a target cell or a target cell population may include introducing a recombinant expression vector comprising a) a first coding sequence encoding a portion of a polypeptide of interest, wherein a first recombinase recognition site is positioned 5' to the first coding sequence; b) a second coding sequence positioned 3' to the first coding sequence, the second coding sequence encoding a portion of the polypeptide of interest; c) a first non-coding sequence comprising a first recombinase recognition site and a second recombinase recognition site positioned between the first coding sequence and the second coding sequence; d) a third coding sequence positioned 3' to the second coding sequence, the third coding sequence encoding a portion of the polypeptide of interest, wherein a third recombinase recognition site is positioned 3' to the third coding sequence; and e) a second non-coding sequence comprising a second recombinase recognition site and third recombinase recognition site positioned between the second coding sequence and the third coding sequence into the target cell or the target cell population.

As summarized above, in some instances, the methods include introducing a recombinant expression vector into a target cell or a target cell population. The introduction may occur by any suitable means. In some aspects, recombinant expression vectors disclosed herein (for example, an AAV vector) can be delivered directly to a neuron or population of neurons with a needle, catheter, or related device, using neurosurgical techniques known in the art, such as by stereotactic injection (See, e.g., Stein et al., *J. Virol,* 73:34243429, 1999; Davidson et al., *PNAS,* 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties) or fluoroscopy.

In some instances, a target cell or population of cells is genetically modified with an expression vector as described herein. A cell has been "genetically modified" or "transformed" or "transfected" by exogenous DNA or exogenous RNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: 50169-409X(12)00283-9. doi: 10.1016/j.addr.2012.09.023), and the like.

The target cell or the target cell population may express any suitable recombinase or combination of recombinases. In some cases, the target cell and/or the target cell population expresses one or more of Cre recombinase, Flp recombinase, Dre recombinase, SCre recombinase, and VCre recombinase. In some cases, the target cell and/or the target cell population expresses a double or triple combination of any of the recombinases disclosed herein. In some cases, a combination of Cre and Flp is expressed. In some cases, a combination of Cre and vCre is expressed. In some cases, a combination of vCre and Flp is expressed. In some cases, a triple combination of Cre, Flp, and VCre is expressed.

As summarized above, in some instances, the method further comprises introducing one or more recombinant expression vectors encoding any of the recombinases described herein to the target cell and/or the target cell population. In some cases, the method further comprises introducing one or more recombinant expression vectors encoding one or more of Cre recombinase, Flp recombinase, and vCre recombinase into the target cell or the target cell population.

In some instances, the method further comprises modulating the amount of one or more recombinases expressed by the target cell or the target cell population. In some cases, the method further comprises modulating the amount of Cre recombinase, Flp recombinase, and vCre recombinase (or any combination thereof) expressed by the target cell or the target cell population. In some cases, the method includes modulating the amount of one or more expression vectors encoding one or more of Cre recombinase, Flp recombinase, and vCre recombinase (or any combination thereof) introduced into the target cell and/or target cell population. In some cases, the method includes modulating the ratio of any double or triple combination of recombinases, e.g., Cre recombinase Flp recombinase, and vCre recombinase, expressed by the target cell and/or target cell population. The ratios may include a ratio of the expressed amounts of any combination of recombinases disclosed herein such as, e.g., a Flp:Cre ratio, a Cre:vCre ratio, a Flp:vCre ratio, or a Cre:Flp:vCre ratio. In some cases, the ratio of a double combination of recombinases is, e.g., 15:1, 10:1, 8:1, 5:1, 4:1, 3:1, or 2:1. In some cases, the ratio of a triple combination of recombinases is, e.g., 15:1:15, 15:1:1, 10:1:10, 10:1:1, 5:1:5, 5:1:1, 2:1:1, or 2:1:2.

Cells

Suitable target cells include any human or non-human animal cell, including any cell of any tissue or organ. Suitable target cells include epithelial cells, endothelial cells, osteoclasts, osteoblasts, retinal cells, skeletal muscle cells, smooth muscle cells, immune cells (e.g., B cells, T cells, etc.), dendritic cells, and the like. The target tissue can be a human target tissue (e.g., an in vivo, in vitro, or ex vivo target tissue). The target tissue can be a non-human animal target tissue (e.g., an in vivo, in vitro, or ex vivo target tissue). Non-human animals include non-human primates, murines (e.g., rats, mice), lagomorphs (e.g., rabbits), ungulates, felines, canines, acid the like. The target tissue can be in a live human or non-human animal. The target tissue can be in a freely-moving human or non-human animal.

Suitable target cells include cells that carry or transmit electrical impulses, such as nerve cells. Target cells include neurons, cardiac cells, and stem cells. In some case, a target cell is a neuron. In some case, a target cell is a sensory neuron, a motor neuron, or an interneuron. Target cells can include cells of the central nervous system and/or cells of the peripheral nervous system. Target cells can be present in a target tissue. In some cases, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some cases, a target tissue may be a portion of an individual cell, such as specific axon of a nerve cell.

In some instances, the target cells are a collection of neurons. In some cases, a collection of neurons is defined by a known functional classification. Any convenient functional classification may be used to define the collection of neuron. In some cases, the collection of neurons includes excitatory neurons, inhibitory neurons, sensory neurons, motor neurons, interneurons, etc. In some cases, the collection of neurons includes dopaminergic, cholinergic, GABAergic, glutamatergic, or peptidergic neurons. In some cases, the collection of neurons includes Purkinje cells, pyramidal cells, golgi cells, Lugaro cells, basket cells, candelabrum cells, granule cells, stellate cells, unipolar brush cells, medium spiny neurons, Renshaw cells, spindle cells, etc. The different functional cells may be labeled specifically with a cellular electrical activity-dependent fluorescent moiety using any suitable method. In some cases, a cell-specific promoter, or a combination of different cell-specific promoters, may be used to control expression of a genetically-encoded cellular electrical activity-dependent fluorescent moiety, e.g., a genetically-encoded calcium indicator, specifically in a functionally-defined collection of neurons.

In some instances, the target cell is a first neuron in a first neural region. In some instances, the first neuron expresses one or more recombinase(s), as described herein. The first neuron may be in communication, e.g., via an axon, with another neuron, e.g., a second neuron, a third neuron, etc. In some instances, the first neuron includes an axon extending to a second neuron in a second neural region. In some instances, the first neuron includes an axon extending to a third neuron in a third neural region.

Devices

Aspects of the present disclosure include a light generating device. In some cases, the light generating device is configured to detect a signal from any of the polypeptides of interest disclosed herein, e.g., a light activated or light emitting polypeptide. In some cases, the light generating device is configured to detect the expression of a polypeptide of interest over time, e.g., in vivo. In some cases, the device is configured to detect the expression of a polypeptide of interest over any suitable period of time ranging from 1 day to 5 weeks including, e.g., from 1 day to 3 weeks, from 1 day to 2 weeks, from 1 day to 1 week, from one to ten days, from one to two weeks, from one to three weeks, or from one week to four weeks.

In certain embodiments, the light generating device includes: a) one or more optical fibers, b) a light source, and c) a spectrometer for detecting visible light. In some cases, the light source includes a light emitting diode. In some cases, the one or more optical fibers comprises an implantable optical fiber. In certain embodiments, the device further includes a filter box comprising, e.g., a dichroic mirror and/or dichroic filter.

Light-generating devices in accordance with embodiments of the present disclosure can generally produce light of a variety of different wavelengths from one or more light sources on the device. In some cases, a light-generating device may include a light cuff or sleeve that can be placed around or near target cells expressing a light-activated polypeptide of the present disclosure. In some cases, a portion of the light source or the entire light source is implantable. The subject light-generating devices may be of any useful configuration for stimulating the light-activated proteins disclosed herein. In some cases, for example, a light-generating device (i.e., optical applicator) may comprise components that facilitate exclusive illumination of a target cell or tissue. For example, in some cases, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For example, in some embodiments, a light-generating device may be configured to illuminate an axon of a nerve cell, but not to illuminate any other portion of the nerve cell. In this way, the light from the light-generating device only affects light-activated proteins in the specific target structure that is illuminated.

Aspects of the disclosure include light delivery devices (i.e., optical applicators) that include one or more optical sources that are configured to deliver light in one or more 2-dimensional and/or 3-dimensional patterns to one or more target locations, including but not limited to one or more portions (e.g., multiple layers) of a target tissue and/or anatomical structure. In certain instances, a light delivery device may include a plurality of light sources (e.g., a plurality of laser light sources, light-emitting diodes (LEDs), and the like), as well as any suitable number of light guides that are configured to bend or shape light in a desired manner Examples of light delivery devices are provided in U.S. Pat. No. 8,545,543, the disclosure of which is hereby incorporated by reference in its entirety.

In some cases, a light-generating device (i.e., optical applicator) may not completely surround the region containing a target cell expressing a light-activated protein, but, rather, can have a U-shape. In some cases, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some cases, the subject light-generating devices may comprise an inner body, the inner body having at least one means for generating light which is connected to a power source. In some embodiments, the power source can be an internal battery for powering the light-generating device. In some cases, an implantable light-generating device may comprise an external antenna for receiving wirelessly transmitted electromagnetic energy from an external source for powering the device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art. In some cases, the light-generating device produces continuous light (i.e., light that is not pulsed).

In some cases, the light-generating device comprises a light emitting diode (LED). In some embodiments, the LED can generate blue and/or green light. In other embodiments, the LED can generate amber and/or yellow light. In some cases, several micro LEDs are embedded into the inner body of the light-generating device. In other cases, the light-generating device is a solid state laser diode or any other means capable of generating light. The light-generating device can generate light having a wavelength and intensity sufficient to activate a light-activated polypeptide of the present disclosure. In some cases, a light-generating device produces light having an intensity of any of about 0.05 $mW/mm^2$, 0.1 $mW/mm^2$, 0.2 $mW/mm^2$, 0.3 $mW/mm^2$, 0.4 $mW/mm^2$, 0.5 $mW/mm^2$, about 0.6 $mW/mm^2$, about 0.7 $mW/mm^2$, about 0.8 $mW/mm^2$, about 0.9 $mW/mm^2$, about 1.0 $mW/mm^2$, about 1.1 $mW/mm^2$, about 1.2 $mW/mm^2$, about 1.3 $mW/mm^2$, about 1.4 $mW/mm^2$, about 1.5 $mW/mm^2$, about 1.6 $mW/mm^2$, about 1.7 $mW/mm^2$, about 1.8 $mW/mm^2$, about 1.9 $mW/mm^2$, about 2.0 $mW/mm^2$, about 2.1 $mW/mm^2$, about 2.2 $mW/mm^2$, about 2.3 $mW/mm^2$, about 2.4 $mW/mm^2$, about 2.5 $mW/mm^2$, about 3 $mW/mm^2$, about 3.5 $mW/mm^2$, about 4 $mW/mm^2$, about 4.5 $mW/mm^2$, about 5 $mW/mm^2$, about 5.5 $mW/mm^2$, about 6 $mW/mm^2$, about 7 $mW/mm^2$, about 8 $mW/mm^2$, about 9 $mW/mm^2$, or about 10 $mW/mm^2$, inclusive, including values in between these numbers. In some embodiments, the light-generating device produces light at a frequency of at least about 5 Hz, such as up to about 20 Hz, at least about 10 Hz, such as up to about 25 Hz, such as up to about 50 Hz, such as up to about 75 Hz, such as up to about 100 Hz.

The subject light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 475 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 635 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm. Subject light-generating devices of the present disclosure are capable of generating light having a wavelength sufficient to activate a subject light-activated protein. Such light-generating devices are capable of generating light having a wavelength ranging from about 550 nm to about 650 nm, from about 600 nm to about 700 nm, from about 650 nm to about 750 nm.

In some cases, a light generating device may generate red light having a wavelength ranging from about 600 nm to about 775 nm. For example, a light generating device may generate red light having a wavelength ranging from about 600 nm to about 650 nm, from about 625 nm to about 675 nm, from about 650 nm to about 700 nm, from about 675 nm to about 725 nm, from about 700 nm to about 750 nm, from about 725 nm to about 775 nm, from about 600 nm to about 700 nm.

In some cases, a suitable light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some cases, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

Any suitable optical fibers may be used in the device. The optical fiber may be a multimode optical fiber. In some instances, a multimode optical fiber supports more than one propagation mode. For example, a multimode optical fiber may be configured to carry a range of wavelengths of light, where each wavelength of light propagates at a different speed. The optical fiber may include a core defining a core diameter, where light from the light source passes through the core. The core may be further surrounded by a cladding. The core diameter of an individual optical fiber that is used to probe a single region in the tissue may vary, and may be any suitable core diameter. In some cases, the core diameter is greater than the wavelength of light carried by the optical fiber. For example, the core diameter of an optical fiber may be 10μm or more. e.g., 50μm or more, 100μm or more, 200μm or more, including 300μm or more, and may be 1,000μm or less, e.g., 900μm or less, 800μm or less, 700μm or less, including, 600μm or less. In some embodiments, the core diameter of the individual optical fiber may be in the range of 10 to 1,000μm, e.g., 50 to 1,000μm, 100 to 1,000μm, 200 to 800μm, including 300 to 600μm.

In some cases, the subject light-generating devices may comprise a plurality of light sources that can be used to illuminate a target tissue with different wavelengths of light. For example, in some cases, a light-generating device may comprise a first light source that generates light of a first wavelength, e.g., red light, and a second light source that generates light of a second wavelength, e.g., blue light. Such light-generating devices may be used to simultaneously illuminate the same target tissue with light of both wavelengths, or may alternately illuminate the target tissue with light of the first wavelength and light of the second wavelength. In some cases, such light generating devices may be used to deliver light from the same light source to different target tissues. For example, in some instances a light-generating device may deliver light of a first wavelength to a first target tissue, and may deliver light of a second wavelength to a different target tissue. Suitable light-generating devices can comprise an implantable optical applicator which is configured to deliver light to a target area, and an operatively coupled light source which is configured to generate light of certain intensities and wavelengths.

Control Devices

Aspects of the disclosure include a controller, processor (e.g., a computer) and computer readable medium that are configured or adapted to control or operate one or more components of the subject devices or systems. In some cases, a system includes a controller that is in communication with one or more components of the systems, e.g., any component of a light generating device, and is configured to control aspects of the systems and/or execute one or more operations or functions of the subject systems. In some cases, a system includes a processor and a computer-readable medium, which may include memory media and/or storage media. Applications and/or operating systems embodied as computer-readable instructions on computer-readable memory can be executed by the processor to provide some or all of the functionalities described herein.

In some cases, a system includes a user interface, such as a graphical user interface (GUI), that is adapted or configured to receive input from a user, and to execute one or more of the methods as described herein. In some embodiments, a GUI is configured to display data or information to a user.

Aspects of the present disclosure include control devices that can control, or modulate, the amount of light that is emitted from the subject light-generating devices. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up to about 1 pulse per minute, up to about 1 pulse per 10 minutes, up to about 1 pulse per 20 minutes, up to about 1 pulse per 30 minutes.

In some cases, a subject control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an external antenna of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon 1826, (8): Spring, 2010).

Utility

The subject recombinant expression vectors, methods, and devices may find use in a variety of applications including clinical or research applications. In some instances, the subject recombinant expression vector, methods, and devices find use in applications that include the modulation of gene expression. Applications of interest may involve tissue-specific gene expression or inducible gene expression. The recombinant expression vector and methods may be used in applications where it is desirable to target expression of a polypeptide to a cell or population of cells.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-29 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant expression vector comprising:

a) a first coding sequence encoding a portion of a polypeptide of interest, wherein a first recombinase recognition site is positioned 5' to the first coding sequence;

b) a second coding sequence positioned 3' to the first coding sequence, the second coding sequence encoding a portion of the polypeptide of interest;

c) a first non-coding sequence comprising a first recombinase recognition site and a second recombinase recognition site positioned between the first coding sequence and the second coding sequence;

d) a third coding sequence positioned 3' to the second coding sequence, the third coding sequence encoding a portion of the polypeptide of interest, wherein a third recombinase recognition site is positioned 3' to the third coding sequence; and e) a second non-coding sequence comprising a second recombinase recognition site and a third recombinase recognition site positioned between the second coding sequence and the third coding sequence.

Aspect 2. The recombinant expression vector of aspect 1, wherein the first coding sequence is in reverse complement orientation.

Aspect 3. The recombinant expression vector of any of aspects 1-2, wherein the second coding sequence is in reverse complement orientation.

Aspect 4. The recombinant expression vector of any of aspects 1-3, wherein the third coding sequence is in reverse complement orientation.

Aspect 5. The recombinant expression vector of aspect 1, wherein the first coding sequence, the second coding sequence, and the third coding sequence are in reverse complement orientation.

Aspect 6. The recombinant expression vector of any of aspects 1-5 wherein the polypeptide of interest comprises any one of a fluorescent polypeptide, a calcium indicator, an excitatory opsin, and an inhibitory opsin.

Aspect 7. The recombinant expression vector of any of aspects 1-6, wherein the first recombinase recognition site is a Cre recombinase recognition site.

Aspect 8. The recombinant expression vector of aspect 7, wherein the Cre recombinase recognition site comprises a loxP sequence, lox2722 sequence, loxN sequence, vloxP sequence, or vlox2722 sequence.

Aspect 9. The recombinant expression vector of any of aspects 1-8, wherein the second recombinase recognition site is a Flp recombinase recognition site.

Aspect 10. The recombinant expression vector of aspect 9, wherein the Flp recombinase recognition site comprises a F3 sequence, F5 sequence, FRT sequence, variant FRT sequence, or F72 sequence.

Aspect 11. The recombinant expression vector of any of aspects 1-10, wherein the third recombinase recognition site is a vCre recombinase recognition site.

Aspect 12. A method for modulating production of a polypeptide of interest in a target cell or a target cell population, the method comprising:

introducing a recombinant expression vector comprising a) a first coding sequence encoding a portion of a polypeptide of interest, wherein a first recombinase recognition site is positioned 5' to the first coding sequence;

b) a second coding sequence positioned 3' to the first coding sequence, the second coding sequence encoding a portion of the polypeptide of interest;

c) a first non-coding sequence comprising a first recombinase recognition site and a second recombinase recognition site positioned between the first coding sequence and the second coding sequence;

d) a third coding sequence positioned 3' to the second coding sequence, the third coding sequence encoding a portion of the polypeptide of interest, wherein a third recombinase recognition site is positioned 3' to the third coding sequence; and e) a second non-coding sequence comprising a second recombinase recognition site and a third recombinase recognition site positioned between the second coding sequence and the third coding sequence into the target cell or the target cell population.

Aspect 13. The method of aspect 12, wherein the target cell or the target cell population expresses one or more of Cre recombinase, Flp recombinase, and vCre recombinase.

Aspect 14. The method of aspect 13, wherein the method further comprises introducing one or more recombinant expression vectors encoding Cre recombinase, Flp recombinase, or vCre recombinase into the target cell or the target cell population.

Aspect 15. The method of aspect 14, wherein the method further comprises modulating the amount of Cre recombinase, Flp recombinase, and vCre recombinase expressed by the target cell or the target cell population.

Aspect 16. The method of any of aspects 12-15, wherein the first coding sequence is in reverse complement orientation.

Aspect 17. The method of any of aspects 12-16, wherein the second coding sequence is in reverse complement orientation.

Aspect 18. The method of any of aspects 12-17, wherein the third coding sequence is in reverse complement orientation.

Aspect 19. The method of aspect 12, wherein the first coding sequence, the second coding sequence, and the third coding sequence are in reverse complement orientation.

Aspect 20. The method of any of aspects 12-19 wherein the polypeptide of interest comprises any one of a fluorescent protein, a calcium indicator, an excitatory opsin, and an inhibitory opsin.

Aspect 21. The method of any of aspects 12-20, wherein the first recombinase recognition site is a Cre recombinase recognition site.

Aspect 22. The method of aspect 21, wherein the Cre recombinase recognition site comprises a loxP sequence, lox2722 sequence, loxN sequence, vloxP sequence, or vlox2722 sequence.

Aspect 23. The method of any of aspects 12-22, wherein the second recombinase recognition site is a Flp recombinase recognition site.

Aspect 24. The method of aspect 23, wherein the Flp recombinase recognition site comprises a F3 sequence, F5 sequence, FRT sequence, variant FRT sequence, or F72 sequence.

Aspect 25. The recombinant expression vector of any of aspects 12-24, wherein the third recombinase recognition site is a vCre recombinase recognition site.

Aspect 26. A light generating device for detecting a polypeptide of interest comprising:

a) one or more optical fibers, b) a light source, and c) a spectrometer for detecting visible light.

Aspect 27. The device of aspect 26, wherein the light source comprises a light emitting diode.

Aspect 28. The device of any of aspects 26-27, wherein the one or more optical fibers comprises an implantable optical fiber.

Aspect 29. The device of any of aspects 26-28, wherein the device further comprises a dichroic filter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Figure 1D:
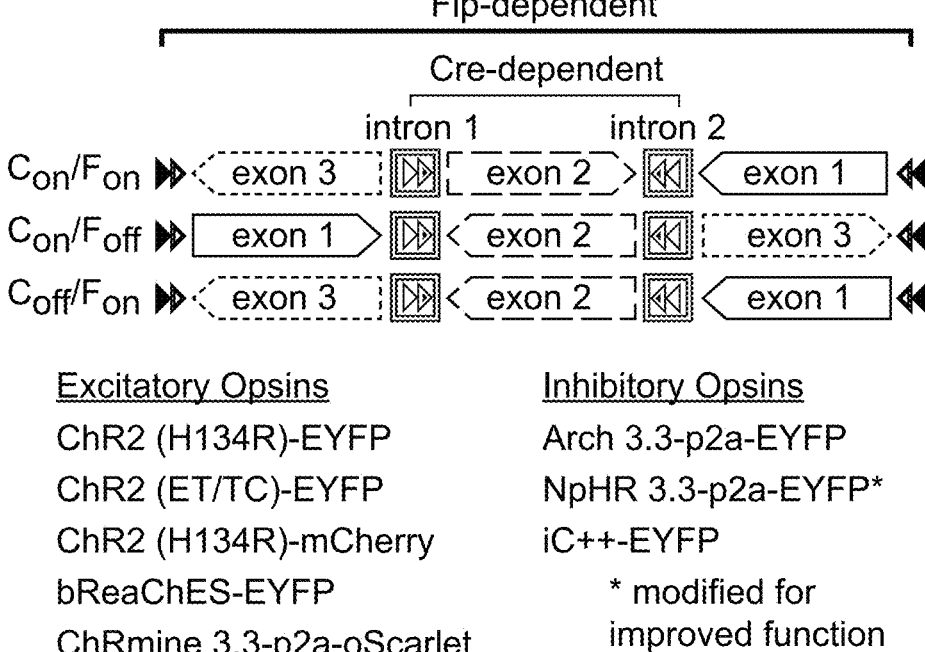
Figure 1E:
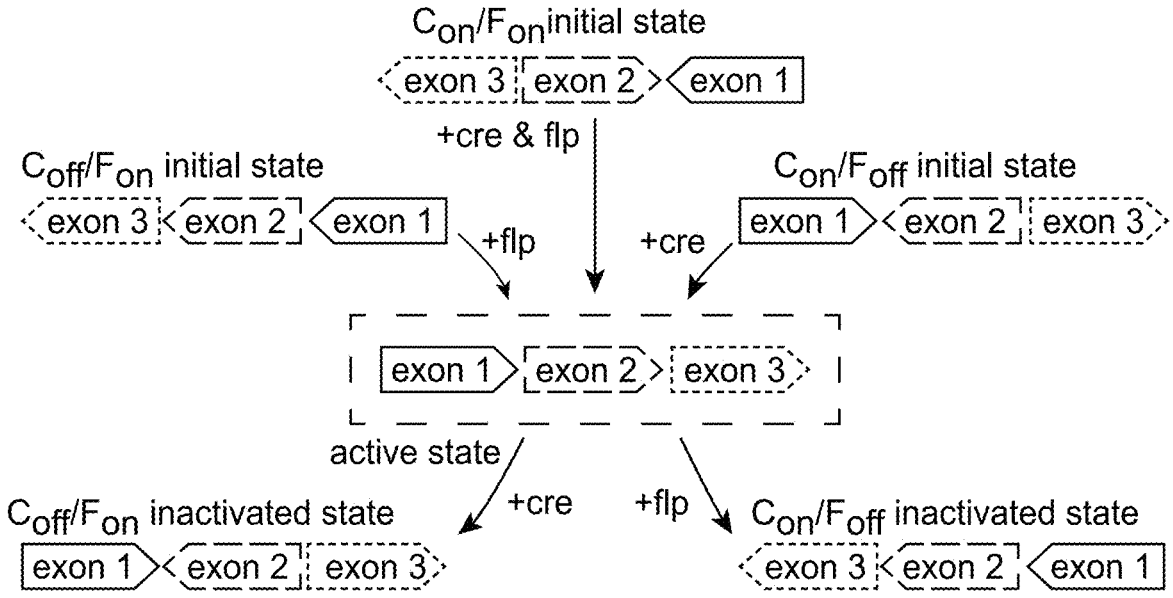
Figure 1F:
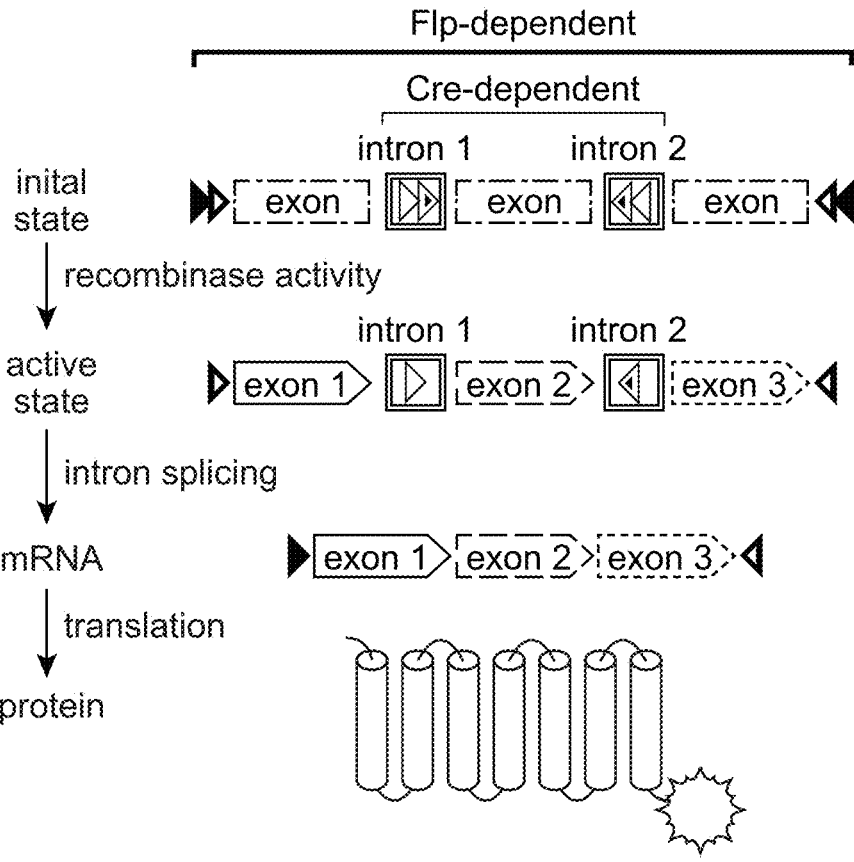

Results
Engineering and Validation of a Comprehensive INTRSECT Optical Neuroscience Toolbox INTRSECT is designed as a modular, molecular system that combines synthetic introns and multiple recombinases to restrict functional expression of a molecular tool to pre-defined neuron subpopulations. To accomplish this, a single intron is inserted within the coding sequence of molecules with a single reading frame (such as fluorophores and genetically-encoded calcium indicators [GECI]; FIG. 1a-c), while two introns are inserted in molecules with two reading frames (such as opsin-fluorophores fusions; FIG. 1d-f). The starting configuration of the exons between which logical combination of Cre and Flp will enable expression (FIG. 1b,e). Only after the activity of the pre-determined pattern of recombinases is completed are all exons are in the correct order and orientation, relative to the promoter, which then allows the synthetic introns containing recombinase recognition sites to be removed during mRNA splicing, and functional protein to be expressed (FIG. 1c,f). The use of introns ensures that sequence elements necessary for the action of recombinases (e.g. lox and FRT sites) do not interfere with the amino acid sequence of the protein. In order to construct an INTRSECT toolbox for optical neuroscience, a standard production pipeline was designed (FIG. 1g), where the pipeline progresses sequentially through in silico molecular design for intron placement, cloning, RT-PCR of transfected HEK293 cells to evaluate proper splicing of synthetic introns, flow cytometry of HEK293 cells, co-transfection with INTRSECT construct and combinations of recombinases to assay expression in the proper configuration and lack of off-target expression, and functional analysis in primary neuron cultures to compare function of the INTRSECT construct with the non-recombinase-dependent, source tool (wild-type 'WT'). INTRSECT variants of a representative set of commonly-used optical tools, including fluorescent proteins (mTagBFP, mCherry, oScarlet; FIG. 7), calcium indicators (GCaMP6f, GCaMP6m, sRGECO1a; FIG. 8), excitatory opsins (ChR2 (H134R)-mCherry, bReaChES-EYFP, ChR2(E123T; T159C)-EYFP, ChRmine3.3-p2a-oScarlet; FIG. 9), and inhibitory opsins (NpHR3.3-p2a-EYFP, Arch3.3-p2a-EYFP, iC++-EYFP; FIG. 10) were created to complement INTRSECT versions of EYFP and ChR2(H134R)-EYFP.

Figure 7A:
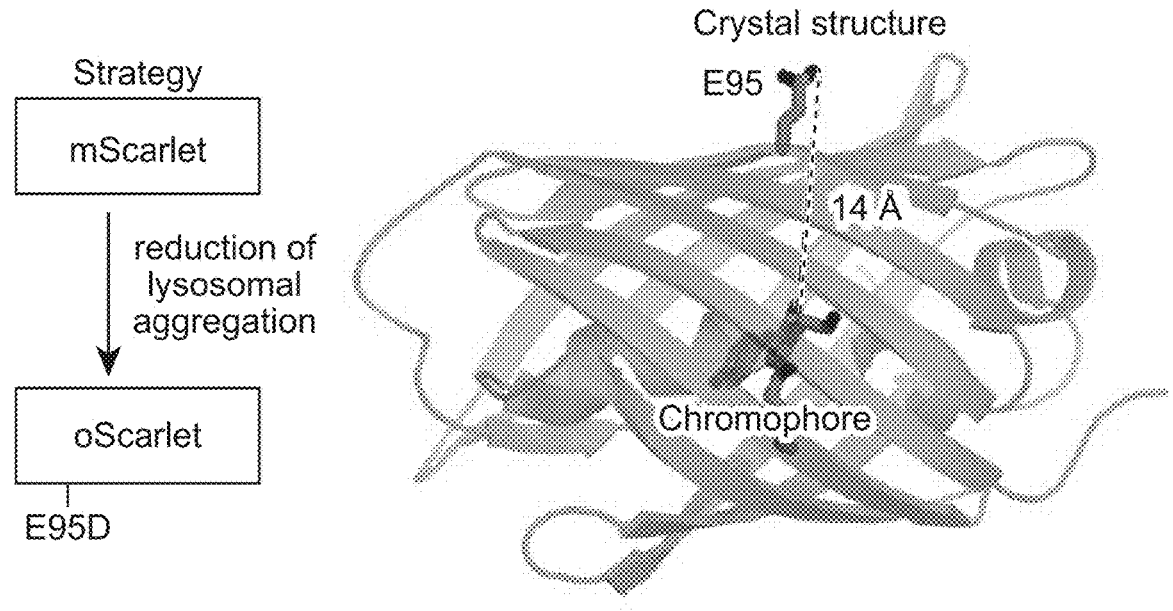
Figure 7B:
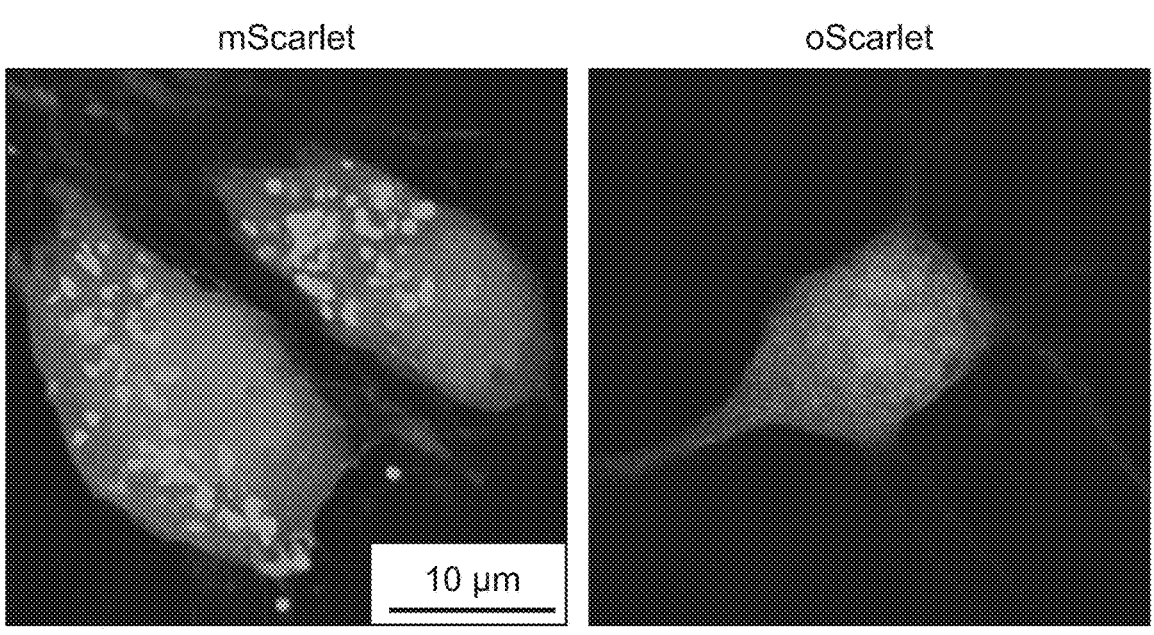
Figures 7C, 7D:
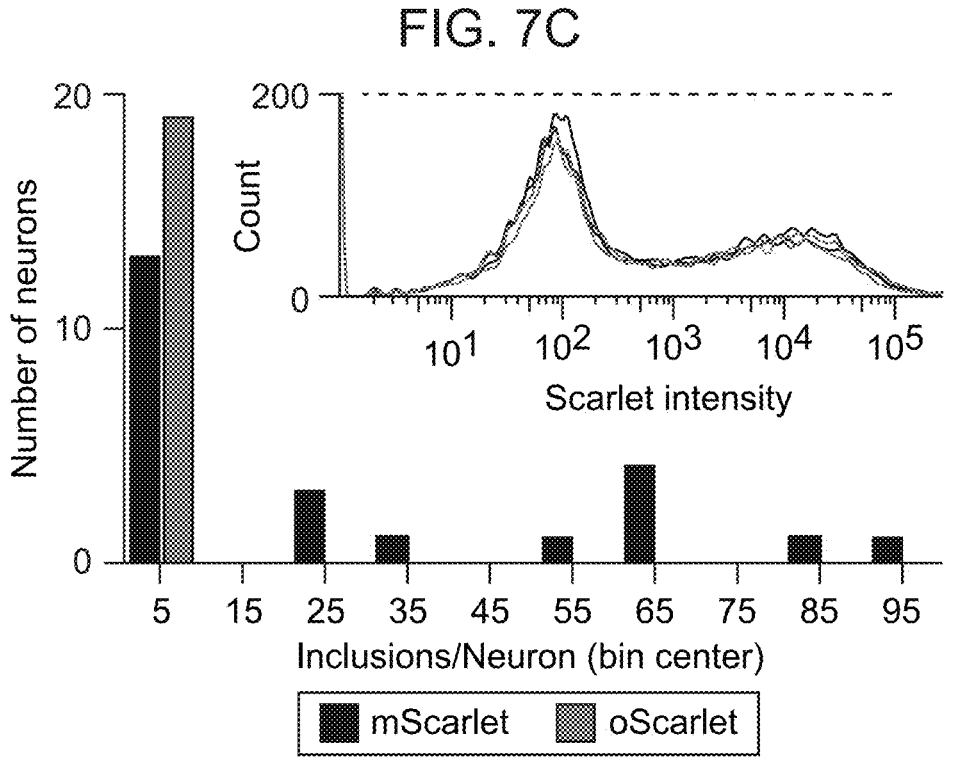
Figures 8D, 8E:
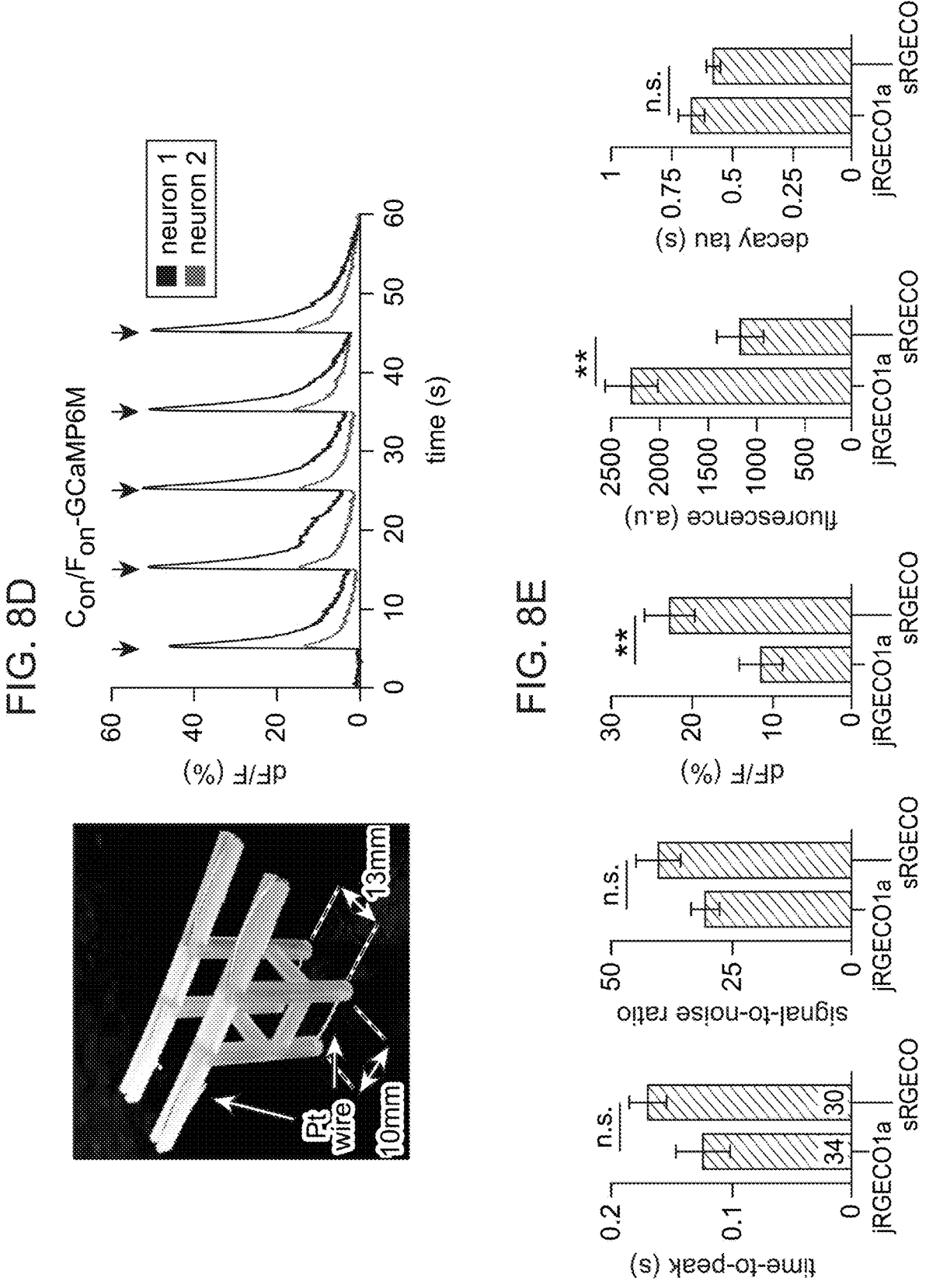
FIGS. 8A-8N depicts INTRSECT GECI development.
Figure 8F:
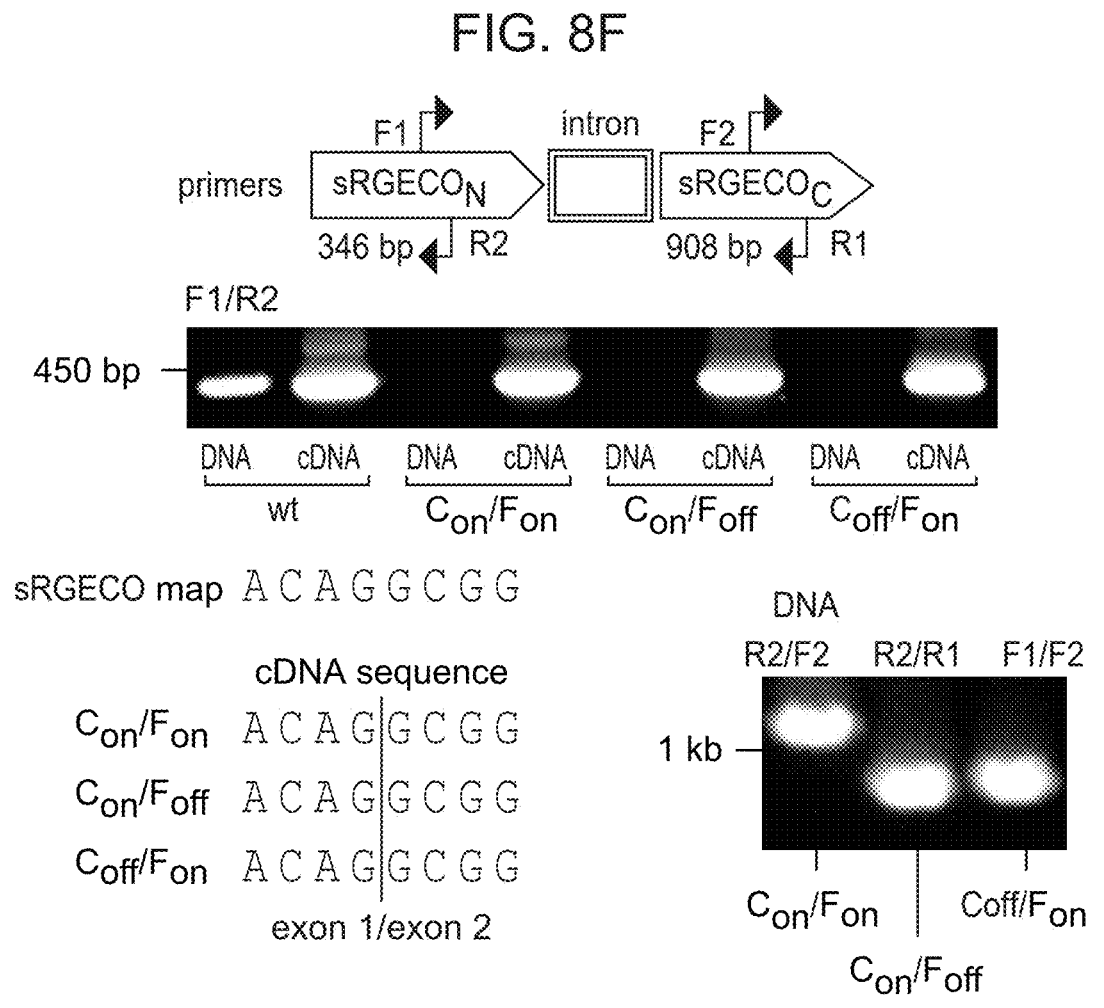
Figure 8H:
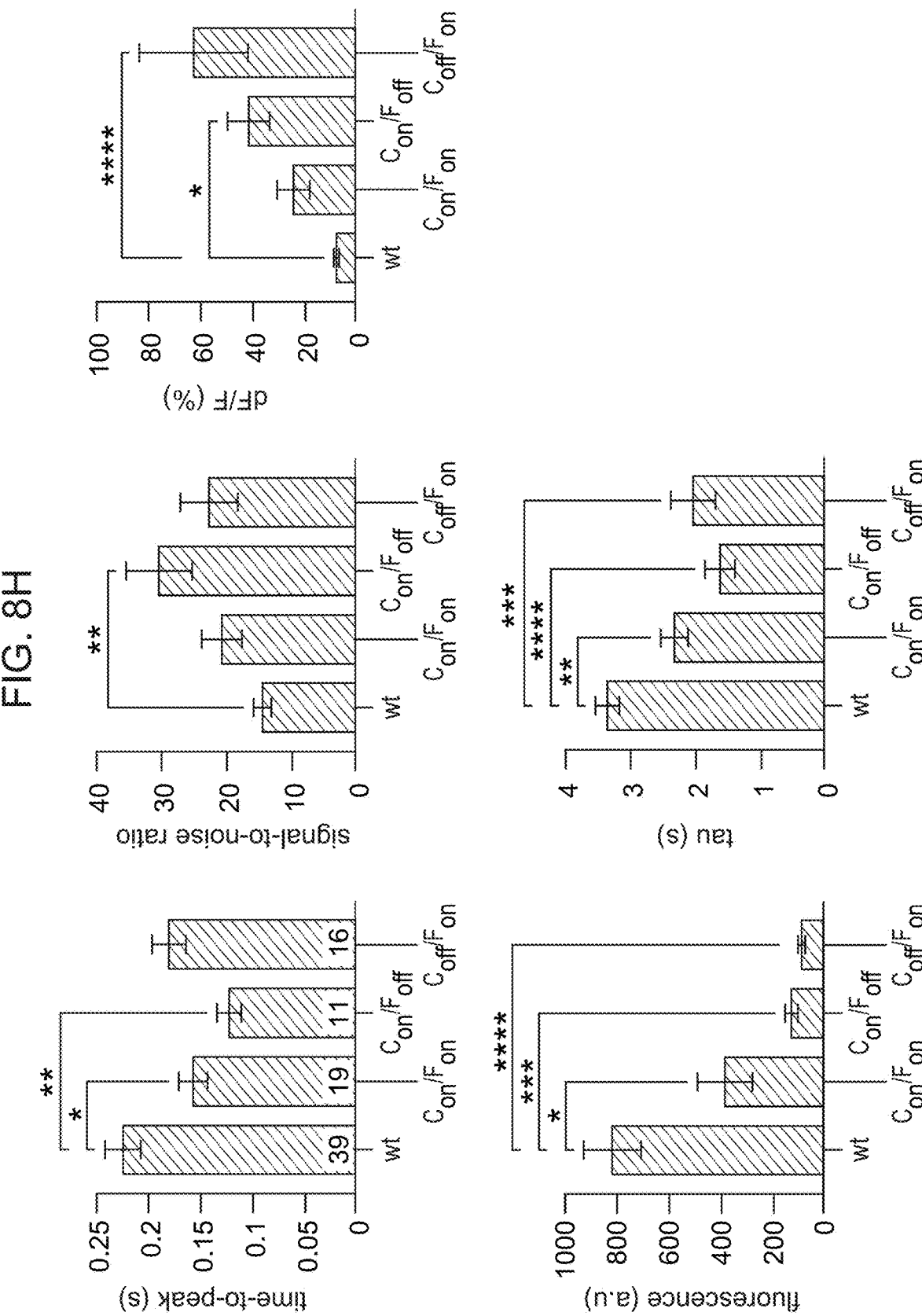
Figure 8I:
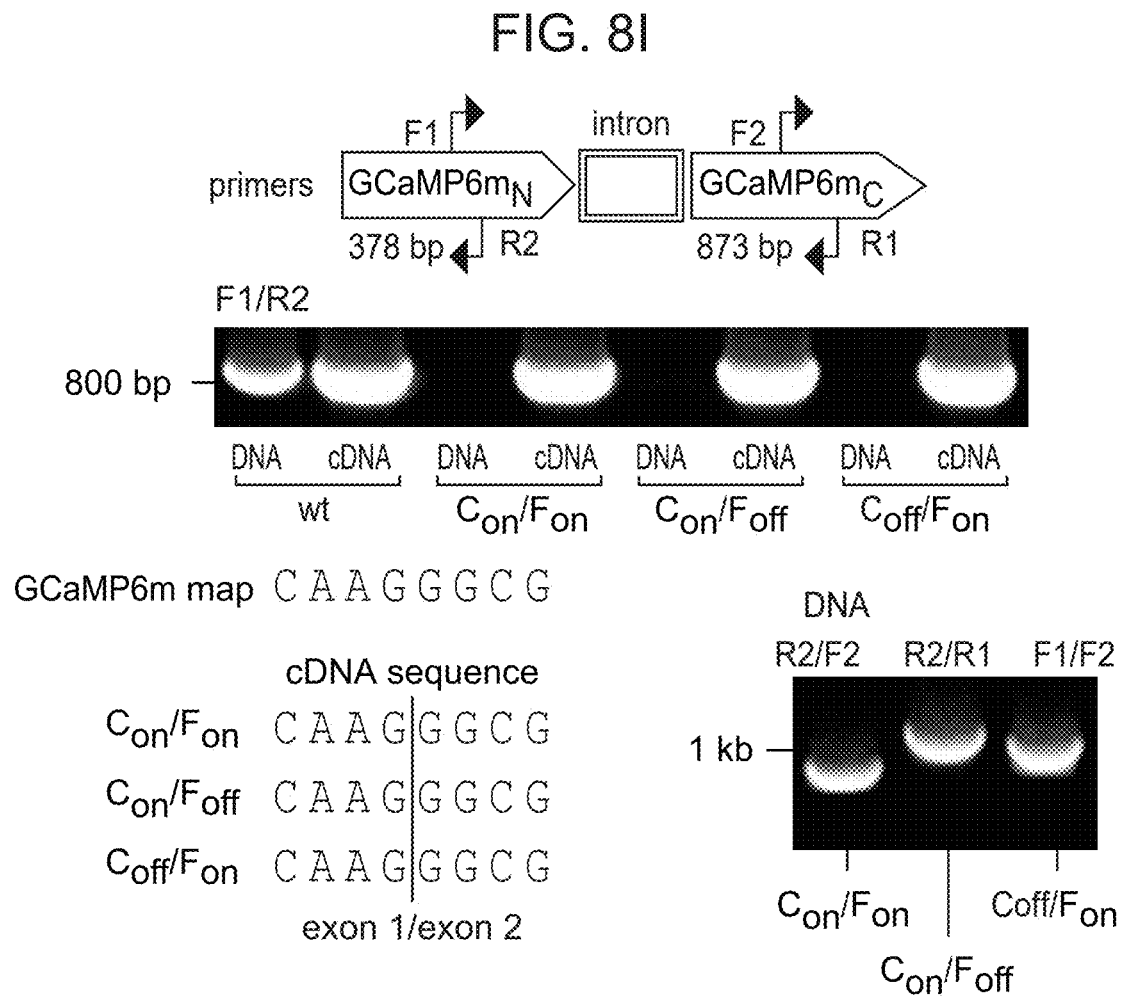
Figure 8L:
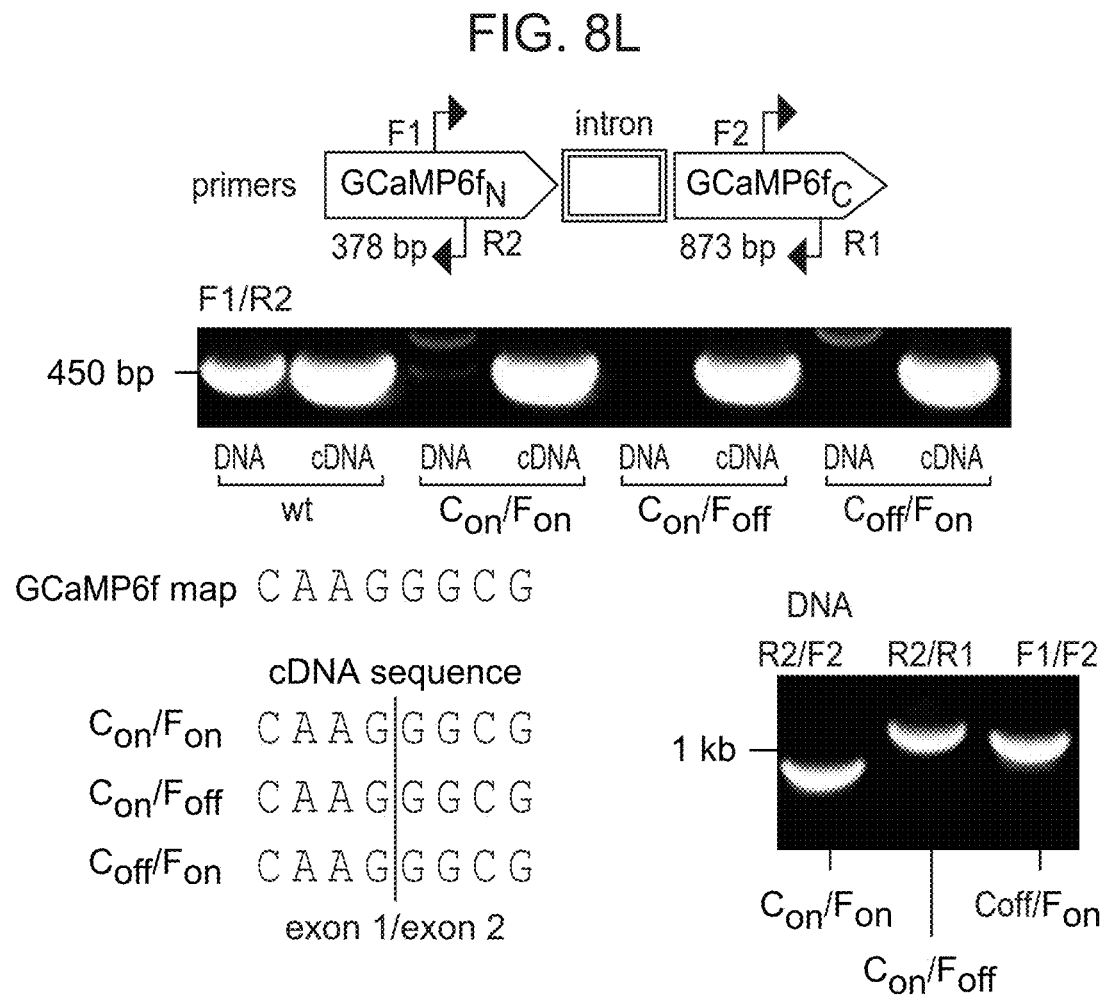
Figure 9A:
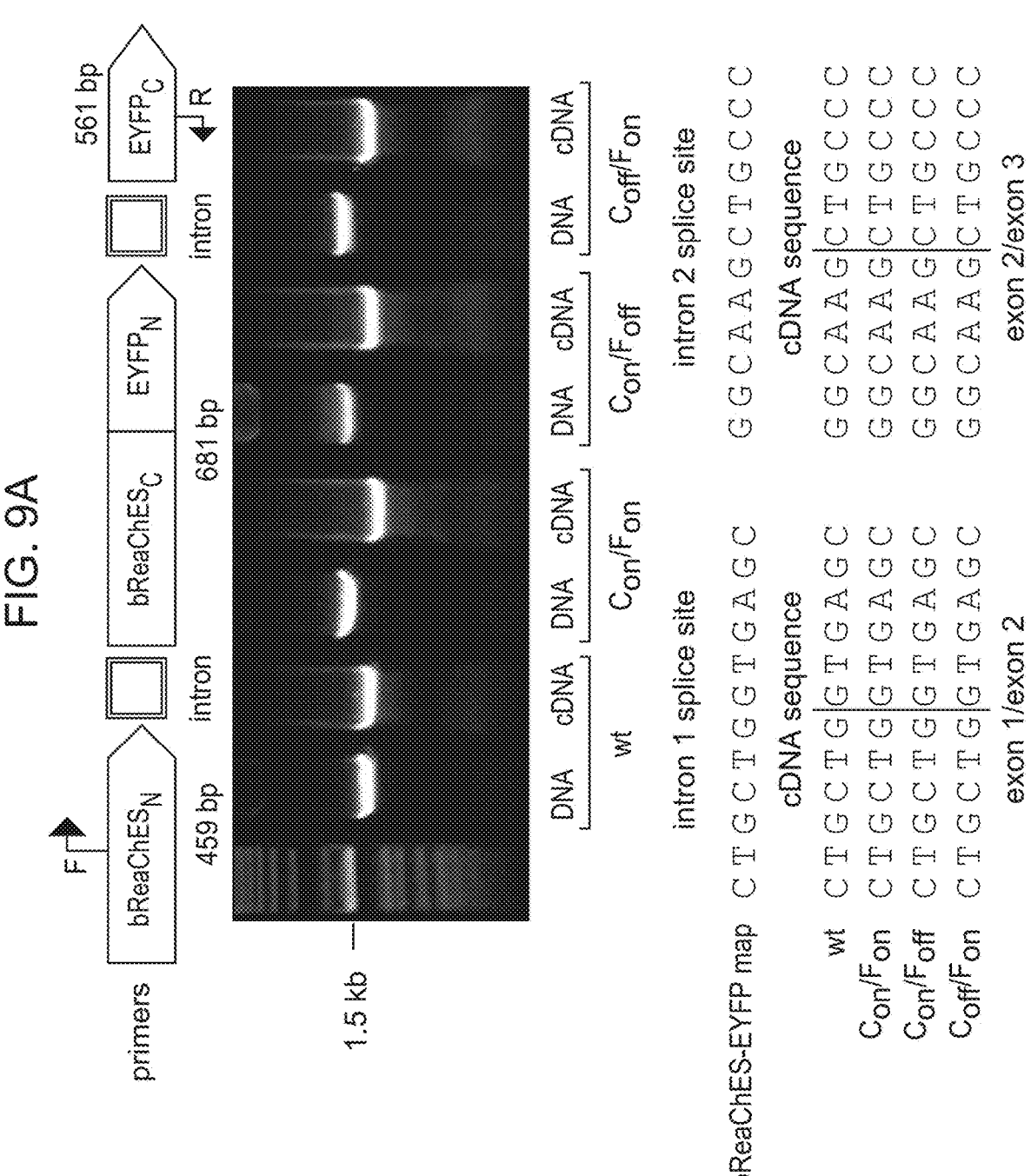
Figures 9C, 9D:
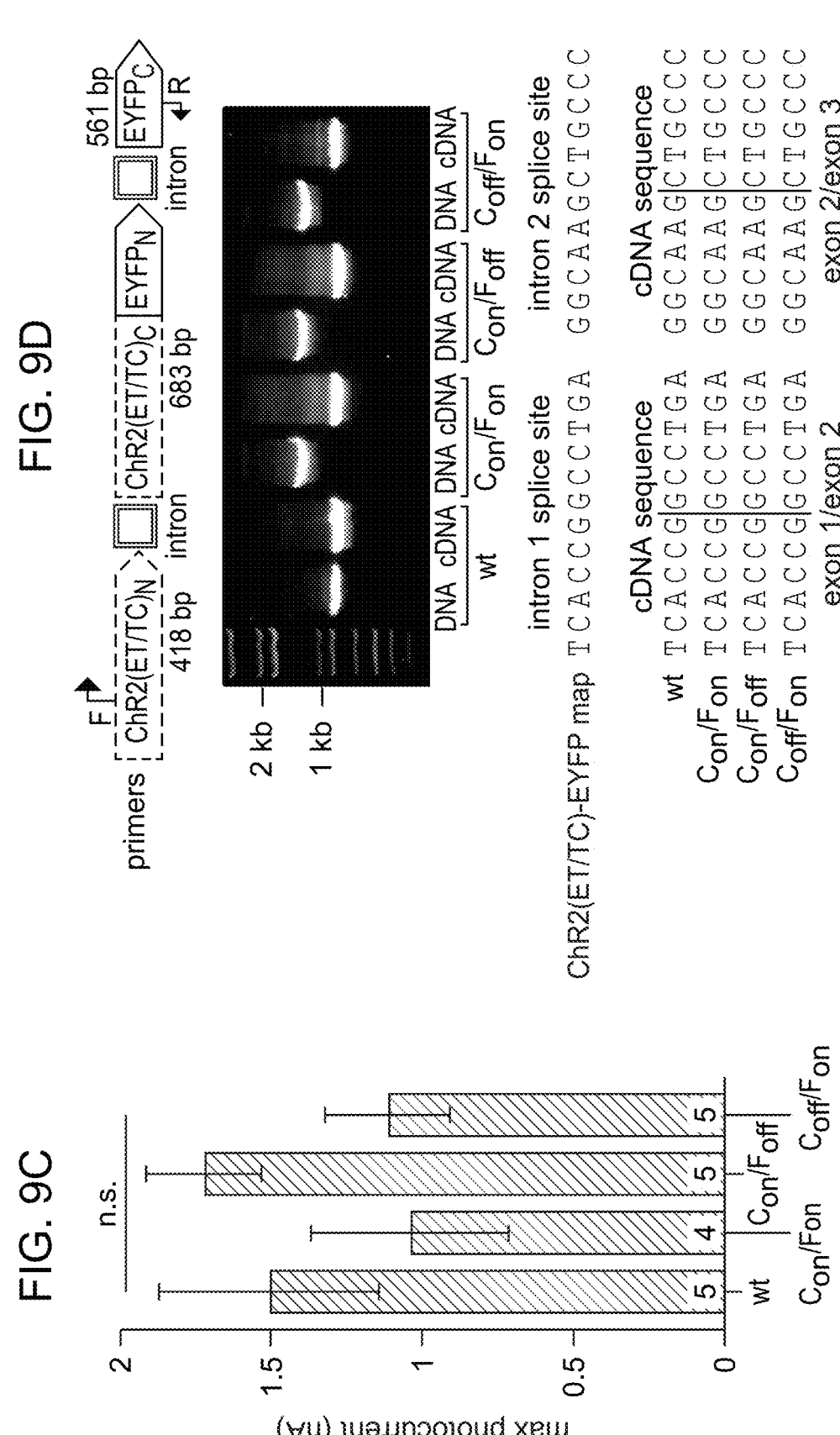
Figure 9E:
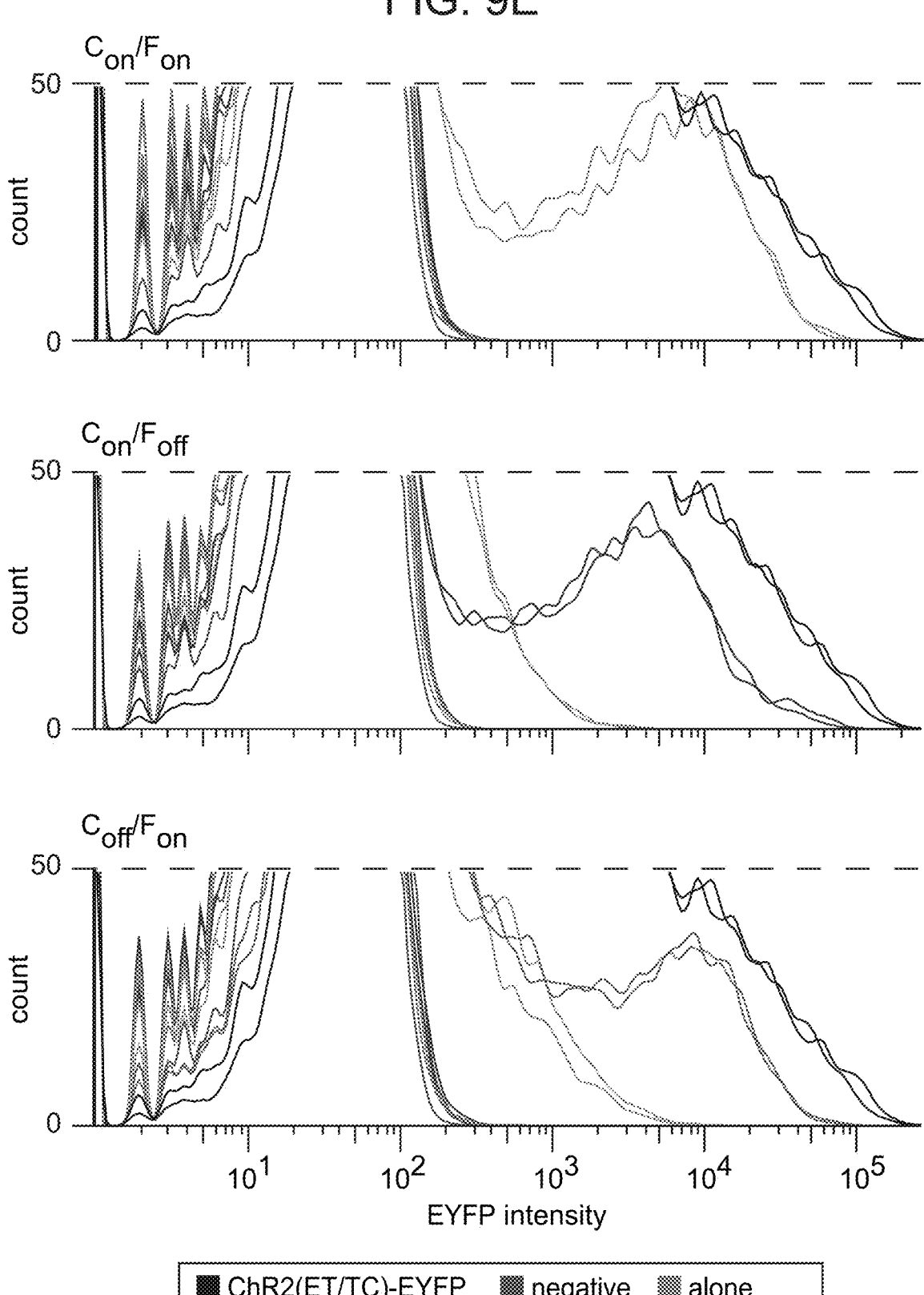
Figures 9F, 9G:
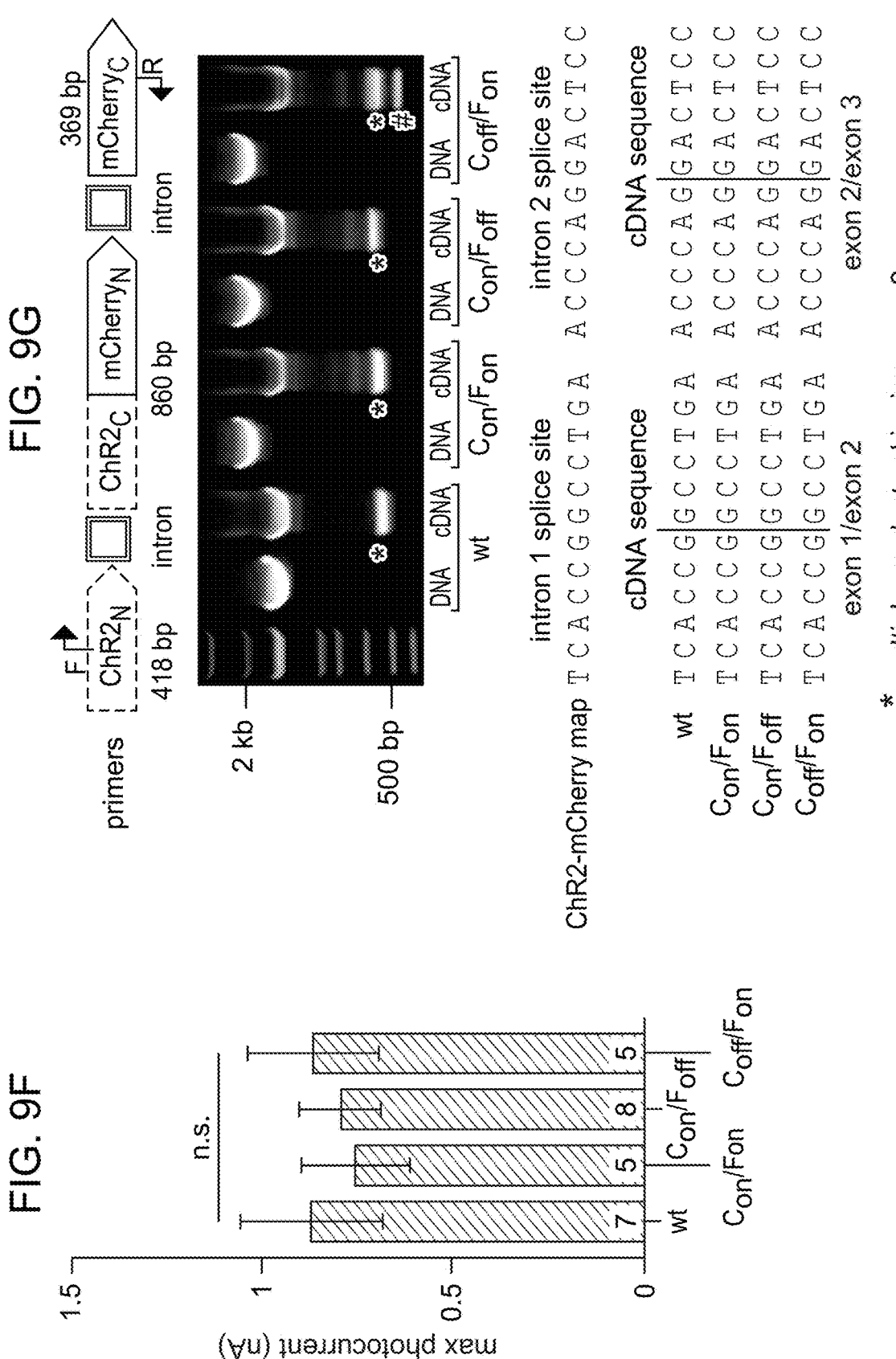
Figures 9I, 9J:
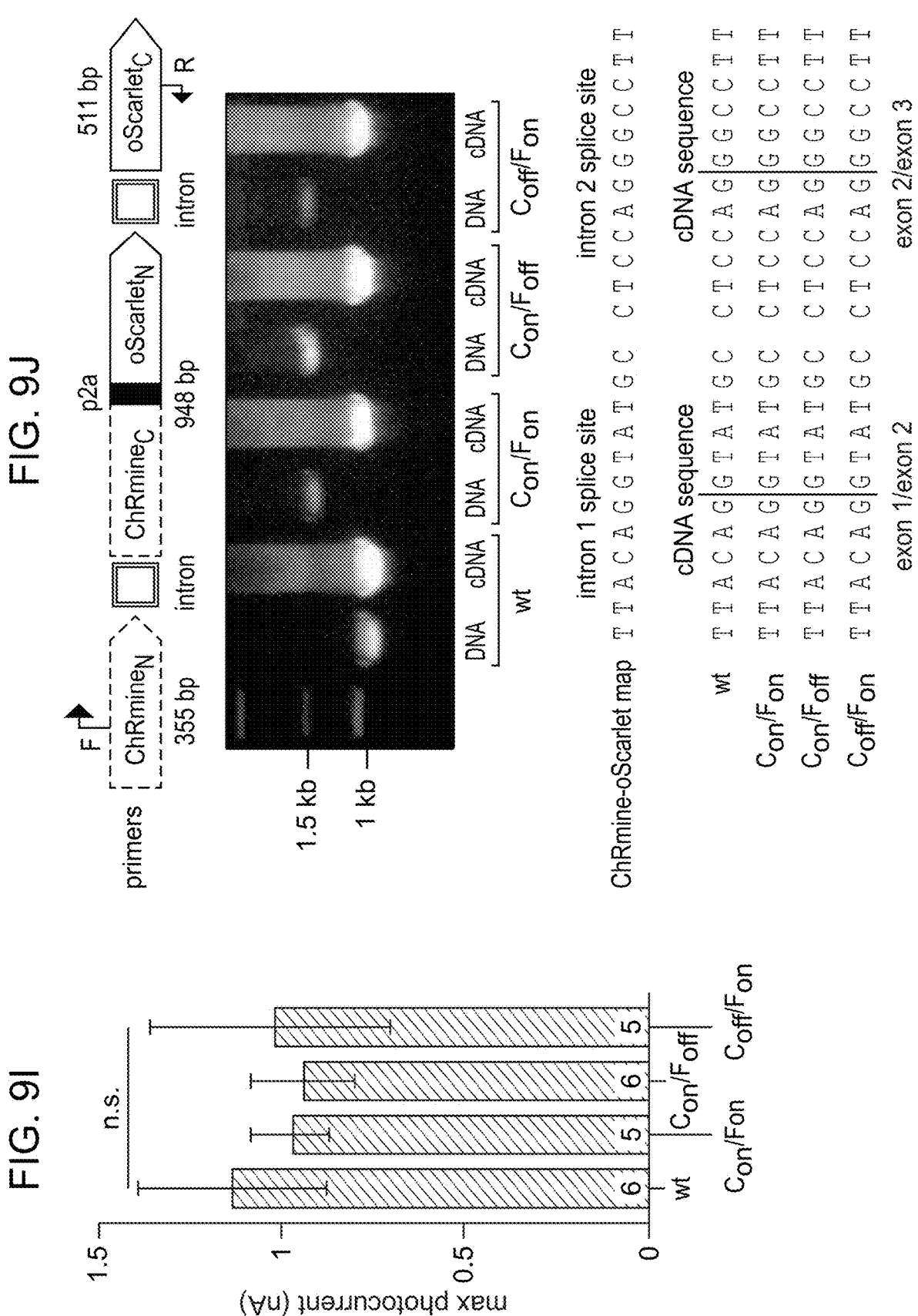

Prior to entering mScarlet and jRGECO1a into the INTRSECT production pipeline, fluorescent puncta (assumed to be protein aggregates) were observed when expressed either in vitro (mScarlet; FIG. 7b) or in vivo (jRGECO1a; FIG. 8b). Both are based on monomeric Red Fluorescent Protein (Bindels et al. (2017) Nat. Methods 14:53-6, Dana et al. (2016) Elife 5), which is known to be degradation-resistant and accumulate in lysosomes (Katayama et al. (2008) 33:1-12). It was found that the unconventional lysosomal targeting motif tryptophan-glutamic acid (Piccirillo et al. (2006) J Cell Sci 119:2003-14) was conserved in both of these tools. To overcome this aggregation problem this motif was mutated, mScarlet(E95D) ('oScarlet'; FIG. 7a) and jRGECO1a(E217D) ('sRGECO'; FIG. 8a). oScarlet had significantly fewer aggregates in cultured neurons (25.9 per neuron in mScarlet, 0.58 per neuron in oScarlet, p=0.0012, unpaired t-test), with no obvious difference in fluorescence intensity as assayed by flow cytometry (FIG. 7b,c). Significantly fewer aggregates were also observed in confocal images of virally-expressed sRGECO relative to jRGECO1a in mouse mPFC (6.96 per neuron in jRGECO1a vs. 5.73 per neuron in sRGECO, p=0.0365, unpaired t-test), without a difference in total fluorescence across the imaged cortical slices (FIG. 8b,c; p=0.1867, unpaired t-test). To characterize this improved GECI more thoroughly, a small, 3D-printable well insert for electrical stimulation of cultured neurons using a 100 mA source applied through platinum wires was designed (FIG. 8d). In vitro characterization of sRGECO and jRGECO1a (FIG. 8e) revealed a difference in basal fluorescence and related differences in signal magnitude, but intact function. Considering the improved expression patterns of oScarlet and sRGECO, these versions were used as the sequence base for creating their INTRSECT variants.

Figures 1G, 2A:
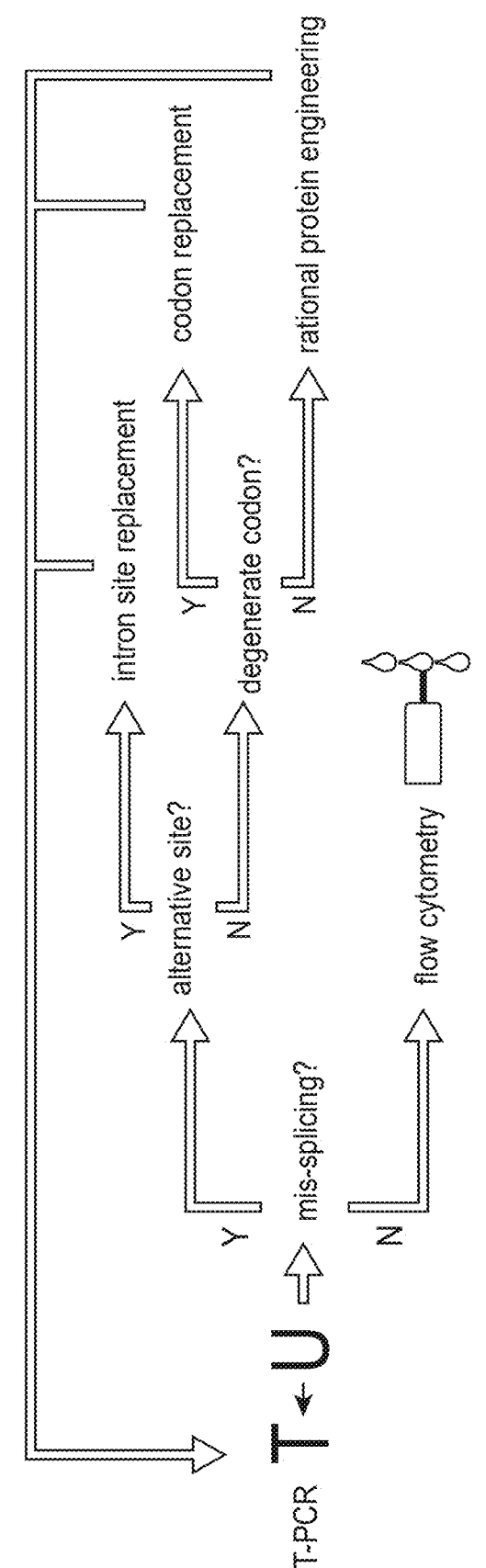
Figure 2B:
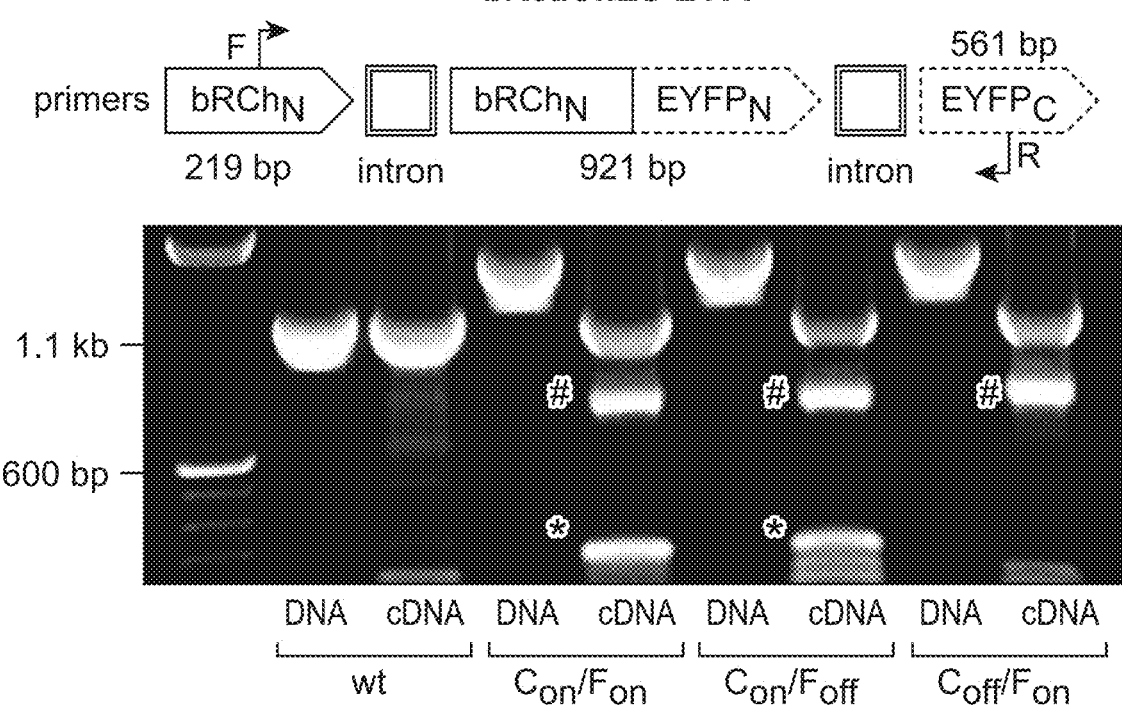
Figure 2C:
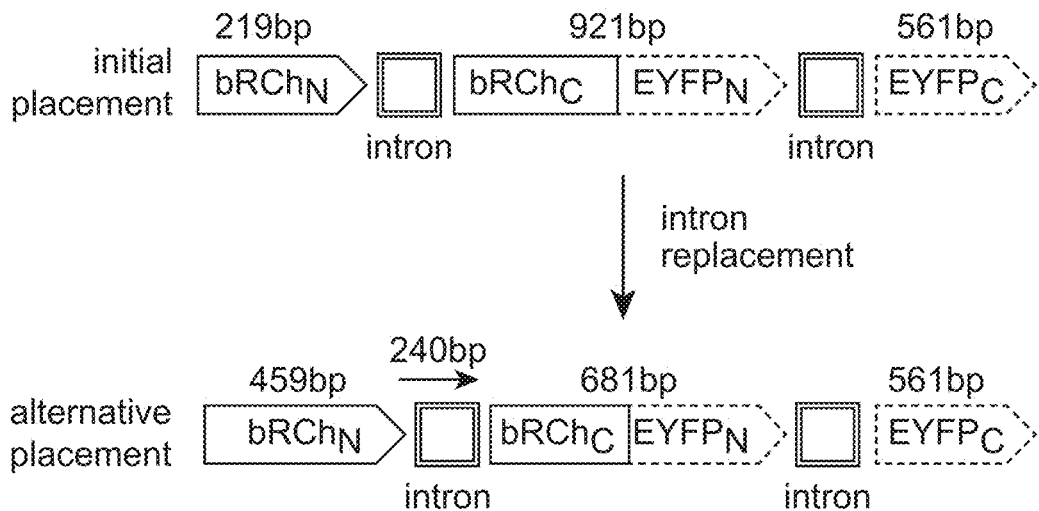
Figure 2D:
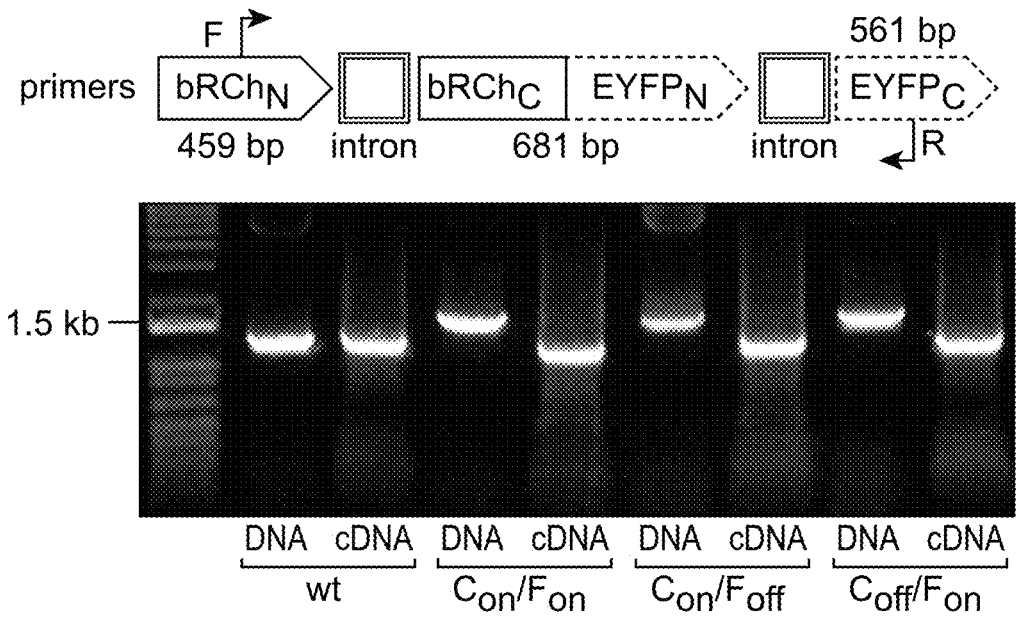
Figure 2E:
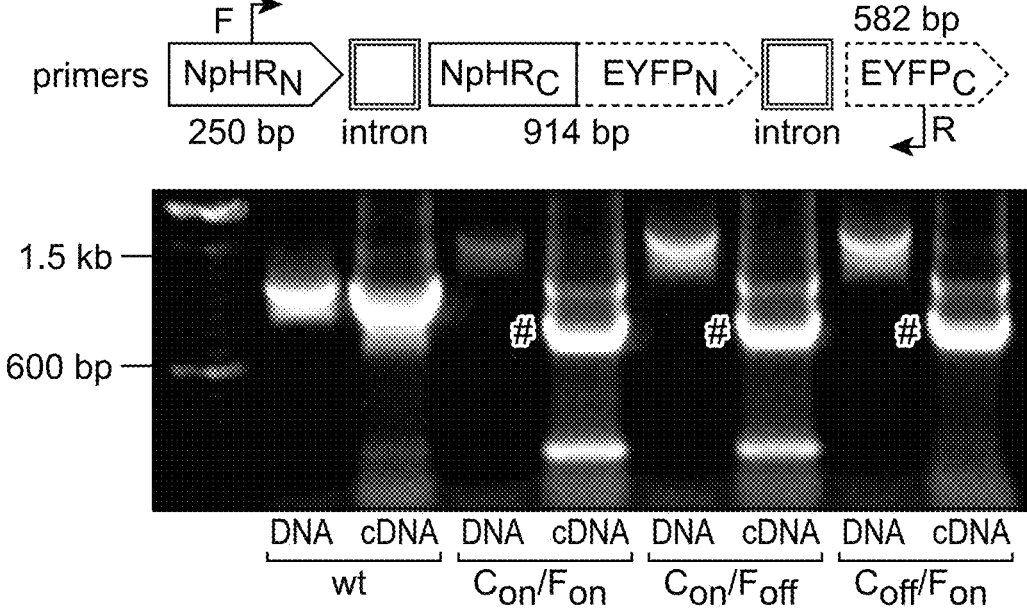
Figure 2F:
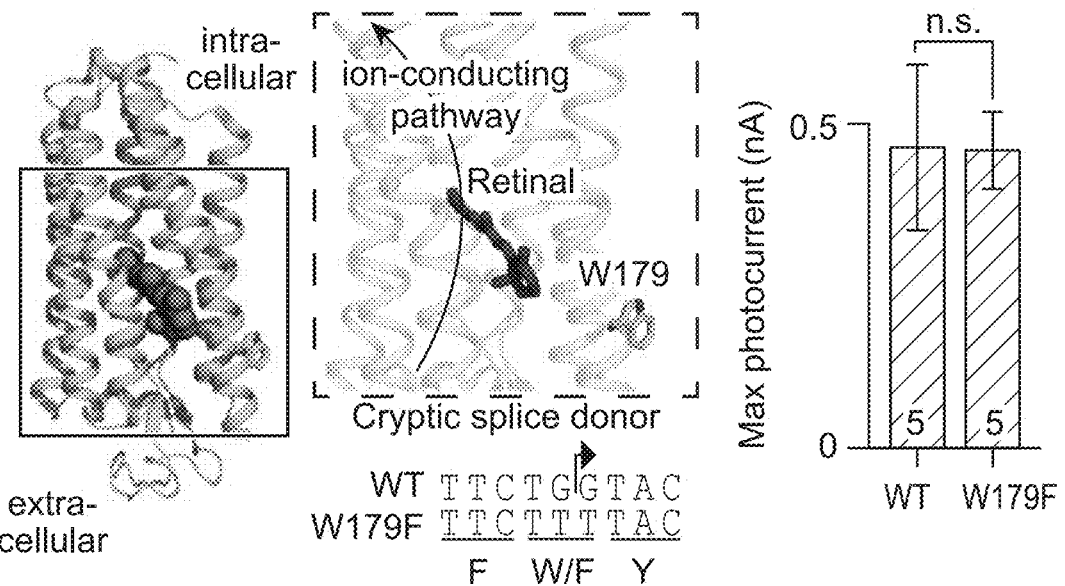
Figure 2G:
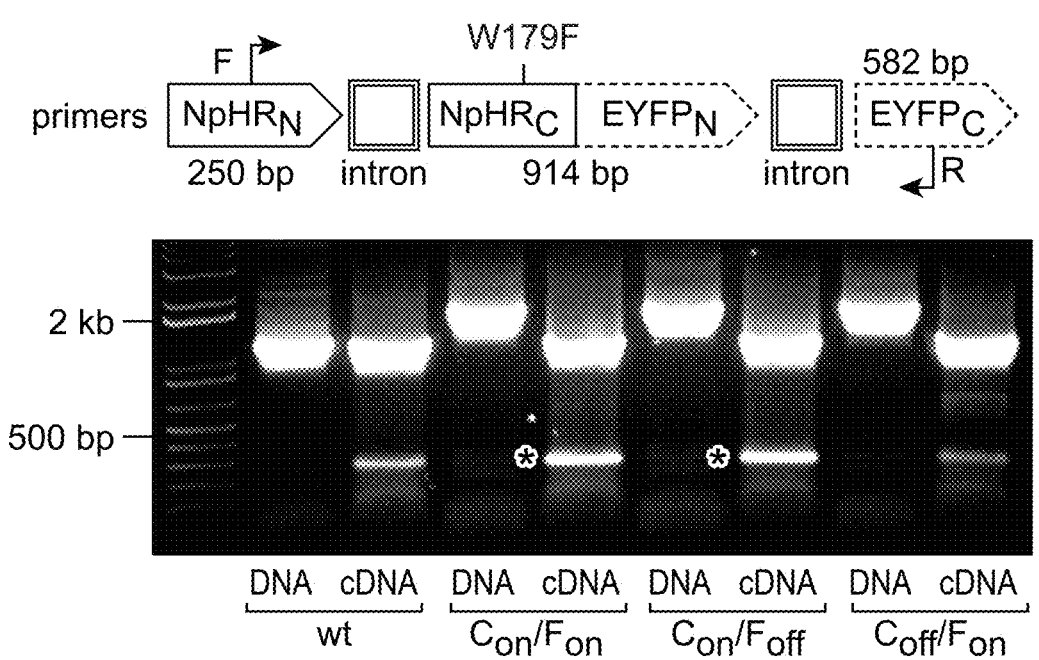
Figure 2H:
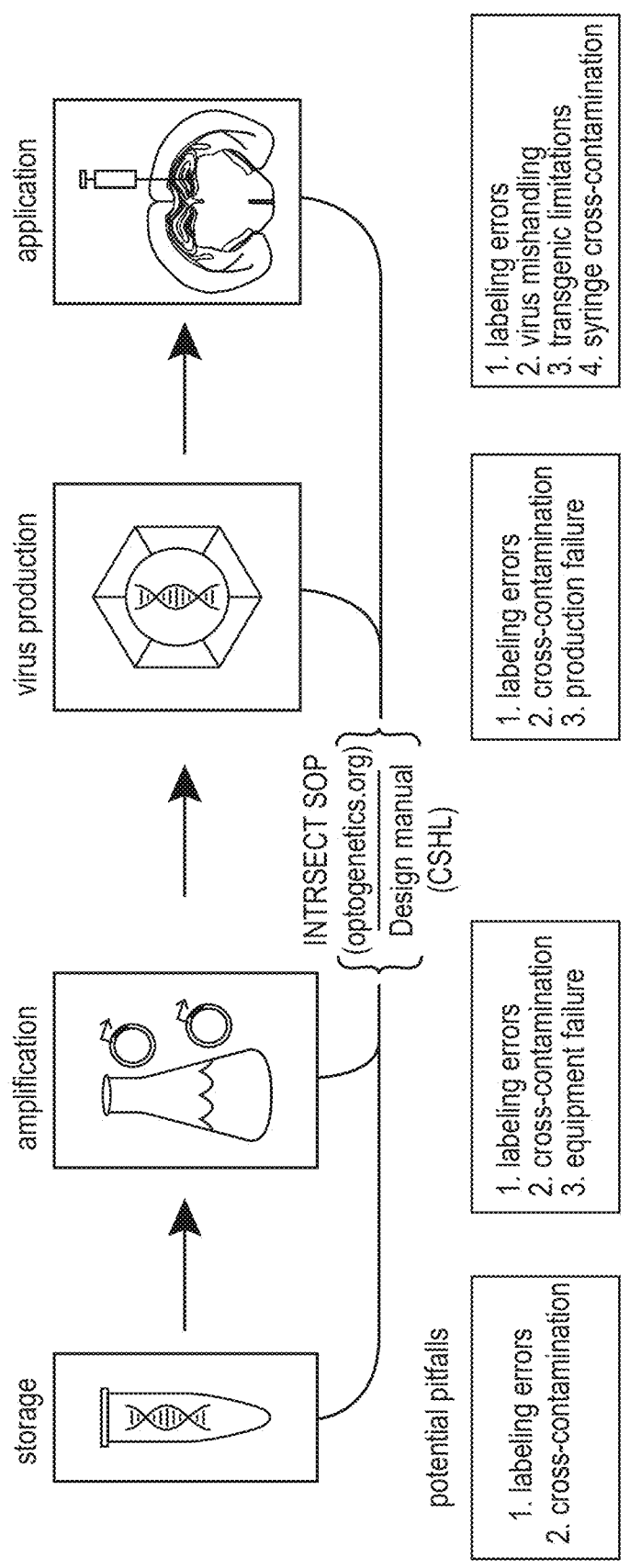

The pipeline approach to INTRSECT construct production (FIG. 1g, FIG. 2) was validated by both the general success of the informatics-based intron placement in generating properly spliced products and by RT-PCR identification of the small number of two intron constructs with spurious splice products, which allowed the modification of these prior to further characterization in vitro or experimental use in vivo. When necessary, improving splice fidelity required individualized strategies based on the sequence of the mis-spliced products (FIG. 2a). For example, a preferred, cryptic splice site within the second exon of bReaChES-EYFP was observed as well as direct splicing of exon 1 to exon 3 (FIG. 2b). In this case, simply moving the first intron to a position further 3' at a secondary candidate splice site was sufficient to eliminate both the cryptic site and exon skipping (FIG. 2c,d). Separately, mis-splicing at a cryptic site was found with NpHR3.3-p2a-EYFP (FIG. 2e). In this case, the sequence of NpHR did not offer an additional splice site option and codon degeneracy was not able to be used to disrupt the cryptic splice site. Instead the available crystal structure of NpHR was leveraged (Kouyama et al. (2010) J Mol Biol. 396:564-79), to hypothesize that the distance (more than 8 angstroms) of the residue encoded by the cryptic splice site from the critical light-sensing retinal binding pocket made it unlikely to be integral to protein function (FIG. 2f—left). This was confirmed, as the introduced mutation, W179F, did not negatively impact opsin function (FIG. 2f—right; p=0.9754, unpaired t-test) and resolved mis-splicing (FIG. 2g).

Aside from rare, cryptic splice sites, direct exon 1 to exon 3 splicing was a frequently observed minor splice variant in two-intron (three-exon) constructs. A number of approaches were used in working to attenuate this phenomenon, with Con/Fon Arch3.3-p2a-EYFP as a platform, including modifying the splice acceptor polypyrimidine tract C/T content, increasing intron sequence length, and increasing the distance between the introns. None of these approaches resolved exon 1 to exon 3 direct splicing (data not shown). Interestingly, in some cases, including NpHR3.3(W179F)-p2a-EYFP (FIG. 10a) and ChR2(H134R)-mCherry (FIG. 9g) the WT cDNA included the same splice product with the same sequence, suggesting that there may be inherent splicing occurring even without the addition of synthetic introns.

Across all constructs, flow cytometry analysis 5d post-transfection in HEK293 cells revealed expression largely as expected, with no expression in the absence of recombinases and expression comparable with WT when paired with activating recombinases. No off-target expression was noted with any of the Cre AND Flp (Con/Fon) vectors; this is as expected, as the design of these constructs precludes expression in the absence of both recombinases (FIG. 1b,e). In the Flp AND NOT Cre (Coff/Fon) constructs, co-transfection with Flp induced expression that was within one order of magnitude of the WT and the range of expression differences appeared to be associated with tool class. Fluorophores and GECI had expression approximately 1-fold lower than WT (FIG. 7e,h,k; FIG. 8g,j,m), excitatory opsins were either the same or slightly lower (FIG. 9b,e,h,k), and inhibitory opsins were indistinguishable (FIG. 10b,e,h). Inactivation of Coff/Fon constructs after co-transfection with both Cre and Flp was highly effective at diminishing expression to levels similar to negative controls. In the Cre AND NOT Flp (Con/Foff) constructs, co-transfection with Cre induced expression that was indistinguishable from the parental construct. Inactivation of Con/Foff constructs by co-transfection with both Cre and Flp diminished expression with a range of results. Some constructs were diminished to levels similar to negative controls, while others were decreased by more than an order of magnitude, but still with obvious expression at 5d post-transfection. Both Con/Foff and Coff/Fon constructs have the potential for transient off-target expression in cells co-expressing Cre and Flp (e.g. if Cre acts before Flp in Con/Foff or if Flp acts before Cre in Coff/Fon), an important consideration considering the well-characterized higher efficacy of Cre relative to Flp (Ringrose et al. (1998) J Mol Biol. 284:363-84); Approaches to further address this discrepancy included a parallel engineering effort (see Improvement of the FRT cassette below).

Figure 7F:
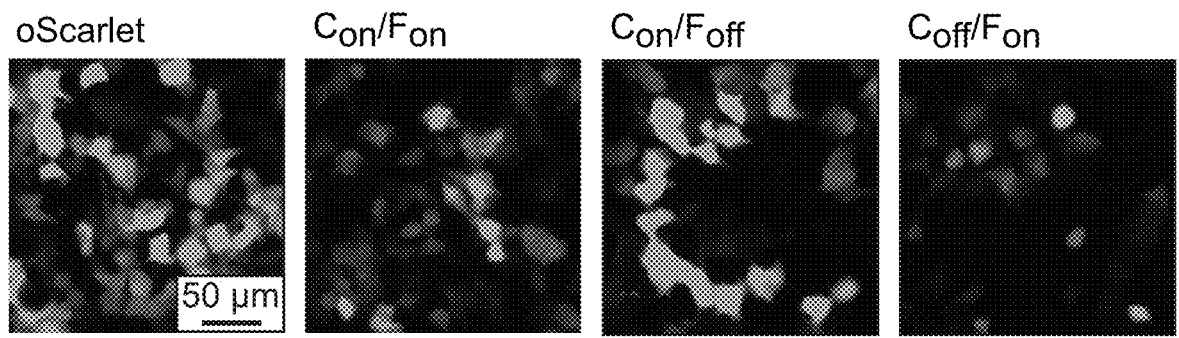
Figure 7G:
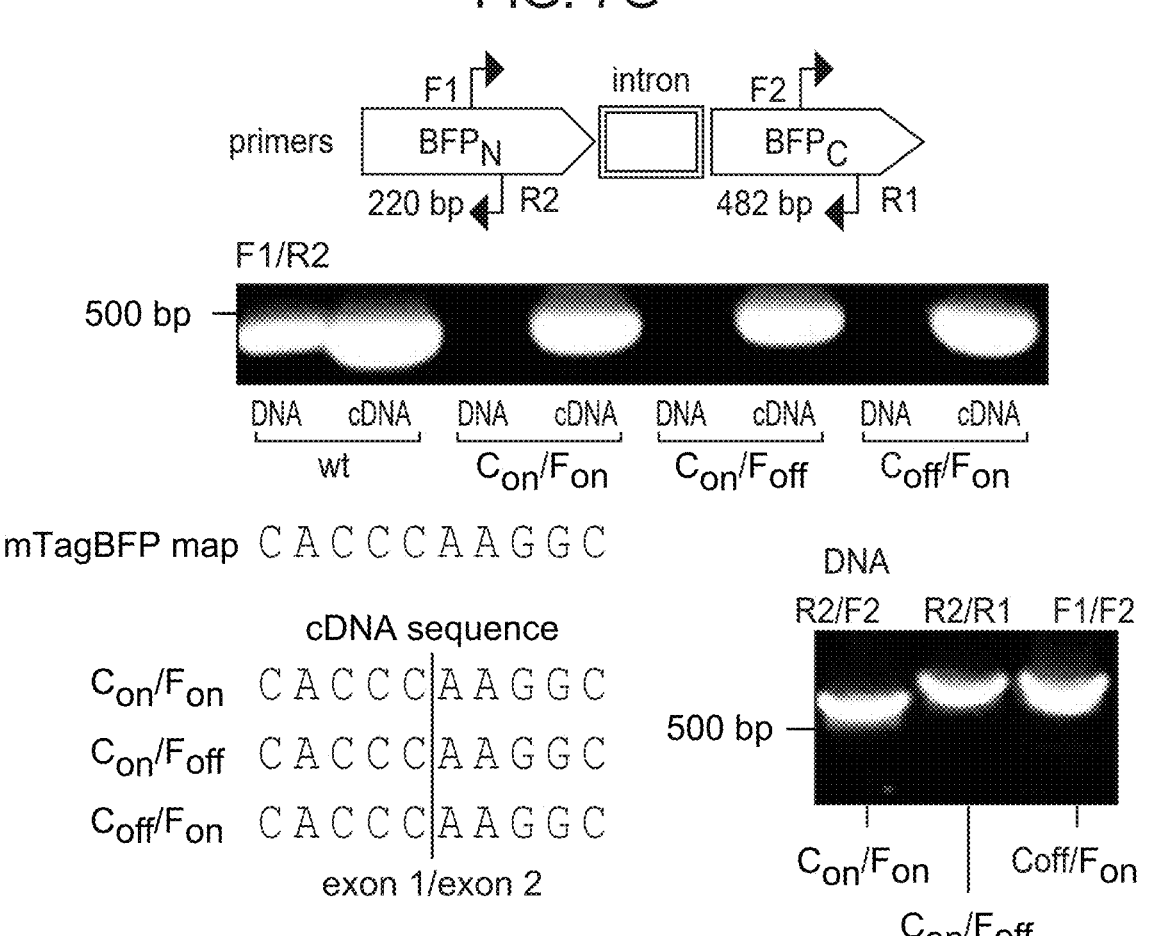
Figures 7I, 7J:
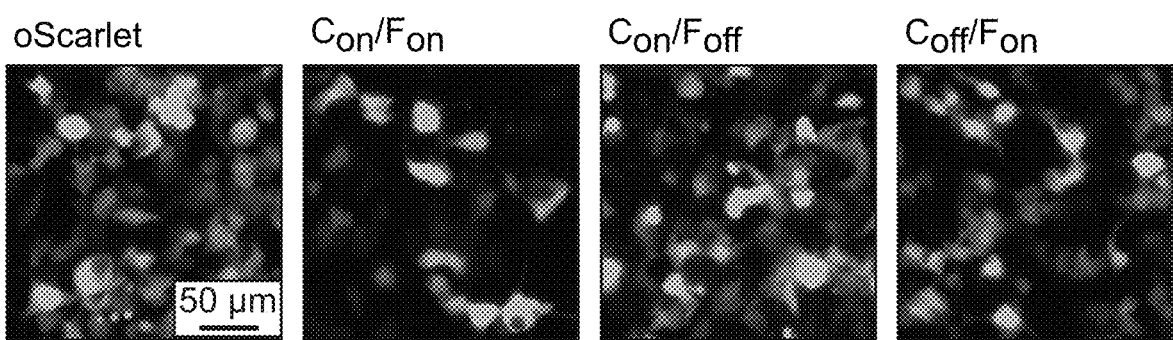
Figure 7L:
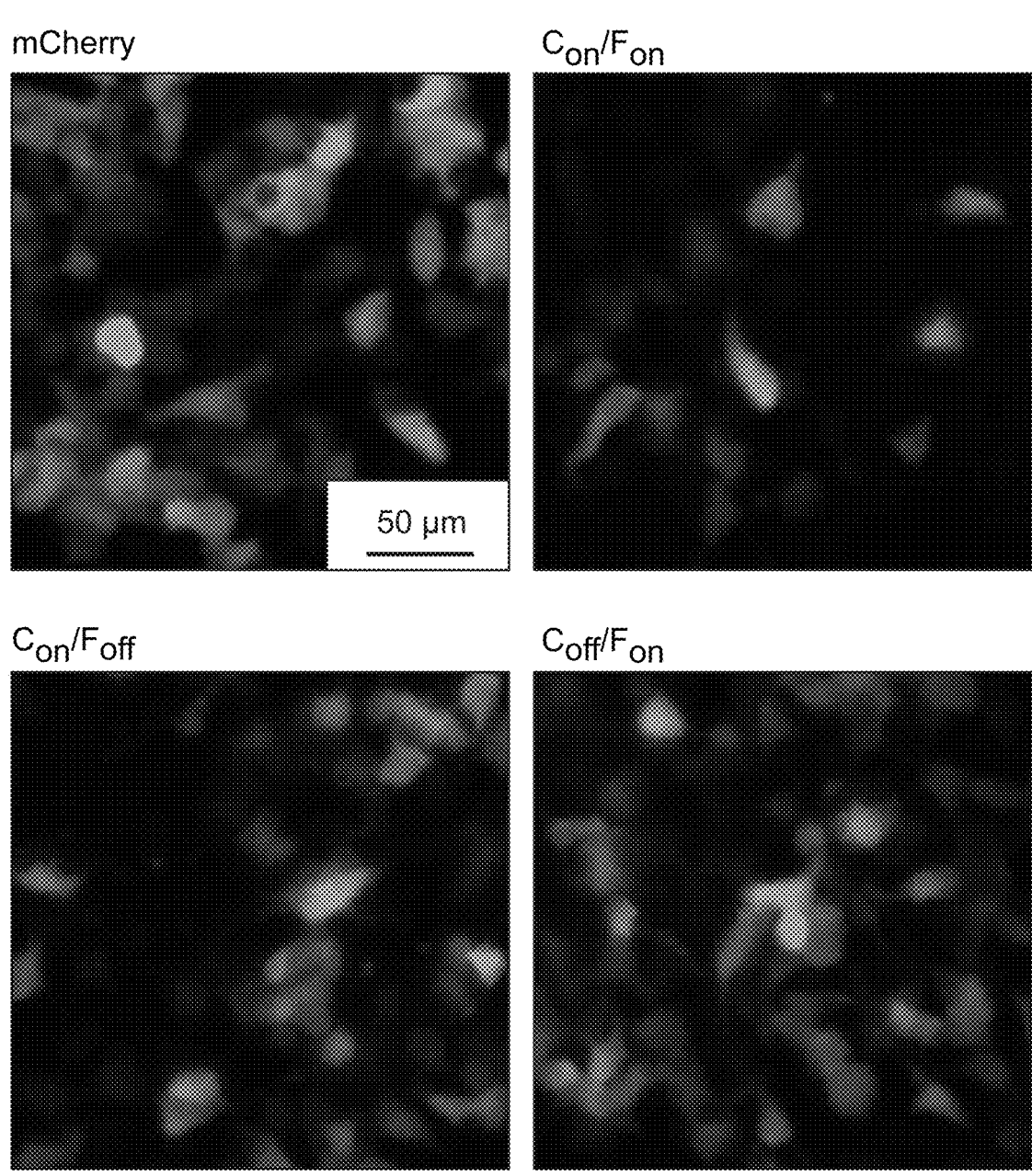
Figures 10C, 10D:
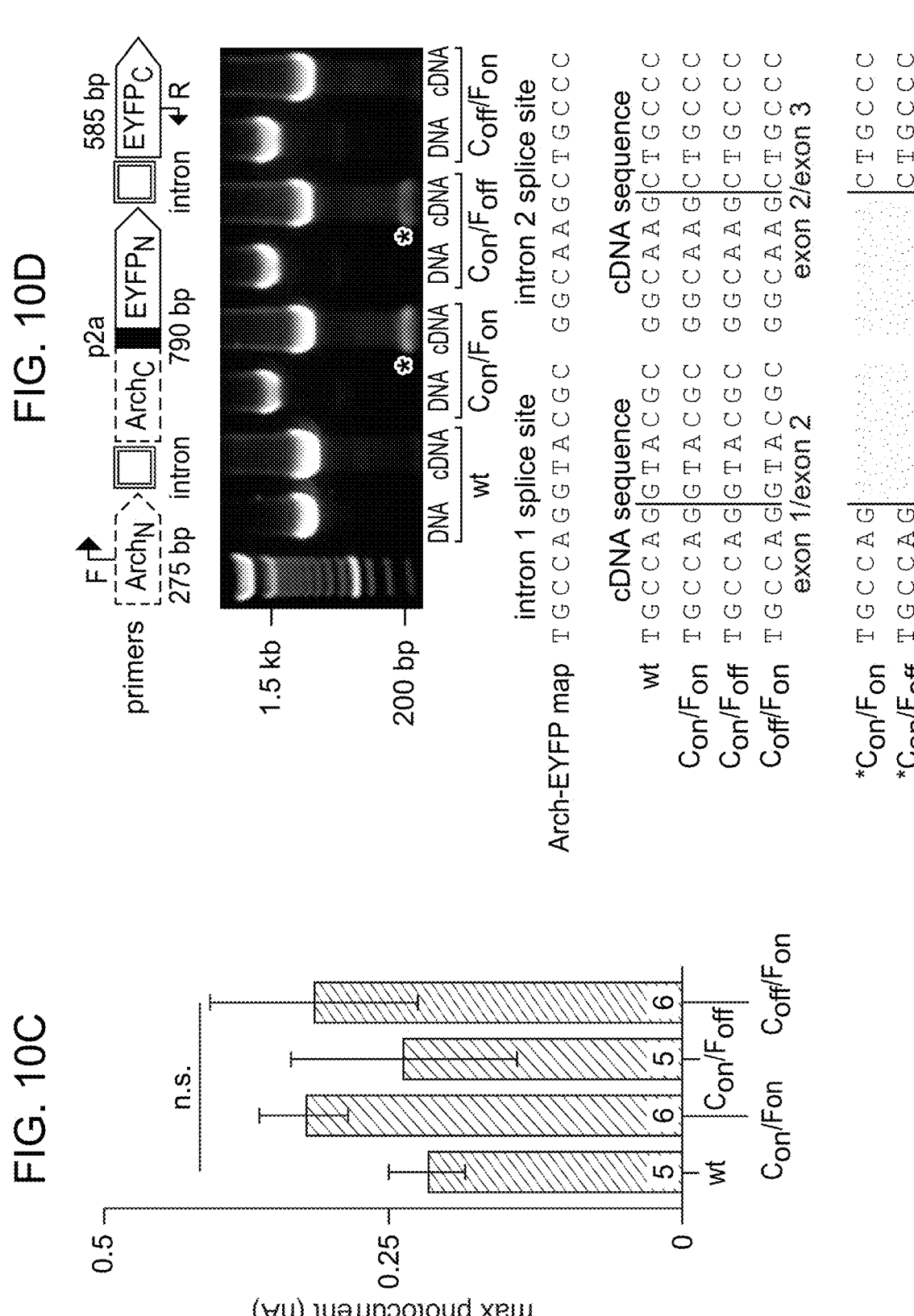
Figure 10F:
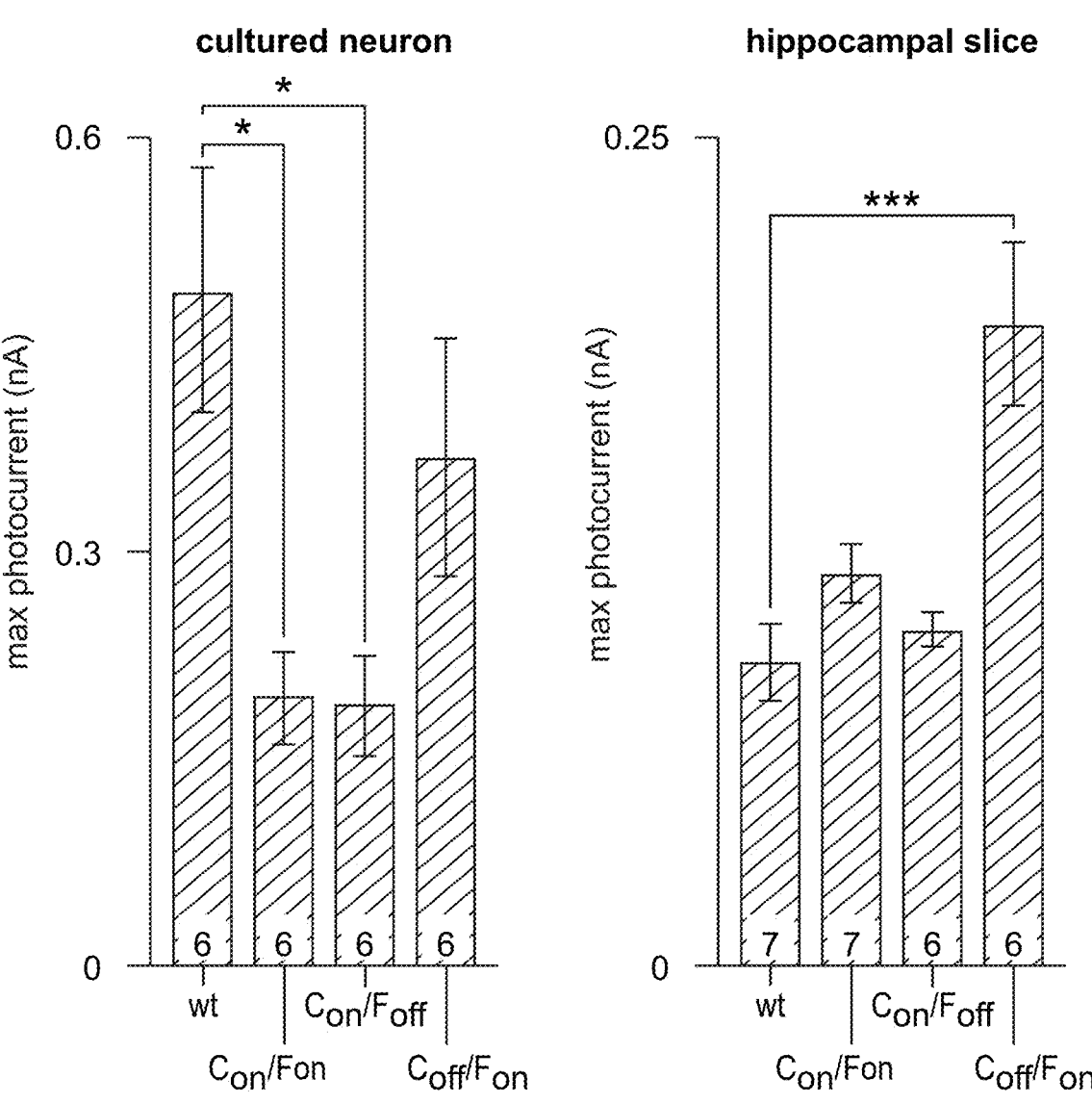
Figure 10G:
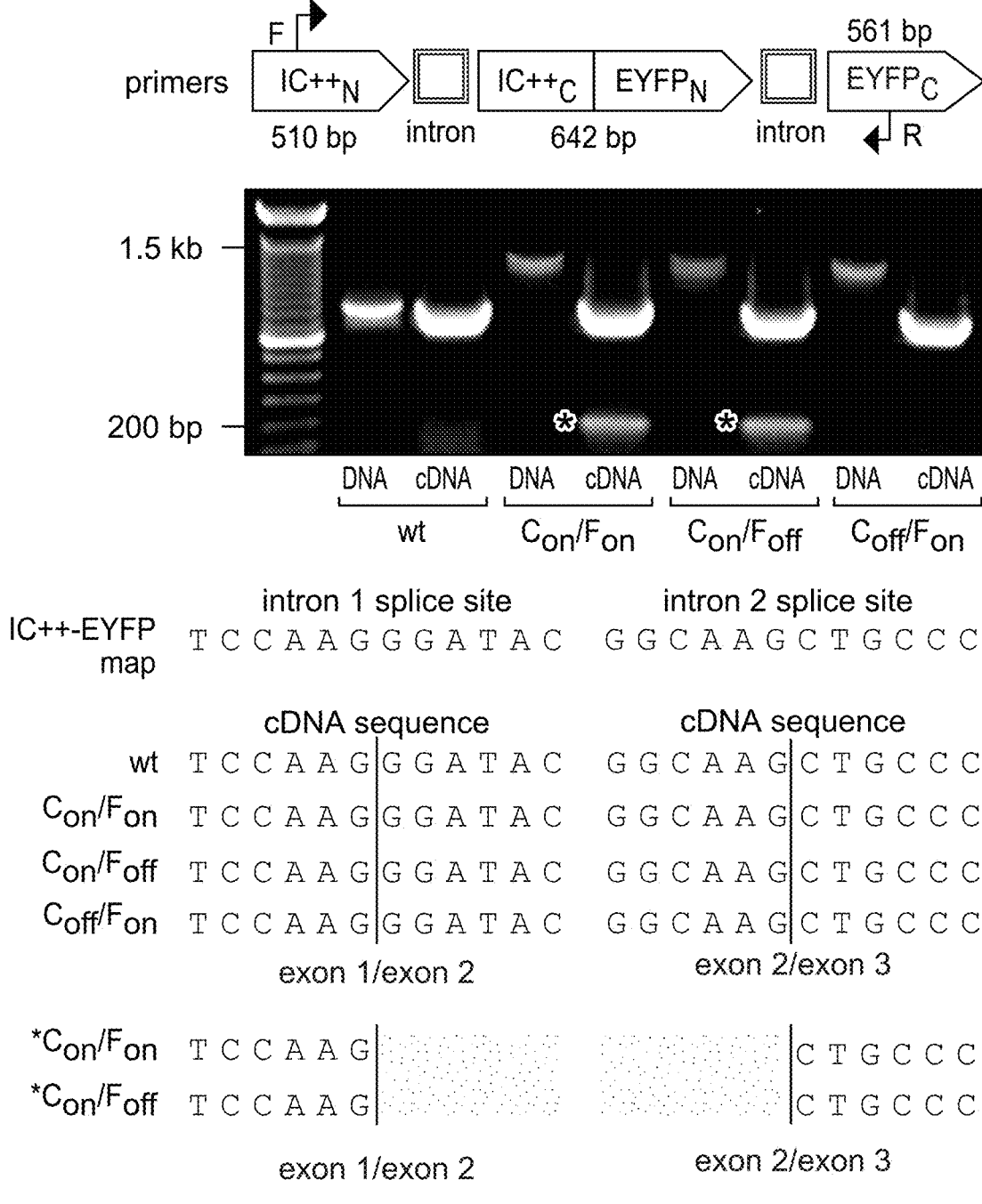
Figure 10I:
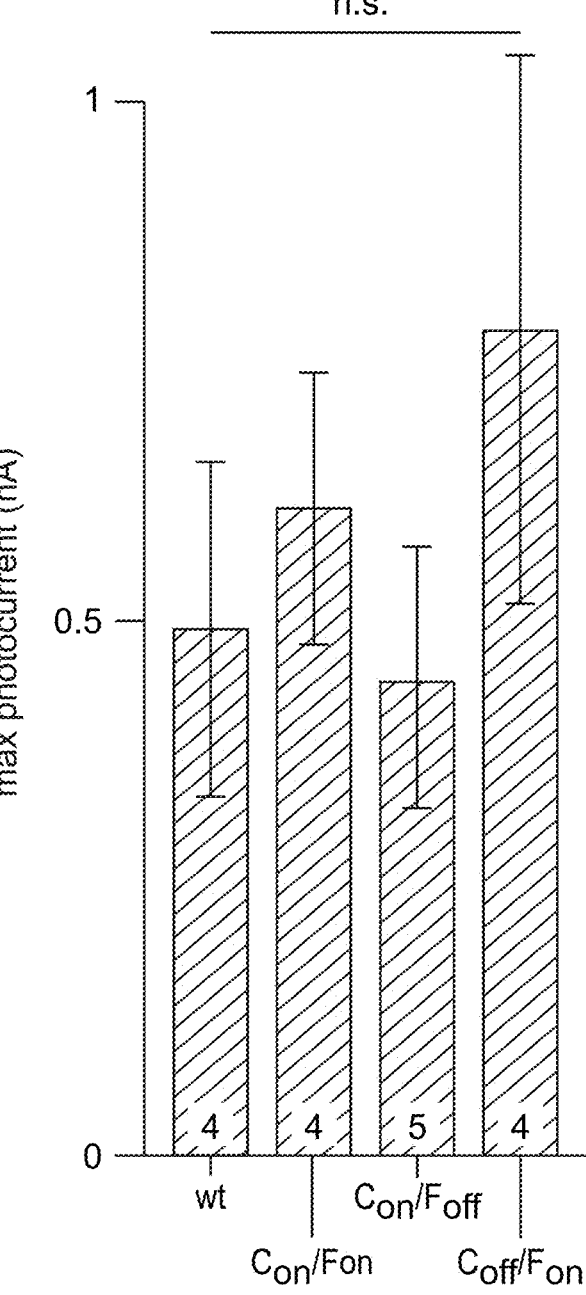

Functional evaluation of the toolbox was performed by class. Fluorophores were tested by flow cytometry, but images were taken for visualization (FIG. 7f,i,l). GECI were transfected in neuron primary cultures and assayed by field stimulation and imaging of single cells. All INTRSECT variants of all GECI (sRGECO, GCaMP6f, GCaMP6m) generated reliable fluorescent signal in response to field stimulation. To more thoroughly evaluate the function of this subset of INTRSECT tools, basal fluorescence, time-to-peak (TTP), signal-to-noise (SNR), delta F/F, and decay kinetics were further assayed. Basal expression in transfected neuron cultures broadly mimicked flow cytometry results, and was significantly decreased relative to parental tool in some cases (FIG. 8h,k; all vs. WT; sRGECO Con/Fon p<0.001, Con/Foff and Coff/Fon p<0.0001; GCaMP6m Coff/Fon p<0.05, ANOVA with Dunnett's test). Calcium signal magnitude (delta F/F) reflected differences in expression with lower basal fluorescence associated with higher-than-WT values (FIG. 8h,n; sRGECO Coff/Fon p<0.0005, GCaMP6f Coff/Fon p<0.001, ANOVA with Dunnet's test). Miscellaneous additional differences were noted sporadically, mostly in sRGECO. Whole cell electrophysiology recordings with photostimulation of INTRSECT opsin variants showed function that was indistinguishable from parental constructs (FIG. 9c,f,I,l; FIG. 10c,i), with the exception of Arch3.3-p2a-EYFP, where Con/Fon and Con/Foff had diminished photocurrents in culture (FIG. 10f—left, p<0.05 for both, ANOVA with Dunnett's test). To further characterize this discrepancy, adeno-associated virus (AAV) of the parental and INTRSECT Arch3.3-p2a-EYFP constructs were produced and these with AAV encoding activating recombinases (Ef1a-Cre, Ef1a-Flp, and Ef1a-Flp-2a-Cre) were co-injected into mouse hippocampus for further evaluation by slice electrophysiology. It was found that functional expression of INTRSECT Arch3.3-p2a-EYFP expressing neurons in slice were either equivalent or had higher photocurrent relative to WT Arch3.3-p2a-EYFP (FIG. 10f—right, Con/Fon p=0.3966, Con/Foff p=0.9286, Coff/Fon p<0.0001, ANOVA with Dunnett's test).

Together with EYFP and ChR2(H134R)-EYFP, the constructs that have been generated and described brings the total number of molecular tools available in INTRSECT configuration to 45. In addition to generating a large variety of INTRSECT constructs for precise, optical neuroscience, a pipeline for the production of additional constructs has been built to efficiently design constructs in silico that largely function well out of the box after cloning (FIG. 1g). In cases that mis-splicing did occur, problems were able to be identified and resolved early in the production process (FIG. 2a). The flow cytometry data largely matched functional expression data when constructs were paired with correct recombinases. A minor population of cells with residual expression was consistently identified 5d after transfection of Con/Foff constructs co-expressed with Cre and Flp, which likely reflects inefficiency of Flp relative to Cre. To further expand the range of experimental contexts available to targeting with Con/Foff, the next step included further characterizing and improving the Con/Foff configuration.

Improvement of the FRT cassette

Figure 3A:
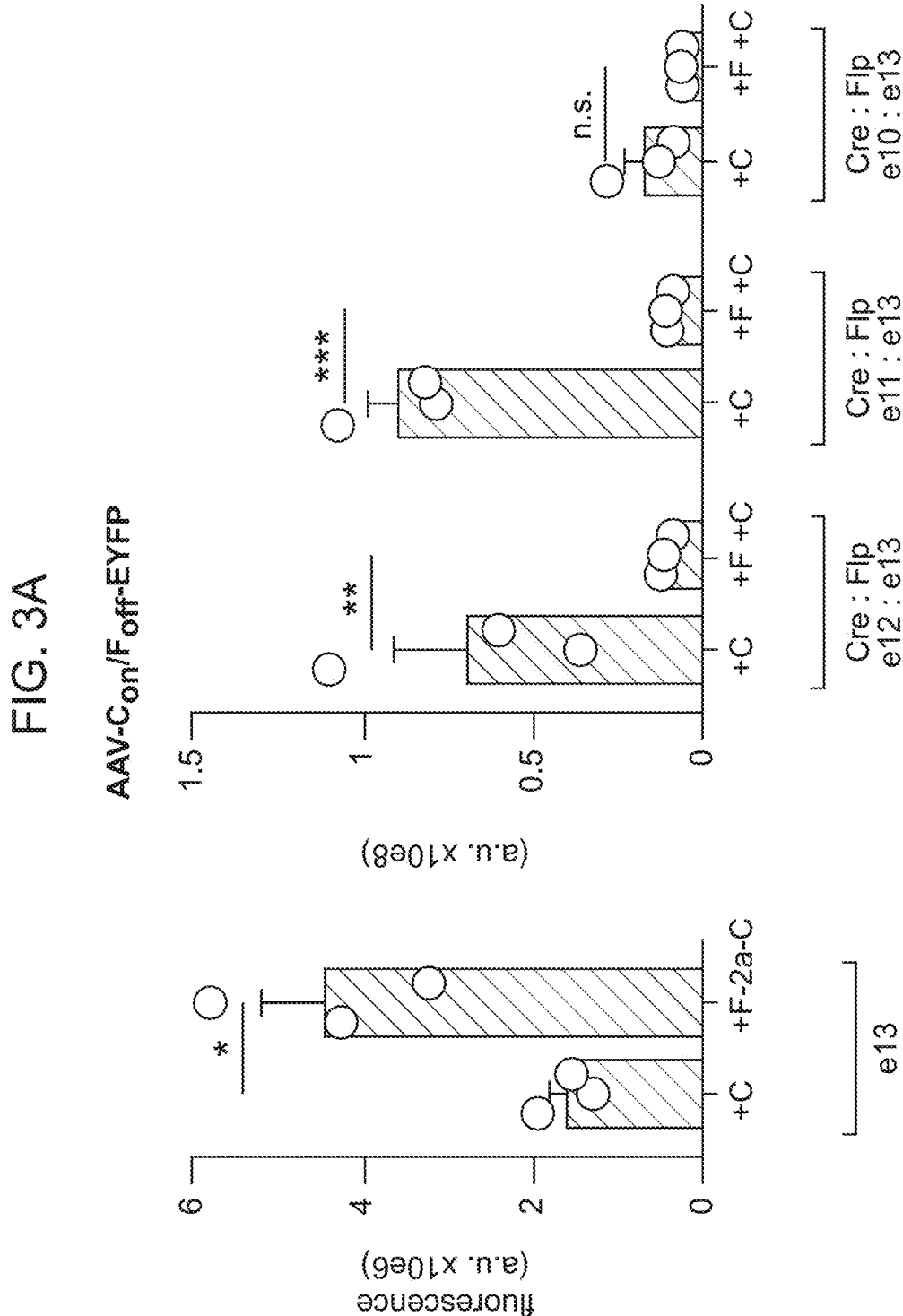
FIGS. 3A-3H depicts Con/Foff 2.0.

It was hypothesized that observed residual expression in some Con/Foff constructs co-expressing both Cre and Flp might result from the known inefficiency of Flp relative to Cre, characterized to be an order of magnitude less efficient at equimolar concentrations in vitro (Ringrose et al. (2017) supra). To test this directly, animals were co-injected with a fixed amount of AAV-Con/Foff-EYFP and either AAV-Cre or AAV-Flp-2a-Cre (FIG. 3a—left). EYFP signal was significantly increased in the AAV-Flp-2a-Cre condition relative to the AAV-Cre alone, potentially due to Cre toxicity in the AAV-Cre condition (see below). Next, the amount of viral Flp and Cre was varied by co-injecting a fixed amount of AAV-Con/Foff-EYFP with variable ratios of AAV-Cre and AAV-Flp. In contrast to the results with co-infection with AAV-Flp-2a-Cre, varying the individual titers of AAV-Flp and AAV-Cre, to increase the relative amount of Flp, resulted in robust extinction of EYFP expression in the Flp AND Cre condition, while high expression was maintained in a wide range of conditions injected with AAV-Cre alone (FIG. 3a—right). Taken together, these data show that the relative amounts of Cre and Flp must be taken into account when using Con/Foff INTRSECT viruses (and likely other multi-recombinase expression platforms), as there is a window of relative expression of Cre and Flp above which there will be over-expression in off-target populations and below which there will be under-expression in the on-target population.

Figure 3B:
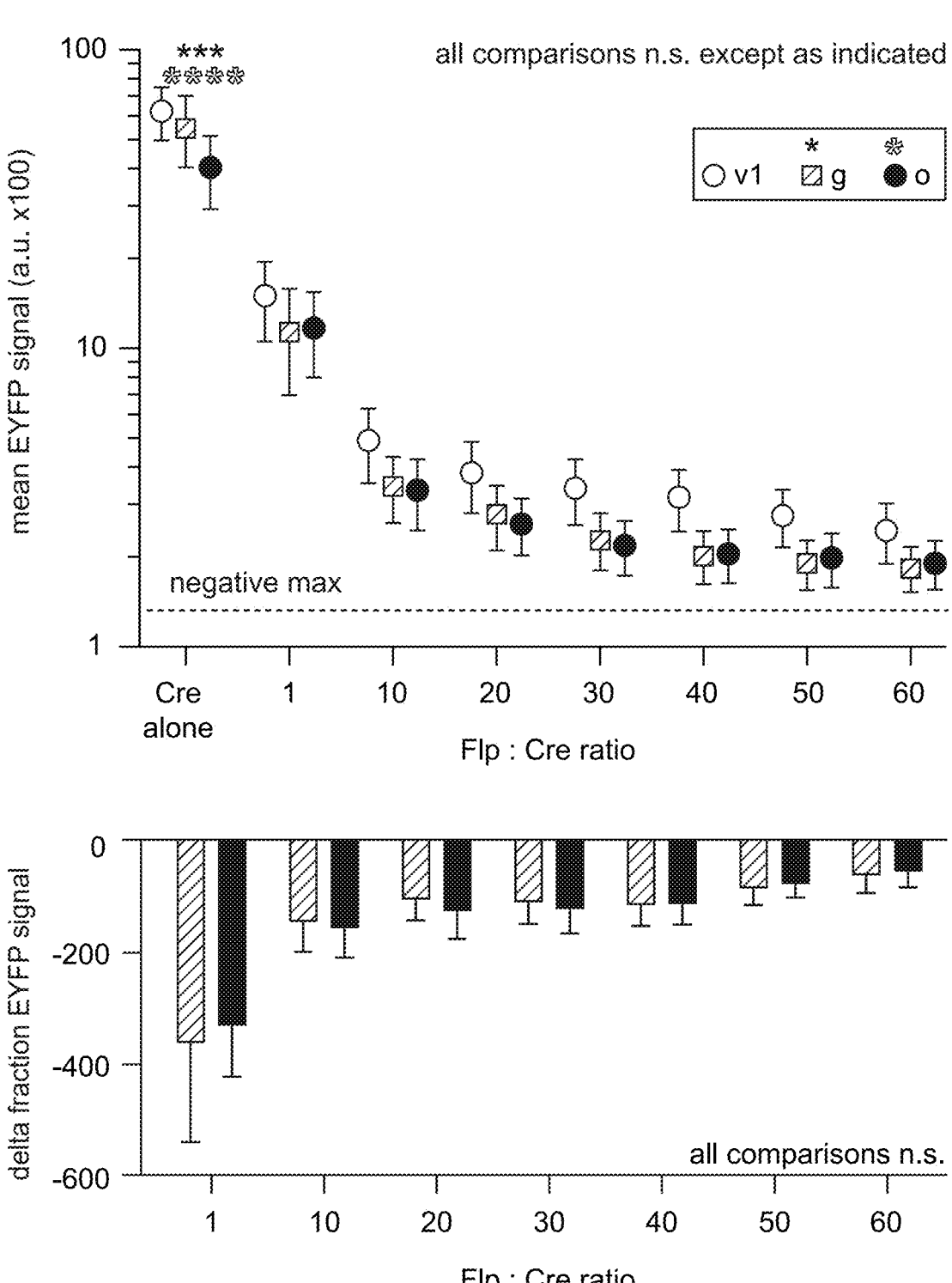
Figure 3C:
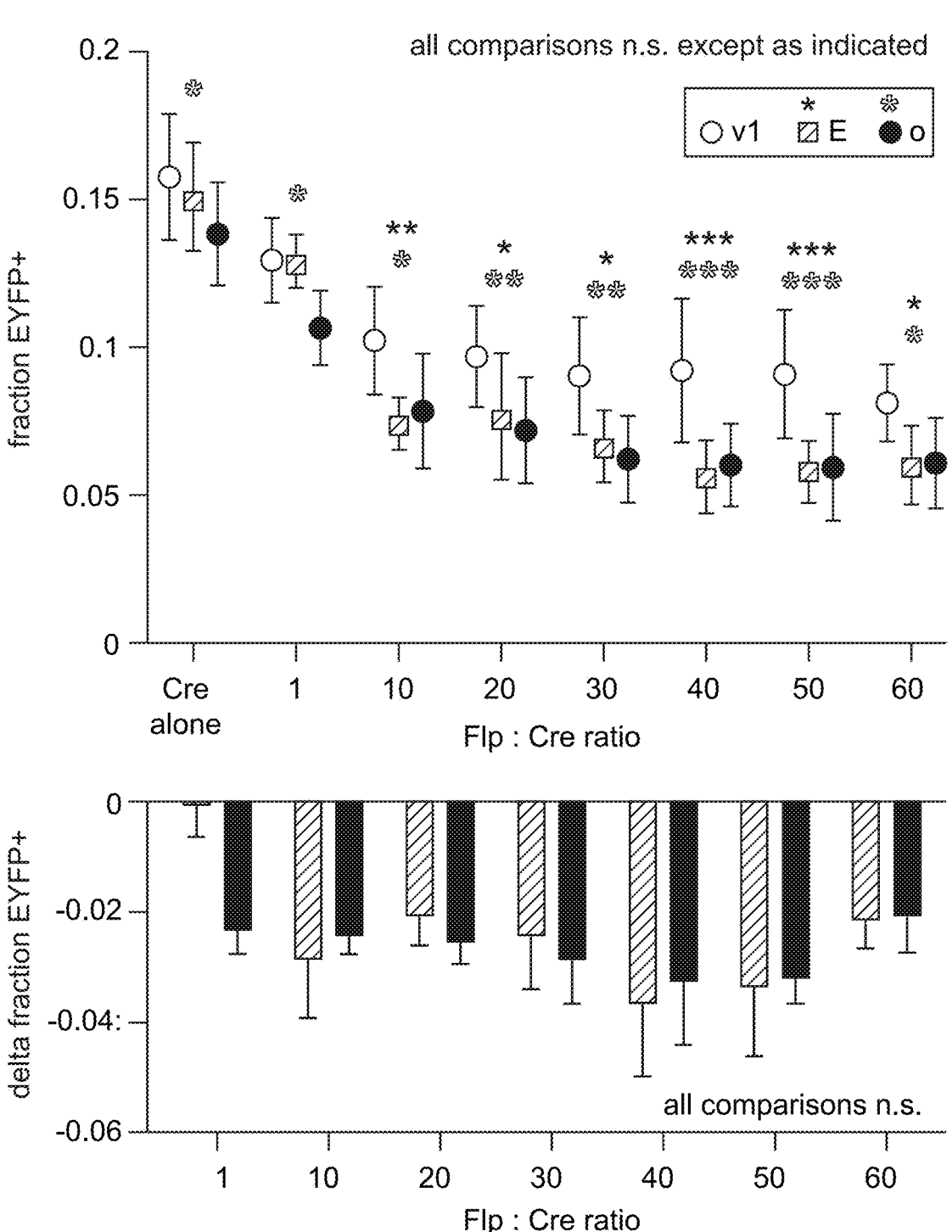
Figure 11A:
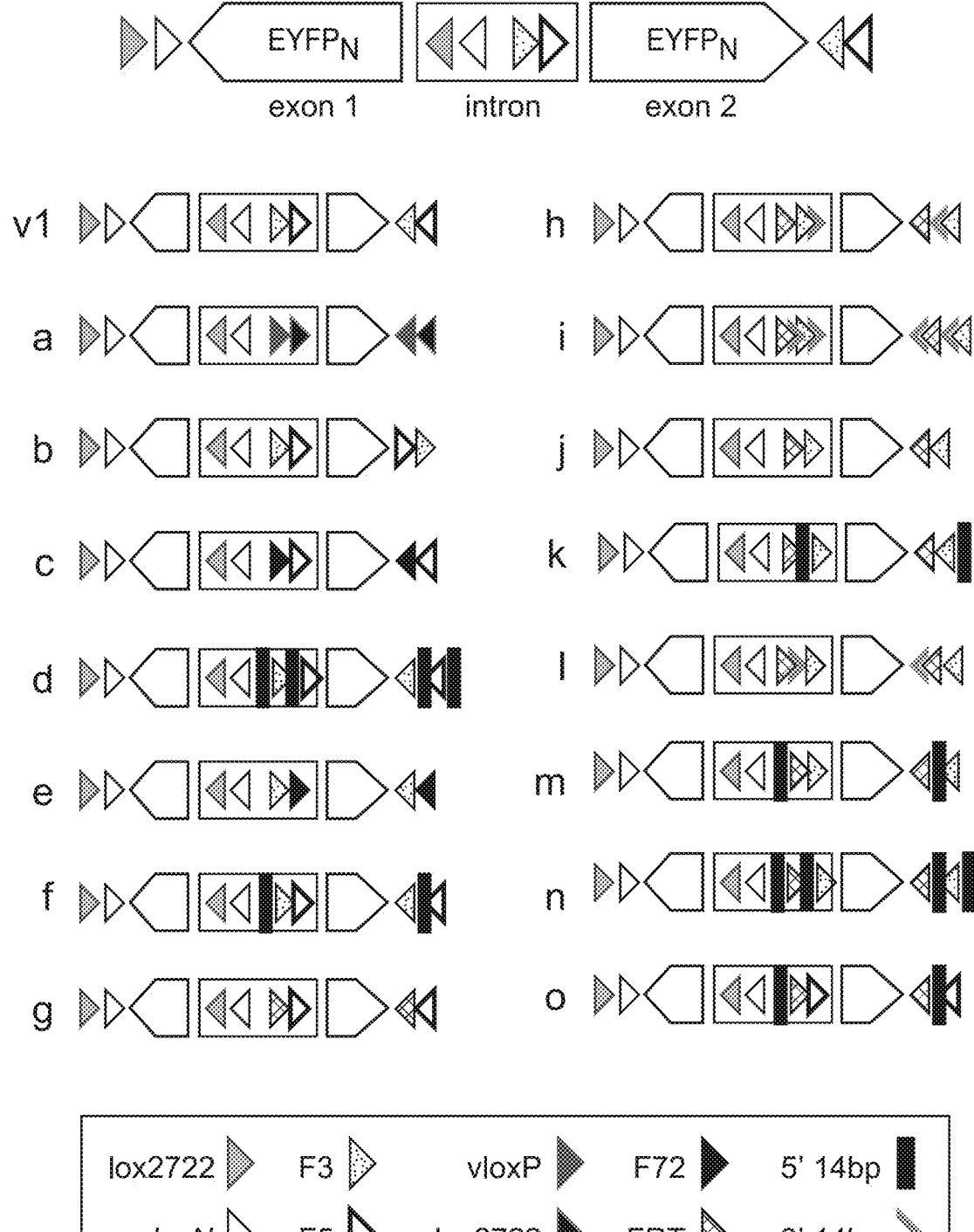
Figure 11C:
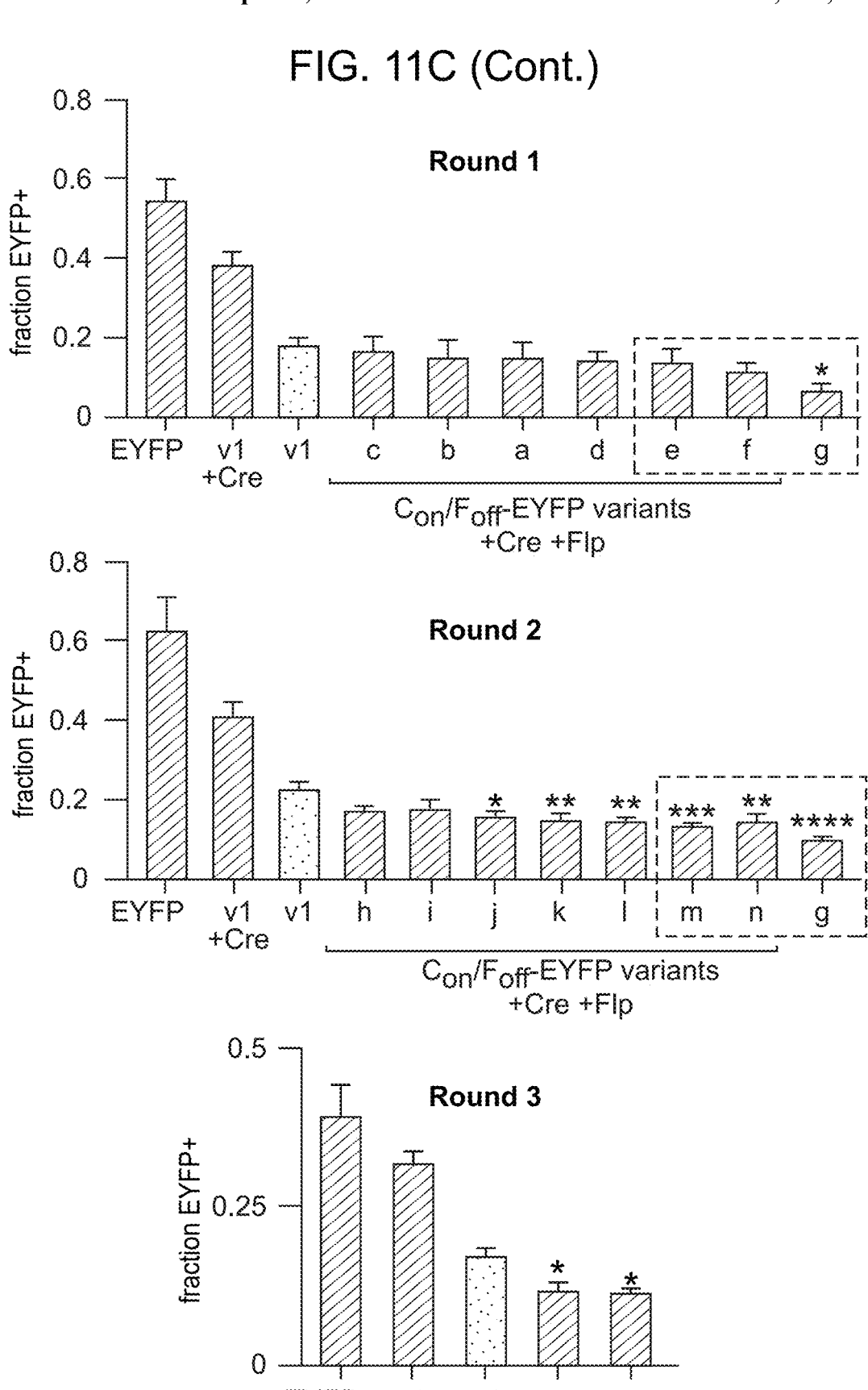

The next aim included expanding this window by screening Con/Foff variants containing modifications of the Flp-dependent elements for increased sensitivity to Flp-mediated recombination. The Flp-dependent cassette (FIG. 11a—top) utilizes two independent Flp recognition elements in the double-floxed inverted open-reading-frame (Atasoy et al. (2008) J Neurosci. 28:7025, Sohal et al. (2009) Nature 459:698) configuration to enable recombinase-dependent inversion of exons. The original INTRSECT design utilizes the F3 and F5 sequences (Schlake et al. (1994) Biochemistry 33:12746), chosen to avoid potential intermolecular recombination between virus and the genome of transgenic Cre-expressing animal lines, which may contain a residual FRT sequence. A rational screening approach that started with a wide range of Con/Foff-EYFP variants was used and promising ones were further modified (FIG. 11a—bottom). Flow cytometry was used to assay candidates in vitro and the mean EYFP intensity of the residual population as well as the percentage of the parent population that these residuals represent were evaluated (FIG. 11b). It was found that replacing the F3 site with FRT or a modified form of FRT containing an additional 14 bp palindromic sequence significantly decreased both the residual expression signal as well as the percentage of cells that continued to aberrantly express EYFP at 5d post-transfection (FIG. 11c). A next step involved assaying whether this improvement in function at an equimolar Flp:Cre ratio was maintained across other Flp:Cre ratios by comparing the original Con/Foff-EYFP to these two variants and systematically varying the relative amounts of Cre and Flp. Both variants maintained their improved expression pattern across a wide range of recombinase ratios (FIG. 3b,c—top). Increasing ratios of Flp:Cre beyond 1:1 continued to reduce residual expression, while ratios greater than 10:1 contributed marginal improvement as expression neared fitted floor values for both mean expression and fraction of the population with residual expression (r2 mean expression v1=0.8028, g=0.7114, o=0.6921; r2 fraction with residual expression v1=0.2793 g=0.5848, o=0.3983). The magnitude of the improvement was equivalent between these two variants (FIG. 3b,c-bottom; all p>0.25 ANOVA with Sidak's test).

Figures 3D, 3E:
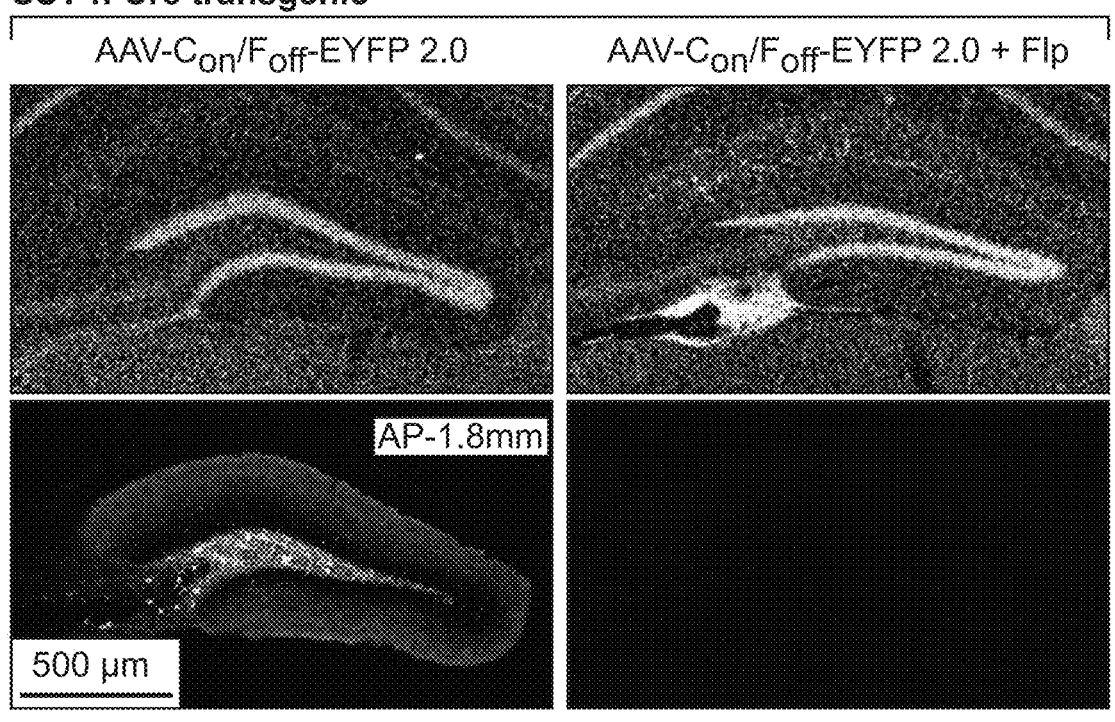
Figure 3F:
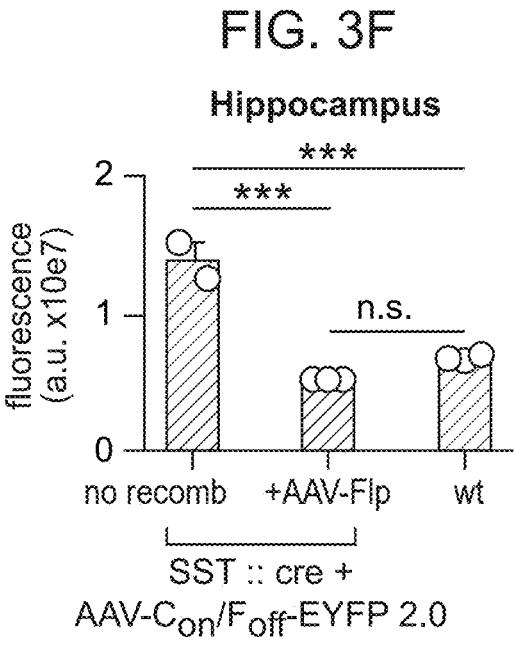
Figure 3H:
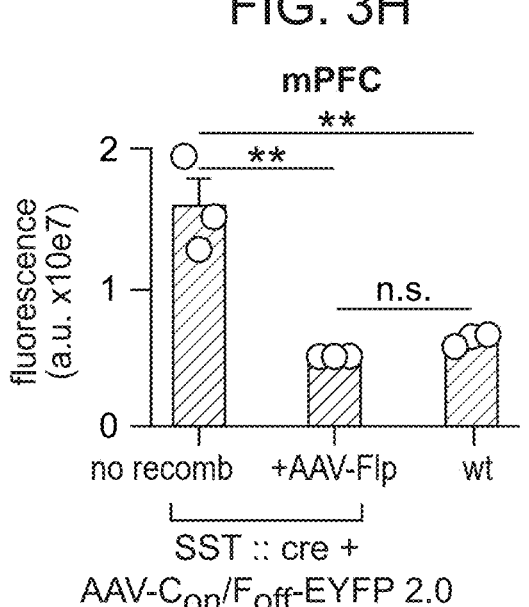
Figure 3G:
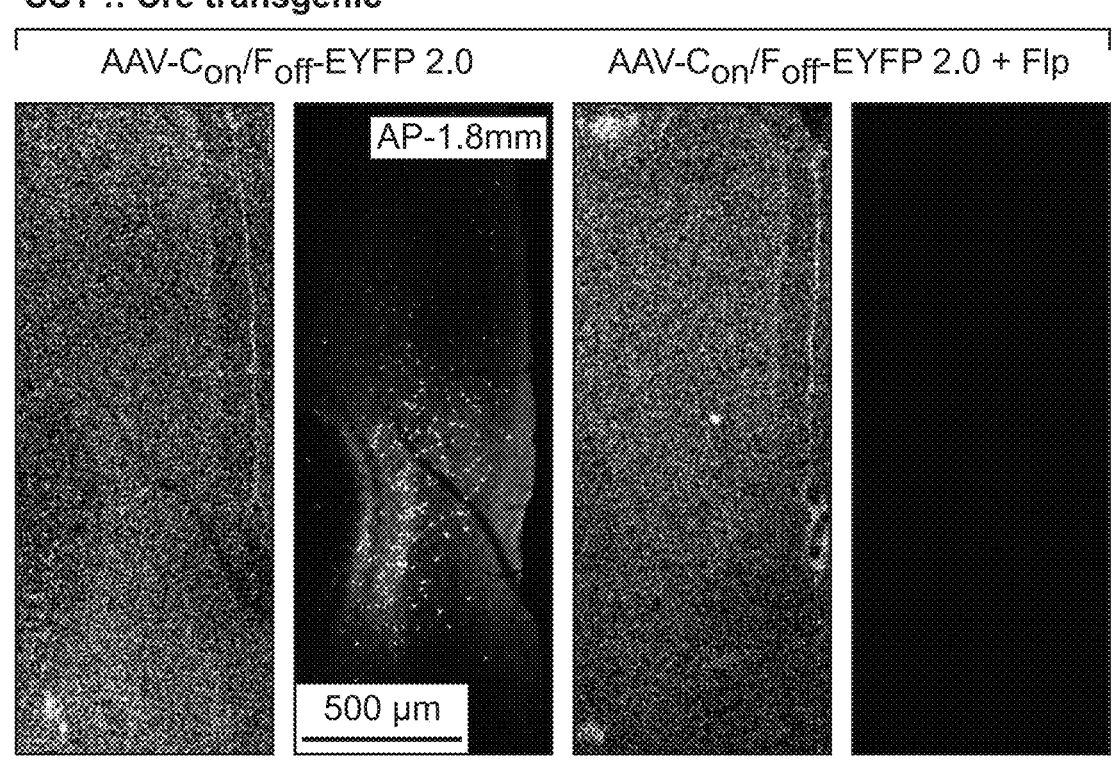
Figure 11D:
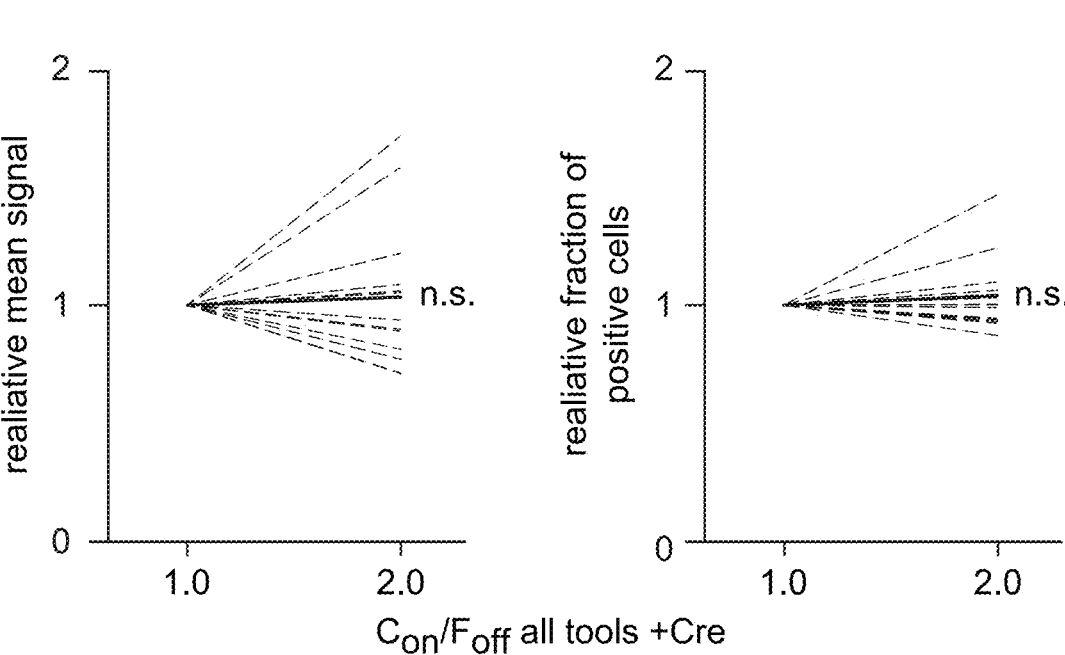
Figure 11E:
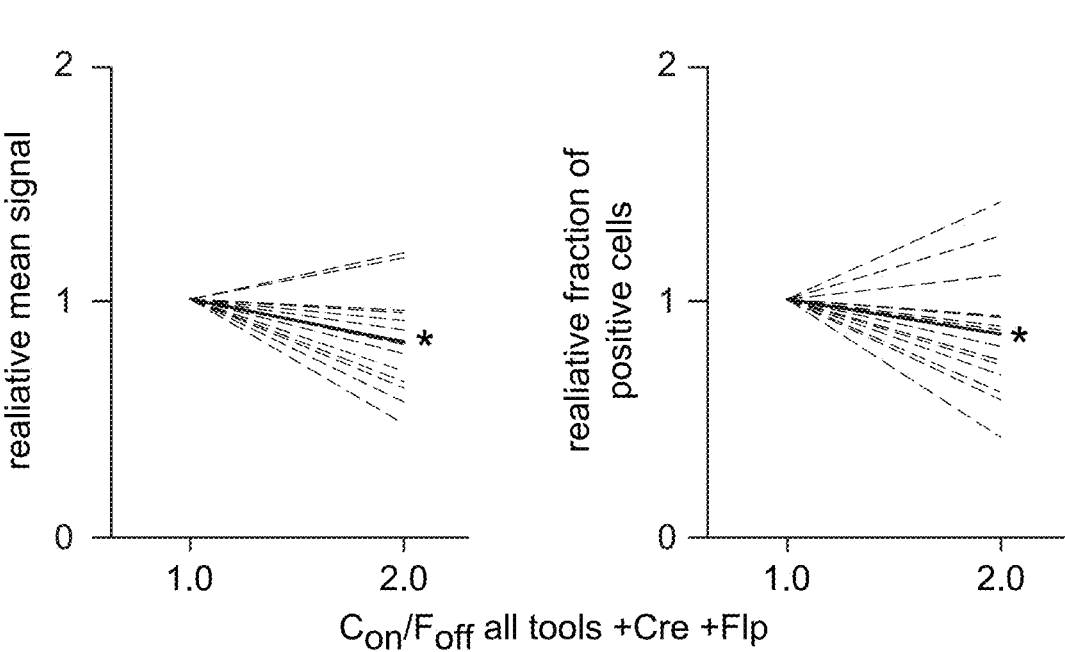

Next, as variants with consistently improved Flp-responsiveness in vitro had been identified, AAV was made to further assess function in vivo. Mouse mPFC was co-injected with either the original AAV-Con/Foff-EYFP or variants and equimolar AAV-Flp-p2a-Cre. In contrast to the original F3/F5-based Con/Foff-EYFP, both variants had reduced off-target expression relative to the Cre alone condition (FIG. 3d; 'v1' 2.213 relative expression, p=0.008, variant 'g' 0.9000 relative expression, p=0.3321, variant 'o' 0.8861 relative expression, p=0.4576, all unpaired t-tests). As these two variants appeared equivalent both in vitro and in vivo, the F5/FRT-based variant was chosen for simplicity and Con/Foff constructs with this cassette were designated '2.0'. To assess the function of Con/Foff-EYFP 2.0 in vivo, AAV-Con/Foff-EYFP 2.0 was injected into the mPFC and dorsal hippocampus of SST-Cre animals, either alone or with AAV-Flp (FIG. 3e-h); as hypothesized, robust expression of EYFP was observed when injected alone and extinguished expression that was indistinguishable from uninjected, wild-type controls when co-infected with Flp was observed. Last, this improved Flp cassette was integrated into all Con/Foff constructs from the comprehensive INTRSECT toolbox and the original (1.0) and improved (2.0) versions (FIG. 11d,e) were compared in all tools. As expected, no significant difference between original and improved versions were found in either the mean signal or fraction of positive cells in the active condition co-transfected with Cre alone (FIG. 11d; Con/Foff-EYFP 1.0 vs Con/Foff-EYFP 2.0, mean signal p=0.89, fraction positive cells p=0.50, paired t-tests). In contrast, when co-transfected with equimolar amounts of Cre and Flp, the 2.0 constructs performed significantly better than their 1.0 counterparts (FIG. 11e; Con/Foff-EYFP 1.0 vs Con/Foff-EYFP 2.0, mean signal p=0.02, fraction positive cells p=0.035, paired t-tests). This characterization of the Flp cassette, and the function of the INTRSECT Con/Foff backbone in particular, illustrate the importance of controlling for potential off-target expression, as well as provide a practical evaluation framework to enable wider adoption of the INTRSECT expression platform specifically, and Flp-dependent constructs more generally.

Modeling INTRSECT Virus Kinetics In Vivo Using a Novel, Spectroscopy Device

Figure 4A:
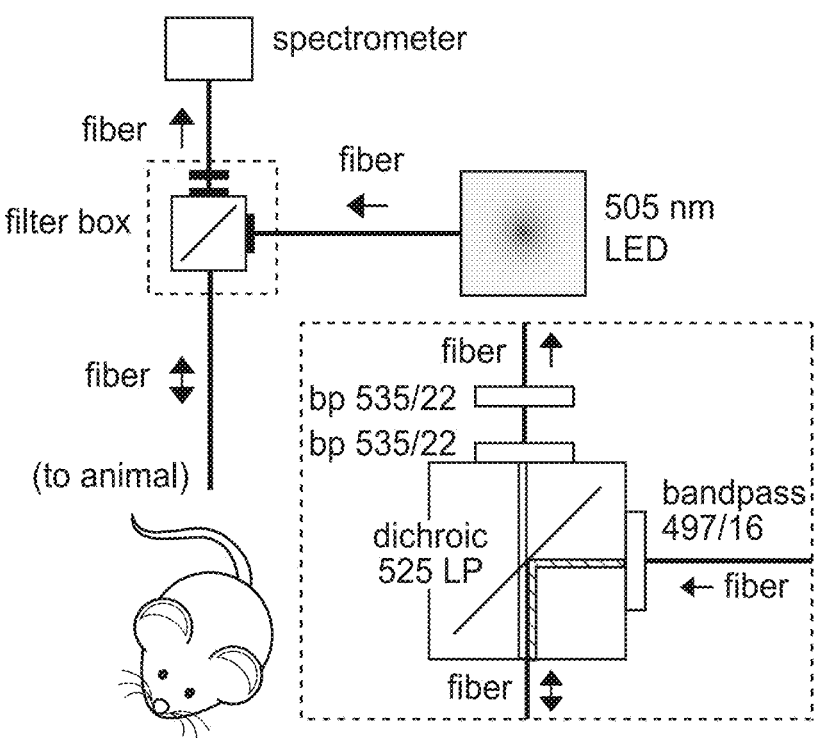
Figure 4B:
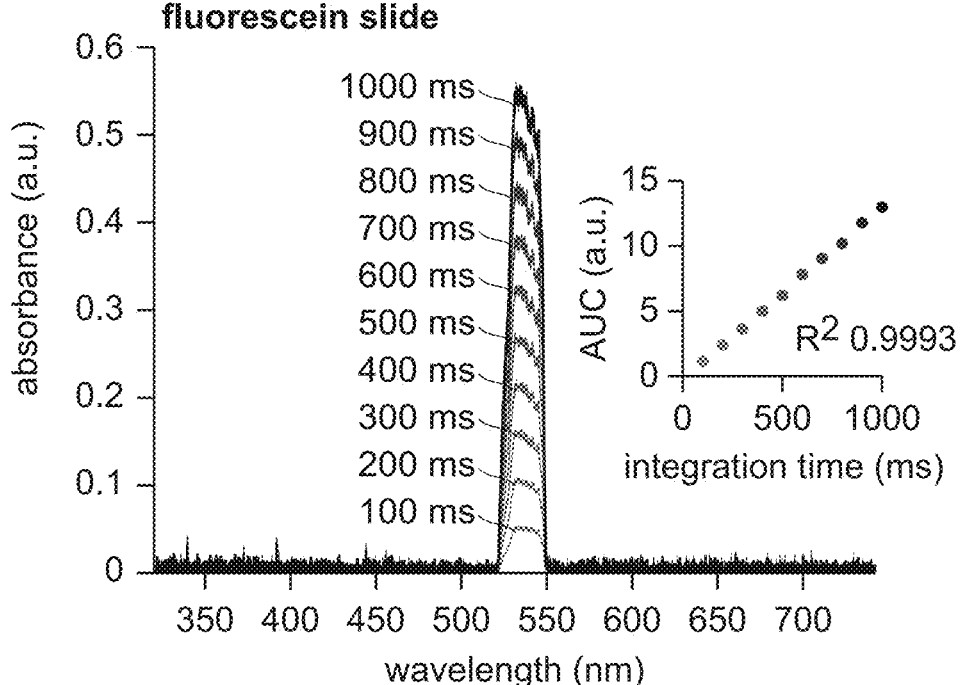
Figure 4G:
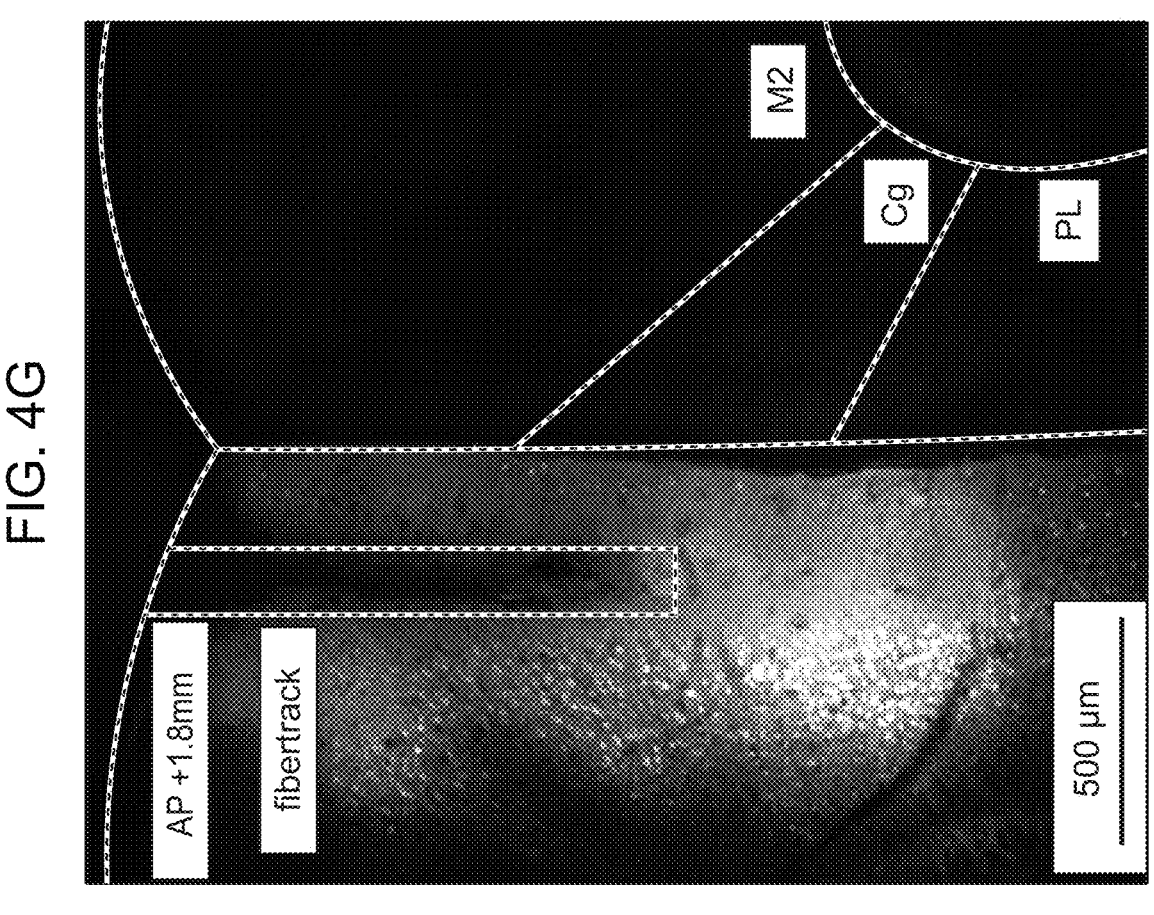
Figure 4F:
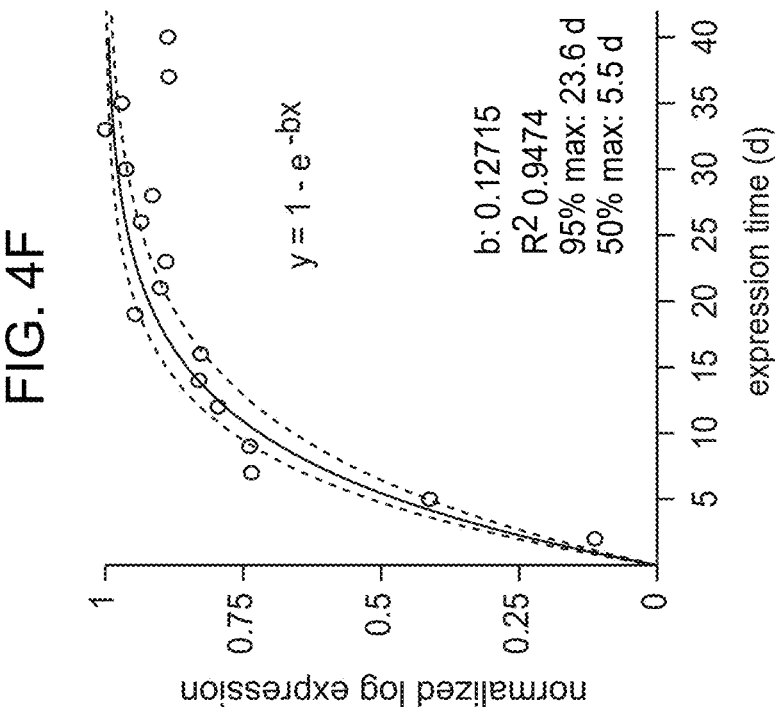

Next, attention was turned to characterizing the in vivo dynamics of INTRSECT viruses. The expression kinetics of AAV8 have been previously characterized by histology (Reimsnider et al. (2007) Mol Ther. 15:1504, Klein et al. (2006) Mol Ther. 13:517) showing that expression velocity peaks sometime between weeks two and three followed by expression plateau. There has not been a study describing the expression time course of commonly employed optical tools in vivo; this knowledge void is one of a number of viral expression parameters that has not been rigorously characterized and has led to variation in experimental design across optogenetic experiments, with typical expression times of between two and four weeks. As behavioral experiments are frequently conducted over days to weeks, not waiting until peak viral expression may result in recruitment of different populations of neurons as expression builds over time, or, conversely, recruiting fewer neurons if expression falls over time. To remedy this data void, an inexpensive device was constructed using off-the-shelf components. The device assays fluorophore expression through an implanted optical fiber (e.g. a typical 200 um fiber used for optogenetic experiments), uses a LED for optical stimulation and a visible wavelength spectrometer for read-out (FIG. 4a). This device has a linear relationship between spectrometer integration time and the area under the curve ('AUC'; FIG. 4b; $R^2=0.9993$). This linear relationship holds for integration times within the dynamic range of the device (e.g. non-zero, non-saturated) in vivo, in virally-expressed EYFP (FIG. 4c,d; $R^2=0.9997$). To assay expression over weeks, a wide range of integration times was chosen to enable sensitivity to low expression (with longer integration times) while maintaining the ability to quantify high expression (with shorter integration times). Next steps included calculating AUC for integration times within the dynamic range of the spectrometer, normalizing to the integration time, then averaging the values to create a daily 'expression score' (FIG. 4e). These scores ranged across multiple orders of magnitude, so to pool data across animals and model expression, the scores were log-transformed and normalized (FIG. 4f), which allowed the modeling of expression using an exponential equation. The histologic appearance of EYFP expression was typical for an animal with implanted fiber optic (FIG. 4g).

Figure 4H:
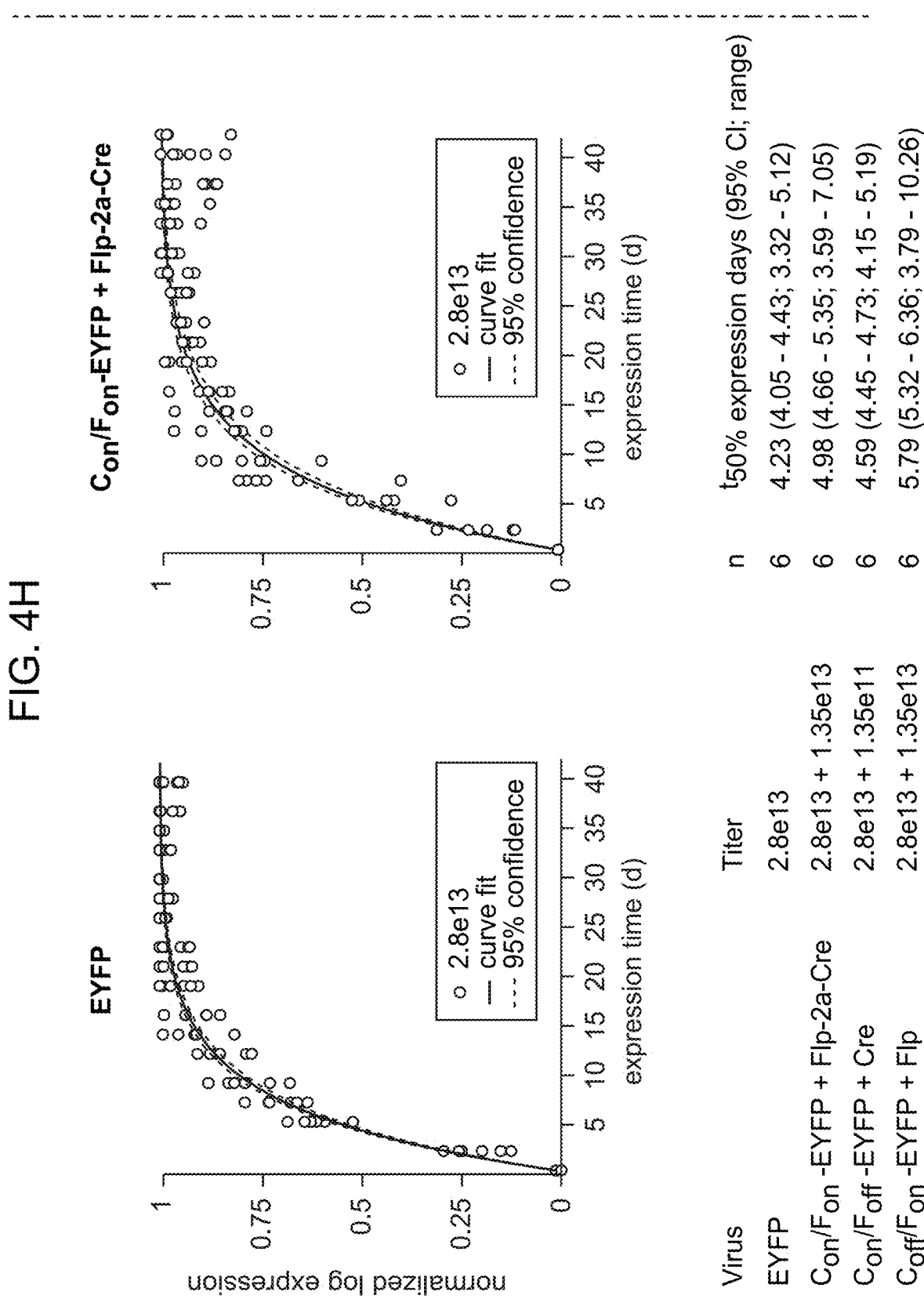
Figure 4H:
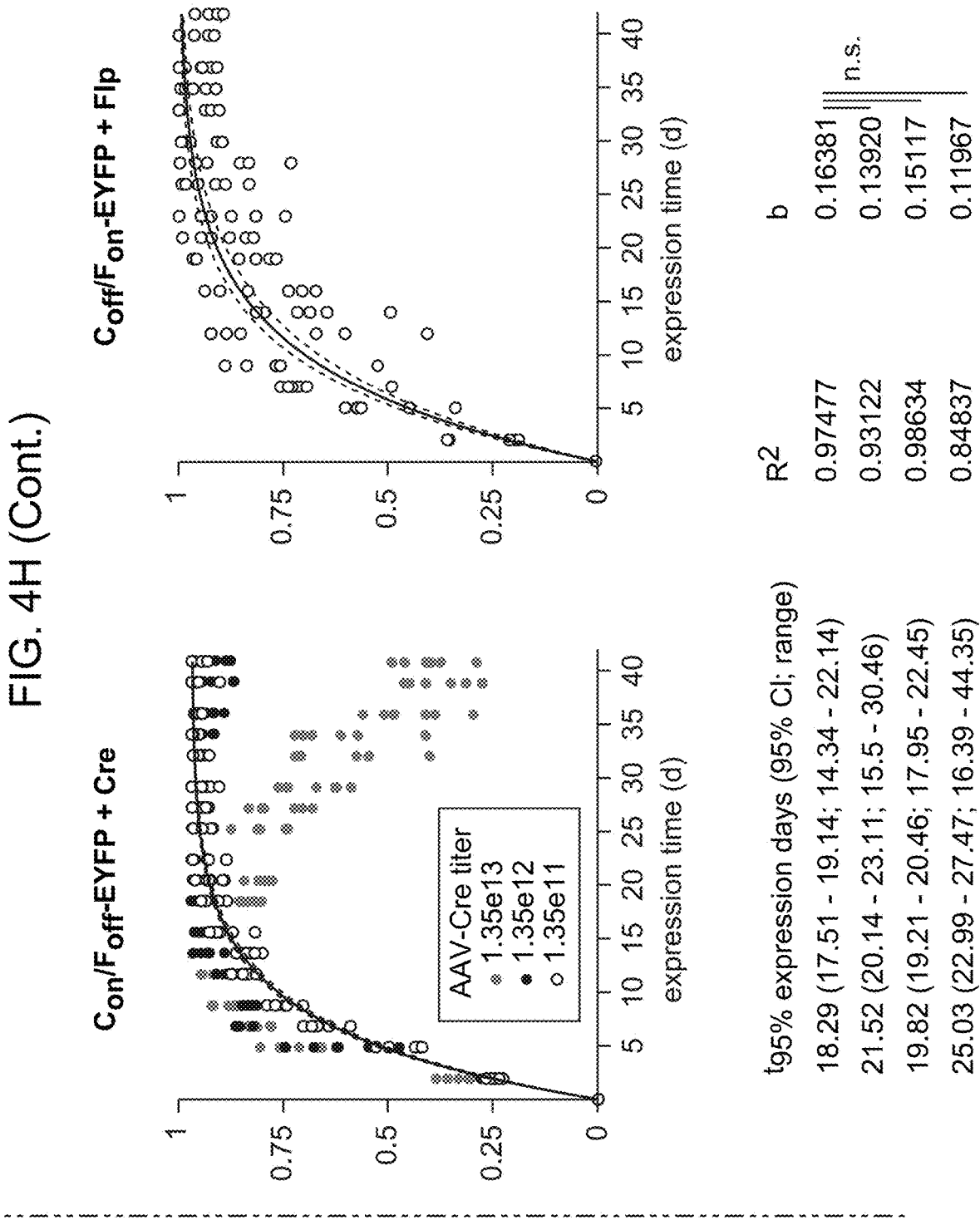
Figure 11F:
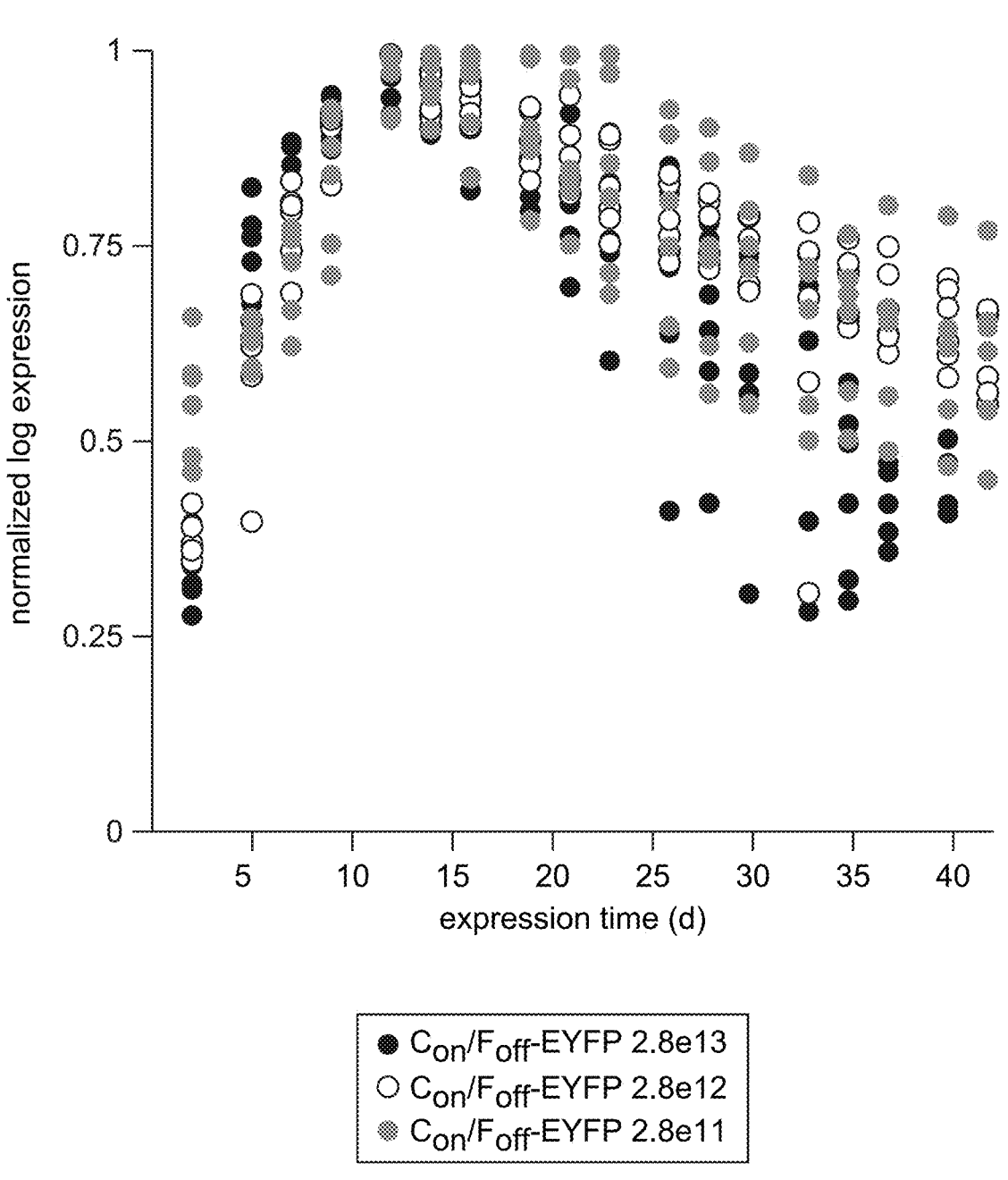

Having established a robust system for assaying expression in vivo, this approach was applied to the three INTR- SECT logical configurations to characterize their expression kinetics and compare them to WT EYFP. Cohorts of animals injected with (all AAV-EF1a-) EYFP, Con/Fon-EYFP+Flp-2a-Cre, Con/Foff-EYFP+Cre, or Coff/Fon-EYFP+Flp were prepared (FIG. 4h). Expression of EYFP was measurable after 2d post-injection and rapidly increased over the first two weeks, before reaching 95% of max expression between weeks two and three. INTRSECT viruses co-injected with recombinases exhibited similar expression kinetics. The fitted expression rate constants for Con/Fon-EYFP, Coff/Fon-EYFP, and Con/Foff-EYFP did not differ significantly compared to non-recombinase-dependent control EYFP (FIG. 4h, column 'b'; all vs. WT, WT b=0.1638, Con/Fon b=0.1392 p=0.4775, Con/Foff b=0.1512 p=0.7728, Coff/Fon b=0.1197 p=0.1380, ANOVA with Dunnett's test). A decrease in the fluorescence readout at high titers (after 26 days for 1×10e12 and after 14 days for 1×10e13) of Cre recombinase (FIG. 4h) was noted, indicating high viral expression of Cre was toxic. This toxicity was not observed with Cre at a titer of 1×10e11, or of Flp or Flp-2a-Cre at high titer (1×10e13). Separate cohorts with co-injections of lower titers of Con/Foff-EYFP and Cre at 1×10e13 show that this toxicity is a result of Cre expression, and not INTRSECT virus toxicity (FIG. 11f).

Figure 4I:
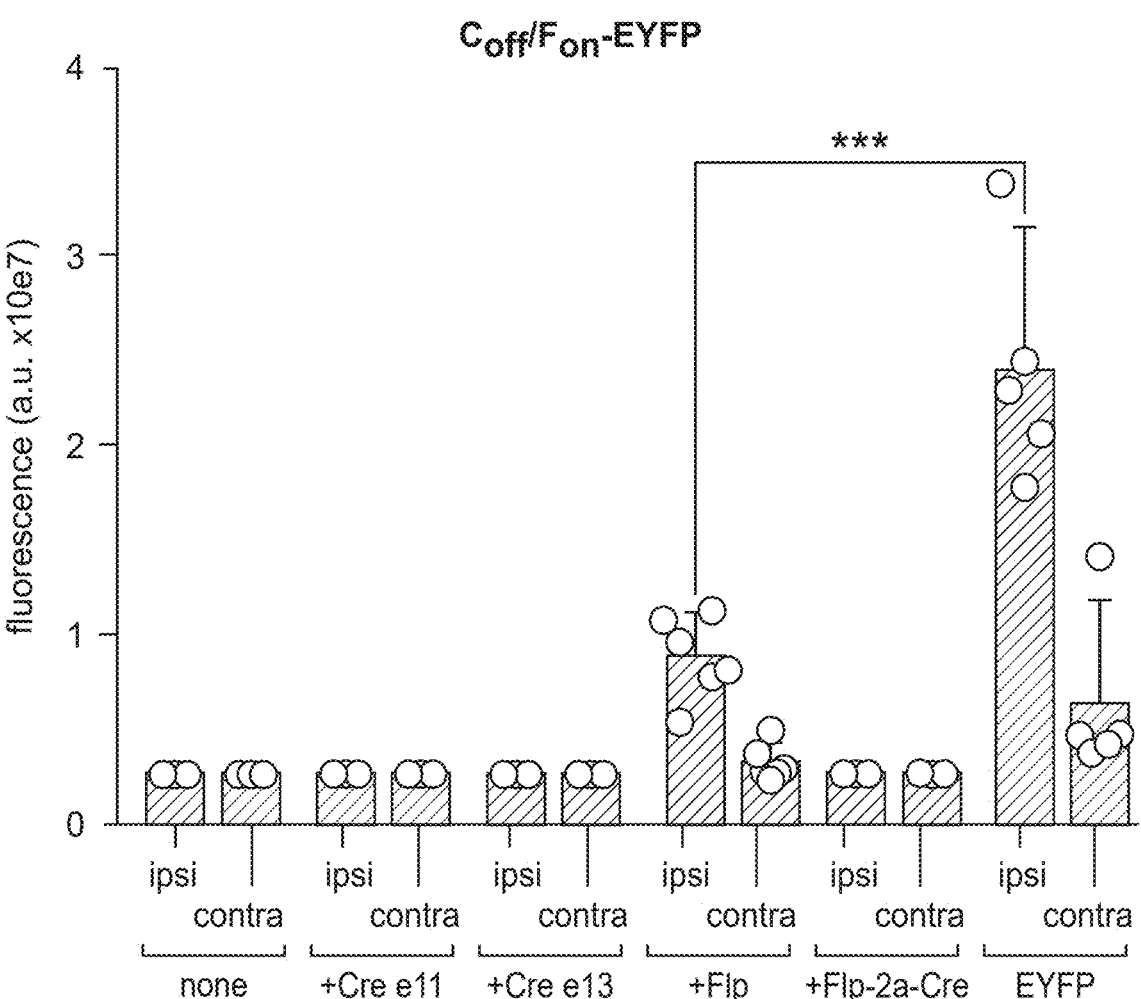
Figure 11G:
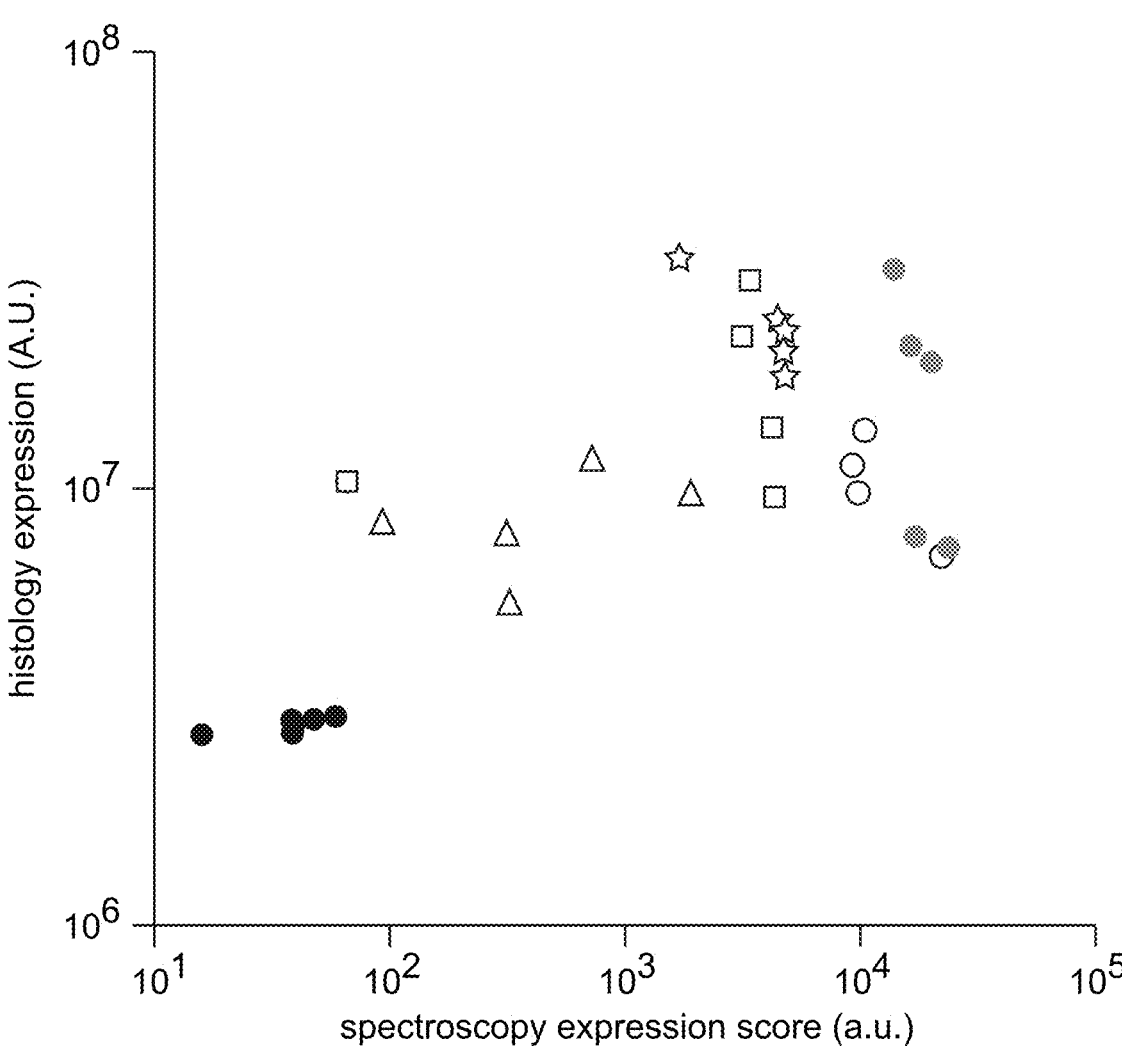

Last, the cohort was used as an opportunity to confirm the expression profile of INTRSECT viruses using a sensitive reporter (EYFP) and efficient actuator (viral recombinase). Separate cohorts were injected with EYFP INTRSECT viruses paired with no recombinase, AAV-Cre alone, AAV-Flp alone, and AAV-Flp-2a-Cre. Cre was injected at both 1×10e11 and 1×10e13, based on previous observations of toxicity with high viral Cre titers. As expected, consistent, high expression in all viruses was seen when paired with their activating recombinases (FIG. 4i); it was notable that AAV-Coff/Fon-EYFP was lower than control AAV-EYFP at equal viral titers (p=0.0003, unpaired t-test). As expected, no off-target expression with AAV-Con/Fon-EYFP or AAV-Coff/Fon-EYFP was observed with any combination of viral recombinases, while co-infection of AAV-Con/Foff-EYFP 2.0 with AAV-Flp-2a-Cre exhibited some residual expression, consistent with prior results (FIG. 3d-h). Comparison of post-hoc confocal imaging results with the last in vivo spectroscopy expression score yielded a positive correlation (FIG. 11g; r=0.7157, p<0.0001, n=30, Pearson correlation). Taken together, the detailed description of the expression patterns over time of multiple AAV, both recombinase-dependent and non-recombinase-dependent, showcases the utility of chronic expression profiling and reveals that, at these titers, recombinase-dependence does not slow viral expression kinetics. The control experiments and histological analysis highlight the specificity of the INTRSECT strategy.

Flp-Expressing Transgenic Mouse Lines for Intersectional Neuroscience

INTRSECT is designed to be a flexible approach that can be integrated with any combination of molecular tool and recombinase expression platform. To facilitate a wide range of experimental designs, academic publications, commercial mouse repositories, and publicly-funded transgenic production projects were searched in order to inventory all of the reported Flp-expressing mouse lines (FIG. 5). 33 mouse lines that represent a total of 27 separate gene targets were found. Of these, five different lines have already been used experimentally with INTRSECT.

Extension of INTRSECT to Three Recombinase-Based Targeting

Figure 12A:
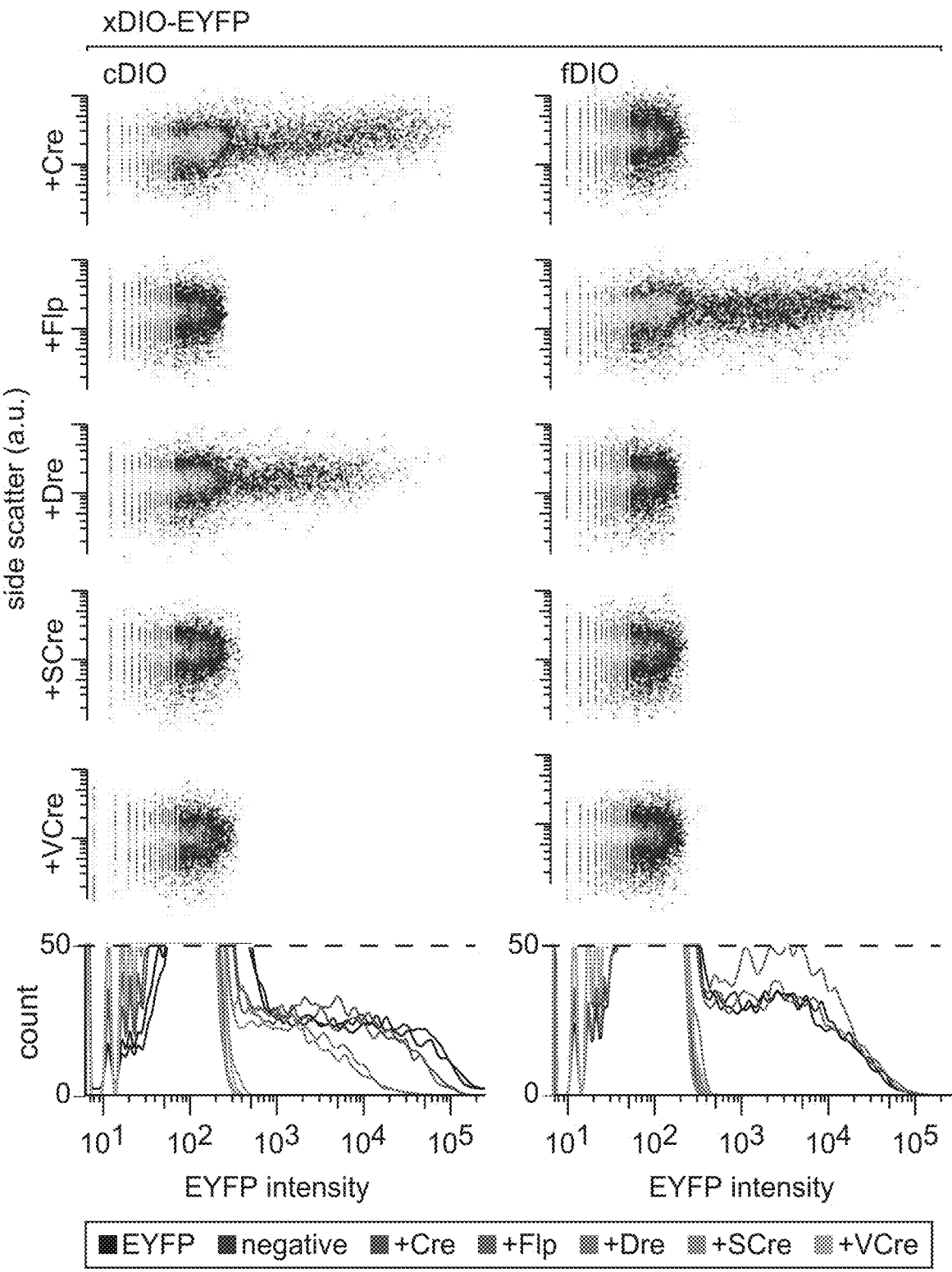
FIGS. 12A-12C depicts identifying and validating a recombinase orthologous to Cre and Flp.
Figure 12A:
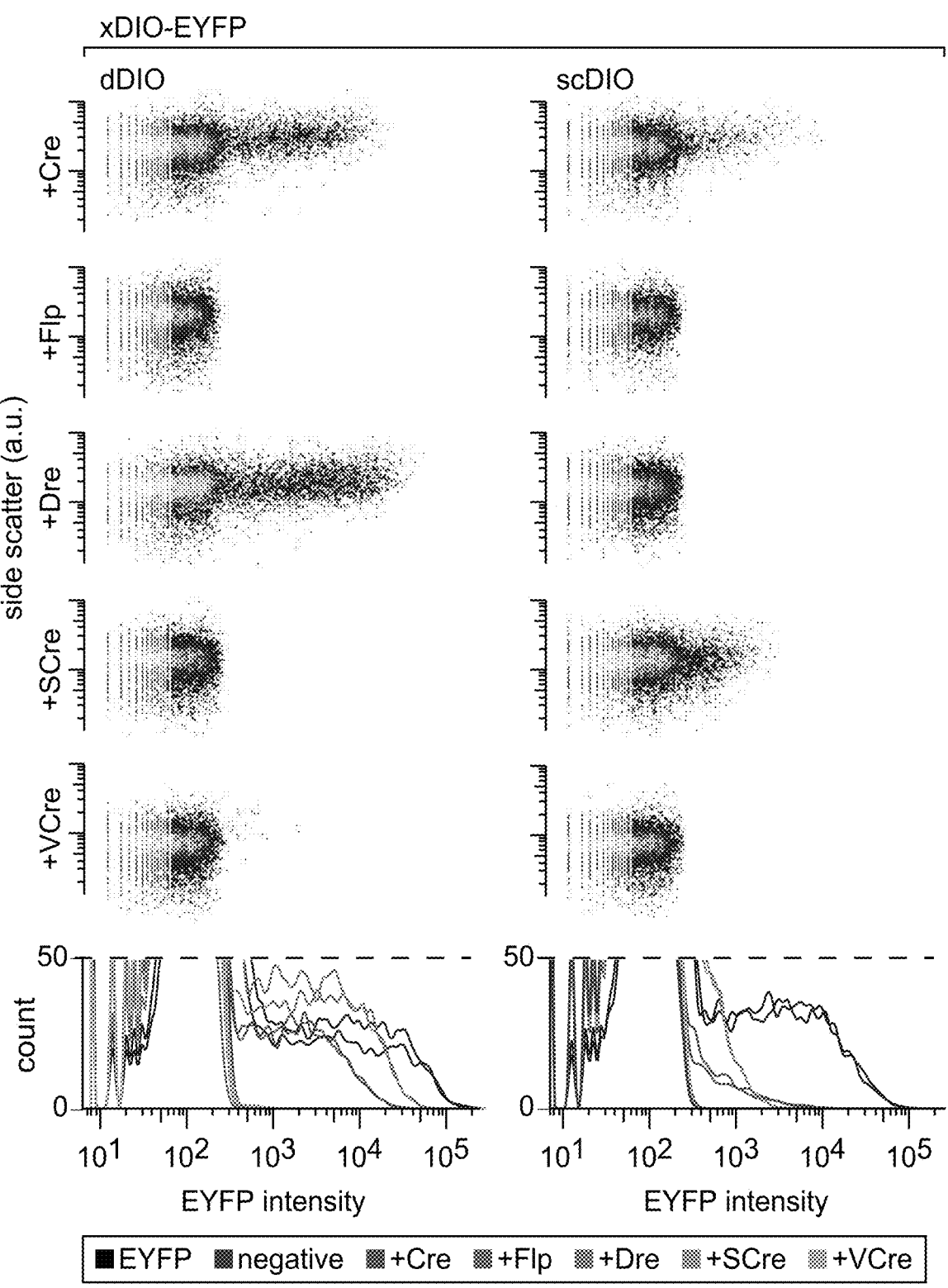
Figure 12A:
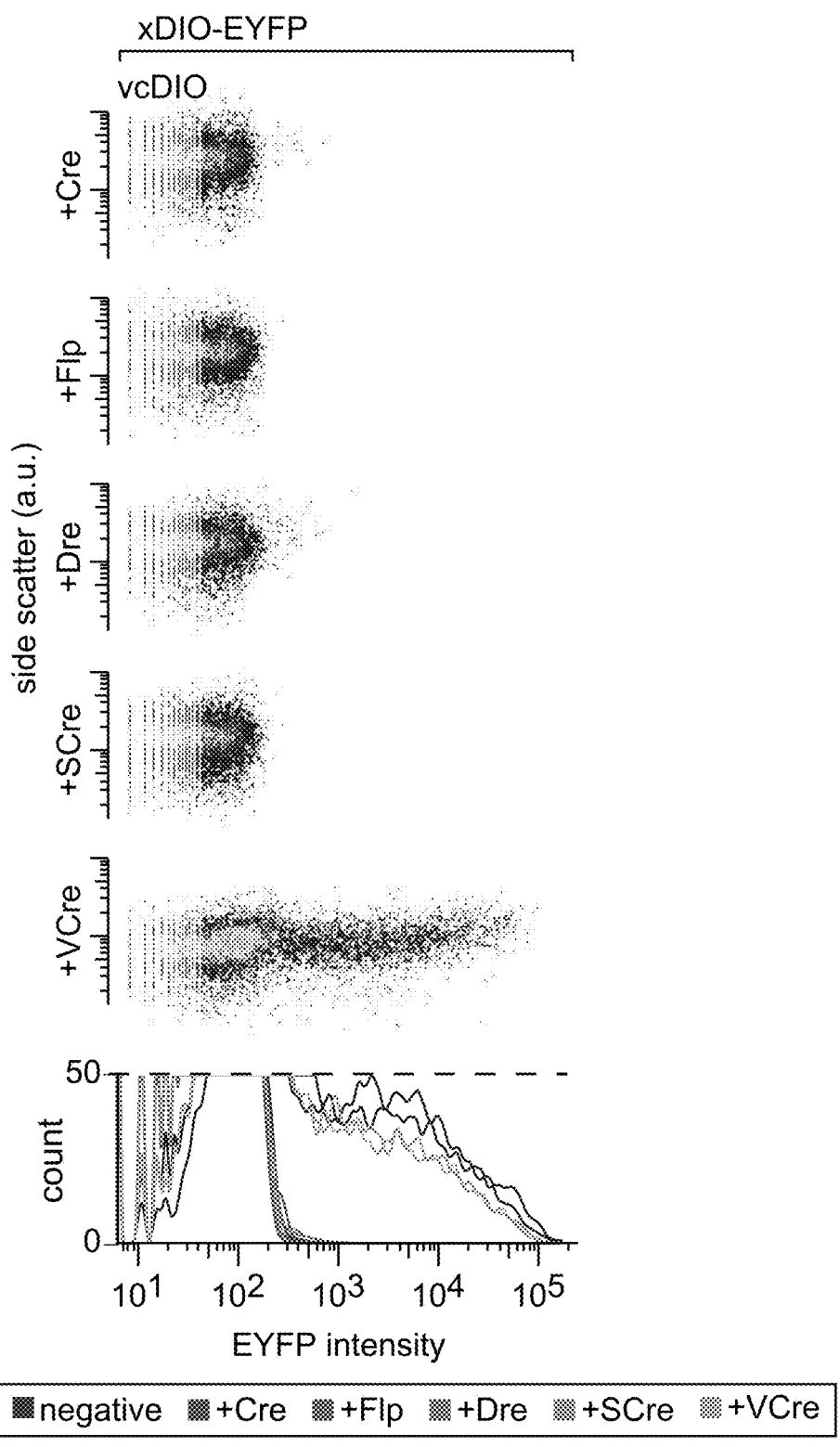
Figure 12B:
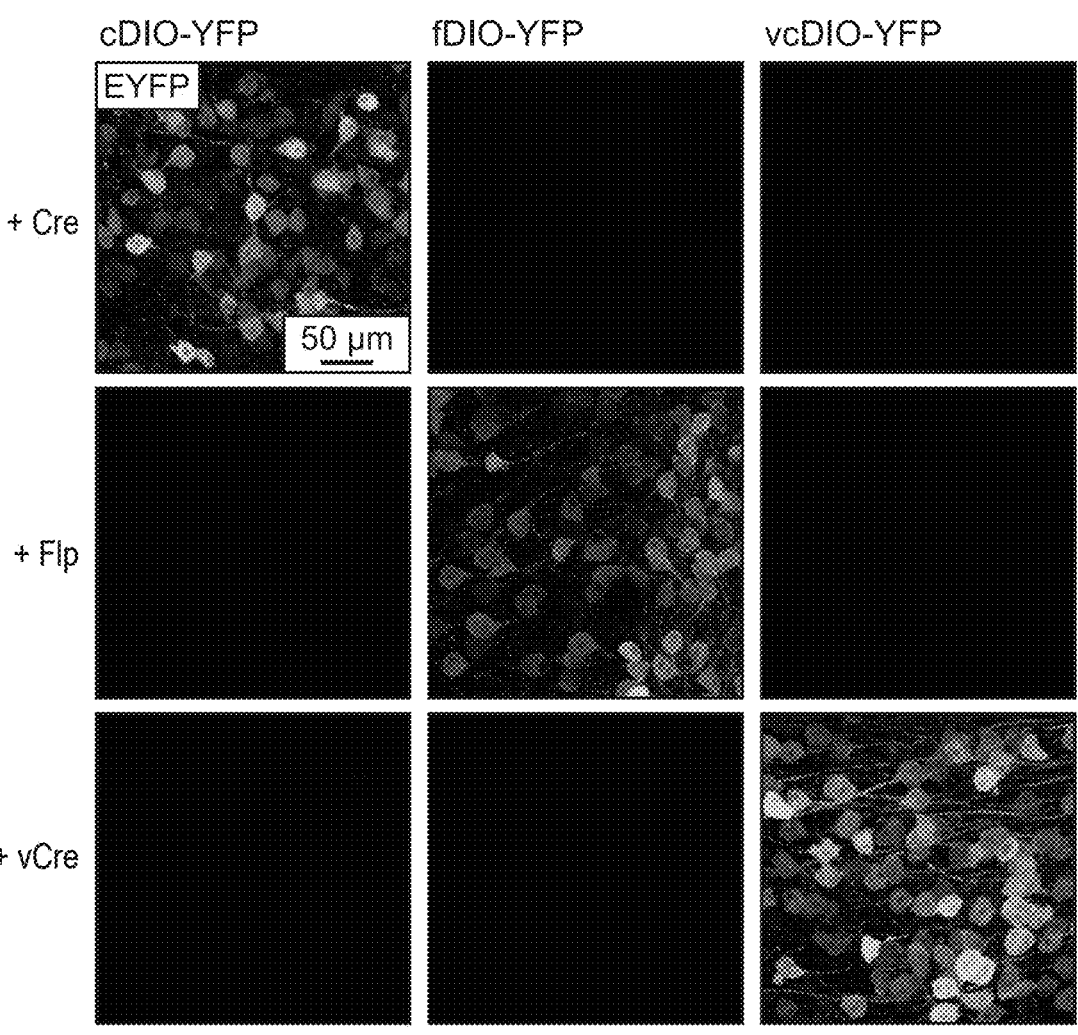
Figure 12C:
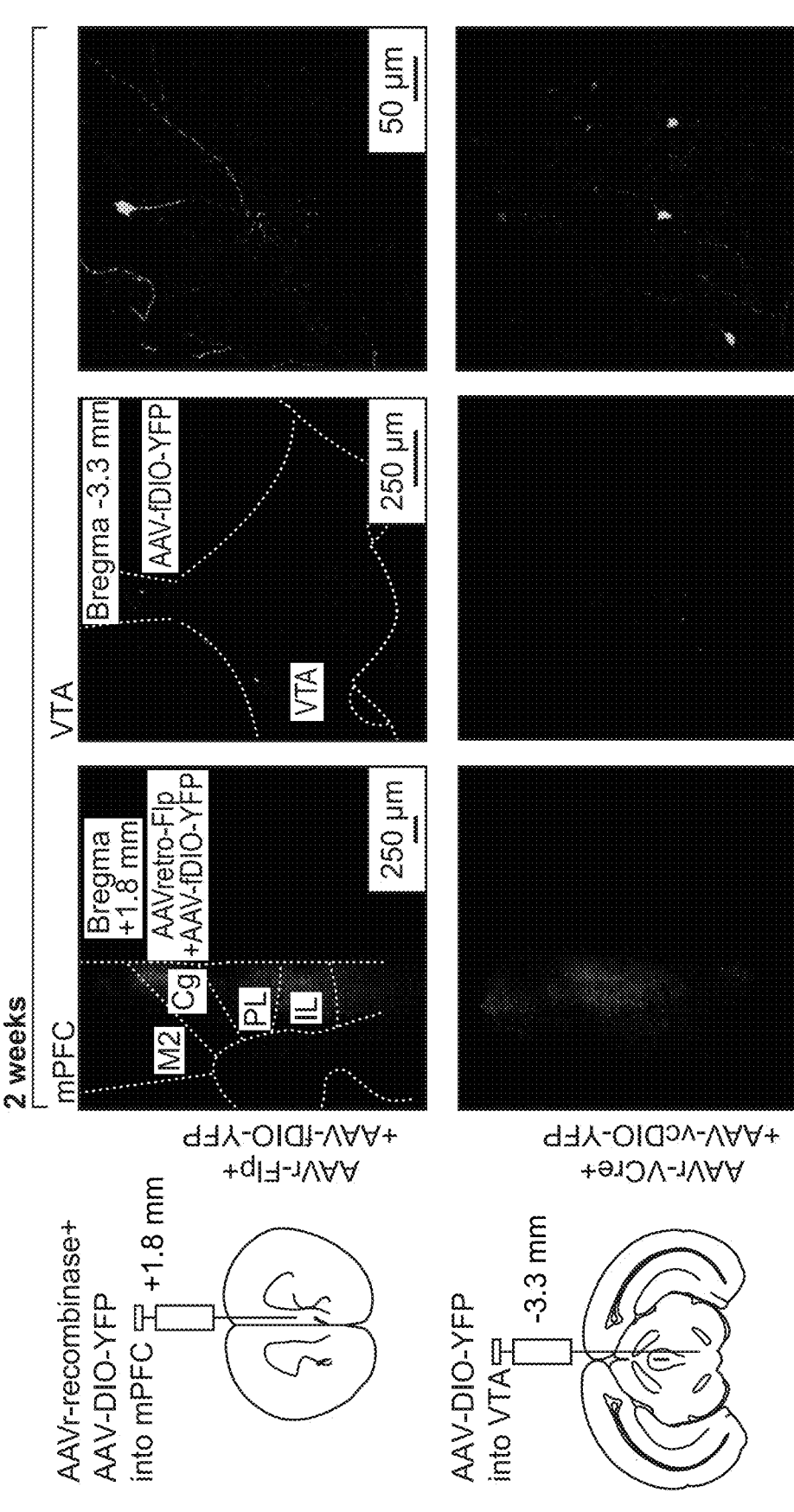

While INTRSECT greatly expands the range of questions that can be assayed using molecular neuroscience tools, it is currently limited to two variables, which are represented by proxy through combinations of Cre and Flp expression. It is known that neuron sub-populations defined by three or more parameters (e.g. 'double projection' neurons defined by genetic and multiple projection features (Jinno et al. (2009) Front Neuroanat. 3:13)) exist, although assessing their functional significance remains beyond the reach of currently available viral targeting approaches for neuroscience. Previously (Fenno et al. (2014) Nat Methods. 11:763) three recombinases (VCre, SCre, Dre) in addition to Cre and Flp were screened for orthogonal activity by assaying expression of recombinase-dependent xDIO-ChR2-EYFP by flow cytometry (where x was one of five recombinases) and identified VCre (Suzuki et al. (2011) Nucleic Acids Res. 39:e49) as a potential third recombinase to be incorporated into INTRESCT. In order to extend the targeting resolution of INTRSECT, this result was first replicated using xDIO-EYFP in place of xDIO-ChR2-EYFP (FIG. 12a). Consistent with previous results, excellent activity of Cre, Flp, Dre, and VCre was found when paired with their respective xDIO-EYFP constructs, with less efficient activation with SCre. Bi-directional, off-target activity between Cre and Dre was again observed, consistent with prior description of this phenomenon. Previous findings that VCre is orthologous to all of the tested recombinases with no indication of cross-activity were replicated, making it ideally suited for use in parallel with Cre and Flp. To confirm the results in vivo, AAV of these three recombinases and xDIO-EYFP constructs were generated and combinations of these were injected into mouse mPFC (FIG. 12b). After four weeks of expression robust expression was found in subjects co-injected with the proper combinations of recombinase/xDIO-EYFP and no cross-expression in improper pairings was found, confirming that this combination of recombinases is suitable for orthologous use in vivo.

Figure 6A:
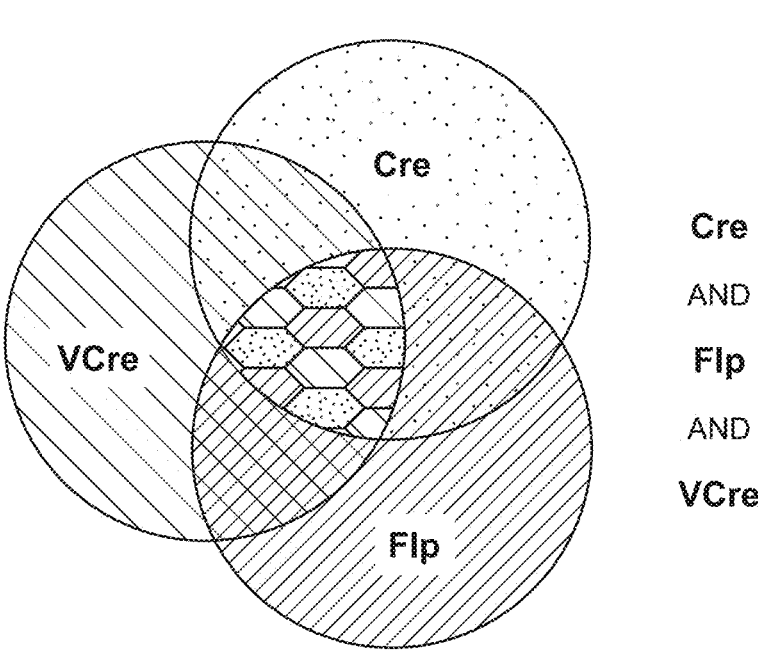
Figure 6B:
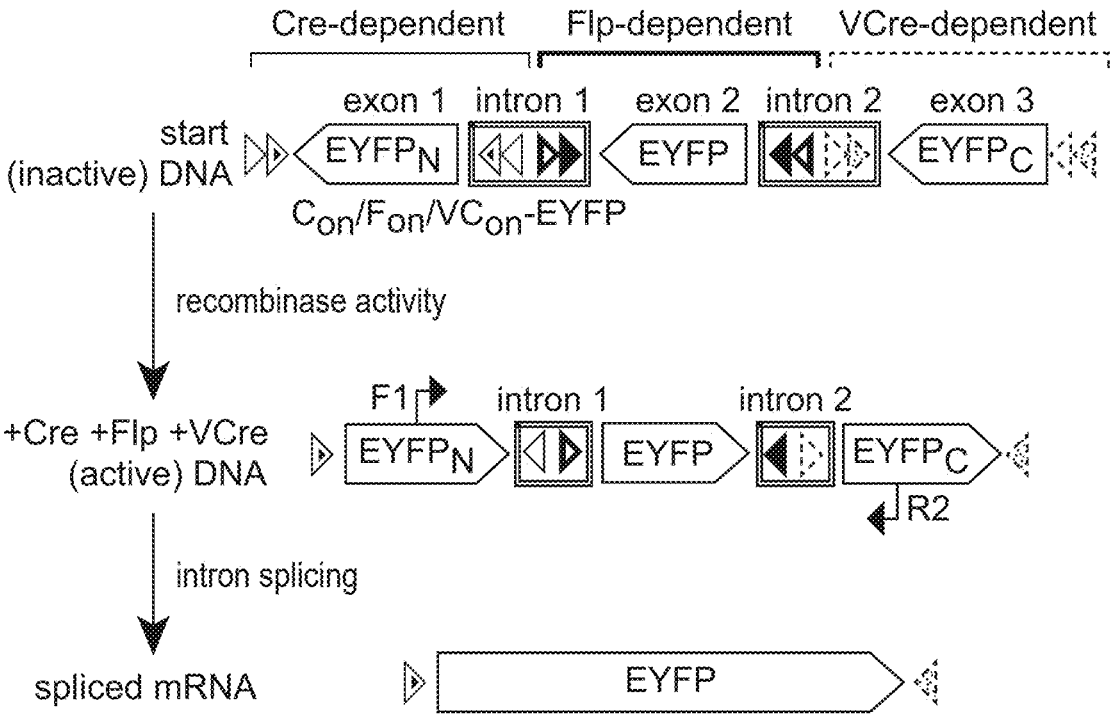
Figure 6E:
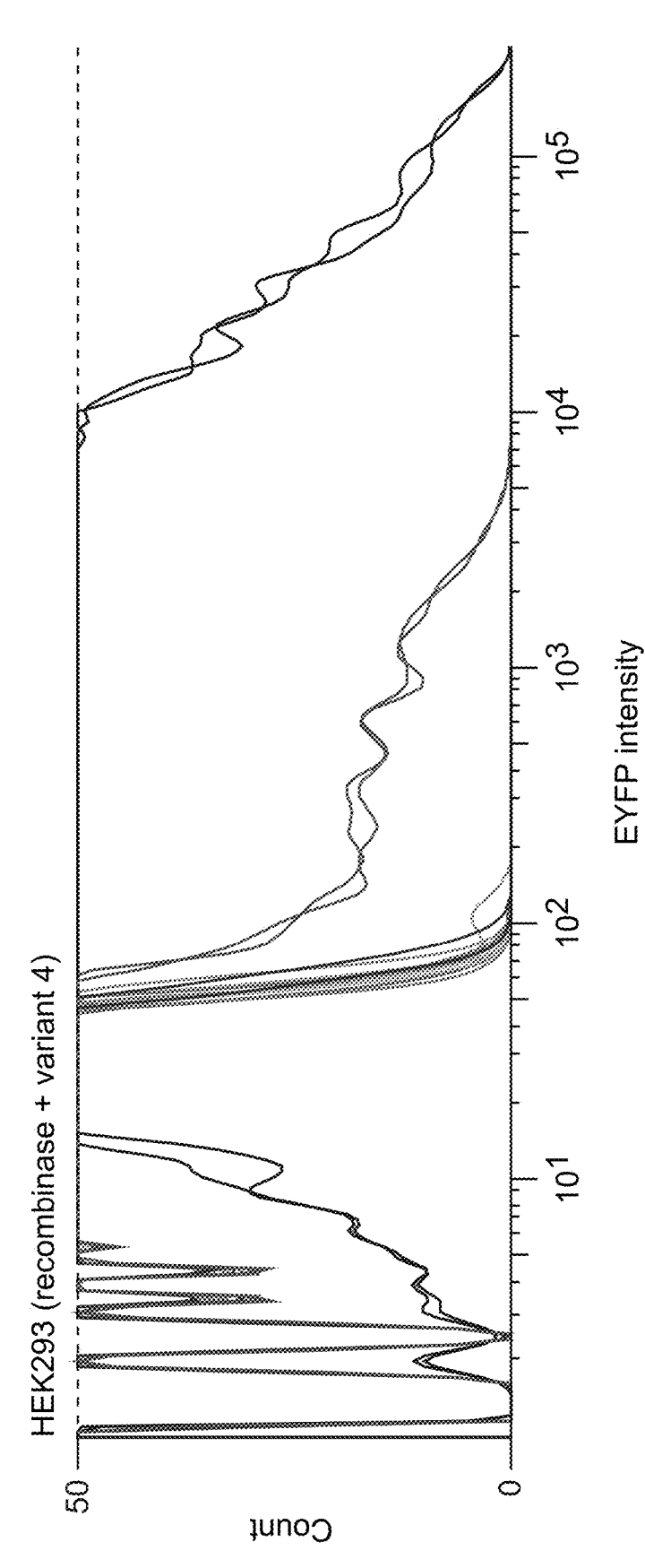
Figure 6F:
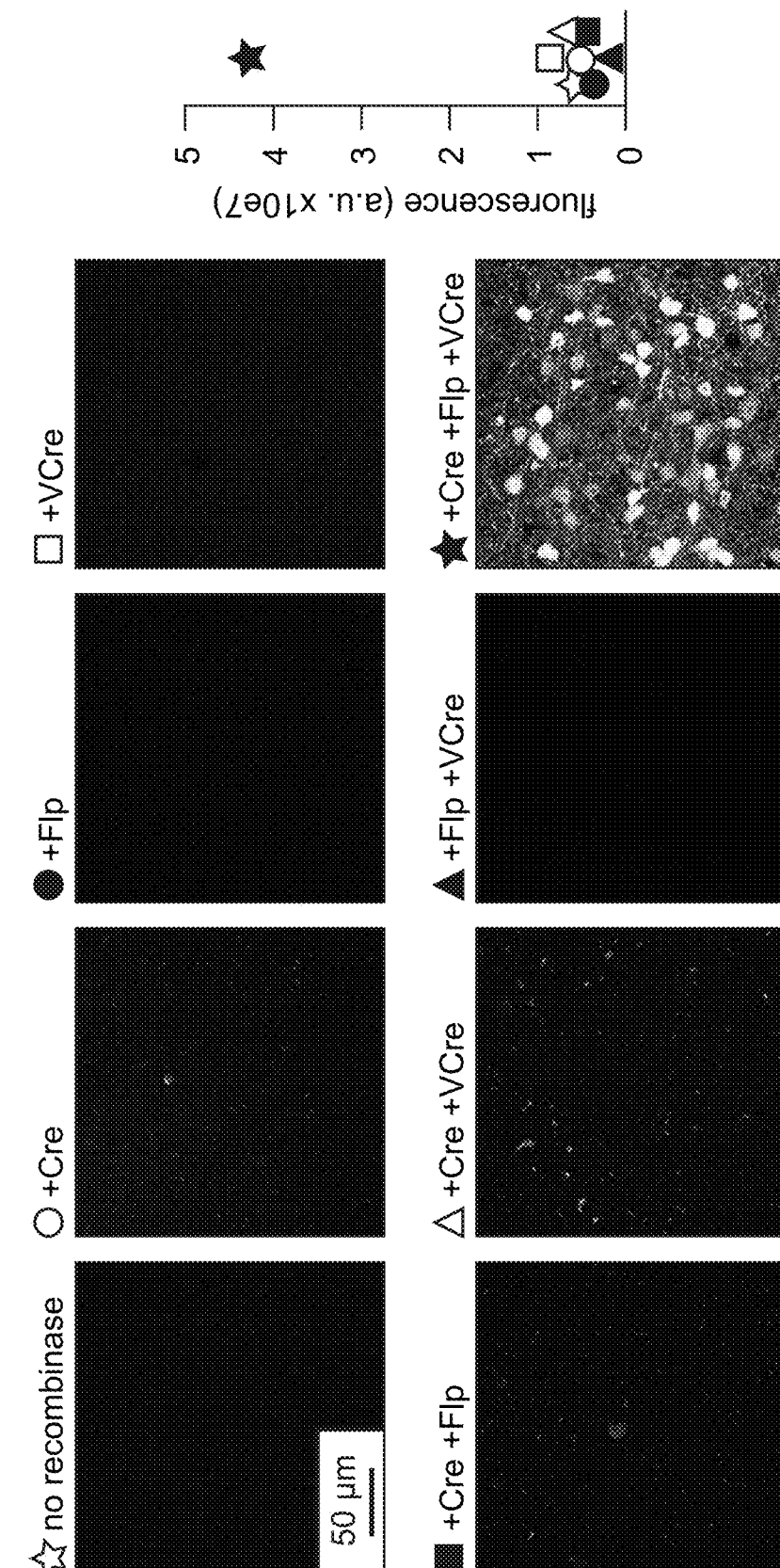

The next goal was to create a construct that would only be active in cells that co-express Cre AND Flp AND VCre, but not in cells with any other combination of recombinases (FIG. 6a). To achieve this, a hybrid version of the one-intron and two-intron INTRSECT constructs was created (FIG. 1a,d) by inserting two introns into EYFP (FIG. 6b). A number of variants with the introns placed at different locations within the EYFP reading frame (FIG. 6c) based on results generated through the engineering pipeline (FIG. 1g) were screened. As expected, the splicing efficiency was accurately reflected in EYFP expression levels of HEK293 cells quadruple-transfected with the three recombinases and Con/Fon/VCon-EYFP variants (FIG. 6d); one of these had excellent expression (from here on '3×-EYFP'). Next, flow cytometry of HEK293 cells co-transfected with various combinations of recombinases and the triple-dependent INTRSECT construct was performed and it was confirmed that expression of 3×-EYFP is limited to cells co-expressing all three recombinases (FIG. 6e). The specificity of 3×-EYFP expression was tested in vivo by injecting the mPFC of mice with AAV-3×-EYFP and combinations of AAV-recombinases, confirming strong, specific expression of this novel triple-recombinase-dependent virus only in cells co-expressing Cre, Flp, and VCre (FIG. 6f).

Figure 6G:
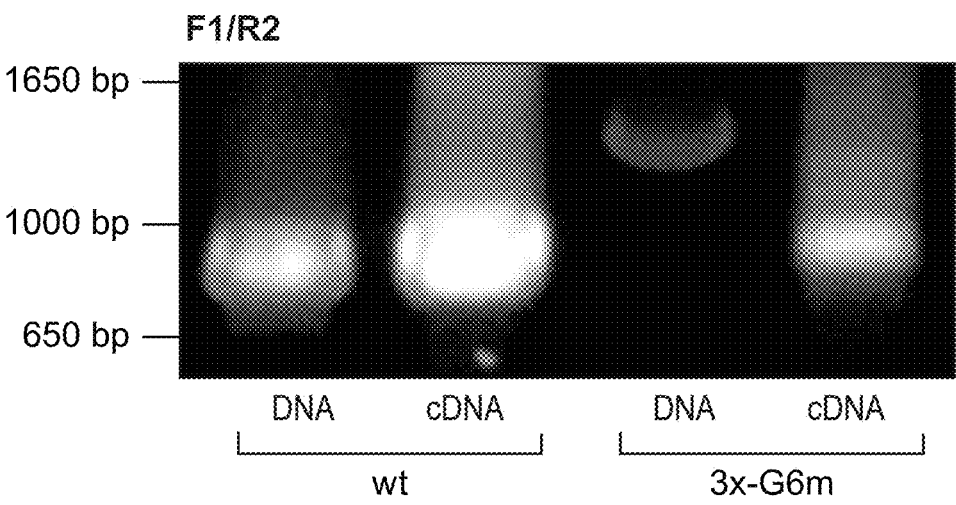
Figure 6H:
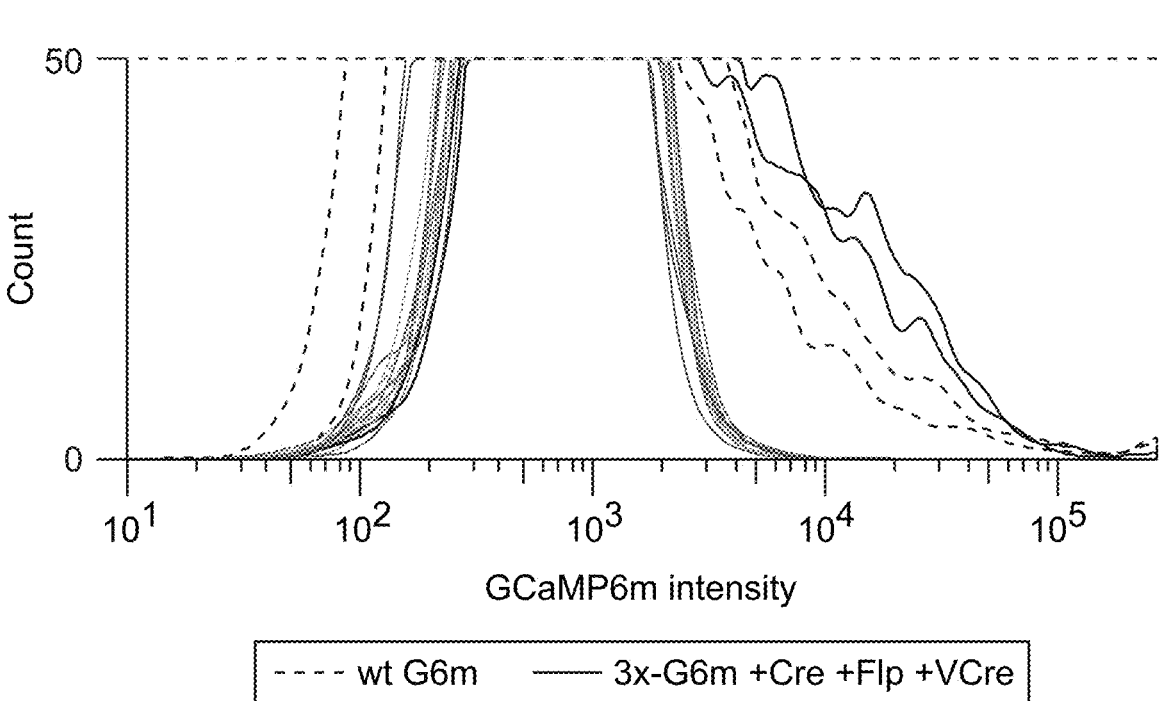
Figure 6J:
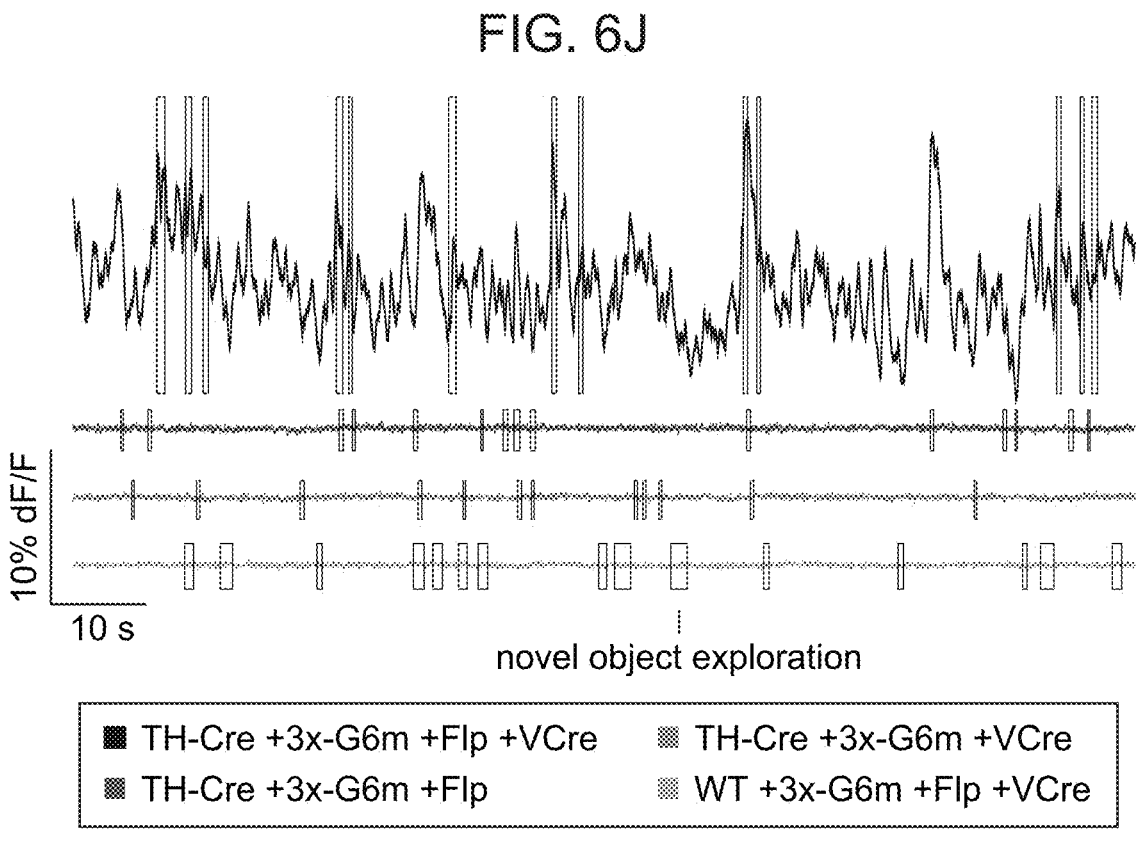
Figure 6K:
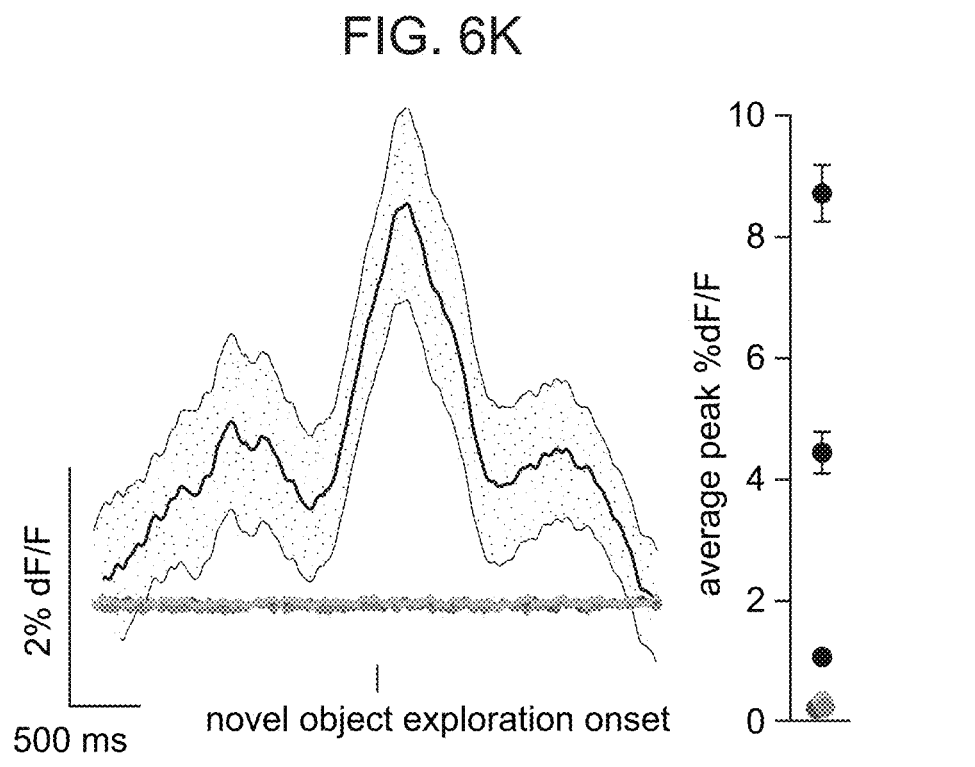
Figure 6L:
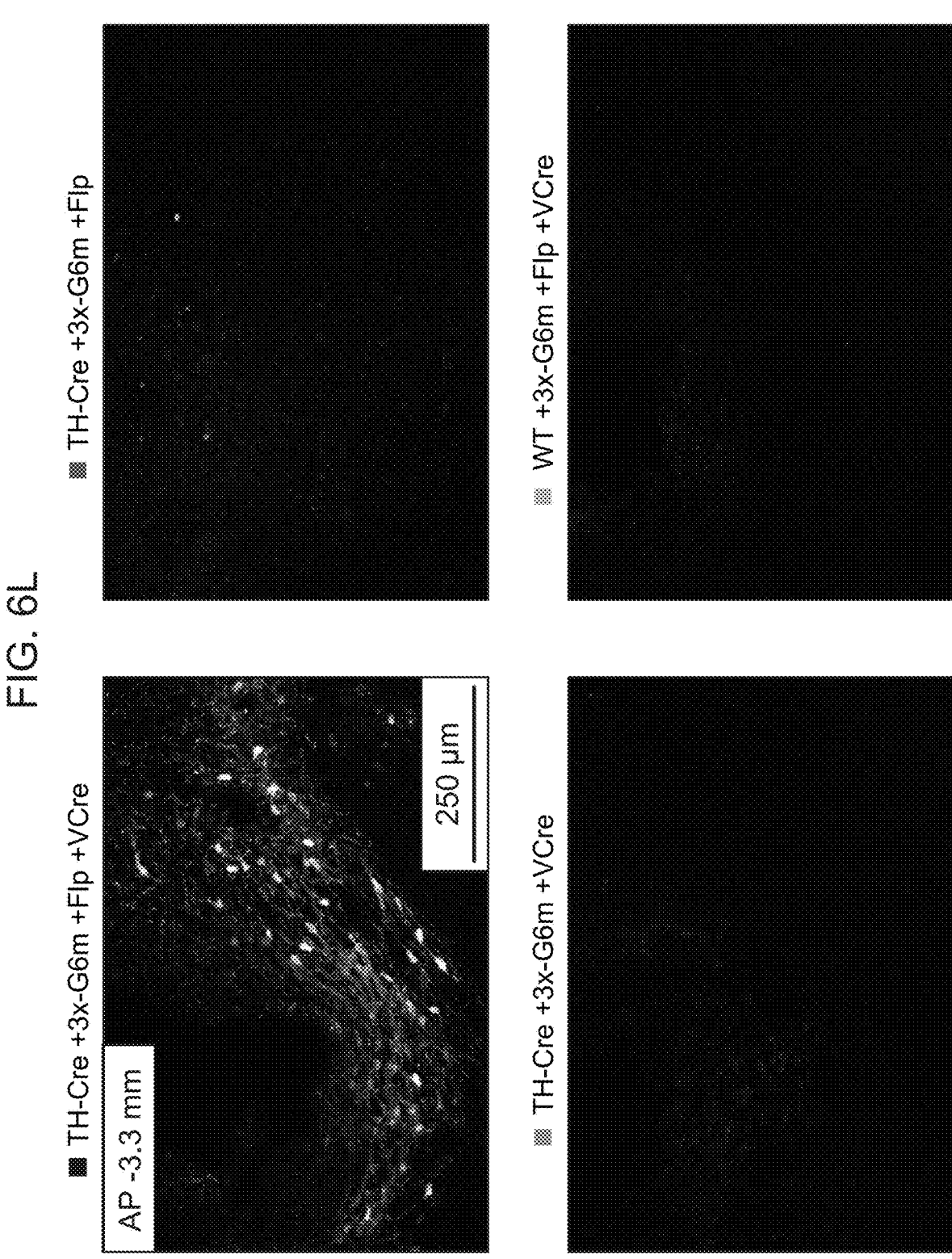

Having created a proof-of-concept, triple-recombinase-dependent 3×-INTRSECT variant of EYFP and confirmed its specific, strong expression in vivo, the next question asked whether this targeting approach is generalizable, by building a 3×-GCaMP6m. Similar to 3×-EYFP, 3×-GCaMP6m spliced efficiently (FIG. 6g) and was only expressed when co-transfected with all three recombinases (FIG. 6h). Biophysical properties of 3×-GCaMP6m compared to WT GCaMP6m in cultured neurons were assayed (FIG. 6i), showing intact function, albeit with lower basal fluorescence and associated properties in vitro. Next in vivo function was assessed by co-injecting AAV-3×-GCaMP6m with viral recombinases in the dorsal hippocampus (FIG. 6j). As expected, photometry recordings from this animal during spontaneous movement showed robust signal (FIG. 6k).

Methods

Molecular Cloning

All single recombinase-dependent plasmids were constructed in an AAV-Ef1α backbone using the double-floxed inverted open-reading-frame (DIO) strategy described previously (Atasoy et al. (2008) supra, Sohal et al. (2009) supra); briefly, the ORF is in the reverse complement orientation between two cassettes of recombinase recognition sites. See Table 1 for information specific to the Cre-dependent (cDIO), Flp-dependent (fDIO) vCre-dependent (vcDIO), Dre-dependent (dDIO), and sCre-dependent (scDIO) iterations. dDIO rox cassette was previously described (Fenno et al. (2014) supra). This, and all constructs used in this example, contain the woodchuck hepatitis virus post-transcriptional regulatory element (WPRE) to enhance expression.

A series of recombinase-expression plasmids were used, as detailed in Table 1. All recombinase expression plasmids were constructed in an AAV-EF1α backbone. These were made as fluorophore-expressing, bicistronic plasmids (using an internal ribosomal entry site or p2a sequence), or without any visual marker, as indicated in the text and figures. FlpO (Raymond et al. (2007) PLos One. 2:e162) was used for Flp-dependent expression.

Mutations to NpHR, jRGECO1a, and mScarlett were introduced via overlapping PCR with primers containing the mutation. The NpHR W179F mutation was chosen from amino acids more than 8 angstroms away from the retinal binding pocket/ion-pumping pathway by analyzing the crystal structure of NpHR (PDB ID: 3A7K; Kouyama et al., 2010). The jRGECO1a (Dana et al. (2016) eLife. 5:e12727) mutation E215D and the mScarlett (Bindels et al. (2017) supra) mutation E95D was chosen to improve functional expression by interrupting a lysosomal import motif (Piccirillo et al. (2006) supra). jRGECO, sRGECO, mScarlet, and oScarlet inclusion quantification was performed by viral infection (jRGECO and sRGECO) or calcium-phosphate transfection (mScarlet and oScarlet) of primary neuron cultures, followed by 4% PFA fixation, mounting, imaging on a confocal, and blinded manual analysis with randomly shuffled and anonymized image labeling.

Tools noted to be '3.3' versions (NpHR, ChRmine, and Arch) include the addition of endoplasmic reticulum and membrane trafficking motifs previously described (Gradinaru et al. (2010) Cell. 141:154), as well as the addition of a p2a bicistronic expression sequence that allows for independent translation of opsin and fluorophore from a single mRNA transcript.

INTRSECT constructs were produced with either one intron (for single ORF, two-recombinase-dependent tools), two introns (for double ORF, two-recombinase-dependent tools), or two introns (for single ORF, three-recombinase-dependent tools).

Single ORF, two-recombinase-dependent INTRSECT plasmids were constructed by splitting the reading frame into two pieces (referred to as 'exon 1' and 'exon 2') after being analyzed for naturally occurring splice-site-like sequences using a public bioinformatics tool (http:// www.cbs.dtu.dk/services/NetGene2/; Brunak et al., 1991), designed as possible to have the splice site out of the reading frame to decrease the chance of partial protein synthesis from exon 2 in the absence of the pre-defined expression criteria. A derivative of the mouse IgE intron 3 (Fenno et al. (2014) supra) containing a cDIO cassette and fDIO cassette was inserted between the exons, with the donor and acceptor sites fused directly to the 3' terminus of exon 1 and 5' terminus of exon 2, respectively. A separate cDIO cassette was added directly after the promoter (5' to the entire coding sequence) and a fDIO cassette was added directly before the WPRE (3' to the entire coding sequence). To create Con/Fon constructs, both exons are in the reverse complement orientation. To create Con/Foff constructs, exon 1 is in the reverse complement orientation and exon 2 is in the sense direction. To create Coff/Fon constructs, exon 1 is in the sense direction and exon 2 is in the reverse complement orientation. All of these plasmids are constructed in an AAV-EF1α backbone with a 3' WPRE and are detailed in Table 1.

Double ORF, two-recombinase-dependent INTRSECT plasmids were constructed by splitting the reading frame into three pieces (referred to as 'exon 1', 'exon 2', and 'exon 3') after being analyzed for naturally occurring splice-site-like sequences using a public bioinformatics tool (http://www.cbs.dtu.dk/services/NetGene2/; Brunak et al., 1991) and choosing a splice site in each of the reading frames, designed as possible to have the splice sites out of the reading frame to decrease the chance of partial protein synthesis from exon 2 or exon 3 in the absence of the pre-defined expression criteria. A derivative of the CMV Towne Variant intron B (Fenno et al. (2014) supra) containing a cDIO cassette was inserted between exon 1 and exon 2, with the donor and acceptor sites fused directly to the 3' terminus of exon 1 and 5' terminus of exon 2, respectively. A derivative of the mouse IgE intron 3 (Fenno et al. (2014) supra) containing a cDIO cassette was inserted between exon 2 and exon 3, with the donor and acceptor sites fused directly to the 3' terminus of exon 2 and 5' terminus of exon 3, respectively. Separate fDIO cassettes were added directly after the promoter (5' to the entire coding sequence) and directly before the WPRE (3' to the entire coding sequence). To create Con/Fon constructs, the exon order is exon 3, exon 2, exon 1, with exons 1 and 3 in the reverse complement orientation and exon 2 in the sense orientation. To create Con/Foff constructs, the exon order is exon 1, exon 2, exon 3, with exons 1 and 3 in the sense orientation and exon 2 in the reverse complement orientation. To create Coff/Fon constructs, the exon order is exon 3, exon 2, exon 1, with all exons in the reverse complement orientation. All of these plasmids are constructed in an AAV-nEF backbone with a 3' WPRE and are detailed in the Table 1.

Single ORF, three-recombinase-dependent INTRSECT plasmids were constructed by splitting the reading frame into three pieces (referred to as 'exon 1', 'exon 2', and 'exon 3') after being analyzed for naturally occurring splice-site-like sequences using a public bioinformatics tool (http://www.cbs.dtu.dk/services/NetGene2/; Brunak et al., 1991), designed as possible to have the splice site out of the reading frame to decrease the chance of partial protein synthesis from exon 2 or exon 3 in the absence of the pre-defined expression criteria. A derivative of the CMV Towne Variant intron B (Fenno et al. (2014) supra) containing a cDIO cassette and fDIO cassette was inserted between exon 1 and exon 2, with the donor and acceptor sites fused directly to the 3' terminus of exon 1 and 5' terminus of exon 2, respectively. A derivative of the mouse IgE intron 3 (Fenno et al. (2014) supra) containing a fDIO cassette and vcDIO cassette was inserted between exon 2 and exon 3, with the donor and acceptor sites fused directly to the 3' terminus of exon 2 and 5' terminus of exon 3, respectively. A separate cDIO cassette was added directly after the promoter (5' to the entire coding sequence) and a vcDIO cassette was added directly before the WPRE (3' to the entire coding sequence). To create Con/Fon/VCon constructs, the exon order is exon 1, exon 2, exon 3, with all exons in the reverse complement orientation. All of these plasmids are constructed in an AAV-nEF backbone with a 3' WPRE and are detailed in the Table 1.

To produce FRT variants for screening Con/Foff improvements, the FRT, F3, F5 (Schlake et al. (1994) Biochemistry. 33:12746), and F72 (Nakano et al. (2001) Microbiol Immunol. 45:657) sequences were built into various combinations of AAV-EF1α-Con/Foff-EYFP as noted in FIG. 11. In addition, a 14 bp addition noted from the genomic FRT sequence (Andrews et al. (1985) Cell. 40:795) was added either to the 5' or 3' (or both) ends of F3, F5, and/or FRT in configurations as noted in FIG. 11. These were synthesized de novo and incorporated into the Flp cassette using standard cloning techniques. After screening, the FRT-F5 cassette (e.g. 'Con/ Foff 2.0') was incorporated into all Con/Foff constructs.

days post transfection, cells were removed by enzymatic dissociation (TrypLE, Gibco), resuspended in cold PBS, pelleted at 200 g for 5 min and resuspended in 500 μL PBS supplemented with 1 μg/mL propidium iodide (PI; Sigma, used with green and blue fluorescent constructs) or 5 μM 4'6-diamidino-2-phenylindole (DAPI; Thermo Fisher, used with red fluorescent constructs), and then placed on ice under aluminum foil until analysis. Flow cytometry was completed on a DxP FACSCAN analyzer at the Stanford Shared FACS Facility using settings optimized for side scatter (SS), forward scatter (FS), vital dye (PI or DAPI) and fluorophore (mTagBFP, EYFP, GCaMP6 (GCaMP6m; GCaMP6f), mCherry, RGECO, or oScarlet) acquisition using positive (non-recombinase-dependent parent construct), negative (empty transfection) and dead (heat-killed; 95° C. for 3 min) conditions as controls. Live-cell populations used in comparisons were isolated from debris and dead cells in post hoc analysis using FlowJo 10.4.2 (FlowJo) by (i) positively gating for the high-density population in plotting FS vs. SS and (ii) negatively gating for vital dye+ cells.

Analysis of FRT cassette variants was completed by exporting the live-cell populations defined as above, then isolating the population of cells with EYFP expression

```
FRT variant sequences (5' repeat|8 bp central motif|3' repeat):
FRT:
                                            (SEQ ID NO: 114)
gaagttcctattc|tctagaaa|gtataggaacttc F3:
                                            (SEQ ID NO: 115)
gaagttcctattc|ttcaaata|gtataggaacttc F5:
                                            (SEQ ID NO: 116)
gaagttcctattc|ttcaaaag|gtataggaacttc F72:
                                            (SEQ ID NO: 117)
gaagttcctattc|tgtagaaa|gtataggaacttc 14 bp addition:
                                            (SEQ ID NO: 118)
gaagttcctattcc
```

Updated maps are available at http://optogenetics.org/.
mRNA Isolation and cDNA Synthesis HEK293FT cells at 90% confluence were transfected with endotoxin-free DNA using Lipofectamine 2000 (Thermo Fisher) following the manufacturer protocol. Five days post transfection, RNA extraction was performed using reagents from the RNeasy Mini Kit (Qiagen). Cells were disrupted with lysis buffer and homogenized using QiaShredder homogenizer columns. Combined first-strand cDNA/PCR using the SuperScript III One-Step RT-PCR System (Thermo Fisher) was performed with the following reaction conditions: 45° C. 30 min, 94° C. 2 min, 40 cycles of 94° C. 15 s, 45° C. 30 s, 68° C. 1 min, ending with 68° C. 5 min using various combinations of primers (F, forward; R, reverse) as noted in the Table 1. The PCR product was electrophoresed on a 0.8% agarose gel, photographed and DNA bands purified from the gel and sequenced to determine splice junctions.
Flow Cytometry HEK293FT cells (Thermo Fisher) were grown in 24-well tissue culture plates to 90% confluence and transfected in duplicate with 800 ng total DNA with Lipofectamine 2000 (Thermo Fisher) following the manufacturer protocol. Five higher than the maximum expression value of the negative population ('residual population'). Calculations were performed, where the calculations included calculating the (i) mean fluorescence of the residual population and (ii) the percentage of the total cells represented by the residual population. Flp titration experiments were completed by transfecting a fixed amount of $C_{on}/F_{off}$-EYFP variant, Cre, and a varying amount of Flp to create molar ratios as indicated in the figure. A constant amount of DNA was transfected in each condition, with the difference between conditions made up with empty vector.
Primary Neuronal Cultures Primary cultured hippocampal neurons were prepared from P0 Sprague-Dawley rat pups (Charles River). CA1 and CA3 were isolated, digested with 0.4 mg ml⁻¹ papain (Worthington), and plated onto glass coverslips precoated with 1:30 Matrigel (Becton Dickinson Labware). Cultures were maintained in a 5% $CO_2$ humid incubator with Neurobasal-A medium (Thermo Fisher) containing 1.25% FBS (HyClone), 4% B-27 supplement (Gibco), 2 mM Glutamax (Gibco) and 2 mg/ml fluorodeoxyuridine (FUDR, Sigma), and grown on coverslips in a 24-well plate at a density of 65,000 cells per well. 2 ug total DNA of mixture of recombinase and INTRSECT construct, or an equivalent amount of the parental tool expression construct, was mixed with 1.875 μl 2 M $CaCl_2$) (final $Ca^{2+}$ concentration 250 mM) in 15 μl $H_2O$. To DNA-$CaCl_2$ 15 μl of 2×HEPES-buffered saline (pH 7.05) were added. After 20 min at room temperature (20-22° C.), the mix was added dropwise into each well (from which the growth medium had been removed and replaced with pre-warmed minimal essential medium (MEM)) and transfection proceeded for 45-60 min at 37° C., after which each well was washed with 3×1 ml warm MEM before the original growth medium was returned. Neurons were allowed to express transfected DNA for 6-8 days prior to experimentation.

to a cage and kept on a reverse 12-h light/dark cycle with ad libitum food and water. Experimental protocols were approved by Stanford University IACUC and meet guidelines of the US National Institutes of Health guide for the Care and Use of Laboratory Animals See Table 1 for specific transgenic animal strain information.

Flp Line Database

To locate transgenic, Flp-expressing mouse lines, the following websites were searched using the term 'Flp' (with the exception of Google Scholar, where the term 'Flp driver mouse line' was used) in September, 2018, and the results were manually assessed. The initial publications describing the production of the lines were assessed for the construction method, promoter, and Flp variant.

| | |
|---|---|
| Jackson Laboratories | https://www.jax.org/mouse-search |
| MMRRC | https://www.mmrrc.org/catalog/StrainCatalogSearchForm.php |
| APF | http://pb.apf.edu.au/phenbank/findstrains.html |
| NIH Blueprint | http://www.credrivermice.org/ |
| GENSAT | http://www.gensat.org/cre.jsp |
| Taconic | https://www.taconic.com/find-your-model/ |
| Mousebook | https://www.mousebook.org/stock-list |

Primary Culture Electrophysiology

Recordings of neurons prepared and transfected as above were obtained in Tyrode's medium (in mM: 150 NaCl, 4 KCl, 2 $MgCl_2$, 2 $CaCl_2$, 10 d-glucose, 10 HEPES, adjusted to pH 7.3-7.4 with NaOH, 320-330 osmolarity) supplemented with Tetrodotoxin (TTX; Tocris, 1 μM), (2R)-2-amino-5-phosphonopentanoic acid (APV; Tocris, 10 μM), and 6-cyano-7-nitroquinoxaline-2,3-dione (CNQX; Tocris, 25 μM) as indicated, with a standard internal solution (in mM: 130 K-gluconate, 10 KCl, 10 HEPES, 10 EGTA, 2 $MgCl_2$, to pH 7.25 with KOH, 300-310 osmolarity) in 3- to 6-Me glass pipettes. Light from a SPECTRA-X Light Engine (Lumencor) with LEDs with individual light power adjusted for uniform light power density of 1 mW/mm² across wavelengths and 470/15, 513/15, and 585/29 filters were used for blue, green and orange illumination, respectively. The Spectra X was coupled with a liquid light guide to an inverted microscope Leica DM-LFSA. All data collected from whole-cell recordings. Recordings were made using a MultiClamp700B amplifier (Molecular Devices). Signals were filtered at 4 kHz and digitized at 10 kHz with a Digidata 1440A analog-digital interface (Molecular Devices). pClamp10.6 software (Molecular Devices) was used to record and analyze data. Peak photocurrents were measured from a 1.5 s light pulse in voltage-clamp mode. Input resistance and capacitance were both calculated from the response to 10 mV voltage steps in voltage clamp, using steady-state current amplitude and recovery from the capacitive transient, respectively.

Culture Calcium Imaging

Calcium imaging conducted on neurons prepared and transfected as above in Tyrode media equivalent to primary culture electrophysiology media, including blockers, except with (mM) 1 MgCl2 and 3 $CaCl_2$. A custom-designed and 3D-printed stimulation insert with platinum wires 1 cm apart was attached to a Bipolar stimulator (Warner Instruments #SIU-102) generator time-locked to imaging software (MetaMorph). Stimulation was conducted a 100 uA, 3 ms pulse width, 0.1 hz, with 5 pulses per imaging field. Bulk signal was extracted from manually drawn ROIs and further processed with MatLab code to extract pertinent parameters.

Animals

Adult wild-type female and transgenic somatostatin-IRES-Cre (Jax 013044) mice were group housed up to four Virus Production AAV-8 (Y733F), called AAV8 from now on serotype was produced by the Stanford Neuroscience Gene Vector and Virus Core. In brief, AAV-8 was produced by standard triple transfection of AAV 293 cells (Agilent). At 72 h post transfection, the cells were collected and lysed by a freeze-thaw procedure. Viral particles were then purified by an iodixanol step-gradient ultracentrifugation method. The iodixanol was diluted and the AAV was concentrated using a 100-kDa molecular mass—cutoff ultrafiltration device. Genomic titer was determined by quantitative PCR. All viruses were tested in cultured neurons for expected expression patterns prior to use in vivo.

Stereotactic Injections

Stereotactic viral injections were carried using typical technique. Briefly, mice induced and maintained on isoflurane anesthesia were placed in a stereotactic frame (Kopf Instruments) and the head leveled using bregma and lambda skull landmarks. Craniotomies were performed so as to cause minimal damage to cortical tissue using a hand drill. Injections were made using a 10 μL syringe and 33 g-36 g beveled needle (World Precision Instruments). 1000 nl of viral suspension was infused at a rate of 100 nl/min at the indicated locations (coordinates in mm below). The needle was left in place for 10 minutes after the completion of injection before being withdrawn under supervision. Skin was approximated with suture.

| | |
|---|---|
| Medial Prefrontal Cortex | A/P: +1.5, M/L: 0.3, D/V: −2.5 |
| | A/P: +1.85, M/L: 0.3, D/V: −2.5 |
| VTA | A/P: −3.3, M/L: 0.5, D/V: −4.0 |

Slice Electrophysiology

To prepare coronal slices (300 μm) from mice previously injected with virus, subjects were first trans-cardially perfused with ice-cold, NMDG-HEPES recovery solution ('NMDG solution'; Ting et al., 2014; in mM): 93 NMDG, 2.5 KCl, 1.2 $NaH_2PO_4$, 30 $NaHCO_3$, 20 HEPES, 25 glucose, 5 sodium ascorbate, 2 thiourea, 3 sodium pyruvate, 10 $MgSO_4$, 0.4 $CaCl_2$, adjusted to pH 7.3-7.4 with HCl/NaOH. A vibratome with ice-cold, bubbled (5% $CO_2$ 'carbogen') NMDG solution was used to cut slices, which were then recovered for 12-14 minutes in carbogen-bubbled NMDG solution at 32° C. before being recovered for 1 hr in RT (22-25° C.) carbogen-bubbled artificial cerebrospinal fluid ('aCSF; in mM): 124 NaCl, 2.5 KCl, 1.2 $NaH_2PO_4$, 24 $NaHCO_3$, 5 HEPES, 12.5 glucose, 2 $MgSO_4$, 2 $CaCl_2$, adjusted to pH 7.3-7.4 with NaOH. Synaptic transmission blockers APV (25 µM), CNQX (10 µM) and sodium channel blocker TTX (1 µM) are used as indicated. Electrophysiological recordings were performed at RT. Slices were visualized with an upright microscope LEICA DM LFSA equipped with a 40× water-immersion objective. Individual neuron recordings were obtained after identifying fluorescent protein expression without interruption of ACSF perfusion. Filtered light from a Spectra X Light engine (Lumencor) was coupled to the fluorescence port of the microscope and used to both view fluorescence and deliver light pulses for opsin activation. Whole-cell recordings were obtained with patch pipettes pulled from borosilicate glass capillaries (Sutter Instruments) with a horizontal puller (P-2000, Sutter Instruments) and contained the following internal solution (in mM): 130 K-gluconate, 10 KCl, 10 HEPES, 10 EGTA, 2 $MgCl_2$, to pH 7.25 with KOH. Recordings were made using a MultiClamp700B amplifier (Molecular Devices). Signals were filtered at 4 kHz and digitized at 10 kHz with a Digidata 1440A analog-digital interface (Molecular Devices). pClamp10.6 software (Molecular Devices) was used to record and analyze data. Peak photocurrents were measured from a 1.5 s light pulse in voltage-clamp mode. Input resistance and capacitance were both calculated from the response to 10-mV voltage steps in voltage clamp, using steady-state current amplitude and recovery from the capacitive transient, respectively.

Spectrophotometry and Viral Kinetic Analysis

A complete parts list is available in the Table 1. Briefly, semi-quantitative data describing viral expression kinetics in vivo were collected with an inexpensive device consisting of a 505 nm LED (Thorlabs M505F1) coupled to a dichroic filter mount via multi-mode fiber optic patch cable (Thorlabs m76L01). Excitation light was band-pass filtered (497 nm/16 nm FWHM, Thorlabs MF497-16) and reflected by dichroic (525 nm long-pass, Chroma T5251pxr) into a 200 µm, 0.53 NA (Doric) fiber optic patch cable to the sample. Emission light then passed through the same dichroic, then through two identical clean-up filters (535 nm/22 nm FWHM, Thorlabs MF535-22), and to a visible wavelength, compact CCD spectrometer (Thorlabs CCS100) via a round-to-linear fiber bundle (Thorlabs BFL200LS02). The spectrometer was connected by USB to a computer running Windows and data acquired with the bundled Thorlabs spectrometer software.

EYFP expression data were acquired from individual animals injected with various AAV8 viruses as indicated (FIG. 3) and fitted with 200 µm, 0.53 NA fiber optic implants (Doric) with the fiber tip placed at the injection site Animals were injected on Wednesdays (day 0) and the first reading taken on Friday (day 2) with (in ms), 5, 10, 50, 100, 500, 1000, 3000, 5000, 10000, 20000, and 30000 integration times, with a large range designed to be sensitive to low expression (longer integration time), but also not saturated with high expression (shorter integration time). Readings were taken every Monday, Wednesday, and Friday thereafter for 6 weeks (18 timepoints) Animals were sacrificed after timepoint 18 for expression analysis by confocal (described below). Prior to recording each day, the excitation LED was calibrated to 0.214 mW using a power meter (ThorLabs) and readings from a fluorescein slide (***) and purified EYFP were taken to ensure consistent system performance. The raw data were stored as .txt files.

To calculate the 'expression score' of an individual time point, raw data were imported into MATLAB, signal from 528 nm-540 nm were segmented from the dataset, and the area under the curve was calculated using the trapz function across this signal subset for each integration timepoint. Timepoints with zero or saturated values were excluded. Integration timepoints within the dynamic range of the spectrometer were normalized to the longest integration timepoint and averaged, to create the expression score.

Virus-dependent expression kinetics were modeled in MATLAB by first log-transforming individual animal expression score datasets, normalizing these log-transformed data to the subject maximum, and pooling the samples within a condition. This combined dataset was then fit with the equation $y=1*(1-\exp(-b*x))$ where y is fraction of max expression, x is the days of expression, and b is solved for using the MATLAB fit function. Days of expression to a certain fraction of normalized log maximum expression was calculated from fitted curves by solving for x (days of expression) for a given y (fraction of maximum). 95% confidence interval of the fit and the solved days of expression were calculated by using the 95% CI values of b.

Fiber Photometry

Mice were injected in VTA with combinations of 3×-GCaMP6m and recombinase AAV and fitted with 400 µm, 0.66 NA fiber optic implants (Doric). After four weeks of expression, bulk fluorescence was collected as previously described. Calcium signal was collected by recording bulk fluorescence using a single optical fiber while simultaneously delivering excitation light as previously described. A385 nm LED (M385F1, Thorlabs) was used for movement correction and 490 nm LED (M490F3, Thorlabs) for calcium signal recording. LEDS were filtered with 386-23 nm (FF01-386/23-25, Semrock) and 488-10 nm (FF01-488/10-25, Semrock) bandpass filters. LED beams were combined using a 425 nm longpass dichroic mirror (T4251pxr, Chroma) before being coupled into an optical fiber patch cable (400 nm diameter, 0.66 NA, Doric Lenses) using a multiband dichroic (ZT405/488/561rpc, Chroma). The far end of the patch cord is end-end coupled to the fiber implant in the animal using 2.5 mm ferrules and zirconia or bronze sleeves. Fluorescent calcium signal emission light was passed through a 555 nm dichroic mirror (FF555-Di03-25× 36, Semrock) which was filtered through a 447/522 nm dual band filter (ZET405/488 nm-custom narrow green, Chroma) and then focused onto a femtowatt photoreceiver (Model 2151, Newport) use a lens (62-561, Edmund Optics). The signal was sampled at 6.1 kHz and independent signals were recovered using synchronous demodulation techniques, low-pass filtered (corner frequency of 15 Hz, decimated to 382 Hz, then recorded to disk. Calcium signal was calculated for each continuous behavioral recording with custom written MATLAB scripts. First, the 405 nm signal was subtracted from the calcium signal for motion correction. Next, a double exponential was fitted to a thresholded version of the fluorescence time series and the best fit was subtracted from the un-thresholded signal to account for slow bleaching. The fluorescence signal was normalized within each mouse by calculating the dF/F as (F median (F))/median (F), where the median was taken over the first 100 s of the trial.

Novel object trials were conducted by placing subjects in a new cage after connecting them to the fiber photometry apparatus by fiber optic patch cable (Doric). Behavior was recorded using an overhead mounted camera and synchronized with fiber photometry using a trial-triggered LED that was mounted below the cage to be out of view of the subject Animals explored the environment for two minutes before novel objects were introduced Animals were allowed to continue exploring for five additional minutes before the trial was ended. Videos were scored manually for physical object interactions.

Histology

Following virus injection, mice were trans-cardially perfused with 10 mL of ice-cold PBS followed by 10 mL of 4% paraformaldehyde (PFA). After an overnight post-fix in PFA, brains were equilibrated in sterile 30% sucrose/PBS for at least 24 h (or until they sunk in the tube). Tissue was sectioned at 60 μm using a freezing microtome (Leica) and mounted with DAPI-containing hard-mount solution (H-1500; Vector Laboratories). Images were obtained on a Leica confocal microscope using 5×, 40×, and 63× objectives. For comparative expression analysis, z-stacks with the same settings (z-distance, number of optical slices, acquisition parameters) were taken from the slice judged to have maximum expression. These were analyzed in the Fiji Image-J implementation by calculating the sum of the total integrated fluorescence extracted from every optical section using a standard ROI.

FIG. 1. The INTRSECT strategy, function, and engineering pipeline are designed for robust flexibility. A,D) Schematics of generic INTRSECT molecular designs for single open reading frame ('ORF'; A) and double ORF (D) in three boolean configurations (Cre AND Flp, Cre AND NOT Flp, Flp AND NOT Cre). Molecular reagents available in each configuration are listed. B,E) Step-wise schematic describing the activity of Cre and Flp on DNA structure to move the different single ORF (B) and double ORF (E) INTRSECT starting configurations (top) to the active (dotted box, middle), and inactivated (bottom) states. C,F) Step-wise schematic showing, from top to bottom, how the initial DNA configuration for single ORF (C) and double ORF (F) constructs transition to the active DNA state after recombinase-dependent rearrangement, mRNA processing that removes introns containing recombinase recognition sites, and protein translation without the addition of extraneous sequence. G) Standardized engineering pipeline for the production of novel INTRSECT constructs consisting of (left to right) design of intron placement and cloning, RT-PCR to ensure proper intron splicing, flow cytometry to assay proper expression and lack of inappropriate expression, and functional testing (in cultured neurons or HEK cells) to compare function with the parent tool.

FIG. 2. Standardized approaches to the INTRSECT design and implementation improve tool and experiment quality. A) Detailed view of RT-PCR testing and mis-splicing resolution approach for new INTRSECT constructs. B,E) Mis-spliced RT-PCR results for INTRSECT bReaChES-EYFP and NpHR3.3-p2a-EYFP. bReaChES-EYFP (B) and NpHR3.3-p2a-EYFP (E) were found to have major and minor splice variants resulting from cryptic splicing. C,F) The bReaChES-EYFP intron was moved to an alternative, candidate splice site (C), while NpHR3.3-p2a-EYFP did not have either a separate candidate splice site or degenerate codon sequence options and so the published crystal structure was used to disrupt the cryptic splice site (F-arrow) by introduction the mutation W179F (F—left), which did not affect opsin function (F—right; p=0.9754, unpaired t-test). D,G) These second iterations of both bReaChES-EYFP (D) and NpHR3.3-p2a-EYFP (G) were found to generate either single spliced products (D), or the correct major product and an exon 1-exon 3 minor splice variant (G). H) Major errors can occur at multiple stages during INTRSECT scaling and implementation and result in experimental failure. A protocol for making new INTRSECT tools (Fenno et al. (2017) Curr Protoc Neurosci. 2017:4.39.1) has been published and a Standard Operating Procedure is maintained (http://www.optogenetics.org/intrsect_sop.pdf).

FIG. 3. Con/Foff 2.0 improves Flp efficiency. A) AAV-Con/Foff-EYFP expression in mPFC is highly expressed when co-expressed with AAV-Cre, but does not efficiently inactivate when co-expressed with equal amounts of Flp and Cre expressed with AAV-Flp-2a-Cre (n=3 animals each, p=0.0214, unpaired t-test). Con/Foff does inactivate efficiently when co-expressed with increased Flp:Cre ratios (Cre alone compared to Flp-2a-Cre, e13:e12, p=0.0044; e13:e11, p=0.0002; e13:e10, p=0.8526, ANOVA with Sidak's test). B,C) Two Con/Foff-EYFP variants ('g', 'o') decrease residual expression mean EYFP fluorescence (B) and the fraction of residual cells (C) compared to Con/Foff-EYFP 1.0 ('O') over a broad range of Flp:Cre ratios in co-transfected HEK293 cells (compared to v1, *p<0.05, p<0.01, *p<0.001, ****p<0.0001, n=5 independent experiments, ANOVA with Dunnett's test), although further increasing the ratio beyond 10:1 showed marginal further increase toward the fitted plateau values (r2 mean expression v1=0.8028, g=0.7114, o=0.6921; r2 fraction of residual cells v1=0.2793 g=0.5848, o=0.3983). There was no significant difference in the magnitude of improvement for either residual fluorescence (B—bottom) or fraction of residual EYFP+ cells (C—bottom) between the two improved variants (p>0.25 for all comparisons, ANOVA with Sidak's test). D) Improvement in the function of Con/Foff-EYFP seen in vitro is reflected in improved residual expression in vivo when mPFC is co-infected AAV-Con/Foff-EYFP and either AAV-Cre or AAV-Flp-p2a-Cre. Relative fluorescence is again observed to be increased compared to Cre alone in Con/Foff-EYFP 1.0 (p=0.008, unpaired t-test), while both Con/Foff-EYFP variants have lower average expression than AAV-Cre alone, with no significant difference in expression (variant g, p=0.3321; variant o, p=0.4576; unpaired t-tests). Based on these results, the variant g Con/Foff backbone modifications were labeled as Con/Foff 2.0. E-H) AAV-Con/Foff-EYFP 2.0 is highly expressed in a Cre transgenic mouse and is inactivated by AAV-Flp. E,G) Injection of AAV-Con/Foff-EYFP 2.0 in the hippocampus (E) or mPFC (G) of a SST-Cre transgenic mouse shows expected high expression when injected alone (bottom-left) which is inactivated when co-injected with AAV-Flp (bottom-right). DAPI for comparison (top). F,H) SST-Cre animals show a consistently high level of expression when injected with AAV-Con/Foff-EYFP 2.0 alone in the hippocampus (vs. AAV-Flp p=0.0003; vs WT p=0.0007; ANOVA with Tukey's test) or mPFC (vs. AAV-Flp p=0.0014; vs WT p=0.0027, ANOVA with Tukey's test), while expression in animals co-injected with AAV-Flp is indistinguishable from wild-type animals (hippocampus p=0.1481, mPFC p=0.7208, ANOVA with Tukey's test).

FIG. 4. Chronic monitoring of viral expression shows INTRSECT and WT virus expression kinetics are equivalent. A) A novel, inexpensive, viral expression monitoring device consisting of a LED light source fed into a filter cube and coupled to a visible wavelength spectrometer for emissions detection. B) This device has a linear input-output relationship between area under the curve ('AUC') of the collected light signal and the integration time set on the spectrophotometer ($r^2$=0.9993). C-G) Exemplar data collected from an animal co-injected in mPFC with AAV-Con/Fon-EYFP and AAV-Flp-2a-Cre. (C) A wide range of spectrometer integration times ensures a continuous dynamic range of non-zero, non-saturated signal from early, weak expression through late, strong expression. D) The linear relationship between AUC and integration time for integration times within the dynamic range of the spectrophotometer is maintained in vivo ($r^2$=0.9997). E) Expression score is calculated by normalizing AUC to integration time and averaging all expression scores for a given time point that are within the spectrometer dynamic range; the time point from panels C and D is noted by the arrow. F) Viral expression kinetics can be modeled by fitting an exponential curve to chronic expression monitoring over weeks. G) Chronic viral monitoring does not require additional components from those used in a typical optogenetic experiment (here with a 200 um fiber). H) Comparison of WT EYFP expression all three INTRSECT logical expression variants of EYFP co-injected with indicated recombinase viruses. Note that high titers of Cre recombinase virus are initially expressed but cause toxicity over time (Con/Foff-EYFP+ Cre-green dots), which would not have been readily apparent without a chronic monitoring approach. Expression kinetics between INTRSECT and non-INTRSECT EYFP viruses are equivalent (comparison of rate constant b between WT and Con/Fon p=0.4775, WT and Con/Foff p=0.7728, WT and Coff/Fon p=0.1380, n=6 animals per condition, ANOVA with Dunnett's test). I) Comparison of in vivo expression of all INTRSECT logical AAV-EYFP variants co-injected with all combinations of AAV recombinases as assayed by confocal total integrated fluorescence. There is no difference between expression of WT EYFP and Con/Fon-EYFP (p=0.7615, unpaired t-test) or WT EYFP and Con/Foff-EYFP (p=0.2559, unpaired t-test). Coff/Fon-EYFP expression was lower than WT EYFP (EYFP 2.41× 10e7 A.U. vs. 8.96×10e6 A.U., p=0.0003, unpaired t-test).

FIG. 5. Published Flp-expressing transgenic mouse lines. Mouse lines were found through searches in September, 2018 and October, 2019 of public databases of academic publications as well as commercial and public transgenic mouse repositories as detailed in the methods.

FIG. 6. Engineering, optimization, testing, and in vivo function of three-recombinase-dependent INTRSECT 3× constructs. A) Potential intersectional populations available with three-recombinase expression. Cre AND Flp AND VCre intersectional population denoted by central pattern. B) Detailed diagram of EYFP divided into three exons with addition of two introns and recombinase recognition sites (top). The activity of Cre AND Flp AND VCre, reorients exons in the sense direction (middle). Introns are removed during RNA processing (bottom), ending with an intact mRNA encoding EYFP; this three-recombinase-dependent approach was labeled 3×-EYFP. C,D) Multiple 3×-EYFP construct variants with different intron placement were generated; variants 1-3 spliced poorly (C), while variant 4 spliced efficiently, as verified by sequencing (bottom); (D) splicing results were mirrored by expression patterns in HEK293 cells co-transfected with 3×-EYFP variants and Cre, Flp, and VCre. Therefore, variant 4 was used going forward. E,F) No expression of 3×-EYFP was observed in the absence of all three recombinases as assayed in vitro by flow cytometry of HEK293 cells transfected with indicated constructs (E) or in vivo in animals injected with 3×-EYFP and recombinase viruses as noted (F). G-K) Next, the 3× engineering approach was applied to the genetically-encoded calcium sensor GCaMP6m (3×-G6m), which showed a similar pattern of proper intron splicing (G) and lack of off-target expression by flow cytometry of HEK293 cells (H; coloring as in E). I) In vitro functional analysis and comparison of 3×-G6m (quadruple transfected with Cre, Flp, and VCre) with WT G6m showed intact function, albeit with reduced basal fluorescence level (Time-to-peak: unpaired, two-tailed t-test, p=0.0178. SNR: unpaired, two-tailed t-test, p=0.0031. dF/F: unpaired, two-tailed t-test, p<0.0001. Basal F: unpaired, two-tailed t-test, p<0.0001. Tau: unpaired, two-tailed t-test, p=0.0008. 3×-G6m n=32, WT n=43). J-K) Viral co-infection of 3×-G6m with separate viruses encoding Cre, Flp, and VCre in the hippocampus was highly expressed (J) and generated spontaneous calcium signal during free behavior in the home cage (K), indicating robust, in vivo, function of triple-recombinase-dependent GCaMP6m.

FIG. 7. INTRSECT fluorophore development. A-C) Optimization of mScarlet. A) It was hypothesized that disrupting a lysosomal targeting motif by introducing mutation E95D would reduce aggregation without impairing fluorophore function. B) Cultured neurons expressing mScarlet show obvious aggregates while the mScarlet (E95D) mutant ('oScarlet') do not. C) Summary histogram of aggregates in neurons transfected with mScarlet (red, n=24) or oScarlet (blue, n=19) showing reduced aggregation of oScarlet (mean aggregates oScarlet=0.579 per neuron, mScarlet=25.92 per neuron, p=0.0012, unpaired t-test), while flow cytometry profiling of HEK293 cells transfected with these constructs show equivalent expression (inset). Development of INTRSECT oScarlet (D-F), INTRSECT mTagBFP (G-I), and INTRSECT mCherry (J-L). D,G,J) PCR of INTRSECT plasmid DNA does not generate an amplicon while PCR of cDNA from cells co-transfected with same plasmids and activating recombinases results in single expected band (middle); the sequences of these cDNA bands are seamless across the exon junction (bottom-left). PCR of INTRSECT plasmid DNA generated expected bands with orientation-specific primers (bottom-right). E,H,K) Flow cytometry of cells transfected with INTRSECT constructs and indicated recombinases shows high expression for Con/Fon and Con/Foff, while Coff/Fon is modestly lower than WT. Con/Foff shows diminished, but residual, expression when co-transfected with Cre and Flp, while Coff/Fon expression is either indistinguishable from negative control (E) or has a minor, dim residual population (H,K) when co-transfected with Cre and Flp. F,I,L) INTRSECT fluorophores are highly expressed in HEK293 cells when co-transfected with activating recombinases.

FIG. 8. INTRSECT GECI development. A-E) Optimization of jRGECO1a. A) To reduce payload size and decrease observed in vivo aggregation, the RSET sequence was removed and a putative lysosomal targeting motif was disrupted by introducing mutation E217D to create sRGECO. B) Representative neurons from mouse mPFC four weeks after infection with either jRGECO1a (left) or sRGECO (right). C) Summary histogram of aggregates per neuron after four weeks of expression in vivo (left). Average number of aggregates per neuron in sRGECO (middle; 5.732, n=235) was significantly less than jRGECO1a (6.958, n=240; p=0.0365, unpaired t-test). Fluorescence expression did not differ between constructs in vivo (right; n=4 injection sites each, mean total integrated fluorescence sRGECO=2.47×10e7 A.U., jRGECO1a=1.86×10e7 A.U., p=0.1867, unpaired t-test). D) To characterize sRGECO function, a 3D-printed well insert for field stimulation (left) that reliably drove signal in cultured neurons expressing GCaMP6m (right) was constructed. E) sRGECO and jRGECO1a had broadly similar biophysical properties in cultured neurons, albeit with lower basal fluorescence of sRGECO with associated increase in dF/F (p<0.01, unpaired t-tests, n as indicated). Development of INTRSECT sRGECO (F-H), INTRSECT GCaMP6m (I-K), and INTRSECT GCaMP6f (L-N). F,I,L) PCR of INTRSECT plasmid DNA does not generate an amplicon while PCR of cDNA from cells co-transfected with same plasmids and activating recombinases results in single expected band (middle); the sequences of these cDNA bands are seamless across the exon junction (bottom-left). PCR of sRGECO plasmid DNA generated expected bands with orientation-specific primers (bottom-right). G,J,M) Flow cytometry of cells transfected with INTRSECT tools and indicated recombinases show generally high expression comparable to WT, with diminished lower expression in the active configuration of Con/Fon and Coff/Fon. A minor population of Con/Foff cells co-transfected with inactivating Cre and Flp is observed. H,K,N) INTRSECT tools co-transfected in cultured neurons generate reliable calcium signal in response to field stimulation, with some scattered differences in biophysical properties (n as indicated, *p<0.05, p<0.01, *p<0.005, ****p<0.0005, ANOVA with Dunnett's test).

FIG. 9. INTRSECT excitatory opsin development. Development of INTRSECT bReaChES-EYFP (A-C), INTRSECT ChR2(ET/TC)-EYFP (D-F), INTRSECT ChR2 (H134R)-mCherry (G-I), and INTRSECT ChRmine3.3-p2a-oScarlet (J-L). A,D,G,J) PCR of INTRSECT plasmid DNA generates an amplicon larger than WT, while PCR of cDNA from cells co-transfected with same plasmids and activating recombinases results in an amplicon equivalent to WT (middle). The sequences of these cDNA bands are seamless across the exon junctions (bottom). INTRSECT ChR2 (H134R)-mCherry was additionally noted to have a smaller PCR product generated by all four cDNA templates and a second, unique product for Coff/Fon. The shared minor amplicon is a truncated sequence splicing exon 1 to exon 3 directly, including in the non-intron-containing WT. The tertiary product of Coff/Fon represents a cryptic splice site active only in this logical configuration (bottom). B,E,H,K) Flow cytometry of cells transfected with INTRSECT tools and indicated recombinases show expression comparable to WT. Diminished, but residual, expression is observed in all constructs for the Con/Foff configuration and in various constructs (B,E) for the Coff/Fon configuration when co-transfected with Cre and Flp. C,F,I,L) Photocurrents of INTRSECT excitatory opsins co-transfected with activating recombinases in cultured neurons are equivalent to WT (all vs. WT, bReaChES-EYFP p>0.5 for all comparisons, ChR2 (ET/TC)-EYFP p>0.9 for all comparisons, ChR2(H134R)-mCherry p>0.85 for all comparisons, ChRmine3.3-p2a-oScarlett p>0.2 for all comparisons, n as indicated, ANOVA with Dunnett's test).

FIG. 10. INTRSECT inhibitory opsin development. Development of INTRSECT NpHR3.3-p2a-EYFP (A-C), INTRSECT Arch3.3-p2a-EYFP (D-F), and INTRSECT iC++-EYFP (G-I). A,D,G) PCR of INTRSECT plasmid DNA generates an amplicon larger than WT, while PCR of cDNA from cells co-transfected with same plasmids and activating recombinases results in an amplicon equivalent to WT (middle); a smaller PCR product is noted in all tools for Con/Fon and Con/Foff. The sequences of these cDNA bands are seamless across the exon junctions. The shared minor amplicon is a truncated sequence splicing exon 1 to exon 3 directly; high-quality sequencing of minor products for NpHR3.3-p2a-EYFP (A) was only obtained for Con/Fon and Con/Foff PCR products. B,E,H) Flow cytometry of cells transfected with INTRSECT tools and indicated recombinases show expression comparable to WT Diminished, but residual, expression is observed in all constructs for the Con/Foff configuration and in some constructs (E,H) for the Coff/Fon configuration when co-transfected with Cre and Flp. C,F,I) Photocurrents of INTRSECT tools co-transfected with activating recombinases in cultured neurons are equivalent to WT for NpHR3.3-p2a-EYFP and iC++-EYFP (all vs. WT, NpHR3.3-p2a-EYFP p>0.9 for all comparisons, iC++-EYFP p>0.5 for all comparisons, n as indicated, ANOVA with Dunnett's test). INTRSECT Arch3.3-p2a-EYFP showed reduced photocurrents for Con/Fon and Con/Foff (F—left; all vs. WT, Con/Fon p=0.0143, Con/Foff p=0.0123, Coff/Fon p=0.4551, n as indicated, ANOVA with Dunnett's test). Acute mPFC slice recordings from neurons expressing WT and INTRSECT Arch3.3-p2a-EYFP four weeks post-infection showed equivalent photocurrents for these two logical configurations and significantly increased photocurrent for Coff/Fon (F—right; all vs. WT, n as indicated, Con/Fon p=0.3966, Con/Foff p=0.9286, Coff/Fon p=0.0001, ANOVA with Dunnett's test).

FIG. 11. Optimization of the Con/Foff INTRSECT backbone. A) Con/Foff-EYFP variants with modified sequences noted by triangles (recombinase recognition sequences) and bars (additional 14 bp sequences). Triangle direction notes orientation of central recognition site motif relative to promoter. The original T3/F5' cassette is noted throughout by 'v1'. B) Variants were screened by flow cytometry and the residual population was defined as having fluorescence intensity greater than the maximum intensity of the negative control. Mean EYFP signal and percentage of total population were used as the read-out of variant function. C) Variants were refined sequentially through three rounds of screening. FRT/F5 ('g') and 14 bp-FRT/F5 ('o') were consistently superior to v1 with significantly decreased mean signal and percentage of total population (n=5 separate experiments, all vs. v1, *p<0.05, p<0.01, *p<0.001, ****p<0.0005; ANOVA with Dunnett's test). Dashed blue boxes indicate variants further modified in subsequent screening round. Variant 'g' was chosen for the Con/Foff INTRSECT 2.0 backbone. D-E) Comparison of mean signal (left) and percentage of total population (right) of 2.0 INTRSECT Con/Foff tools relative to 1.0 versions in HEK293 cells co-transfected with Cre alone (D; active configuration; mean relative signal of 2.0=1.014, p=0.7788, relative percentage of total population=1.038, p=0.4733) or co-transfected with Cre AND Flp (E; inactivated configuration, relative mean signal=0.8255, p=0.0168, relative percentage of total population=0.8685, p=0.0395, n=15 individual constructs, all comparisons paired t-tests). F) Observed in vivo viral toxicity of AAV-Con/Foff-EYFP 2.0 co-injected with AAV-Cre is independent of INTRSECT virus titer. G) Comparison of the measured in vivo viral expression score immediately prior to animal sacrifice and post-hoc total integrated fluorescence measured by confocal are positively correlated (r=0.7157, p<0.0001, n=30, Pearson correlation of log-transformed data).

FIG. 12. Identifying and validating a recombinase orthologous to Cre and Flp. A) Co-transfected HEK293 cells with combinations of recombinase expression constructs (rows) and recombinase-dependent EYFP expression constructs (xDIO-EYFP; columns) were analyzed by flow cytometry. Cre and Dre showed obvious, bi-directional cross-activity, with some additional cross-activity noted when Cre was paired with scDIO-EYFP. VCre showed expected robust action on its vcDIO-EYFP partner without any noted in vitro cross-activity. B) AAV-Cre, -Flp, and -VCre show expected robust activity when co-injected with their partner AAV-xDIO-EYFP without any evidence of cross-activity after four weeks of expression in mPFC at either low magnification (left) or high magnification (right). Needle track and cellular debris were used to identify injection sites in samples without expression. C) rAAV serotypes of Flp and VCre were generated and these were co-injected with their respective AAV-xDIO-EYFP in mPFC, while also injecting AAV-xDIO-EYFP into the VTA. After two weeks (left), sparse EYFP expression was observed in mPFC and VTA, with high levels of expression in both sites, driven by both recombinases, after four weeks (right).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant expression vector comprising:
   a) a first coding sequence encoding a portion of a polypeptide of interest, wherein a first recombinase recognition site is positioned 5' to the first coding sequence;
   b) a second coding sequence positioned 3' to the first coding sequence, the second coding sequence encoding a portion of the polypeptide of interest;
   c) a first non-coding sequence comprising a first recombinase recognition site and a second recombinase recognition site positioned between the first coding sequence and the second coding sequence;
   d) a third coding sequence positioned 3' to the second coding sequence, the third coding sequence encoding a portion of the polypeptide of interest, wherein a third recombinase recognition site is positioned 3' to the third coding sequence; and
   e) a second non-coding sequence comprising a second recombinase recognition site and a third recombinase recognition site positioned between the second coding sequence and the third coding sequence.

2. The recombinant expression vector of claim 1, wherein the first coding sequence is in reverse complement orientation.

3. The recombinant expression vector of claim 1 or claim 2, wherein the second coding sequence is in reverse complement orientation.

4. The recombinant expression vector of claim 1, wherein the third coding sequence is in reverse complement orientation.

5. The recombinant expression vector of claim 1, wherein the first coding sequence, the second coding sequence, and the third coding sequence are in reverse complement orientation.

6. The recombinant expression vector of claim 1, wherein the polypeptide of interest comprises any one of a fluorescent polypeptide, a calcium indicator, an excitatory opsin, and an inhibitory opsin.

7. The recombinant expression vector of claim 1, wherein the first recombinase recognition site is a Cre recombinase recognition site.

8. The recombinant expression vector of claim 7, wherein the Cre recombinase recognition site comprises a loxP sequence, lox2722 sequence, loxN sequence, vloxP sequence, or vlox2722 sequence.

9. The recombinant expression vector of claim 1, wherein the second recombinase recognition site is a Flp recombinase recognition site.

10. The recombinant expression vector of claim 9, wherein the Flp recombinase recognition site comprises a F3 sequence, F5 sequence, FRT sequence, variant FRT sequence, or F72 sequence.

11. The recombinant expression vector of claim 1, wherein the third recombinase recognition site is a vCre recombinase recognition site.

12. A method for modulating production of a polypeptide of interest in a target cell or a target cell population, the method comprising:
   introducing a recombinant expression vector comprising
   a) a first coding sequence encoding a portion of a polypeptide of interest, wherein a first recombinase recognition site is positioned 5' to the first coding sequence;
   b) a second coding sequence positioned 3' to the first coding sequence, the second coding sequence encoding a portion of the polypeptide of interest;
   c) a first non-coding sequence comprising a first recombinase recognition site and a second recombinase recognition site positioned between the first coding sequence and the second coding sequence;
   d) a third coding sequence positioned 3' to the second coding sequence, the third coding sequence encoding a portion of the polypeptide of interest, wherein a third recombinase recognition site is positioned 3' to the third coding sequence; and
   e) a second non-coding sequence comprising a second recombinase recognition site and a third recombinase recognition site positioned between the second coding sequence and the third coding sequence
   into the target cell or the target cell population.

13. The method of claim 12, wherein the target cell or the target cell population expresses one or more of Cre recombinase, Flp recombinase, and vCre recombinase.

14. The method of claim 13, wherein the method further comprises introducing one or more recombinant expression vectors encoding one or more of Cre recombinase, Flp recombinase, and vCre recombinase into the target cell or the target cell population.

15. The method of claim 14, wherein the method further comprises modulating the amount of Cre recombinase, Flp recombinase, vCre recombinase, or any combination thereof expressed by the target cell or the target cell population.

16. The method of claim 12, wherein the first coding sequence is in reverse complement orientation.

17. The method of claim 12, wherein the second coding sequence is in reverse complement orientation.

18. The method of claim 12, wherein the third coding sequence is in reverse complement orientation.

19. The method of claim 12, wherein the first coding sequence, the second coding sequence, and the third coding sequence are in reverse complement orientation.

20. The method of claim 12, wherein the polypeptide of interest comprises any one of a fluorescent protein, a calcium indicator, an excitatory opsin, and an inhibitory opsin.

21. The method of claim 12, wherein the first recombinase recognition site is a Cre recombinase recognition site.

22. The method of claim 21, wherein the Cre recombinase recognition site comprises a loxP sequence, lox2722 sequence, loxN sequence, vloxP sequence, or vlox2722 sequence.

23. The method of claim 12, wherein the second recombinase recognition site is a Flp recombinase recognition site.

24. The method of claim 23, wherein the Flp recombinase recognition site comprises a F3 sequence, F5 sequence, FRT sequence, variant FRT sequence, or F72 sequence.

25. The method of claim 12, wherein the third recombinase recognition site is a vCre recombinase recognition site.

\* \* \* \* \*

SEQUENCE LISTING

```
<160> NUMBER OF SEQ ID NOS: 118

<210> SEQ ID NO 1
<211> LENGTH: 9
<212> TYPE: DNA
<213> ORGANISM: Artificial sequence
<220> FEATURE:
<223> OTHER INFORMATION: synthetic sequence

<400> SEQUENCE: 1 ttctggtac                                                          9

<210> SEQ ID NO 2
<211> LENGTH: 9
<212> TYPE: DNA
<213> ORGANISM: Artificial sequence
<220> FEATURE:
<223> OTHER INFORMATION: synthetic sequence

<400> SEQUENCE: 2 ttcttttac                                                          9

<210> SEQ ID NO 3
<211> LENGTH: 12
<212> TYPE: DNA
<213> ORGANISM: Artificial sequence
<220> FEATURE:
<223> OTHER INFORMATION: synthetic sequence

<400> SEQUENCE: 3
ggcaagctgc cc                                                     12

<210> SEQ ID NO 4
<211> LENGTH: 12
<212> TYPE: DNA
<213> ORGANISM: Artificial sequence
<220> FEATURE:
<223> OTHER INFORMATION: synthetic sequence

<400> SEQUENCE: 4
gtccaggagc gc                                                     12

<210> SEQ ID NO 5
<211> LENGTH: 10
<212> TYPE: DNA
<213> ORGANISM: Artificial sequence
<220> FEATURE:
<223> OTHER INFORMATION: synthetic sequence

<400> SEQUENCE: 5
tccagggcct                                                        10

<210> SEQ ID NO 6
<211> LENGTH: 10
<212> TYPE: DNA
```

-continued

```
<213> ORGANISM: Artificial sequence
<220> FEATURE:
<223> OTHER INFORMATION: synthetic sequence

<400> SEQUENCE: 6
cacccaaggc                                                                    10

<210> SEQ ID NO 7
<211> LENGTH: 10
<212> TYPE: DNA
<213> ORGANISM: Artificial sequence
<220> FEATURE:
<223> OTHER INFORMATION: synthetic sequence

<400> SEQUENCE: 7
cccaggactc                                                                    10

<210> SEQ ID NO 8
<211> LENGTH: 12
<212> TYPE: DNA
<213> ORGANISM: Artificial sequence
<220> FEATURE:
<223> OTHER INFORMATION: synthetic sequence

<400> SEQUENCE: 8
ctgctggtga gc                                                                 12

<210> SEQ ID NO 9
<211> LENGTH: 12
<212> TYPE: DNA
<213> ORGANISM: Artificial sequence
<220> FEATURE:
<223> OTHER INFORMATION: synthetic sequence

<400> SEQUENCE: 9
tcaccggcct ga                                                                 12

<210> SEQ ID NO 10
<211> LENGTH: 12
<212> TYPE: DNA
<213> ORGANISM: Artificial sequence
<220> FEATURE:
<223> OTHER INFORMATION: synthetic sequence

<400> SEQUENCE: 10
acccaggact cc                                                                 12

<210> SEQ ID NO 11
<211> LENGTH: 12
<212> TYPE: DNA
<213> ORGANISM: Artificial sequence
<220> FEATURE:
<223> OTHER INFORMATION: synthetic sequence

<400> SEQUENCE: 11
ttacaggtat gc                                                                 12

<210> SEQ ID NO 12
<211> LENGTH: 12
<212> TYPE: DNA
<213> ORGANISM: Artificial sequence
<220> FEATURE:
<223> OTHER INFORMATION: synthetic sequence

<400> SEQUENCE: 12
ctccagggcc tt                                                                 12
```

```
<210> SEQ ID NO 13
<211> LENGTH: 12
<212> TYPE: DNA
<213> ORGANISM: Artificial sequence
<220> FEATURE:
<223> OTHER INFORMATION: synthetic sequence

<400> SEQUENCE: 13
acactggatt gg                                                       12

<210> SEQ ID NO 14
<211> LENGTH: 12
<212> TYPE: DNA
<213> ORGANISM: Artificial sequence
<220> FEATURE:
<223> OTHER INFORMATION: synthetic sequence

<400> SEQUENCE: 14
tgccaggtac gc                                                       12

<210> SEQ ID NO 15
<211> LENGTH: 12
<212> TYPE: DNA
<213> ORGANISM: Artificial sequence
<220> FEATURE:
<223> OTHER INFORMATION: synthetic sequence

<400> SEQUENCE: 15
tccaagggat ac                                                       12

<210> SEQ ID NO 16
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 16

Xaa Xaa Xaa Xaa Xaa
1               5

<210> SEQ ID NO 17
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 17

Xaa Xaa Xaa Xaa Xaa
1               5

<210> SEQ ID NO 18
<211> LENGTH: 5
<212> TYPE: PRT
<213> ORGANISM: Artificial sequence
<220> FEATURE:
<223> OTHER INFORMATION: synthetic sequence
<220> FEATURE:
```

```
<221> NAME/KEY: misc_feature
<222> LOCATION: (1)..(5)
<223> OTHER INFORMATION: Xaa can be any naturally occurring amino acid

<400> SEQUENCE: 18

Xaa Xaa Xaa Xaa Xaa
1               5

<210> SEQ ID NO 19
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 19

Xaa Xaa Xaa Xaa Xaa
1               5

<210> SEQ ID NO 20
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 20

Xaa Xaa Xaa Xaa Xaa
1               5

<210> SEQ ID NO 21
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 21

Xaa Xaa Xaa Xaa Xaa
1               5

<210> SEQ ID NO 22
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 22

Xaa Xaa Xaa Xaa Xaa
1               5

<210> SEQ ID NO 23
```

```
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 23

Xaa Xaa Xaa Xaa Xaa
1               5

<210> SEQ ID NO 24
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 24

Xaa Xaa Xaa Xaa Xaa
1               5

<210> SEQ ID NO 25
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 25

Xaa Xaa Xaa Xaa Xaa
1               5

<210> SEQ ID NO 26
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 26

Xaa Xaa Xaa Xaa Xaa
1               5

<210> SEQ ID NO 27
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 27
```

```
Xaa Xaa Xaa Xaa Xaa
1               5

<210> SEQ ID NO 28
<211> LENGTH: 450
<212> TYPE: PRT
<213> ORGANISM: Artificial sequence
<220> FEATURE:
<223> OTHER INFORMATION: synthetic sequence

<400> SEQUENCE: 28

Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
                20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350
```

```
Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Thr Asp Ser Glu
    370                 375                 380

Glu Glu Ile Gly Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 29
<211> LENGTH: 451
<212> TYPE: PRT
<213> ORGANISM: Artificial sequence
<220> FEATURE:
<223> OTHER INFORMATION: synthetic sequence

<400> SEQUENCE: 29

Met Arg Gly Ser His His His His His His Gly Met Ala Ser Met Thr
1                   5                   10                  15

Gly Gly Gln Gln Met Gly Arg Asp Leu Tyr Asp Asp Asp Asp Lys Asp
                20                  25                  30

Leu Ala Thr Met Val Asp Ser Ser Arg Arg Lys Trp Asn Lys Thr Gly
            35                  40                  45

His Ala Val Arg Ala Ile Gly Arg Leu Ser Ser Leu Glu Asn Val Tyr
        50                  55                  60

Ile Met Ala Asp Lys Gln Lys Asn Gly Ile Lys Ala Asn Phe Lys Ile
65                  70                  75                  80

Arg His Asn Ile Glu Asp Gly Gly Val Gln Leu Ala Tyr His Tyr Gln
                85                  90                  95

Gln Asn Thr Pro Ile Gly Asp Gly Pro Val Leu Leu Pro Asp Asn His
            100                 105                 110

Tyr Leu Ser Thr Gln Ser Lys Leu Ser Lys Asp Pro Asn Glu Lys Arg
        115                 120                 125

Asp His Met Val Leu Leu Glu Phe Val Thr Ala Ala Gly Ile Thr Leu
    130                 135                 140

Gly Met Asp Glu Leu Tyr Lys Gly Gly Thr Gly Gly Ser Met Val Ser
145                 150                 155                 160

Lys Gly Glu Glu Leu Phe Thr Gly Val Val Pro Ile Leu Val Glu Leu
                165                 170                 175

Asp Gly Asp Val Asn Gly His Lys Phe Ser Val Ser Gly Glu Gly Glu
            180                 185                 190

Gly Asp Ala Thr Tyr Gly Lys Leu Thr Leu Lys Phe Ile Cys Thr Thr
        195                 200                 205

Gly Lys Leu Pro Val Pro Trp Pro Thr Leu Val Thr Thr Leu Thr Tyr
    210                 215                 220

Gly Val Gln Cys Phe Ser Arg Tyr Pro Asp His Met Lys Gln His Asp
225                 230                 235                 240

Phe Phe Lys Ser Ala Met Pro Glu Gly Tyr Ile Gln Glu Arg Thr Ile
                245                 250                 255
```

-continued

```
Phe Phe Lys Asp Asp Gly Asn Tyr Lys Thr Arg Ala Glu Val Lys Phe
            260                 265                 270

Glu Gly Asp Thr Leu Val Asn Arg Ile Glu Leu Lys Gly Ile Asp Phe
            275                 280                 285

Lys Glu Asp Gly Asn Ile Leu Gly His Lys Leu Glu Tyr Asn Thr Arg
            290                 295                 300

Asp Gln Leu Thr Glu Glu Gln Ile Ala Glu Phe Lys Glu Ala Phe Ser
305                 310                 315                 320

Leu Phe Asp Lys Asp Gly Asp Gly Thr Ile Thr Thr Lys Glu Leu Gly
            325                 330                 335

Thr Val Met Arg Ser Leu Gly Gln Asn Pro Thr Glu Ala Glu Leu Gln
            340                 345                 350

Asp Met Ile Asn Glu Val Asp Ala Asp Gly Asn Gly Thr Ile Asp Phe
            355                 360                 365

Pro Glu Phe Leu Thr Met Met Ala Arg Lys Met Lys Asp Thr Asp Ser
    370                 375                 380

Glu Glu Glu Ile Arg Glu Ala Phe Arg Val Phe Asp Lys Asp Gly Asn
385                 390                 395                 400

Gly Tyr Ile Ser Ala Ala Glu Leu Arg His Val Met Thr Asn Leu Gly
            405                 410                 415

Glu Lys Leu Thr Asp Glu Glu Val Asp Glu Met Ile Arg Glu Ala Asp
            420                 425                 430

Ile Asp Gly Asp Gly Gln Val Asn Tyr Glu Glu Phe Val Gln Met Met
            435                 440                 445

Thr Ala Lys
    450
```

```
<210> SEQ ID NO 30
<211> LENGTH: 450
<212> TYPE: PRT
<213> ORGANISM: Artificial sequence
<220> FEATURE:
<223> OTHER INFORMATION: synthetic sequence

<400> SEQUENCE: 30
```

```
Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
            50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
            85                  90                  95

Asn Thr Pro Ile Gly Asp Gly Pro Val Leu Leu Pro Asp Asn His Tyr
            100                 105                 110

Leu Ser Thr Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
            130                 135                 140

Met Asp Glu Leu Tyr Lys Gly Gly Thr Gly Gly Ser Met Val Ser Lys
145                 150                 155                 160
```

-continued

```
Gly Glu Glu Leu Phe Thr Gly Val Val Pro Ile Leu Val Glu Leu Asp
            165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
            210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
            355                 360                 365

Glu Phe Leu Thr Met Met Ala Arg Lys Met Lys Asp Thr Asp Ser Glu
        370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450
```

```
<210> SEQ ID NO 31
<211> LENGTH: 450
<212> TYPE: PRT
<213> ORGANISM: Artificial sequence
<220> FEATURE:
<223> OTHER INFORMATION: synthetic sequence

<400> SEQUENCE: 31
```

```
Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60
```

-continued

```
Met Ala Asp Lys Gln Lys Asn Gly Ile Lys Ala Asn Phe Lys Ile Arg
65              70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
        370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450
```

```
<210> SEQ ID NO 32
<211> LENGTH: 450
```

```
<212> TYPE: PRT
<213> ORGANISM: Artificial sequence
<220> FEATURE:
<223> OTHER INFORMATION: synthetic sequence

<400> SEQUENCE: 32

Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Cys Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380
```

-continued

```
Glu Glu Ile Arg Glu Ala Phe Arg Val Phe Asp Lys Asp Gly Asn Gly
385             390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450
```

<210> SEQ ID NO 33
<211> LENGTH: 450
<212> TYPE: PRT
<213> ORGANISM: Artificial sequence
<220> FEATURE:
<223> OTHER INFORMATION: synthetic sequence

<400> SEQUENCE: 33

```
Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285
```

-continued

```
Glu Asp Gly Asn Ile Leu Gly His Lys Leu Glu Tyr Asn Thr Arg Asp
    290             295             300

Gln Leu Thr Glu Glu Gln Ile Ala Glu Phe Lys Glu Ala Phe Ser Leu
305             310             315             320

Phe Asp Lys Asp Gly Asp Gly Thr Ile Thr Thr Lys Glu Leu Gly Thr
            325             330             335

Val Met Arg Ser Leu Gly Gln Asn Pro Thr Glu Ala Glu Leu Gln Asp
            340             345             350

Met Ile Asn Glu Val Asp Ala Asp Gly Asn Gly Thr Ile Asp Phe Pro
            355             360             365

Glu Phe Leu Thr Met Met Ala Arg Lys Met Lys Asp Thr Asp Ser Glu
    370             375             380

Glu Glu Ile Arg Glu Ala Phe Arg Val Phe Asp Lys Asp Gly Asn Gly
385             390             395             400

Tyr Ile Ser Ala Ala Glu Leu Arg His Val Met Thr Asn Leu Gly Glu
            405             410             415

Lys Leu Thr Asp Glu Glu Val Asp Glu Met Ile Arg Glu Ala Asp Ile
            420             425             430

Asp Gly Asp Gly Gln Val Asn Tyr Glu Glu Phe Val Gln Met Met Thr
            435             440             445

Ala Lys
    450

<210> SEQ ID NO 34
<211> LENGTH: 450
<212> TYPE: PRT
<213> ORGANISM: Artificial sequence
<220> FEATURE:
<223> OTHER INFORMATION: synthetic sequence

<400> SEQUENCE: 34

Met Gly Ser His His His His His His Gly Met Ala Ser Met Thr Gly
1               5               10              15

Gly Gln Gln Met Gly Arg Asp Leu Tyr Asp Asp Asp Asp Lys Asp Leu
                20              25              30

Ala Thr Met Val Asp Ser Ser Arg Arg Lys Trp Asn Lys Thr Gly His
            35              40              45

Ala Val Arg Ala Ile Gly Arg Leu Ser Ser Leu Glu Asn Val Tyr Ile
    50              55              60

Met Ala Asp Lys Gln Lys Asn Gly Ile Lys Ala Asn Phe Lys Ile Arg
65              70              75              80

His Asn Ile Glu Asp Gly Gly Val Gln Leu Ala Tyr His Tyr Gln Gln
                85              90              95

Asn Thr Pro Ile Gly Asp Gly Pro Val Leu Leu Pro Asp Asn His Tyr
                100             105             110

Leu Ser Val Gln Ser Lys Leu Ser Lys Asp Pro Asn Glu Lys Arg Asp
            115             120             125

His Met Val Leu Leu Glu Phe Val Thr Ala Ala Gly Ile Thr Leu Gly
            130             135             140

Met Asp Glu Leu Tyr Lys Gly Gly Thr Gly Gly Ser Met Val Ser Lys
145             150             155             160

Gly Glu Glu Leu Phe Thr Gly Val Val Pro Ile Leu Val Glu Leu Asp
                165             170             175

Gly Asp Val Asn Gly His Lys Phe Ser Val Ser Gly Glu Gly Glu Gly
            180             185             190
```

-continued

```
Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
                355                 360                 365

Glu Phe Leu Thr Met Met Ala Arg Lys Met Lys Asp Thr Asp Ser Glu
        370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
                435                 440                 445

Ala Lys
    450
```

```
<210> SEQ ID NO 35
<211> LENGTH: 450
<212> TYPE: PRT
<213> ORGANISM: Artificial sequence
<220> FEATURE:
<223> OTHER INFORMATION: synthetic sequence

<400> SEQUENCE: 35
```

```
Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
                20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95
```

-continued

```
Asn Thr Pro Ile Gly Asp Gly Pro Val Leu Leu Pro Asp Asn His Tyr
            100             105             110

Leu Ser Val Gln Ser Lys Leu Ser Lys Asp Pro Asn Glu Lys Arg Asp
            115             120             125

His Met Val Leu Leu Glu Phe Val Thr Ala Ala Gly Ile Thr Leu Gly
            130             135             140

Met Asp Glu Leu Tyr Lys Gly Gly Thr Gly Gly Ser Met Val Ser Lys
145             150             155             160

Gly Glu Glu Leu Phe Thr Gly Val Val Pro Ile Leu Val Glu Leu Asp
                165             170             175

Gly Asp Val Asn Gly His Lys Phe Ser Val Ser Gly Glu Gly Glu Gly
            180             185             190

Asp Ala Thr Tyr Gly Lys Leu Thr Leu Lys Phe Ile Cys Thr Thr Gly
            195             200             205

Lys Leu Pro Val Pro Trp Pro Thr Leu Val Thr Thr Leu Thr Tyr Gly
            210             215             220

Val Gln Cys Phe Ser Arg Tyr Pro Asp His Met Lys Gln His Asp Phe
225             230             235             240

Phe Lys Ser Ala Met Pro Glu Gly Tyr Ile Gln Glu Arg Thr Ile Phe
                245             250             255

Phe Lys Asp Asp Gly Asn Tyr Lys Thr Arg Ala Glu Val Lys Phe Glu
            260             265             270

Gly Asp Thr Leu Val Asn Arg Ile Glu Leu Lys Gly Ile Asp Phe Lys
            275             280             285

Glu Asp Gly Asn Ile Leu Gly His Lys Leu Glu Tyr Asn Thr Arg Asp
            290             295             300

Gln Leu Thr Glu Glu Gln Ile Ala Glu Phe Lys Glu Ala Phe Ser Leu
305             310             315             320

Phe Asp Lys Asp Gly Asp Gly Thr Ile Thr Thr Lys Glu Leu Gly Thr
                325             330             335

Val Met Arg Ser Leu Gly Gln Asn Pro Thr Glu Ala Glu Leu Gln Asp
            340             345             350

Met Ile Asn Glu Val Asp Ala Asp Gly Asp Gly Thr Ile Asp Phe Pro
            355             360             365

Glu Phe Leu Thr Met Met Ala Arg Lys Met Lys Asp Thr Asp Ser Glu
            370             375             380

Glu Glu Ile Arg Glu Ala Phe Arg Val Phe Asp Lys Asp Gly Asn Gly
385             390             395             400

Tyr Ile Ser Ala Ala Glu Leu Arg His Val Met Thr Asn Leu Gly Glu
                405             410             415

Lys Leu Thr Asp Glu Glu Val Asp Glu Met Ile Arg Glu Ala Asp Ile
            420             425             430

Asp Gly Asp Gly Gln Val Asn Tyr Glu Glu Phe Val Gln Met Met Thr
            435             440             445

Ala Lys
    450
```

<210> SEQ ID NO 36
<211> LENGTH: 450
<212> TYPE: PRT
<213> ORGANISM: Artificial sequence
<220> FEATURE:
<223> OTHER INFORMATION: synthetic sequence

<400> SEQUENCE: 36

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
```

-continued

```
                420                 425                 430

Asp Gly Asp Gly Gln Val Asn Tyr Glu Glu Phe Val Gln Met Met Thr
        435                 440                 445

Ala Lys
    450

<210> SEQ ID NO 37
<211> LENGTH: 450
<212> TYPE: PRT
<213> ORGANISM: Artificial sequence
<220> FEATURE:
<223> OTHER INFORMATION: synthetic sequence

<400> SEQUENCE: 37

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
```

```
                325            330                335

Val Met Arg Ser Leu Gly Gln Asn Pro Thr Glu Ala Glu Leu Gln Asp
            340            345                350

Met Ile Asn Glu Val Asp Ala Asp Gly Asp Gly Thr Ile Asp Phe Pro
            355            360                365

Glu Phe Leu Thr Met Met Ala Arg Lys Gly Ser Tyr Arg Asp Thr Glu
        370            375                380

Glu Glu Ile Arg Glu Ala Phe Gly Val Phe Asp Lys Asp Gly Asn Gly
    385                390                395            400

Tyr Ile Ser Ala Ala Glu Leu Arg His Val Met Thr Asn Leu Gly Glu
                405            410                415

Lys Leu Thr Asp Glu Glu Val Asp Glu Met Ile Arg Glu Ala Asp Ile
            420            425                430

Asp Gly Asp Gly Gln Val Asn Tyr Glu Glu Phe Val Gln Met Met Thr
            435            440                445

Ala Lys
    450

<210> SEQ ID NO 38
<211> LENGTH: 450
<212> TYPE: PRT
<213> ORGANISM: Artificial sequence
<220> FEATURE:
<223> OTHER INFORMATION: synthetic sequence

<400> SEQUENCE: 38

Met Gly Ser His His His His His His Gly Met Ala Ser Met Thr Gly
1               5               10                15

Gly Gln Gln Met Gly Arg Asp Leu Tyr Asp Asp Asp Asp Lys Asp Leu
            20            25                30

Ala Thr Met Val Asp Ser Ser Arg Arg Lys Trp Asn Lys Thr Gly His
        35            40                45

Ala Val Arg Ala Ile Gly Arg Leu Ser Ser Leu Glu Asn Val Tyr Ile
    50                55                60

Lys Ala Asp Lys Gln Lys Asn Gly Ile Lys Ala Asn Phe His Ile Arg
65                70            75                80

His Asn Ile Glu Asp Gly Gly Val Gln Leu Ala Tyr His Tyr Gln Gln
                85            90                95

Asn Thr Pro Ile Gly Asp Gly Pro Val Leu Leu Pro Asp Asn His Tyr
            100            105                110

Leu Ser Val Gln Ser Lys Leu Ser Lys Asp Pro Asn Glu Lys Arg Asp
        115            120                125

His Met Val Leu Leu Glu Phe Val Thr Ala Ala Gly Ile Thr Leu Gly
        130            135                140

Met Asp Glu Leu Tyr Lys Gly Gly Thr Gly Gly Ser Met Val Ser Lys
145                150            155                160

Gly Glu Glu Leu Phe Thr Gly Val Val Pro Ile Leu Val Glu Leu Asp
                165            170                175

Gly Asp Val Asn Gly His Lys Phe Ser Val Ser Gly Glu Gly Glu Gly
            180            185                190

Asp Ala Thr Tyr Gly Lys Leu Thr Leu Lys Phe Ile Cys Thr Thr Gly
            195            200                205

Lys Leu Pro Val Pro Trp Pro Thr Leu Val Thr Thr Leu Thr Tyr Gly
        210            215                220

Val Gln Cys Phe Ser Arg Tyr Pro Asp His Met Lys Gln His Asp Phe
```

```
225                230                235                240

Phe Lys Ser Ala Met Pro Glu Gly Tyr Ile Gln Glu Arg Thr Ile Phe
            245                250                255

Phe Lys Asp Asp Gly Asn Tyr Lys Thr Arg Ala Glu Val Lys Phe Glu
            260                265                270

Gly Asp Thr Leu Val Asn Arg Ile Glu Leu Lys Gly Ile Asp Phe Lys
            275                280                285

Glu Asp Gly Asn Ile Leu Gly His Lys Leu Glu Tyr Asn Leu Pro Asp
            290                295                300

Gln Leu Thr Glu Glu Gln Ile Ala Glu Phe Lys Glu Ala Phe Ser Leu
305                310                315                320

Phe Asp Lys Asp Gly Asp Gly Thr Ile Thr Thr Lys Glu Leu Gly Thr
            325                330                335

Val Met Arg Ser Leu Gly Gln Asn Pro Thr Glu Ala Glu Leu Gln Asp
            340                345                350

Met Ile Asn Glu Val Asp Ala Asp Gly Asp Gly Thr Ile Asp Phe Pro
            355                360                365

Glu Phe Leu Thr Met Met Ala Arg Lys Met Lys Tyr Arg Asp Thr Glu
            370                375                380

Glu Glu Ile Arg Glu Ala Phe Gly Val Phe Asp Lys Asp Gly Asn Gly
385                390                395                400

Tyr Ile Ser Ala Ala Glu Leu Arg His Val Met Thr Asn Leu Gly Glu
            405                410                415

Lys Leu Thr Asp Glu Glu Val Asp Glu Met Ile Arg Glu Ala Asp Ile
            420                425                430

Asp Gly Asp Gly Gln Val Asn Tyr Glu Glu Phe Val Gln Met Met Thr
            435                440                445

Ala Lys
    450

<210> SEQ ID NO 39
<211> LENGTH: 450
<212> TYPE: PRT
<213> ORGANISM: Artificial sequence
<220> FEATURE:
<223> OTHER INFORMATION: synthetic sequence

<400> SEQUENCE: 39

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
```

-continued

```
            130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
            210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
            290                 295                 300

Gln Leu Thr Glu Glu Gln Ile Ala Glu Phe Lys Glu Glu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
                355                 360                 365

Glu Phe Leu Thr Met Met Ala Arg Lys Met Lys Tyr Arg Asp Thr Glu
            370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 40
<211> LENGTH: 415
<212> TYPE: PRT
<213> ORGANISM: Artificial sequence
<220> FEATURE:
<223> OTHER INFORMATION: synthetic sequence

<400> SEQUENCE: 40

Met Val Asp Ser Ser Arg Arg Lys Trp Asn Lys Thr Gly His Ala Val
1                   5                   10                  15

Arg Ala Ile Gly Arg Leu Ser Ser Pro Glu Asn Val Tyr Ile Lys Ala
                20                  25                  30

Asp Glu Gln Lys Asn Gly Ile Lys Ala Tyr Phe Lys Ile Arg His Asn
```

-continued

```
                  35                  40                  45

Ile Glu Gly Gly Gly Val Gln Leu Ala Tyr His Tyr Gln Gln Ile Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
                100                 105                 110

Glu Leu Tyr Lys Gly Gly Ser Gly Gly Met Val Ser Lys Gly Glu Glu
                115                 120                 125

Leu Phe Thr Gly Val Val Pro Ile Gln Val Glu Leu Asp Gly Asp Val
    130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
                165                 170                 175

Val Pro Trp Pro Thr Leu Val Thr Thr Leu Ser Tyr Gly Val Gln Cys
                180                 185                 190

Phe Ser Arg Tyr Pro Asp His Met Lys Gln His Asp Phe Phe Lys Ser
                195                 200                 205

Ala Met Pro Glu Gly Tyr Ile Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
                245                 250                 255

Asn Ile Leu Gly His Lys Leu Glu Tyr Ser Thr Arg Asp Gln Leu Thr
                260                 265                 270

Glu Glu Gln Ile Ala Glu Phe Lys Glu Ala Phe Ser Leu Phe Asp Lys
                275                 280                 285

Asp Gly Asp Gly Thr Ile Thr Thr Lys Glu Leu Gly Thr Val Met Arg
    290                 295                 300

Ser Leu Gly Gln Asn Pro Thr Glu Ala Glu Leu Gln Asp Met Ile Asn
305                 310                 315                 320

Glu Val Asp Ala Asp Gly Asp Gly Thr Ile Asp Phe Pro Glu Phe Leu
                325                 330                 335

Thr Met Met Ala Pro Lys Met Gln Asp Thr Asp Ser Glu Glu Glu Ile
                340                 345                 350

Arg Glu Ala Phe Arg Val Phe Asp Lys Asp Gly Asn Gly Tyr Ile Gly
                355                 360                 365

Ala Ala Glu Leu Arg His Val Met Thr Asn Leu Gly Glu Lys Leu Thr
    370                 375                 380

Asp Glu Glu Val Asp Glu Met Ile Arg Val Ala Asp Ile Asp Gly Asp
385                 390                 395                 400

Gly Gln Val Asn Tyr Glu Glu Phe Val Gln Met Met Thr Ala Lys
                405                 410                 415
```

<210> SEQ ID NO 41
<211> LENGTH: 416
<212> TYPE: PRT
<213> ORGANISM: Artificial sequence
<220> FEATURE:
<223> OTHER INFORMATION: synthetic sequence -continued

<400> SEQUENCE: 41

```
Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
                20                  25                  30

Asp Glu Gln Lys Asn Gly Ile Lys Ala Asn Phe Lys Ile Arg His Asn
                35                  40                  45

Ile Glu Asp Gly Gly Val Gln Leu Ala Tyr His Tyr Gln Gln Asn Thr
        50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
                100                 105                 110

Glu Leu Tyr Lys Gly Gly Thr Gly Gly Ser Met Val Ser Lys Gly Glu
                115                 120                 125

Glu Leu Phe Thr Gly Val Val Pro Ile Gln Val Glu Leu Asp Gly Asp
        130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Ser Tyr Gly Val Gln
                180                 185                 190

Cys Phe Ser Arg Tyr Pro Asp His Met Lys Gln His Asp Phe Phe Lys
                195                 200                 205

Ser Ala Met Pro Glu Gly Tyr Ile Gln Glu Arg Thr Ile Phe Phe Lys
        210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
                260                 265                 270

Thr Glu Glu Gln Ile Ala Glu Leu Lys Glu Ala Phe Ser Leu Phe Asp
        275                 280                 285

Lys Asp Gly Asp Gly Thr Ile Thr Thr Lys Glu Leu Gly Thr Val Met
        290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Leu Pro Glu Phe
                325                 330                 335

Gln Thr Met Met Ala Arg Lys Met Asn Asp Thr Asp Ser Glu Glu Glu
        340                 345                 350

Ile Arg Glu Ala Phe Arg Val Phe Asp Lys Asp Gly Asn Gly Tyr Ile
        355                 360                 365

Gly Ala Ala Glu Leu Arg His Val Met Thr Asn Leu Gly Glu Lys Leu
        370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
                405                 410                 415
```

```
<210> SEQ ID NO 42
<211> LENGTH: 417
<212> TYPE: PRT
<213> ORGANISM: Artificial sequence
<220> FEATURE:
<223> OTHER INFORMATION: synthetic sequence

<400> SEQUENCE: 42

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
    50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
            115                 120                 125

Ala Ile Ile Lys Glu Phe Met Arg Phe Lys Val His Met Glu Gly Ser
    130                 135                 140

Val Asn Gly His Glu Phe Glu Ile Glu Gly Glu Gly Glu Gly Arg Pro
145                 150                 155                 160

Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
            180                 185                 190

Lys Ala Tyr Ile Lys His Pro Ala Asp Ile Pro Asp Tyr Phe Lys Leu
            195                 200                 205

Ser Phe Pro Glu Gly Phe Arg Trp Glu Arg Val Met Asn Phe Glu Asp
    210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Ala Thr Arg Asp Gln
            260                 265                 270

Leu Thr Glu Glu Gln Ile Ala Glu Phe Lys Glu Ala Phe Ser Leu Phe
            275                 280                 285

Asp Lys Asp Gly Asp Gly Thr Ile Thr Thr Lys Glu Leu Gly Thr Val
    290                 295                 300

Met Arg Ser Leu Gly Gln Asn Pro Thr Glu Ala Glu Leu Gln Asp Met
305                 310                 315                 320

Ile Asn Glu Val Asp Ala Asp Gly Asp Gly Thr Phe Asp Phe Pro Glu
                325                 330                 335

Phe Leu Thr Met Met Ala Arg Lys Met Asn Asp Thr Asp Ser Glu Glu
            340                 345                 350

Glu Ile Arg Glu Ala Phe Arg Val Phe Asp Lys Asp Gly Asn Gly Tyr
            355                 360                 365
```

```
Ile Gly Ala Ala Glu Leu Arg His Val Met Thr Asp Leu Gly Glu Lys
    370             375             380

Leu Thr Asp Glu Glu Val Asp Glu Met Ile Arg Val Ala Asp Ile Asp
385             390             395             400

Gly Asp Gly Gln Val Asn Tyr Glu Glu Phe Val Gln Met Met Thr Ala
            405             410             415

Lys

<210> SEQ ID NO 43
<211> LENGTH: 418
<212> TYPE: PRT
<213> ORGANISM: Artificial sequence
<220> FEATURE:
<223> OTHER INFORMATION: synthetic sequence

<400> SEQUENCE: 43

Met Val Asp Ser Pro Arg Arg Lys Trp Asn Lys Thr Gly His Ala Val
1               5               10              15

Arg Ala Ile Gly Arg Leu Ser Ser Pro Glu Asn Val Tyr Ile Lys Ala
            20              25              30

Asp Lys Gln Lys Asn Gly Ile Lys Ala Asn Phe Lys Ile Arg His Asn
        35              40              45

Ile Glu Gly Gly Gly Val Gln Leu Ala Tyr His Tyr Gln Gln Asn Thr
    50              55              60

Pro Ile Gly Asp Gly Pro Val Leu Leu Pro Asp Asn His Tyr Leu Ser
65              70              75              80

Val Gln Ser Ile Leu Ser Lys Asp Pro Asn Glu Lys Arg Asp His Met
            85              90              95

Val Leu Leu Glu Phe Val Thr Ala Ala Gly Ile Thr Leu Gly Met Asp
            100             105             110

Glu Leu Tyr Lys Gly Gly Thr Gly Gly Ser Glu Ser Met Val Ser Lys
            115             120             125

Gly Glu Glu Leu Phe Thr Gly Val Val Pro Ile Gln Val Glu Leu Asp
            130             135             140

Gly Asp Val Asn Gly His Lys Phe Ser Val Ser Gly Glu Gly Glu Gly
145             150             155             160

Asp Ala Thr Tyr Gly Lys Leu Thr Leu Lys Phe Ile Cys Thr Thr Gly
            165             170             175

Lys Leu Pro Val Pro Trp Pro Thr Leu Val Thr Thr Leu Ser His Gly
            180             185             190

Val Gln Cys Phe Ser Arg Tyr Pro Asp His Met Lys Gln His Asp Phe
            195             200             205

Phe Lys Ser Ala Met Pro Gly Gly Tyr Ile Gln Glu Arg Thr Ile Phe
    210             215             220

Phe Lys Asp Asp Gly Asn Tyr Lys Thr Arg Ala Glu Val Lys Phe Glu
225             230             235             240

Gly Asp Thr Leu Val Asn Arg Ile Glu Leu Lys Gly Ile Asp Phe Lys
            245             250             255

Glu Asp Gly Asn Ile Leu Gly His Lys Leu Glu Tyr Asn Thr Arg Gly
            260             265             270

Gln Leu Thr Glu Glu Gln Ile Ala Glu Phe Lys Glu Ala Phe Ser Leu
            275             280             285

Phe Asp Lys Asp Gly Asp Gly Thr Ile Thr Thr Lys Glu Leu Gly Thr
    290             295             300
```

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Pro Lys Met Gln Asp Thr Asp Ser Glu
                340                 345                 350

Glu Glu Ile Arg Glu Ala Phe Arg Val Phe Asp Lys Asp Gly Asn Gly
                355                 360                 365

Tyr Ile Gly Ala Ala Glu Leu Arg His Val Met Thr Asn Leu Gly Glu
            370                 375                 380

Lys Leu Thr Asp Glu Glu Val Asp Glu Met Ile Arg Glu Ala Asp Ile
385                 390                 395                 400

Asp Gly Asp Gly Gln Val Asn Tyr Glu Glu Phe Val Gln Met Met Thr
                405                 410                 415

Ala Lys

<210> SEQ ID NO 44
<211> LENGTH: 416
<212> TYPE: PRT
<213> ORGANISM: Artificial sequence
<220> FEATURE:
<223> OTHER INFORMATION: synthetic sequence

<400> SEQUENCE: 44

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
                20                  25                  30

Asp Lys Gln Lys Asn Gly Ile Lys Ala Asn Phe Lys Ile Arg His Asn
            35                  40                  45

Ile Glu Asp Gly Gly Val Gln Leu Ala Tyr His Tyr Gln Gln Asn Thr
        50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
                100                 105                 110

Glu Leu Tyr Lys Gly Gly Thr Gly Gly Ser Met Val Ser Lys Gly Glu
            115                 120                 125

Glu Leu Phe Thr Gly Val Val Pro Ile Gln Val Glu Leu Asp Gly Asp
        130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
                180                 185                 190

Cys Phe Ser Arg Tyr Pro Asp His Met Lys Gln His Asp Phe Phe Lys
            195                 200                 205

Ser Ala Met Pro Glu Gly Tyr Ile Gln Glu Arg Thr Ile Phe Phe Lys
        210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp

```
                    245              250              255

Gly Asn Ile Leu Gly His Lys Leu Glu Tyr Asn Thr Arg Asp Gln Leu
            260              265              270

Thr Glu Glu Gln Ile Ala Glu Phe Lys Glu Ala Phe Ser Leu Phe Asp
        275              280              285

Lys Asp Gly Asp Gly Thr Ile Thr Thr Lys Glu Leu Gly Thr Val Met
    290              295              300

Arg Ser Leu Gly Gln Asn Pro Thr Glu Ala Glu Leu Gln Asp Met Ile
305              310              315              320

Asn Glu Val Asp Ala Asp Gly Asp Gly Thr Ile Asp Phe Pro Glu Phe
            325              330              335

Leu Thr Met Met Ala Arg Lys Met Lys Asp Thr Asp Ser Glu Glu Glu
            340              345              350

Ile Arg Glu Ala Phe Arg Val Phe Asp Lys Asp Gly Asn Gly Tyr Ile
            355              360              365

Gly Ala Ala Glu Leu Arg His Val Met Thr Asn Leu Gly Glu Lys Leu
    370              375              380

Thr Asp Glu Glu Val Asp Glu Met Ile Arg Val Ala Asp Ile Asp Gly
385              390              395              400

Asp Gly Gln Val Asn Tyr Glu Glu Phe Val Gln Met Met Thr Ala Lys
            405              410              415
```

<210> SEQ ID NO 45
<211> LENGTH: 416
<212> TYPE: PRT
<213> ORGANISM: Artificial sequence
<220> FEATURE:
<223> OTHER INFORMATION: synthetic sequence

<400> SEQUENCE: 45

```
Met Val Asp Ser Ser Arg Arg Lys Trp Asn Lys Thr Gly His Ala Val
1               5               10              15

Arg Ala Ile Gly Arg Leu Ser Ser Leu Glu Asn Val Tyr Ile Lys Ala
            20              25              30

Asp Glu Gln Lys Asn Gly Ile Lys Ala Tyr Phe Lys Ile Arg His Asn
        35              40              45

Ile Glu Gly Gly Gly Val Gln Leu Ala Tyr His Tyr Gln Gln Asn Thr
    50              55              60

Pro Ile Gly Asp Gly Pro Val Leu Leu Pro Asp Asn His Tyr Leu Ser
65              70              75              80

Val Gln Ser Ile Leu Ser Lys Asp Pro Asn Glu Lys Arg Asp His Met
            85              90              95

Val Leu Leu Glu Phe Val Thr Ala Ala Gly Ile Thr Leu Gly Met Asp
            100             105             110

Glu Leu Tyr Lys Gly Gly Thr Gly Gly Ser Met Val Ser Lys Gly Glu
        115             120             125

Glu Leu Phe Thr Gly Val Val Pro Ile Gln Val Glu Leu Asp Gly Asp
    130             135             140

Val Asn Gly His Lys Phe Ser Val Ser Gly Glu Gly Glu Gly Asp Ala
145             150             155             160

Thr Tyr Gly Lys Leu Thr Leu Lys Phe Ile Cys Thr Thr Gly Lys Leu
            165             170             175

Pro Val Pro Trp Pro Thr Leu Val Thr Thr Leu Thr Tyr Gly Val Gln
        180             185             190

Cys Phe Ser Arg Tyr Pro Asp His Met Lys Gln His Asp Phe Phe Lys
```

-continued

```
              195                200                205

Ser Ala Met Pro Glu Gly Tyr Ile Gln Glu Arg Thr Ile Phe Phe Lys
    210                215                220

Asp Asp Gly Asn Tyr Lys Thr Arg Ala Glu Val Lys Phe Glu Gly Asp
225                230                235                240

Thr Leu Val Asn Arg Ile Glu Leu Lys Gly Ile Asp Phe Lys Glu Asp
                245                250                255

Gly Asn Ile Leu Gly His Lys Leu Glu Tyr Asn Thr Arg Asp Gln Leu
                260                265                270

Thr Glu Glu Gln Ile Ala Glu Phe Lys Glu Ala Phe Ser Leu Phe Asp
                275                280                285

Lys Asp Gly Asp Gly Thr Ile Thr Thr Lys Glu Leu Gly Thr Val Met
    290                295                300

Arg Ser Leu Gly Gln Asn Pro Thr Glu Ala Glu Leu Gln Asp Met Ile
305                310                315                320

Asn Glu Val Asp Ala Asp Gly Asp Gly Thr Ile Asp Phe Pro Glu Phe
                325                330                335

Leu Thr Met Met Ala Arg Lys Met Asn Asp Thr Asp Ser Glu Glu Glu
                340                345                350

Ile Arg Glu Ala Phe Arg Val Phe Asp Lys Asp Gly Asn Gly Tyr Ile
                355                360                365

Gly Ala Ala Glu Leu Arg His Val Met Thr Asn Leu Gly Glu Lys Leu
    370                375                380

Thr Asp Glu Glu Val Asp Glu Met Ile Arg Val Ala Asp Ile Asp Gly
385                390                395                400

Asp Gly Gln Val Asn Tyr Glu Glu Phe Val Gln Met Met Thr Ala Lys
                405                410                415
```

```
<210> SEQ ID NO 46
<211> LENGTH: 418
<212> TYPE: PRT
<213> ORGANISM: Artificial sequence
<220> FEATURE:
<223> OTHER INFORMATION: synthetic sequence

<400> SEQUENCE: 46

Met Val Asp Ser Ser Arg Arg Lys Trp Asn Lys Thr Gly His Ala Val
1               5                10                15

Arg Ala Ile Gly Arg Leu Ser Ser Leu Glu Asn Val Tyr Ile Lys Ala
                20                25                30

Asp Glu Gln Lys Asn Gly Ile Lys Ala Tyr Phe Lys Ile Arg His Asn
        35                40                45

Ile Glu Gly Gly Gly Val Gln Leu Ala Tyr His Tyr Gln Gln Asn Thr
    50                55                60

Pro Ile Gly Asp Gly Pro Val Leu Leu Pro Asp Asn His Tyr Leu Ser
65                70                75                80

Val Gln Ser Met Leu Ser Lys Asp Pro Asn Glu Lys Arg Asp His Met
                85                90                95

Val Leu Leu Glu Phe Val Thr Ala Ala Gly Ile Thr Leu Gly Met Asp
                100                105                110

Glu Leu Tyr Lys Gly Gly Thr Gly Gly Ser Glu Ser Met Val Ser Lys
        115                120                125

Gly Glu Glu Leu Phe Thr Gly Val Val Pro Ile Gln Val Glu Leu Asp
    130                135                140

Gly Asp Val Asn Gly His Lys Phe Ser Val Ser Gly Glu Gly Glu Gly
```

```
145             150             155             160

Asp Ala Thr Tyr Gly Lys Leu Thr Leu Lys Phe Ile Cys Thr Thr Gly
                165             170             175

Lys Leu Pro Val Pro Trp Pro Thr Leu Val Thr Thr Leu Thr Tyr Gly
                180             185             190

Val Gln Cys Phe Ser Arg Tyr Pro Asp His Met Lys Gln His Asp Phe
                195             200             205

Phe Lys Ser Ala Met Pro Glu Gly Tyr Ile Gln Glu Arg Thr Ile Phe
        210             215             220

Phe Lys Gly Asp Gly Asn Tyr Lys Thr Arg Ala Glu Val Lys Phe Glu
225             230             235             240

Gly Asp Thr Leu Val Asn Arg Ile Glu Leu Lys Gly Ile Asp Phe Lys
                245             250             255

Glu Asp Gly Asn Ile Leu Gly His Lys Leu Glu Tyr Asn Thr Arg Asp
                260             265             270

Gln Leu Thr Glu Glu Gln Ile Ala Glu Phe Lys Glu Ala Phe Ser Leu
                275             280             285

Phe Asp Lys Asp Gly Asp Gly Thr Ile Thr Thr Lys Glu Leu Gly Thr
        290             295             300

Val Met Arg Ser Leu Gly Gln Asn Pro Thr Glu Ala Glu Leu Gln Asp
305             310             315             320

Met Ile Asn Glu Val Asp Ala Asp Gly Asp Gly Thr Ile Asp Phe Pro
                325             330             335

Glu Phe Leu Thr Met Met Ala Arg Lys Met Lys Asp Thr Asp Ser Glu
                340             345             350

Glu Glu Ile Arg Glu Ala Phe Arg Val Phe Asp Lys Asp Gly Asn Gly
                355             360             365

Tyr Ile Gly Ala Ala Glu Leu Arg His Val Met Thr Asn Leu Gly Glu
        370             375             380

Lys Leu Thr Asp Glu Glu Val Asp Glu Met Ile Arg Val Ala Asp Ile
385             390             395             400

Asp Gly Asp Gly Gln Val Asn Tyr Glu Glu Phe Val Gln Met Met Thr
                405             410             415

Ala Lys

<210> SEQ ID NO 47
<211> LENGTH: 619
<212> TYPE: PRT
<213> ORGANISM: Artificial sequence
<220> FEATURE:
<223> OTHER INFORMATION: synthetic sequence

<400> SEQUENCE: 47

Met Val Ser Lys Gly Glu Glu Leu Phe Thr Gly Val Val Pro Ile Leu
1               5               10              15

Val Glu Leu Asp Gly Asp Val Asn Gly His Lys Phe Ser Val Arg Gly
                20              25              30

Glu Gly Glu Gly Asp Ala Thr Asn Gly Lys Leu Thr Leu Lys Phe Ile
                35              40              45

Cys Thr Thr Gly Lys Leu Pro Val Pro Trp Pro Thr Leu Val Thr Thr
        50              55              60

Leu Thr Trp Gly Val Gln Cys Phe Ser Arg Tyr Pro Asp His Met Lys
65              70              75              80

Gln His Asp Phe Phe Lys Ser Ala Met Pro Glu Gly Tyr Val Gln Glu
                85              90              95
```

-continued

```
Arg Thr Ile Phe Phe Lys Asp Asp Gly Asn Tyr Lys Thr Arg Ala Glu
            100              105              110

Val Lys Phe Glu Gly Asp Thr Leu Val Asn Arg Ile Glu Leu Lys Gly
            115              120              125

Ile Asp Phe Lys Glu Asp Gly Asn Ile Leu Gly His Lys Leu Glu Tyr
            130              135              140

Asn Tyr Ile Ser His Asn Val Tyr Ile Thr Ala Asp Lys Gln Lys Asn
145              150              155              160

Gly Ile Lys Ala His Phe Lys Ile Arg His Asn Ile Glu Asp Gly Ser
            165              170              175

Val Gln Leu Ala Asp His Tyr Gln Gln Asn Thr Pro Ile Gly Asp Gly
            180              185              190

Pro Val Leu Leu Pro Asp Asn His Tyr Leu Ser Thr Gln Ser Lys Leu
            195              200              205

Ser Lys Asp Pro Asn Glu Lys Arg Asp His Met Val Leu Leu Glu Phe
            210              215              220

Val Thr Ala Ala Arg Met Leu Ser Glu Glu Glu Leu Ala Asn Cys Phe
225              230              235              240

Arg Ile Phe Asp Lys Asp Ala Asn Gly Phe Ile Asp Ile Glu Glu Leu
            245              250              255

Gly Glu Ile Leu Arg Ala Thr Gly Glu His Val Thr Glu Glu Asp Ile
            260              265              270

Glu Asp Leu Met Lys Asp Ser Asp Lys Asn Asn Asp Gly Arg Ile Asp
            275              280              285

Phe Asp Glu Phe Leu Lys Met Met Glu Gly Val Gln Gly Thr Ser Glu
            290              295              300

Glu Glu Leu Ala Asn Cys Phe Arg Ile Phe Asp Lys Asp Ala Asn Gly
305              310              315              320

Phe Ile Asp Ile Glu Glu Leu Gly Glu Ile Leu Arg Ala Thr Gly Glu
            325              330              335

His Val Thr Glu Glu Asp Ile Glu Asp Leu Met Lys Asp Ser Asp Lys
            340              345              350

Asn Asn Asp Gly Arg Ile Asp Phe Asp Glu Phe Leu Lys Met Met Glu
            355              360              365

Gly Val Gln Glu Leu Met Gly Gly Val Gln Leu Ala Asp His Tyr Gln
            370              375              380

Gln Asn Thr Pro Ile Gly Asp Gly Pro Val Leu Leu Pro Asp Asn His
385              390              395              400

Tyr Leu Ser Tyr Gln Ser Lys Leu Ser Lys Asp Pro Asn Glu Lys Arg
            405              410              415

Asp His Met Val Leu Leu Glu Phe Val Thr Ala Ala Gly Ile Thr Leu
            420              425              430

Gly Met Asp Glu Leu Tyr Lys Gly Gly Thr Gly Gly Ser Met Val Ser
            435              440              445

Lys Gly Glu Glu Leu Phe Thr Gly Val Val Pro Ile Leu Val Glu Leu
            450              455              460

Asp Gly Asp Val Asn Gly His Lys Phe Ser Val Arg Gly Glu Gly Glu
465              470              475              480

Gly Asp Ala Thr Asn Gly Lys Leu Thr Leu Lys Phe Ile Cys Thr Thr
            485              490              495

Gly Lys Leu Pro Val Pro Trp Pro Thr Leu Val Thr Thr Leu Gly Tyr
            500              505              510
```

```
Gly Leu Met Cys Phe Ala Arg Tyr Pro Asp His Met Lys Gln His Asp
        515                 520                 525

Phe Phe Lys Ser Ala Met Pro Glu Gly Tyr Val Gln Glu Arg Thr Ile
        530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
                565                 570                 575

Lys Glu Asp Gly Asn Ile Leu Gly His Lys Leu Glu Tyr Asn Tyr Asn
                580                 585                 590

Ser His Asn Val Tyr Ile Met Ala Asp Lys Gln Lys Asn Gly Ile Lys
        595                 600                 605

Ala Asn Phe Lys Ile Arg His Asn Ile Glu Asp
        610                 615
```

```
<210> SEQ ID NO 48
<211> LENGTH: 673
<212> TYPE: PRT
<213> ORGANISM: Artificial sequence
<220> FEATURE:
<223> OTHER INFORMATION: synthetic sequence

<400> SEQUENCE: 48
```

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
        210                 215                 220

Val Thr Ala Ala Arg Met His Asp Gln Leu Thr Glu Glu Gln Ile Ala
225                 230                 235                 240

Glu Phe Lys Glu Ala Phe Ser Leu Phe Asp Lys Asp Gly Asp Gly Thr
                245                 250                 255
```

-continued

```
Ile Thr Thr Lys Glu Leu Gly Thr Val Met Arg Ser Leu Gly Gln Asn
            260                 265                 270

Pro Thr Glu Ala Glu Leu Gln Asp Met Ile Asn Glu Val Asp Ala Asp
            275                 280                 285

Gly Asn Gly Thr Ile Tyr Phe Pro Glu Phe Leu Thr Met Met Ala Arg
    290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Gln Leu Arg
                325                 330                 335

His Val Met Thr Asn Leu Gly Glu Lys Leu Thr Asp Glu Glu Val Asp
            340                 345                 350

Glu Met Ile Arg Glu Ala Asp Ile Asp Gly Asp Gly Gln Val Asn Tyr
            355                 360                 365

Glu Glu Phe Val Gln Met Met Thr Ala Lys Gly Gly Lys Arg Arg Trp
    370                 375                 380

Lys Lys Asn Phe Ile Ala Val Ser Ala Ala Asn Arg Phe Lys Lys Ile
385                 390                 395                 400

Ser Ser Ser Gly Ala Leu Glu Leu Met Asp Gly Gly Val Gln Leu Ala
                405                 410                 415

Asp His Tyr Gln Gln Asn Thr Pro Ile Gly Asp Gly Pro Val Leu Leu
            420                 425                 430

Pro Asp Asn His Tyr Leu Ser Tyr Gln Ser Ala Leu Ser Lys Asp Pro
            435                 440                 445

Asn Glu Lys Arg Asp His Met Val Leu Leu Glu Phe Val Thr Ala Ala
    450                 455                 460

Gly Ile Thr Leu Gly Met Asp Glu Leu Tyr Lys Gly Gly Ser Gly Gly
465                 470                 475                 480

Met Val Ser Lys Gly Glu Glu Leu Phe Thr Gly Val Val Pro Ile Leu
                485                 490                 495

Val Glu Leu Asp Gly Asp Val Asn Gly His Lys Phe Ser Val Ser Gly
            500                 505                 510

Glu Gly Glu Gly Asp Ala Thr Tyr Gly Lys Leu Thr Leu Lys Leu Ile
            515                 520                 525

Cys Thr Thr Gly Lys Leu Pro Val Pro Trp Pro Thr Leu Val Thr Thr
    530                 535                 540

Leu Gly Tyr Gly Leu Gln Cys Phe Ala Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
            595                 600                 605

Ile Asp Phe Lys Glu Asp Gly Asn Ile Leu Gly His Lys Leu Glu Tyr
    610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu Leu Ser Arg
                645                 650                 655

Gly Pro Gly Thr Ser Ala Glu Ile Tyr Ala Cys Arg Leu Glu Ile Ser
            660                 665                 670

Asn
```

```
<210> SEQ ID NO 49
<211> LENGTH: 653
<212> TYPE: PRT
<213> ORGANISM: Artificial sequence
<220> FEATURE:
<223> OTHER INFORMATION: synthetic sequence

<400> SEQUENCE: 49

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Arg Met His Asp Gln Leu Thr Glu Glu Gln Ile Ala
225                 230                 235                 240

Glu Phe Lys Glu Ala Phe Ser Leu Leu Asp Lys Asp Gly Asp Gly Thr
                245                 250                 255

Ile Thr Thr Lys Glu Leu Gly Thr Ala Leu Arg Ser Leu Gly Gln Asn
                260                 265                 270

Pro Thr Glu Ala Glu Leu Gln Asp Met Ile Asn Glu Val Asp Ala Asp
            275                 280                 285

Gly Asn Gly Thr Ile Tyr Phe Pro Glu Phe Leu Thr Met Met Ala Arg
        290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Glu Leu Arg
                325                 330                 335

His Val Met Thr Asn Leu Gly Glu Lys Leu Thr Asp Glu Glu Val Asp
            340                 345                 350

Glu Met Ile Arg Glu Ala Asp Ile Asp Gly Asp Gly Gln Val Asn Tyr
            355                 360                 365
```

```
Glu Glu Phe Val Gln Met Met Thr Ala Lys Gly Gly Lys Arg Arg Trp
    370             375             380

Gln Lys Thr Gly His Ala Val Arg Ala Phe Gly Arg Leu Lys Lys Ile
385             390             395             400

Ser Ser Ser Gly Ala Leu Glu Leu Met Asp Gly Gly Val Gln Leu Ala
            405             410             415

Asp His Tyr Gln Gln Asn Thr Pro Ile Gly Asp Gly Pro Val Leu Leu
            420             425             430

Pro Asp Asn His Tyr Leu Ser Tyr Gln Ser Ala Leu Ser Lys Asp Pro
            435             440             445

Asn Glu Lys Arg Asp His Met Val Leu Leu Glu Phe Val Thr Ala Ala
    450             455             460

Gly Ile Thr Leu Gly Met Asp Glu Leu Tyr Lys Gly Gly Ser Gly Gly
465             470             475             480

Met Val Ser Lys Gly Glu Glu Leu Phe Thr Gly Val Val Pro Ile Leu
            485             490             495

Val Glu Leu Asp Gly Asp Val Asn Gly His Lys Phe Ser Val Ser Gly
            500             505             510

Glu Gly Glu Gly Asp Ala Thr Tyr Gly Lys Leu Thr Leu Lys Leu Ile
            515             520             525

Cys Thr Thr Gly Lys Leu Pro Val Pro Trp Pro Thr Leu Val Thr Thr
    530             535             540

Leu Gly Tyr Gly Leu Gln Cys Phe Ala Arg Tyr Pro Asp His Met Lys
545             550             555             560

Gln His Asp Phe Phe Lys Ser Ala Met Pro Glu Gly Tyr Val Gln Glu
            565             570             575

Arg Thr Ile Phe Phe Lys Asp Asp Gly Asn Tyr Lys Thr Arg Ala Glu
            580             585             590

Val Lys Phe Glu Gly Asp Thr Leu Val Asn Arg Ile Glu Leu Lys Gly
            595             600             605

Ile Asp Phe Lys Glu Asp Gly Asn Ile Leu Gly His Lys Leu Glu Tyr
    610             615             620

Asn Tyr Asn Ser His Asn Val Tyr Ile Thr Ala Asp Lys Gln Lys Asn
625             630             635             640

Gly Ile Lys Ala Asn Phe Lys Ile Arg His Asn Ile Glu
            645             650
```

```
<210> SEQ ID NO 50
<211> LENGTH: 344
<212> TYPE: PRT
<213> ORGANISM: Artificial sequence
<220> FEATURE:
<223> OTHER INFORMATION: synthetic sequence

<400> SEQUENCE: 50

Met Ser Arg Arg Pro Trp Leu Leu Ala Leu Ala Leu Ala Val Ala Leu
1               5               10              15

Ala Ala Gly Ser Ala Gly Ala Ser Thr Gly Ser Asp Ala Thr Val Pro
            20              25              30

Val Ala Thr Gln Asp Gly Pro Asp Tyr Val Phe His Arg Ala His Glu
        35              40              45

Arg Met Leu Phe Gln Thr Ser Tyr Thr Leu Glu Asn Asn Gly Ser Val
    50              55              60

Ile Cys Ile Pro Asn Asn Gly Gln Cys Phe Cys Leu Ala Trp Leu Lys
65              70              75              80
```

```
Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
            165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
            245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
            275                 280                 285

Ala Ile Leu Asp Leu Ala Ser Lys Asn Ala Trp Ser Met Met Gly His
    290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
            325                 330                 335

Thr Met Val His Glu Glu Asp Asp
            340
```

```
<210> SEQ ID NO 51
<211> LENGTH: 310
<212> TYPE: PRT
<213> ORGANISM: Artificial sequence
<220> FEATURE:
<223> OTHER INFORMATION: synthetic sequence

<400> SEQUENCE: 51
```

```
Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
            85                  90                  95
```

```
Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 52
<211> LENGTH: 310
<212> TYPE: PRT
<213> ORGANISM: Artificial sequence
<220> FEATURE:
<223> OTHER INFORMATION: synthetic sequence

<400> SEQUENCE: 52

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140
```

```
Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 53
<211> LENGTH: 310
<212> TYPE: PRT
<213> ORGANISM: Artificial sequence
<220> FEATURE:
<223> OTHER INFORMATION: synthetic sequence

<400> SEQUENCE: 53

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190
```

-continued

```
Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 54
<211> LENGTH: 300
<212> TYPE: PRT
<213> ORGANISM: Artificial sequence
<220> FEATURE:
<223> OTHER INFORMATION: synthetic sequence

<400> SEQUENCE: 54

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240
```

-continued

```
Ala Ile Gly His Ser Ile Leu Asp Leu Ile Ala Lys Asn Met Trp Gly
              245                 250                 255

Val Leu Gly Asn Tyr Leu Arg Val Lys Ile His Glu His Ile Leu Leu
              260                 265                 270

Tyr Gly Asp Ile Arg Lys Lys Gln Lys Ile Thr Ile Ala Gly Gln Glu
              275                 280                 285

Met Glu Val Glu Thr Leu Val Ala Glu Glu Glu Asp
     290                 295                 300

<210> SEQ ID NO 55
<211> LENGTH: 300
<212> TYPE: PRT
<213> ORGANISM: Artificial sequence
<220> FEATURE:
<223> OTHER INFORMATION: synthetic sequence

<400> SEQUENCE: 55

Met Asp Tyr Pro Val Ala Arg Ser Leu Ile Val Arg Tyr Pro Thr Asp
1                 5                 10                  15

Leu Gly Asn Gly Thr Val Cys Met Pro Arg Gly Gln Cys Tyr Cys Glu
              20                  25                  30

Gly Trp Leu Arg Ser Arg Gly Thr Ser Ile Glu Lys Thr Ile Ala Ile
              35                  40                  45

Thr Leu Gln Trp Val Val Phe Ala Leu Ser Val Ala Cys Leu Gly Trp
     50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
              85                  90                  95

Phe Asp Ser Pro Ala Thr Leu Trp Leu Ser Ser Gly Asn Gly Val Val
              100                 105                 110

Trp Met Arg Tyr Gly Glu Trp Leu Leu Thr Ser Pro Val Leu Leu Ile
              115                 120                 125

His Leu Ser Asn Leu Thr Gly Leu Lys Asp Asp Tyr Ser Lys Arg Thr
     130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
              165                 170                 175

Leu Ser Tyr Gly Met Tyr Thr Tyr Phe His Ala Ala Lys Val Tyr Ile
              180                 185                 190

Glu Ala Phe His Thr Val Pro Lys Gly Ile Cys Arg Glu Leu Val Arg
              195                 200                 205

Val Met Ala Trp Thr Phe Phe Val Ala Trp Gly Met Phe Pro Val Leu
     210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
              245                 250                 255

Val Leu Gly Asn Tyr Leu Arg Val Lys Ile His Glu His Ile Leu Leu
              260                 265                 270

Tyr Gly Asp Ile Arg Lys Lys Gln Lys Ile Thr Ile Ala Gly Gln Glu
              275                 280                 285

Met Glu Val Glu Thr Leu Val Ala Glu Glu Glu Asp
     290                 295                 300
```

```
<210> SEQ ID NO 56
<211> LENGTH: 300
<212> TYPE: PRT
<213> ORGANISM: Artificial sequence
<220> FEATURE:
<223> OTHER INFORMATION: synthetic sequence

<400> SEQUENCE: 56

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
    130                 135                 140

Met Gly Leu Leu Val Ser Ala Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Glu Asp
    290                 295                 300

<210> SEQ ID NO 57
<211> LENGTH: 344
<212> TYPE: PRT
<213> ORGANISM: Artificial sequence
<220> FEATURE:
<223> OTHER INFORMATION: synthetic sequence

<400> SEQUENCE: 57

Met Ser Arg Arg Pro Trp Leu Leu Ala Leu Ala Leu Ala Val Ala Leu
```

-continued

```
1                    5                    10                   15

Ala Ala Gly Ser Ala Gly Ala Ser Thr Gly Ser Asp Ala Thr Val Pro
             20                   25                   30

Val Ala Thr Gln Asp Gly Pro Asp Tyr Val Phe His Arg Ala His Glu
             35                   40                   45

Arg Met Leu Phe Gln Thr Ser Tyr Thr Leu Glu Asn Asn Gly Ser Val
             50                   55                   60

Ile Cys Ile Pro Asn Asn Gly Gln Cys Phe Cys Leu Ala Trp Leu Lys
65                   70                   75                   80

Ser Asn Gly Thr Asn Ala Glu Lys Leu Ala Ala Asn Ile Leu Gln Trp
             85                   90                   95

Ile Thr Phe Ala Leu Ser Ala Leu Cys Leu Met Phe Tyr Gly Tyr Gln
             100                  105                  110

Thr Trp Lys Ser Thr Cys Gly Trp Glu Glu Ile Tyr Val Ala Thr Ile
             115                  120                  125

Glu Met Ile Lys Phe Ile Ile Glu Tyr Phe His Glu Phe Asp Glu Pro
             130                  135                  140

Ala Val Ile Tyr Ser Ser Asn Gly Asn Lys Thr Val Trp Leu Arg Tyr
145                  150                  155                  160

Ala Glu Trp Leu Leu Thr Cys Pro Val Leu Leu Ile His Leu Ser Asn
             165                  170                  175

Leu Thr Gly Leu Lys Asp Asp Tyr Ser Lys Arg Thr Met Gly Leu Leu
             180                  185                  190

Val Ser Asp Val Gly Cys Ile Val Trp Gly Ala Thr Ser Ala Met Cys
             195                  200                  205

Thr Gly Trp Thr Lys Ile Leu Phe Phe Leu Ile Ser Leu Ser Tyr Gly
             210                  215                  220

Met Tyr Thr Tyr Phe His Ala Ala Lys Val Tyr Ile Glu Ala Phe His
225                  230                  235                  240

Thr Val Pro Lys Gly Ile Cys Arg Glu Leu Val Arg Val Met Ala Trp
             245                  250                  255

Thr Phe Phe Val Ala Trp Gly Met Phe Pro Val Leu Phe Leu Leu Gly
             260                  265                  270

Thr Glu Gly Phe Gly His Ile Ser Pro Tyr Gly Ser Ala Ile Gly His
             275                  280                  285

Ser Ile Leu Asp Leu Ile Ala Lys Asn Met Trp Gly Val Leu Gly Asn
             290                  295                  300

Tyr Leu Arg Val Lys Ile His Glu His Ile Leu Leu Tyr Gly Asp Ile
305                  310                  315                  320

Arg Lys Lys Gln Lys Ile Thr Ile Ala Gly Gln Glu Met Glu Val Glu
             325                  330                  335

Thr Leu Val Ala Glu Glu Glu Asp
             340
```

```
<210> SEQ ID NO 58
<211> LENGTH: 348
<212> TYPE: PRT
<213> ORGANISM: Artificial sequence
<220> FEATURE:
<223> OTHER INFORMATION: synthetic sequence

<400> SEQUENCE: 58

Met Ser Arg Arg Pro Trp Leu Leu Ala Leu Ala Leu Ala Val Ala Leu
1                    5                    10                   15

Ala Ala Gly Ser Ala Gly Ala Ser Thr Gly Ser Asp Ala Thr Val Pro
```

-continued

```
                20                    25                    30

Val Ala Thr Gln Asp Gly Pro Asp Tyr Val Phe His Arg Ala His Glu
            35                    40                    45

Arg Met Leu Phe Gln Thr Ser Tyr Thr Leu Glu Asn Asn Gly Ser Val
        50                    55                    60

Ile Cys Ile Pro Asn Asn Gly Gln Cys Phe Cys Leu Ala Trp Leu Lys
65                    70                    75                    80

Ser Asn Gly Thr Asn Ala Glu Lys Leu Ala Ala Asn Ile Leu Gln Trp
                85                    90                    95

Ile Thr Phe Ala Leu Ser Ala Leu Cys Leu Met Phe Tyr Gly Tyr Gln
                100                   105                   110

Thr Trp Lys Ser Thr Cys Gly Trp Glu Glu Ile Tyr Val Ala Thr Ile
            115                   120                   125

Glu Met Ile Lys Phe Ile Ile Glu Tyr Phe His Glu Phe Asp Glu Pro
            130                   135                   140

Ala Val Ile Tyr Ser Ser Asn Gly Asn Lys Thr Val Trp Leu Arg Tyr
145                   150                   155                   160

Ala Glu Trp Leu Leu Thr Cys Pro Val Ile Leu Ile His Leu Ser Asn
                165                   170                   175

Leu Thr Gly Leu Ala Asn Asp Tyr Asn Lys Arg Thr Met Gly Leu Leu
                180                   185                   190

Val Ser Asp Ile Gly Thr Ile Val Trp Gly Thr Thr Ala Ala Leu Ser
                195                   200                   205

Lys Gly Tyr Val Arg Val Ile Phe Phe Leu Met Gly Leu Cys Tyr Gly
            210                   215                   220

Ile Tyr Thr Phe Phe Asn Ala Ala Lys Val Tyr Ile Glu Ala Tyr His
225                   230                   235                   240

Thr Val Pro Lys Gly Arg Cys Arg Gln Val Val Thr Gly Met Ala Trp
                245                   250                   255

Leu Phe Phe Val Ser Trp Gly Met Phe Pro Ile Leu Phe Ile Leu Gly
                260                   265                   270

Pro Glu Gly Phe Gly Val Leu Ser Val Tyr Gly Ser Thr Val Gly His
            275                   280                   285

Thr Ile Ile Asp Leu Met Ser Lys Asn Cys Trp Gly Leu Leu Gly His
            290                   295                   300

Tyr Leu Arg Val Leu Ile His Glu His Ile Leu Ile His Gly Asp Ile
305                   310                   315                   320

Arg Lys Thr Thr Lys Leu Asn Ile Gly Gly Thr Glu Ile Glu Val Glu
                325                   330                   335

Thr Leu Val Glu Asp Glu Ala Glu Ala Gly Ala Val
            340                   345
```

```
<210> SEQ ID NO 59
<211> LENGTH: 316
<212> TYPE: PRT
<213> ORGANISM: Artificial sequence
<220> FEATURE:
<223> OTHER INFORMATION: synthetic sequence

<400> SEQUENCE: 59

Met Gly Gly Ala Pro Ala Pro Asp Ala His Ser Ala Pro Pro Gly Asn
1                   5                     10                    15

Asp Ser Ala Gly Gly Ser Glu Tyr His Ala Pro Ala Gly Tyr Gln Val
                20                    25                    30

Asn Pro Pro Tyr His Pro Val His Gly Tyr Glu Glu Gln Cys Ser Ser
```

```
            35                      40                      45
Ile Tyr Ile Tyr Tyr Gly Ala Leu Trp Glu Gln Glu Thr Ala Arg Gly
            50                      55                      60

Phe Gln Trp Phe Ala Val Phe Leu Ser Ala Leu Phe Leu Ala Phe Tyr
65                      70                      75                      80

Gly Trp His Ala Tyr Lys Ala Ser Val Gly Trp Glu Glu Val Tyr Val
                        85                      90                      95

Cys Ser Val Glu Leu Ile Lys Val Ile Leu Glu Ile Tyr Phe Glu Phe
                        100                     105                     110

Thr Ser Pro Ala Met Leu Phe Leu Tyr Gly Gly Asn Ile Thr Pro Trp
                        115                     120                     125

Leu Arg Tyr Ala Glu Trp Leu Leu Thr Cys Pro Val Ile Leu Ile His
            130                     135                     140

Leu Ser Asn Ile Thr Gly Leu Ser Glu Glu Tyr Asn Lys Arg Thr Met
145                     150                     155                     160

Ala Leu Leu Val Ser Asp Leu Gly Thr Ile Cys Met Gly Val Thr Ala
                        165                     170                     175

Ala Leu Ala Thr Gly Trp Val Lys Trp Leu Phe Tyr Cys Ile Gly Leu
                        180                     185                     190

Val Tyr Gly Thr Gln Thr Phe Tyr Asn Ala Gly Ile Ile Tyr Val Glu
                        195                     200                     205

Ser Tyr Tyr Ile Met Pro Ala Gly Gly Cys Lys Lys Leu Val Leu Ala
            210                     215                     220

Met Thr Ala Val Tyr Tyr Ser Ser Trp Leu Met Phe Pro Gly Leu Phe
225                     230                     235                     240

Ile Phe Gly Pro Glu Gly Met His Thr Leu Ser Val Ala Gly Ser Thr
                        245                     250                     255

Ile Gly His Thr Ile Ala Asp Leu Leu Ser Lys Asn Ile Trp Gly Leu
                        260                     265                     270

Leu Gly His Phe Leu Arg Ile Lys Ile His Glu His Ile Ile Met Tyr
            275                     280                     285

Gly Asp Ile Arg Arg Pro Val Ser Ser Gln Phe Leu Gly Arg Lys Val
            290                     295                     300

Asp Val Leu Ala Phe Val Thr Glu Glu Asp Lys Val
305                     310                     315

<210> SEQ ID NO 60
<211> LENGTH: 349
<212> TYPE: PRT
<213> ORGANISM: Artificial sequence
<220> FEATURE:
<223> OTHER INFORMATION: synthetic sequence

<400> SEQUENCE: 60

Met Glu Pro Val Leu Gly Leu Ala Ser Thr Ala Val Arg Glu Leu Thr
1                       5                       10                      15

Ala Gly Gly Ser Gly Asn Pro Tyr Glu Ser Tyr Lys Pro Pro Glu Asp
            20                      25                      30

Pro Cys Ala Leu Thr Pro Phe Gly Cys Leu Thr Asn Phe Trp Cys Asp
            35                      40                      45

Pro Gln Phe Gly Leu Ala Asp Ala Lys Tyr Asp Tyr Cys Tyr Val Lys
            50                      55                      60

Ala Ala Tyr Gly Glu Leu Ala Ile Val Glu Thr Ser Arg Leu Pro Trp
65                      70                      75                      80

Leu Tyr Ser His Gly Ser Asp Ala Glu His Gln Gly Ala Leu Ala Met
```

```
                     85              90              95
Gln Trp Met Ala Phe Ala Leu Cys Ile Ile Cys Leu Val Phe Tyr Ala
            100             105             110

Tyr His Ser Trp Lys Ala Thr Thr Gly Trp Glu Glu Val Tyr Val Cys
        115             120             125

Val Val Glu Leu Val Lys Val Leu Leu Glu Ile Tyr Lys Glu Phe Glu
    130             135             140

Ser Pro Ala Ser Ile Tyr Leu Pro Thr Ala Asn Ala Ala Leu Trp Leu
145             150             155             160

Arg Tyr Gly Glu Trp Leu Leu Thr Cys Pro Val Ile Leu Ile His Leu
            165             170             175

Ser Asn Ile Thr Gly Leu Lys Asp Asp Tyr Asn Lys Arg Thr Met Gln
            180             185             190

Leu Leu Val Ser Asp Ile Gly Cys Val Val Trp Gly Ile Thr Ala Ala
            195             200             205

Phe Ser Val Gly Trp Leu Lys Trp Val Phe Phe Val Leu Gly Leu Leu
    210             215             220

Tyr Gly Ser Asn Thr Tyr Phe His Ala Ala Lys Val Tyr Ile Glu Ser
225             230             235             240

Tyr His Thr Val Pro Lys Gly His Cys Arg Leu Ile Val Arg Leu Met
            245             250             255

Ala Tyr Cys Phe Tyr Val Ala Trp Thr Met Tyr Pro Ile Leu Phe Ile
            260             265             270

Leu Gly Pro Glu Gly Leu Gly His Met Ser Ala Tyr Met Ser Thr Ala
            275             280             285

Leu His Gly Val Ala Asp Met Leu Ser Lys Gln Ile Trp Gly Leu Leu
    290             295             300

Gly His His Leu Arg Val Lys Ile Phe Glu His Ile Leu Ile His Gly
305             310             315             320

Asp Ile Arg Lys Thr Thr Thr Met Gln Val Gly Gly Gln Met Val Gln
            325             330             335

Val Glu Glu Met Val Asp Glu Glu Asp Glu Asp Thr Ile
            340             345
```

<210> SEQ ID NO 61
<211> LENGTH: 345
<212> TYPE: PRT
<213> ORGANISM: Artificial sequence
<220> FEATURE:
<223> OTHER INFORMATION: synthetic sequence

<400> SEQUENCE: 61

```
Met Ser Arg Leu Val Ala Ala Ser Trp Leu Leu Ala Leu Leu Leu Cys
1               5               10              15

Gly Ile Thr Ser Thr Thr Thr Ala Ser Ser Ala Pro Ala Ala Ser Ser
            20              25              30

Thr Asp Gly Thr Ala Ala Ala Ala Val Ser His Tyr Ala Met Asn Gly
            35              40              45

Phe Asp Glu Leu Ala Lys Gly Ala Val Val Pro Glu Asp His Phe Val
    50              55              60

Cys Gly Pro Ala Asp Lys Cys Tyr Cys Ser Ala Trp Leu His Ser Arg
65              70              75              80

Gly Thr Pro Gly Glu Lys Ile Gly Ala Gln Val Cys Gln Trp Ile Ala
            85              90              95

Phe Ser Ile Ala Ile Ala Leu Leu Thr Phe Tyr Gly Phe Ser Ala Trp
```

-continued

```
                 100                 105                 110

Lys Ala Thr Cys Gly Trp Glu Glu Val Tyr Val Cys Cys Val Glu Val
             115                 120                 125

Leu Phe Val Thr Leu Glu Ile Phe Lys Glu Phe Ser Ser Pro Ala Thr
         130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                 165                 170                 175

Gly Leu Lys Asn Asp Tyr Ser Lys Arg Thr Met Gly Leu Ile Val Ser
             180                 185                 190

Cys Val Gly Met Ile Val Phe Gly Met Ala Ala Gly Leu Ala Thr Asp
             195                 200                 205

Trp Leu Lys Trp Leu Leu Tyr Ile Val Ser Cys Ile Tyr Gly Gly Tyr
         210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                 245                 250                 255

Phe Ala Ser Trp Gly Ser Tyr Pro Ile Leu Trp Ala Val Gly Pro Glu
             260                 265                 270

Gly Leu Leu Lys Leu Ser Pro Tyr Ala Asn Ser Ile Gly His Ser Ile
         275                 280                 285

Cys Asp Ile Ile Ala Lys Glu Phe Trp Thr Phe Leu Ala His His Leu
         290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Glu Phe
             325                 330                 335

Val Glu Glu Glu Asp Glu Asp Thr Val
             340                 345
```

```
<210> SEQ ID NO 62
<211> LENGTH: 325
<212> TYPE: PRT
<213> ORGANISM: Artificial sequence
<220> FEATURE:
<223> OTHER INFORMATION: synthetic sequence

<400> SEQUENCE: 62
```

```
Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
             20                  25                  30

Thr Pro Ala Ala Asp Ala His Gly Glu Thr Ser Asn Ala Thr Thr Ala
         35                  40                  45

Gly Ala Asp His Gly Cys Phe Pro His Ile Asn His Gly Thr Glu Leu
     50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                 85                  90                  95

Gly Trp Glu Glu Val Tyr Val Cys Val Ile Glu Leu Val Lys Cys Phe
             100                 105                 110

Ile Glu Leu Phe His Glu Val Asp Ser Pro Ala Thr Val Tyr Gln Thr
```

```
            115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
                180                 185                 190

Leu Phe Phe Met Ile Gly Leu Phe Tyr Gly Val Thr Cys Phe Phe Gln
                195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
                260                 265                 270

Ser Lys Asn Thr Trp Gly Phe Leu Gly His His Leu Arg Val Lys Ile
                275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325

<210> SEQ ID NO 63
<211> LENGTH: 258
<212> TYPE: PRT
<213> ORGANISM: Artificial sequence
<220> FEATURE:
<223> OTHER INFORMATION: synthetic sequence

<400> SEQUENCE: 63

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
```

-continued

```
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp
```

```
<210> SEQ ID NO 64
<211> LENGTH: 248
<212> TYPE: PRT
<213> ORGANISM: Artificial sequence
<220> FEATURE:
<223> OTHER INFORMATION: synthetic sequence

<400> SEQUENCE: 64
```

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Ile Val Lys Gly Trp Gly Val Thr Asp Lys Glu
                35                  40                  45

Ala Arg Glu Tyr Tyr Ser Ile Thr Ile Leu Val Pro Gly Ile Ala Ser
        50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245
```

<210> SEQ ID NO 65
<211> LENGTH: 223
<212> TYPE: PRT
<213> ORGANISM: Artificial sequence
<220> FEATURE:
<223> OTHER INFORMATION: synthetic sequence

<400> SEQUENCE: 65

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Trp Val Ile Ala Pro
    50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
        115                 120                 125

Phe Phe Gly Met Cys Trp Phe Leu His Ile Ile Phe Ala Leu Gly Lys
    130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
        195                 200                 205

Gly Leu Ile Leu Met Ser Gly Ala Ala Thr Gly Tyr Glu Ser Ile
    210                 215                 220

<210> SEQ ID NO 66
<211> LENGTH: 262
<212> TYPE: PRT
<213> ORGANISM: Artificial sequence
<220> FEATURE:
<223> OTHER INFORMATION: synthetic sequence

<400> SEQUENCE: 66

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala

```
                85              90              95

Tyr Arg Tyr Val Asp Trp Leu Leu Thr Val Pro Leu Leu Leu Val Glu
            100             105             110

Leu Ile Leu Val Met Lys Leu Pro Ala Lys Glu Thr Val Cys Leu Ala
        115             120             125

Trp Thr Leu Gly Ile Ala Ser Ala Val Met Val Ala Leu Gly Tyr Pro
    130             135             140

Gly Glu Ile Gln Asp Asp Leu Ser Val Arg Trp Phe Trp Trp Ala Cys
145             150             155             160

Ala Met Val Pro Phe Val Tyr Val Val Gly Thr Leu Val Val Gly Leu
            165             170             175

Gly Ala Ala Thr Ala Lys Gln Pro Glu Gly Val Val Asp Leu Val Ser
            180             185             190

Ala Ala Arg Tyr Leu Thr Val Val Ser Trp Leu Thr Tyr Pro Phe Val
            195             200             205

Tyr Ile Val Lys Asn Ile Gly Leu Ala Gly Ser Thr Ala Thr Met Tyr
    210             215             220

Glu Gln Ile Gly Tyr Ser Ala Ala Asp Val Thr Ala Lys Ala Val Phe
225             230             235             240

Gly Val Leu Ile Trp Ala Ile Ala Asn Ala Lys Ser Arg Leu Glu Glu
            245             250             255

Glu Gly Lys Leu Arg Ala
            260
```

```
<210> SEQ ID NO 67
<211> LENGTH: 313
<212> TYPE: PRT
<213> ORGANISM: Artificial sequence
<220> FEATURE:
<223> OTHER INFORMATION: synthetic sequence

<400> SEQUENCE: 67

Met Ile Val Asp Gln Phe Glu Glu Val Leu Met Lys Thr Ser Gln Leu
1               5               10              15

Phe Pro Leu Pro Thr Ala Thr Gln Ser Ala Gln Pro Thr His Val Ala
            20              25              30

Pro Val Pro Thr Val Leu Pro Asp Thr Pro Ile Tyr Glu Thr Val Gly
        35              40              45

Asp Ser Gly Ser Lys Thr Leu Trp Val Val Phe Val Leu Met Leu Ile
    50              55              60

Ala Ser Ala Ala Phe Thr Ala Leu Ser Trp Lys Ile Pro Val Asn Arg
65              70              75              80

Arg Leu Tyr His Val Ile Thr Thr Ile Ile Thr Leu Thr Ala Ala Leu
            85              90              95

Ser Tyr Phe Ala Met Ala Thr Gly His Gly Val Ala Leu Asn Lys Ile
            100             105             110

Val Ile Arg Thr Gln His Asp His Val Pro Asp Thr Tyr Glu Thr Val
            115             120             125

Tyr Arg Gln Val Tyr Tyr Ala Arg Tyr Ile Asp Trp Ala Ile Thr Thr
            130             135             140

Pro Leu Leu Leu Leu Asp Leu Gly Leu Leu Ala Gly Met Ser Gly Ala
145             150             155             160

His Ile Phe Met Ala Ile Val Ala Asp Leu Ile Met Val Leu Thr Gly
            165             170             175

Leu Phe Ala Ala Phe Gly Ser Glu Gly Thr Pro Gln Lys Trp Gly Trp
```

-continued

```
              180              185              190
Tyr Thr Ile Ala Cys Ile Ala Tyr Ile Phe Val Val Trp His Leu Val
         195              200              205
Leu Asn Gly Gly Ala Asn Ala Arg Val Lys Gly Glu Lys Leu Arg Ser
    210              215              220
Phe Phe Val Ala Ile Gly Ala Tyr Thr Leu Ile Leu Trp Thr Ala Tyr
225              230              235              240
Pro Ile Val Trp Gly Leu Ala Asp Gly Ala Arg Lys Ile Gly Val Asp
              245              250              255
Gly Glu Ile Ile Ala Tyr Ala Val Leu Asp Val Leu Ala Lys Gly Val
         260              265              270
Phe Gly Ala Trp Leu Leu Val Thr His Ala Asn Leu Arg Glu Ser Asp
         275              280              285
Val Glu Leu Asn Gly Phe Trp Ala Asn Gly Leu Asn Arg Glu Gly Ala
    290              295              300
Ile Arg Ile Gly Glu Asp Asp Gly Ala
305              310
```

```
<210> SEQ ID NO 68
<211> LENGTH: 273
<212> TYPE: PRT
<213> ORGANISM: Artificial sequence
<220> FEATURE:
<223> OTHER INFORMATION: synthetic sequence

<400> SEQUENCE: 68
```

```
Val Thr Gln Arg Glu Leu Phe Glu Phe Val Leu Asn Asp Pro Leu Leu
1                 5                10               15
Ala Ser Ser Leu Tyr Ile Asn Ile Ala Leu Ala Gly Leu Ser Ile Leu
         20               25               30
Leu Phe Val Phe Met Thr Arg Gly Leu Asp Asp Pro Arg Ala Lys Leu
         35               40               45
Ile Ala Val Ser Thr Ile Leu Val Pro Val Val Ser Ile Ala Ser Tyr
    50               55               60
Thr Gly Leu Ala Ser Gly Leu Thr Ile Ser Val Leu Glu Met Pro Ala
65               70               75               80
Gly His Phe Ala Glu Gly Ser Ser Val Met Leu Gly Gly Glu Glu Val
              85               90               95
Asp Gly Val Val Thr Met Trp Gly Arg Tyr Leu Thr Trp Ala Leu Ser
         100              105              110
Thr Pro Met Ile Leu Leu Ala Leu Gly Leu Leu Ala Gly Ser Asn Ala
         115              120              125
Thr Lys Leu Phe Thr Ala Ile Thr Phe Asp Ile Ala Met Cys Val Thr
    130              135              140
Gly Leu Ala Ala Ala Leu Thr Thr Ser Ser His Leu Met Arg Trp Phe
145              150              155              160
Trp Tyr Ala Ile Ser Cys Ala Cys Phe Leu Val Val Leu Tyr Ile Leu
              165              170              175
Leu Val Glu Trp Ala Gln Asp Ala Lys Ala Ala Gly Thr Ala Asp Met
         180              185              190
Phe Asn Thr Leu Lys Leu Leu Thr Val Val Met Trp Leu Gly Tyr Pro
         195              200              205
Ile Val Trp Ala Leu Gly Val Glu Gly Ile Ala Val Leu Pro Val Gly
    210              215              220
Val Thr Ser Trp Gly Tyr Ser Phe Leu Asp Ile Val Ala Lys Tyr Ile
```

-continued

```
225               230               235               240

Phe Ala Phe Leu Leu Leu Asn Tyr Leu Thr Ser Asn Glu Ser Val Val
                245               250               255

Ser Gly Ser Ile Leu Asp Val Pro Ser Ala Ser Gly Thr Pro Ala Asp
                260               265               270

Asp

<210> SEQ ID NO 69
<211> LENGTH: 365
<212> TYPE: PRT
<213> ORGANISM: Artificial sequence
<220> FEATURE:
<223> OTHER INFORMATION: synthetic sequence

<400> SEQUENCE: 69

Met Arg Arg Arg Glu Ser Gln Leu Ala Tyr Leu Cys Leu Phe Val Leu
1               5               10               15

Ile Ala Gly Trp Ala Pro Arg Leu Thr Glu Ser Ala Pro Asp Leu Ala
                20               25               30

Glu Arg Arg Pro Pro Ser Glu Arg Asn Thr Pro Tyr Ala Asn Ile Lys
        35               40               45

Lys Val Pro Asn Ile Thr Glu Pro Asn Ala Asn Val Gln Leu Asp Gly
        50               55               60

Trp Ala Leu Tyr Gln Asp Phe Tyr Tyr Leu Ala Gly Ser Asp Lys Glu
65               70               75               80

Trp Val Val Gly Pro Ser Asp Gln Cys Tyr Cys Arg Ala Trp Ser Lys
                85               90               95

Ser His Gly Thr Asp Arg Glu Gly Glu Ala Ala Val Val Trp Ala Tyr
                100               105               110

Ile Val Phe Ala Ile Cys Ile Val Gln Leu Val Tyr Phe Met Phe Ala
                115               120               125

Ala Trp Lys Ala Thr Val Gly Trp Glu Glu Val Tyr Val Asn Ile Ile
        130               135               140

Glu Leu Val His Ile Ala Leu Val Ile Trp Val Glu Phe Asp Lys Pro
145               150               155               160

Ala Met Leu Tyr Leu Asn Asp Gly Gln Met Val Pro Trp Leu Arg Tyr
                165               170               175

Ser Ala Trp Leu Leu Ser Cys Pro Val Ile Leu Ile His Leu Ser Asn
                180               185               190

Leu Thr Gly Leu Lys Gly Asp Tyr Ser Lys Arg Thr Met Gly Leu Leu
                195               200               205

Val Ser Asp Ile Gly Thr Ile Val Phe Gly Thr Ser Ala Ala Leu Ala
        210               215               220

Pro Pro Asn His Val Lys Val Ile Leu Phe Thr Ile Gly Leu Leu Tyr
225               230               235               240

Gly Leu Phe Thr Phe Phe Thr Ala Ala Lys Val Tyr Ile Glu Ala Tyr
                245               250               255

His Thr Val Pro Lys Gly Gln Cys Arg Asn Leu Val Arg Ala Met Ala
                260               265               270

Trp Thr Tyr Phe Val Ser Trp Ala Met Phe Pro Ile Leu Phe Ile Leu
                275               280               285

Gly Arg Glu Gly Phe Gly His Ile Thr Tyr Phe Gly Ser Ser Ile Gly
        290               295               300

His Phe Ile Leu Glu Ile Phe Ser Lys Asn Leu Trp Ser Leu Leu Gly
305               310               315               320
```

His Gly Leu Arg Tyr Arg Ile Arg Gln His Ile Ile Ile His Gly Asn
                325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
        355                 360                 365

<210> SEQ ID NO 70
<211> LENGTH: 1083
<212> TYPE: PRT
<213> ORGANISM: Artificial sequence
<220> FEATURE:
<223> OTHER INFORMATION: synthetic sequence

<400> SEQUENCE: 70

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Lys Ser Arg Ile Thr Ser Glu Gly Glu Tyr Ile Pro Leu Asp
            260                 265                 270

Gln Ile Asp Ile Asn Val Gly Ala Pro Gly Ser Gly Ala Thr Asn Phe
        275                 280                 285

Ser Leu Leu Lys Gln Ala Gly Asp Val Glu Glu Asn Pro Gly Pro Met
        290                 295                 300

Asp Leu Lys Glu Ser Pro Ser Glu Gly Ser Leu Gln Pro Ser Ser Ile
305                 310                 315                 320

```
Gln Ile Phe Ala Asn Thr Ser Thr Leu His Gly Ile Arg His Ile Phe
            325             330             335

Val Tyr Gly Pro Leu Thr Ile Arg Arg Val Leu Trp Ala Val Ala Phe
            340             345             350

Val Gly Ser Leu Gly Leu Leu Leu Val Glu Ser Ser Glu Arg Val Ser
            355             360             365

Tyr Tyr Phe Ser Tyr Gln His Val Thr Lys Val Asp Glu Val Val Ala
    370             375             380

Gln Ser Leu Val Phe Pro Ala Val Thr Leu Cys Asn Leu Asn Gly Phe
385             390             395             400

Arg Phe Ser Arg Leu Thr Thr Asn Asp Leu Tyr His Ala Gly Glu Leu
            405             410             415

Leu Ala Leu Leu Asp Val Asn Leu Gln Ile Pro Asp Pro His Leu Ala
            420             425             430

Asp Pro Thr Val Leu Glu Ala Leu Arg Gln Lys Ala Asn Phe Lys His
            435             440             445

Tyr Lys Pro Lys Gln Phe Ser Met Leu Glu Phe Leu His Arg Val Gly
    450             455             460

His Asp Leu Lys Asp Met Met Leu Tyr Cys Lys Phe Lys Gly Gln Glu
465             470             475             480

Cys Gly His Gln Asp Phe Thr Thr Val Phe Thr Lys Tyr Gly Lys Cys
            485             490             495

Tyr Met Phe Asn Ser Gly Glu Asp Gly Lys Pro Leu Leu Thr Thr Val
            500             505             510

Lys Gly Gly Thr Gly Asn Gly Leu Glu Ile Met Leu Asp Ile Gln Gln
            515             520             525

Asp Glu Tyr Leu Pro Ile Trp Gly Glu Thr Glu Glu Thr Thr Phe Glu
    530             535             540

Ala Gly Val Lys Val Gln Ile His Ser Gln Ser Glu Pro Pro Phe Ile
545             550             555             560

Gln Glu Leu Gly Phe Gly Val Ala Pro Gly Phe Gln Thr Phe Val Ala
            565             570             575

Thr Gln Glu Gln Arg Leu Thr Tyr Leu Pro Pro Pro Trp Gly Glu Cys
            580             585             590

Arg Ser Ser Glu Met Gly Leu Asp Phe Phe Pro Val Tyr Ser Ile Thr
            595             600             605

Ala Cys Arg Ile Asp Cys Glu Thr Arg Tyr Ile Val Glu Asn Cys Asn
    610             615             620

Cys Arg Met Val His Met Pro Gly Asp Ala Pro Phe Cys Thr Pro Glu
625             630             635             640

Gln His Lys Glu Cys Ala Glu Pro Ala Leu Gly Leu Leu Ala Glu Lys
            645             650             655

Asp Ser Asn Tyr Cys Leu Cys Arg Thr Pro Cys Asn Leu Thr Arg Tyr
            660             665             670

Asn Lys Glu Leu Ser Met Val Lys Ile Pro Ser Lys Thr Ser Ala Lys
            675             680             685

Tyr Leu Glu Lys Lys Phe Asn Lys Ser Glu Lys Tyr Ile Ser Glu Asn
    690             695             700

Ile Leu Val Leu Asp Ile Phe Phe Glu Ala Leu Asn Tyr Glu Thr Ile
705             710             715             720

Glu Gln Lys Lys Ala Tyr Glu Val Ala Ala Leu Leu Gly Asp Ile Gly
            725             730             735
```

```
Gly Gln Met Gly Leu Phe Ile Gly Ala Ser Leu Leu Thr Ile Leu Glu
        740                 745                 750

Leu Phe Asp Tyr Ile Tyr Glu Leu Ile Lys Glu Lys Leu Leu Asp Leu
        755                 760                 765

Leu Gly Lys Glu Glu Glu Glu Gly Ser His Asp Glu Asn Met Ser Thr
        770                 775                 780

Cys Asp Thr Met Pro Asn His Ser Glu Thr Ile Ser His Thr Val Asn
785                 790                 795                 800

Val Pro Leu Gln Thr Ala Leu Gly Thr Leu Glu Glu Ile Ala Cys Ala
                805                 810                 815

Ala Ala Lys Ser Arg Ile Thr Ser Glu Gly Glu Tyr Ile Pro Leu Asp
                820                 825                 830

Gln Ile Asp Ile Asn Val Val Ser Lys Gly Glu Glu Leu Phe Thr Gly
        835                 840                 845

Val Val Pro Ile Leu Val Glu Leu Asp Gly Asp Val Asn Gly His Lys
        850                 855                 860

Phe Ser Val Ser Gly Glu Gly Glu Gly Asp Ala Thr Tyr Gly Lys Leu
865                 870                 875                 880

Thr Leu Lys Phe Ile Cys Thr Thr Gly Lys Leu Pro Val Pro Trp Pro
                885                 890                 895

Thr Leu Val Thr Thr Phe Gly Tyr Gly Leu Gln Cys Phe Ala Arg Tyr
                900                 905                 910

Pro Asp His Met Lys Gln His Asp Phe Phe Lys Ser Ala Met Pro Glu
        915                 920                 925

Gly Tyr Val Gln Glu Arg Thr Ile Phe Phe Lys Asp Asp Gly Asn Tyr
        930                 935                 940

Lys Thr Arg Ala Glu Val Lys Phe Glu Gly Asp Thr Leu Val Asn Arg
945                 950                 955                 960

Ile Glu Leu Lys Gly Ile Asp Phe Arg Glu Asp Gly Asn Ile Leu Gly
                965                 970                 975

His Lys Leu Glu Tyr Asn Tyr Asn Ser His Asn Val Tyr Ile Met Ala
        980                 985                 990

Asp Lys Gln Lys Asn Gly Ile Lys  Val Asn Phe Lys Ile  Arg His Asn
        995                 1000                1005

Ile Glu  Asp Gly Ser Val Gln  Leu Ala Asp His Tyr  Gln Gln Asn
    1010                1015                1020

Thr Pro  Ile Gly Asp Gly Pro  Val Leu Leu Pro Asp  Asn His Tyr
    1025                1030                1035

Leu Ser  Tyr Gln Ser Ala Leu  Ser Lys Asp Pro Asn  Glu Lys Arg
    1040                1045                1050

Asp His  Met Val Leu Leu Glu  Phe Val Thr Ala Ala  Gly Ile Thr
    1055                1060                1065

Leu Gly  Met Asp Glu Leu Tyr  Lys Phe Cys Tyr Glu  Asn Glu Val
    1070                1075                1080
```

<210> SEQ ID NO 71
<211> LENGTH: 20
<212> TYPE: DNA
<213> ORGANISM: Artificial sequence
<220> FEATURE:
<223> OTHER INFORMATION: synthetic sequence

<400> SEQUENCE: 71
gaccctgctt gctcaactct                                                                           20

<210> SEQ ID NO 72
<211> LENGTH: 20
<212> TYPE: DNA
<213> ORGANISM: Artificial sequence
<220> FEATURE:
<223> OTHER INFORMATION: synthetic sequence

<400> SEQUENCE: 72
tggaatttgc ccttttttgag                                                               20

<210> SEQ ID NO 73
<211> LENGTH: 21
<212> TYPE: DNA
<213> ORGANISM: Artificial sequence
<220> FEATURE:
<223> OTHER INFORMATION: synthetic sequence

<400> SEQUENCE: 73
gggacgacat gacttaacca g                                                              21

<210> SEQ ID NO 74
<211> LENGTH: 20
<212> TYPE: DNA
<213> ORGANISM: Artificial sequence
<220> FEATURE:
<223> OTHER INFORMATION: synthetic sequence

<400> SEQUENCE: 74
ccagcccttc tcatgttcag                                                               20

<210> SEQ ID NO 75
<211> LENGTH: 20
<212> TYPE: DNA
<213> ORGANISM: Artificial sequence
<220> FEATURE:
<223> OTHER INFORMATION: synthetic sequence

<400> SEQUENCE: 75
cctgtatgtg acccatgtgc                                                               20

<210> SEQ ID NO 76
<211> LENGTH: 20
<212> TYPE: DNA
<213> ORGANISM: Artificial sequence
<220> FEATURE:
<223> OTHER INFORMATION: synthetic sequence

<400> SEQUENCE: 76
gcacatgggt cacatacagg                                                               20

<210> SEQ ID NO 77
<211> LENGTH: 20
<212> TYPE: DNA
<213> ORGANISM: Artificial sequence
<220> FEATURE:
<223> OTHER INFORMATION: synthetic sequence

<400> SEQUENCE: 77
gggccacaac tcctcataaa                                                               20

<210> SEQ ID NO 78
<211> LENGTH: 20
<212> TYPE: DNA
<213> ORGANISM: Artificial sequence
<220> FEATURE:
<223> OTHER INFORMATION: synthetic sequence

<400> SEQUENCE: 78
accgtggaca accatcactt                                          20

<210> SEQ ID NO 79
<211> LENGTH: 20
<212> TYPE: DNA
<213> ORGANISM: Artificial sequence
<220> FEATURE:
<223> OTHER INFORMATION: synthetic sequence

<400> SEQUENCE: 79
atgtcgtttc tgccttccag                                          20

<210> SEQ ID NO 80
<211> LENGTH: 20
<212> TYPE: DNA
<213> ORGANISM: Artificial sequence
<220> FEATURE:
<223> OTHER INFORMATION: synthetic sequence

<400> SEQUENCE: 80
gaccagctac accctggaga                                          20

<210> SEQ ID NO 81
<211> LENGTH: 20
<212> TYPE: DNA
<213> ORGANISM: Artificial sequence
<220> FEATURE:
<223> OTHER INFORMATION: synthetic sequence

<400> SEQUENCE: 81
aagtcgtgct gcttcatgtg                                          20

<210> SEQ ID NO 82
<211> LENGTH: 20
<212> TYPE: DNA
<213> ORGANISM: Artificial sequence
<220> FEATURE:
<223> OTHER INFORMATION: synthetic sequence

<400> SEQUENCE: 82
caatgttact gtgccggatg                                          20

<210> SEQ ID NO 83
<211> LENGTH: 20
<212> TYPE: DNA
<213> ORGANISM: Artificial sequence
<220> FEATURE:
<223> OTHER INFORMATION: synthetic sequence

<400> SEQUENCE: 83
aagtcgtgct gcttcatgtg                                          20

<210> SEQ ID NO 84
<211> LENGTH: 20
<212> TYPE: DNA
<213> ORGANISM: Artificial sequence
<220> FEATURE:
<223> OTHER INFORMATION: synthetic sequence

<400> SEQUENCE: 84
caatgttact gtgccggatg                                          20

<210> SEQ ID NO 85
<211> LENGTH: 20

```
<212> TYPE: DNA
<213> ORGANISM: Artificial sequence
<220> FEATURE:
<223> OTHER INFORMATION: synthetic sequence

<400> SEQUENCE: 85
cttgtacagc tcgtccatgc                                             20

<210> SEQ ID NO 86
<211> LENGTH: 20
<212> TYPE: DNA
<213> ORGANISM: Artificial sequence
<220> FEATURE:
<223> OTHER INFORMATION: synthetic sequence

<400> SEQUENCE: 86
acttcaagat ccgccacaac                                             20

<210> SEQ ID NO 87
<211> LENGTH: 20
<212> TYPE: DNA
<213> ORGANISM: Artificial sequence
<220> FEATURE:
<223> OTHER INFORMATION: synthetic sequence

<400> SEQUENCE: 87
tccccgtcct tgtcaaatag                                             20

<210> SEQ ID NO 88
<211> LENGTH: 20
<212> TYPE: DNA
<213> ORGANISM: Artificial sequence
<220> FEATURE:
<223> OTHER INFORMATION: synthetic sequence

<400> SEQUENCE: 88
acttcaagat ccgccacaac                                             20

<210> SEQ ID NO 89
<211> LENGTH: 20
<212> TYPE: DNA
<213> ORGANISM: Artificial sequence
<220> FEATURE:
<223> OTHER INFORMATION: synthetic sequence

<400> SEQUENCE: 89
tccccgtcct tgtcaaatag                                             20

<210> SEQ ID NO 90
<211> LENGTH: 20
<212> TYPE: DNA
<213> ORGANISM: Artificial sequence
<220> FEATURE:
<223> OTHER INFORMATION: synthetic sequence

<400> SEQUENCE: 90
aacaagcgta ccatgggtct                                             20

<210> SEQ ID NO 91
<211> LENGTH: 20
<212> TYPE: DNA
<213> ORGANISM: Artificial sequence
<220> FEATURE:
<223> OTHER INFORMATION: synthetic sequence

<400> SEQUENCE: 91
```

-continued

```
aagtcgtgct gcttcatgtg                                              20

<210> SEQ ID NO 92
<211> LENGTH: 20
<212> TYPE: DNA
<213> ORGANISM: Artificial sequence
<220> FEATURE:
<223> OTHER INFORMATION: synthetic sequence

<400> SEQUENCE: 92
cctgtcccct cagttcatgt                                              20

<210> SEQ ID NO 93
<211> LENGTH: 20
<212> TYPE: DNA
<213> ORGANISM: Artificial sequence
<220> FEATURE:
<223> OTHER INFORMATION: synthetic sequence

<400> SEQUENCE: 93
cttcagcttc agcctctgct                                              20

<210> SEQ ID NO 94
<211> LENGTH: 20
<212> TYPE: DNA
<213> ORGANISM: Artificial sequence
<220> FEATURE:
<223> OTHER INFORMATION: synthetic sequence

<400> SEQUENCE: 94
gttgttcgag ttcgtgctga                                              20

<210> SEQ ID NO 95
<211> LENGTH: 20
<212> TYPE: DNA
<213> ORGANISM: Artificial sequence
<220> FEATURE:
<223> OTHER INFORMATION: synthetic sequence

<400> SEQUENCE: 95
aagtcgtgct gcttcatgtg                                              20

<210> SEQ ID NO 96
<211> LENGTH: 21
<212> TYPE: DNA
<213> ORGANISM: Artificial sequence
<220> FEATURE:
<223> OTHER INFORMATION: synthetic sequence

<400> SEQUENCE: 96
ccatgaacgg ccacgagttc g                                            21

<210> SEQ ID NO 97
<211> LENGTH: 22
<212> TYPE: DNA
<213> ORGANISM: Artificial sequence
<220> FEATURE:
<223> OTHER INFORMATION: synthetic sequence

<400> SEQUENCE: 97
gtccaacttg cggtccacgt tg                                           22

<210> SEQ ID NO 98
<211> LENGTH: 20
<212> TYPE: DNA
<213> ORGANISM: Artificial sequence
```

```
<220> FEATURE:
<223> OTHER INFORMATION: synthetic sequence

<400> SEQUENCE: 98
caacgaggac tacaccatcg                                          20

<210> SEQ ID NO 99
<211> LENGTH: 20
<212> TYPE: DNA
<213> ORGANISM: Artificial sequence
<220> FEATURE:
<223> OTHER INFORMATION: synthetic sequence

<400> SEQUENCE: 99
gtcctcgaag ttcatcacgc                                          20

<210> SEQ ID NO 100
<211> LENGTH: 112
<212> TYPE: DNA
<213> ORGANISM: Artificial sequence
<220> FEATURE:
<223> OTHER INFORMATION: synthetic sequence

<400> SEQUENCE: 100
gtaagtgtcg gggtttgtgc cccccctttt ttttataaaa ttgtattaat gttatataca    60
tatctcctgt atgtgaccca tgtgcttatg actctatttc tcatgtgttt ag           112

<210> SEQ ID NO 101
<211> LENGTH: 82
<212> TYPE: DNA
<213> ORGANISM: Artificial sequence
<220> FEATURE:
<223> OTHER INFORMATION: synthetic sequence

<400> SEQUENCE: 101
gtgagtacag gaggtggaga gtggccagcc cttctcatgt tcagagaaca tggttaactg    60
gttaagtcat gtcgtcccac ag                                            82

<210> SEQ ID NO 102
<211> LENGTH: 34
<212> TYPE: DNA
<213> ORGANISM: Artificial sequence
<220> FEATURE:
<223> OTHER INFORMATION: synthetic sequence

<400> SEQUENCE: 102
gaagttccta ttctctagaa agtataggaa cttc                         34

<210> SEQ ID NO 103
<211> LENGTH: 13
<212> TYPE: DNA
<213> ORGANISM: Artificial sequence
<220> FEATURE:
<223> OTHER INFORMATION: synthetic sequence

<400> SEQUENCE: 103
gaagttccta ttc                                                13

<210> SEQ ID NO 104
<211> LENGTH: 34
<212> TYPE: DNA
<213> ORGANISM: Artificial sequence
<220> FEATURE:
<223> OTHER INFORMATION: synthetic sequence
<220> FEATURE:
```

-continued

```
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 104
ataacttcgt atannntann ntatacgaag ttat                                          34

<210> SEQ ID NO 105
<211> LENGTH: 8
<212> TYPE: DNA
<213> ORGANISM: Artificial sequence
<220> FEATURE:
<223> OTHER INFORMATION: synthetic sequence

<400> SEQUENCE: 105 atgtatgc                                                                        8

<210> SEQ ID NO 106
<211> LENGTH: 13
<212> TYPE: DNA
<213> ORGANISM: Artificial sequence
<220> FEATURE:
<223> OTHER INFORMATION: synthetic sequence

<400> SEQUENCE: 106
ataacttcgt ata                                                                 13

<210> SEQ ID NO 107
<211> LENGTH: 13
<212> TYPE: DNA
<213> ORGANISM: Artificial sequence
<220> FEATURE:
<223> OTHER INFORMATION: synthetic sequence

<400> SEQUENCE: 107
ataacttcgt ata                                                                 13

<210> SEQ ID NO 108
<211> LENGTH: 13
<212> TYPE: DNA
<213> ORGANISM: Artificial sequence
<220> FEATURE:
<223> OTHER INFORMATION: synthetic sequence

<400> SEQUENCE: 108
ataacttcgt ata                                                                 13

<210> SEQ ID NO 109
<211> LENGTH: 13
<212> TYPE: DNA
<213> ORGANISM: Artificial sequence
<220> FEATURE:
<223> OTHER INFORMATION: synthetic sequence

<400> SEQUENCE: 109
ataacttcgt ata                                                                 13

<210> SEQ ID NO 110
<211> LENGTH: 13
<212> TYPE: DNA
<213> ORGANISM: Artificial sequence
<220> FEATURE:
<223> OTHER INFORMATION: synthetic sequence
```

```
<400> SEQUENCE: 110
tatacgaagt tat                                                              13

<210> SEQ ID NO 111
<211> LENGTH: 13
<212> TYPE: DNA
<213> ORGANISM: Artificial sequence
<220> FEATURE:
<223> OTHER INFORMATION: synthetic sequence

<400> SEQUENCE: 111
tatacgaagt tat                                                              13

<210> SEQ ID NO 112
<211> LENGTH: 13
<212> TYPE: DNA
<213> ORGANISM: Artificial sequence
<220> FEATURE:
<223> OTHER INFORMATION: synthetic sequence

<400> SEQUENCE: 112
tatacgaagt tat                                                              13

<210> SEQ ID NO 113
<211> LENGTH: 13
<212> TYPE: DNA
<213> ORGANISM: Artificial sequence
<220> FEATURE:
<223> OTHER INFORMATION: synthetic sequence

<400> SEQUENCE: 113
tatacgaagt tat                                                              13

<210> SEQ ID NO 114
<211> LENGTH: 34
<212> TYPE: DNA
<213> ORGANISM: Artificial sequence
<220> FEATURE:
<223> OTHER INFORMATION: synthetic sequence

<400> SEQUENCE: 114
gaagttccta ttctctagaa agtataggaa cttc                                       34

<210> SEQ ID NO 115
<211> LENGTH: 34
<212> TYPE: DNA
<213> ORGANISM: Artificial sequence
<220> FEATURE:
<223> OTHER INFORMATION: synthetic sequence

<400> SEQUENCE: 115
gaagttccta ttcttcaaat agtataggaa cttc                                       34

<210> SEQ ID NO 116
<211> LENGTH: 34
<212> TYPE: DNA
<213> ORGANISM: Artificial sequence
<220> FEATURE:
<223> OTHER INFORMATION: synthetic sequence

<400> SEQUENCE: 116
gaagttccta ttcttcaaaa ggtataggaa cttc                                       34

<210> SEQ ID NO 117
```

-continued

```
<211> LENGTH: 34
<212> TYPE: DNA
<213> ORGANISM: Artificial sequence
<220> FEATURE:
<223> OTHER INFORMATION: synthetic sequence

<400> SEQUENCE: 117
gaagttccta ttctgtagaa agtataggaa cttc                                    34

<210> SEQ ID NO 118
<211> LENGTH: 14
<212> TYPE: DNA
<213> ORGANISM: Artificial sequence
<220> FEATURE:
<223> OTHER INFORMATION: synthetic sequence

<400> SEQUENCE: 118
gaagttccta ttcc                                                          14
```